United States Patent
Weber et al.

(10) Patent No.: US 9,085,624 B2
(45) Date of Patent: Jul. 21, 2015

(54) ANTIBODIES DIRECTED TO THE DELETION MUTANTS OF EPIDERMAL GROWTH FACTOR RECEPTOR AND USES THEREOF

(75) Inventors: Richard Weber, San Francisco, CA (US); Xiao Feng, Union City, CA (US); Orit Foord, Foster City, CA (US); Larry Green, San Francisco, CA (US); Jean M. Gudas, Santa Monica, CA (US); Bruce Keyt, Hillsborough, CA (US); Ying Liu, Palo Alto, CA (US); Palaniswami Rathanaswami, Vancouver (CA); Robert Raya, Fremont, CA (US); Xiao Dong Yang, Palo Alto, CA (US); Jose Corvalan, Foster City, CA (US); Ian Foltz, Burnaby (CA); Xiao-Chi Jia, Los Angeles, CA (US); Jaspal S. Kang, Surrey (CA); Chadwick T. King, Vancouver (CA); Scott L. Klakamp, Fremont, CA (US); Qiaojuan Jane Su, San Jose, CA (US)

(73) Assignee: Amgen Fremont Inc., Fremont, CA (US)

( * ) Notice: Subject to any disclaimer, the term of this patent is extended or adjusted under 35 U.S.C. 154(b) by 0 days.

(21) Appl. No.: 12/268,352

(22) Filed: Nov. 10, 2008

(65) Prior Publication Data

US 2009/0155282 A1 Jun. 18, 2009

Related U.S. Application Data

(62) Division of application No. 10/877,774, filed on Jun. 25, 2004, now Pat. No. 7,736,644.

(60) Provisional application No. 60/483,145, filed on Jun. 27, 2003, provisional application No. 60/525,570, filed on Nov. 26, 2003, provisional application No. 60/562,453, filed on Apr. 15, 2004.

(51) Int. Cl.
| | |
|---|---|
| *A61K 39/395* | (2006.01) |
| *C07K 16/28* | (2006.01) |
| *A61K 39/00* | (2006.01) |
| *A61K 47/48* | (2006.01) |
| *B82Y 5/00* | (2011.01) |

(52) U.S. Cl.
CPC ....... *C07K 16/2863* (2013.01); *A61K 47/48384* (2013.01); *A61K 47/48561* (2013.01); *A61K 47/48746* (2013.01); *B82Y 5/00* (2013.01); *A61K 2039/505* (2013.01); *C07K 2317/34* (2013.01); *C07K 2317/92* (2013.01); *Y10S 435/81* (2013.01)
USPC .................. 424/141.1; 424/142.1; 424/143.1; 435/810

(58) Field of Classification Search
CPC ........... C07K 16/2863; C07K 2317/34; C07K 2317/92; A61K 2039/505; A61K 2123/00
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,485,045 A | 11/1984 | Regen |
| 4,544,545 A | 10/1985 | Ryan et al. |
| 4,681,581 A | 7/1987 | Coates |
| 4,735,210 A | 4/1988 | Goldenberg |
| 4,981,979 A | 1/1991 | Sivam |
| 5,055,291 A | 10/1991 | Lam et al. |
| 5,101,827 A | 4/1992 | Goldenberg |
| 5,102,990 A | 4/1992 | Rhodes |
| 5,194,594 A | 3/1993 | Khawli et al. |
| 5,208,020 A | 5/1993 | Chari et al. |
| 5,212,290 A | 5/1993 | Vogelstein et al. |
| 5,401,828 A | 3/1995 | Vogelstein et al. |
| 5,576,288 A | 11/1996 | Lappi et al. |
| 5,627,052 A | 5/1997 | Schrader |
| 5,648,471 A | 7/1997 | Buffram et al. |
| 5,697,902 A | 12/1997 | Goldenberg |
| 5,710,010 A | 1/1998 | Vogelstein et al. |
| 5,770,195 A | 6/1998 | Hudziak et al. |
| 5,814,317 A | 9/1998 | Vogelstein et al. |
| 5,939,598 A | 8/1999 | Kucherlapati et al. |
| 5,981,725 A | 11/1999 | Vogelstein et al. |
| 6,075,181 A | 6/2000 | Kucherlapati et al. |

(Continued)

FOREIGN PATENT DOCUMENTS

| | | |
|---|---|---|
| AU | 639726 B | 4/1991 |
| CA | 2066428 | 8/1990 |

(Continued)

OTHER PUBLICATIONS

Roitt et al, p. 5.8 and 5.9, in Immunology second edition, Gower Medical Publishing New York 1989.*
Henry et al, Cancer Res. 64: 7995-8001, Nov. 1, 2004.*
Stancoviski et al, Proceedings of the National Academy of Science USA 88: 8691-8695, 1991.*
Riemer et al. Mol. Immunol. 42: 1121-1124, 2005.*
Cochran et al, J. Immunol. Meth. 287: 147-158, 2004.*
U.S. Appl. No. 07/404,226, filed Sep. 8, 1989, Vogelstein.
U.S. Appl. No. 07/466,008, filed Jan. 12, 1990, Kucherlapati.
U.S. Appl. No. 07/531,410, filed Jun. 6, 1990, Vogelstein.
U.S. Appl. No. 07/610,515, filed Nov. 8, 1990, Kucherlapati et al.

(Continued)

*Primary Examiner* — Phuong Huynh
(74) *Attorney, Agent, or Firm* — Knobbe, Martens, Olson & Bear, LLP

(57) ABSTRACT

The present invention relates to novel antibodies, particularly antibodies directed against deletion mutants of epidermal growth factor receptor and particularly to the type III deletion mutant, EGFRvIII. The invention also relates to human monoclonal antibodies directed against deletion mutants of epidermal growth factor receptor and particularly to EGFRvIII. Diagnostic and therapeutic formulations of such antibodies, and immunoconjugates thereof, are also provided.

26 Claims, 57 Drawing Sheets

(56) References Cited

U.S. PATENT DOCUMENTS

| | | | |
|---|---|---|---|
| 6,114,598 A | 9/2000 | Kucherlapati et al. | |
| 6,127,126 A | 10/2000 | Vogelstein et al. | |
| 6,150,584 A | 11/2000 | Kucherlapati et al. | |
| 6,162,963 A | 12/2000 | Kucherlapati et al. | |
| 6,180,370 B1 | 1/2001 | Queen et al. | |
| 6,224,868 B1* | 5/2001 | Wong et al. | 424/184.1 |
| 6,235,883 B1 | 5/2001 | Jakobovits et al. | |
| 6,342,219 B1 | 1/2002 | Thorpe | |
| 6,423,513 B1 | 7/2002 | Fitzgerald et al. | |
| 6,441,163 B1 | 8/2002 | Chari et al. | |
| 6,455,498 B1* | 9/2002 | Vogelstein et al. | 424/195.11 |
| 6,492,497 B1 | 12/2002 | Thompson et al. | |
| 6,673,986 B1 | 1/2004 | Kucherlapati et al. | |
| 6,914,128 B1 | 7/2005 | Salfeld et al. | |
| 6,946,543 B2 | 9/2005 | Ward et al. | |
| 6,946,546 B2 | 9/2005 | Vaughan et al. | |
| 7,084,257 B2 | 8/2006 | Deshpande et al. | |
| 7,261,893 B2 | 8/2007 | Weldman et al. | |
| 7,285,269 B2 | 10/2007 | Babcook et al. | |
| 7,438,910 B2 | 10/2008 | Varnum et al. | |
| 7,456,264 B2 | 11/2008 | Keler et al. | |
| 7,566,772 B2 | 7/2009 | Weber et al. | |
| 7,575,748 B1 | 8/2009 | Erickson et al. | |
| 7,628,986 B2* | 12/2009 | Weber et al. | 424/130.1 |
| 7,736,644 B2* | 6/2010 | Weber et al. | 424/130.1 |
| 8,067,544 B2 | 11/2011 | Landes et al. | |
| 8,337,856 B2 | 12/2012 | Blättler et al. | |
| 2002/0045571 A1 | 4/2002 | Lie et al. | |
| 2003/0086930 A1 | 5/2003 | Mueller et al. | |
| 2003/0099647 A1 | 5/2003 | Deshpande et al. | |
| 2003/0170235 A1 | 9/2003 | Cohen | |
| 2003/0223996 A1 | 12/2003 | Ruben et al. | |
| 2004/0043418 A1 | 3/2004 | Holtzman et al. | |
| 2004/0147428 A1 | 7/2004 | Pluenneke | |
| 2005/0053608 A1* | 3/2005 | Weber et al. | 424/155.1 |
| 2005/0059087 A1* | 3/2005 | Weber et al. | 435/7.1 |
| 2005/0084449 A1 | 4/2005 | Landes et al. | |
| 2005/0147612 A1 | 7/2005 | Yayon et al. | |
| 2008/0113930 A1 | 5/2008 | Tan et al. | |
| 2009/0155282 A1* | 6/2009 | Weber et al. | 424/139.1 |
| 2009/0156790 A1* | 6/2009 | Weber et al. | 530/387.9 |
| 2009/0175887 A1* | 7/2009 | Weber et al. | 424/178.1 |
| 2009/0240038 A1* | 9/2009 | Weber et al. | 530/391.7 |
| 2010/0111979 A1* | 5/2010 | Weber et al. | 424/183.1 |
| 2010/0196398 A1 | 8/2010 | Gazit-Bornstein et al. | |
| 2011/0046686 A1* | 2/2011 | Kaplan et al. | 606/86 R |

FOREIGN PATENT DOCUMENTS

| | | |
|---|---|---|
| CN | 1142505 A | 2/1997 |
| DE | 69025946 | 4/1996 |
| EP | 58481 | 8/1982 |
| EP | 88046 | 9/1983 |
| EP | 102324 | 3/1984 |
| EP | 142641 | 10/1988 |
| EP | 143949 | 10/1988 |
| EP | 36676 B2 | 9/1990 |
| EP | 491007 B1 | 6/1992 |
| EP | 0 463 151 B1 | 6/1996 |
| JP | 607934 | 1/1985 |
| JP | 3 068 180 B2 | 3/1991 |
| JP | 3 068 506 B2 | 3/1991 |
| JP | 3 068 507 B2 | 3/1991 |
| JP | 2975679 B2 | 11/1999 |
| KR | 2002-89359 | 11/2002 |
| KR | 2002-90873 | 12/2002 |
| KR | 2003-38557 | 5/2003 |
| WO | WO 91/03489 | 3/1991 |
| WO | WO 94/02602 | 2/1994 |
| WO | WO 96/16988 | 6/1996 |
| WO | WO 96/34096 | 10/1996 |
| WO | WO 98/24893 | 6/1998 |
| WO | WO 98/50433 | 11/1998 |
| WO | WO 00/76310 | 12/2000 |
| WO | WO 01/00244 | 1/2001 |
| WO | WO 01/24763 | 4/2001 |
| WO | WO 01/62931 | 8/2001 |
| WO | WO 02/02641 | 1/2002 |
| WO | WO 03/47336 | 6/2003 |
| WO | WO 2004/018649 | 3/2004 |
| WO | WO2004084823 | 10/2004 |
| WO | WO2007059082 | 5/2007 |
| WO | WO 2008/086395 | 7/2008 |
| WO | WO 2010/32059 | 3/2010 |
| WO | WO 2013/075048 A1 | 5/2013 |

OTHER PUBLICATIONS

U.S. Appl. No. 07/919,297, filed Jul. 30, 1992, Kucherlapati et al.
U.S. Appl. No. 08/112,848, filed Aug. 27, 1993, Kucherlapati et al.
U.S. Appl. No. 08/234,145, filed Apr. 28, 1994, Kucherlapati et al.
U.S. Appl. No. 08/376,279, filed Jan. 20, 1995, Jakobovitz et al.
U.S. Appl. No. 08/430,938, filed Apr. 1995, Kucherlapati et al.
U.S. Appl. No. 08/462,837, filed Jun. 5, 1995, Kucherlapati et al.
U.S. Appl. No. 08/463,191, filed Jun. 5, 1995, Kucherlapati et al.
U.S. Appl. No. 08/464,584, filed Jun. 5, 1995, Jakobovitz et al.
U.S. Appl. No. 08/486,853, filed Jun. 5, 1995, Kucherlapati et al.
U.S. Appl. No. 08/486,859, filed Jun. 5, 1995, Kucherlapati et al.
U.S. Appl. No. 08/759,620, filed Dec. 3, 1996, Jakobovitz et al.
U.S. Appl. No. 12/396,286, filed Mar. 2, 2009, Weber et al.
U.S. Appl. No. 12/396,313, filed Mar. 2, 2009, Weber et al.
U.S. Appl. No. 12/268,363, filed Nov. 10, 2008, Weber et al.
Batra et al. Epidermal growth factor ligand-independent, unregulated, cell-transforming potential of a naturally occurring human mutant EGFRvlll gene. Cell Growth Differ. 6(10):1251-9 (1995).
Dillman et al. Superiority of an Acid-labile Daunorubicin-Monoclonal antibody Immunoconjugate compared to free drug. Cancer Res. (1988) 48:6097-6102.
Francisco et al. cAC10-vcMMAE, an anti-CD30-monomethyl auristatin E conjugate with potent and selective antitumor activity. Blood. Aug. 15, 2003 [Epub ahead of print]. Epub Apr. 24, 2003.
Gammett et al., (1986). Differences in Sequences Encoding the Carboxy-Terminal Epidermal Growth Factor Receptor Correlate with Differences in the Disease Potential of Viral erbB Genes. Proc. Natl. Acad. Sci. USA 83:6053-6057).
Humphrey et al., (1988). Amplification and Expression of the Epidermal Growth Factor Receptor Gene in Human Glioma Xenografts. Cancer Research 48:2231-2238.
Janeway et al. Immunobiology, 1994, p. 3:1-3:3.
Junghans et al. in Cancer Chemotherapy and Biotherapy 655-686 (2d edition, Chafner and Longo, eds., Lippincott Raven (1996).
Kato et al. J. Med. Chem. 27:1602-1607 (1984).
Kobrin et al. "A V region mutation in a phosphocholine-binding monoclonal antibody results in loss of antigen binding" J Immunol 146(6): 2017-2020, Mar. 1991.
Kris et al., (1985). Antibodies Against a Synthetic Peptide as a Probe for the Kinase Activity of the Avian EGF Receptor and v-erB Protein. Cell 40:619-625.
Kuan et al. EGF mutant receptor vIII as a molecular target in cancer therapy. Endocr Relat Cancer. 8(2):83-96 (2001).
Kuan et al. EGFRvIII as a promising target for antibody-based brain tumor therapy. Brain Tumor Pathol. 17(2):71-78 (2000).
Kuan et al. Increased binding affinity enhances targeting of glioma xenografts by EGFRvIII-specific scFv. International Journal of Cancer. 88(6):962-969 (2000).
Kuby et al. Immunology, Second Edition, 1994, p. 86-96.
Lambert et al. in Immunotoxins 175-209 (A. Frankel, ed. 1988).
Lambert et al. J. Biol. Chem. 260:12035-12041 (1985).
Landry et al. Antibody recognition of a conformational epitope in a peptide antigen: Fv-peptide complex of an antibody fragment specific for the mutant EGF receptor, EGFRvIII. Journal of Molecular. Biology 308(5):883-893 (2001).
Libermann et al. (1985). Amplification, Enhanced Expression and Possible Rearrangement of EGF Receptor Gene in Primary Human Brain Tumours of Glial Origin. Nature 313:144-147.
Livneh et al. "Reconstitution of human epidermal growth factor receptors and its deletion mutants in cultured hamster cells" J Biol Chem., vol. 261, Issue 27, 12490-12497, 09, 1986.

(56) References Cited

OTHER PUBLICATIONS

Lonardo et al. "Evidence for the Epidermal Growth Factor Receptor As a Target for Lung Cancer Prevention" Clin Cancer Res, 2002; 8(1): 54-60.
Lorimer et al. "Immunotoxins that target an oncogenic mutant epidermal growth factor receptor expressed in human tumors." Clinical Cancer Research, Aug. 1995, 1(8): 859-864.
Liu et al. Proc. Natl. Acad. Sci. USA, Aug. 1996, 93: 8618-8623.
Luo et al. Int. J. Cancer. 104(6):716-21 (2003).
Luwor et al. "Monoclonal Antibody 806 Inhibits the Growth of Tumor Xenografts Expressing Either the de2-7 or Amplified Epidermal Growth Factor Receptor (EGFR) but not Wild-Type EGFR" Cancer Research 61: 5355-5361, 2001.
Mamot et al. Epidermal Growth Factor Receptor (EGFR)-targeted Immunoliposomes Mediate Specific and Efficient Drug Delivery to EGFR- and EGFRvIII-overexpressing Tumor Cells. Cancer Research 63:3154-3161 (2003).
Martin, et al. J Mol Biol. Nov. 15, 1996;263(5):800-15.
Mendelsohn, The epidermal growth factor receptor as a target for therapy with antireceptor monoclonal antibodies, Semin Cancer Biol, Oct. 1990; 1(5):339-44.
Mendez et al. Functional transplant of megabase human immunoglobulin loci recapitulates human antibody response in mice. Nat Genet.15(2):146-56 (1997).
Mohammad et al. Clin Cancer Res, May 1998, 4(5): 1337-1343.
Ohkawa et al. Cancer Immumol. Immunother. 23:81-86 (1986).
Pederson et al. "The type III epidermal growth factor receptor mutation. Biological significance and potential target for anti-cancer therapy." Annals of Oncology / ESMO Jun. 2001, 12(6): 745-760.
Reist et al. Astatine-211 labeling of internalizing anti-EGFRvIII monoclonal antibody using N-succinimidyl 5-[211At]astato-3-pyridinecarboxylate. Nuclear Medicine and Biology. 26(4):405-411 (1999).
Tsukuda et al. Br. J. Cancer 52:111-116 (1985).
Vitetta et al. Immunotoxins: magic bullets or misguided missiles? Immunol Today 14:252 (1993).
Wikstrand et al. The class III variant of the epidermal growth factor receptor (EGFRvIII): characterization and utilization as an immunotherapeutic target. J.Neurovirol. 4(2):148-158 (1998).
U.S. Appl. No. 12/649,179, filed Dec. 29, 2009, Weber et al.
Office Action dated Jan. 22, 2013 received in Japanese Patent Application 2010-262796 (with English translation).
Office Action dated Sep. 6, 2013 in U.S. Appl. No. 12/649,179.
Office Action issued Nov. 24, 2011 by the European Patent Office, received in European Patent Application No. 04 777 034.2.
Office Action issued Nov. 24, 2011 by the European Patent Office, received in European Patent Application No. 04 777 147.2.
Office Action dated Feb. 6, 2013 received in Australian Patent Application No. 2011265359.
Office Action and English translation received in Chinese Application No. 200480018185.3, dated Nov. 5, 2012.
Foote et al., "Antibody Framework Residues Affecting the Conformation of the Hypervariable Loops." Journal of Molecular Biology 224.2 (1992):487-499.
Hearing Notification dated Mar. 18, 2011, received in Indian Patent Appl. No. 6074/DELNP/2005.
Hearing Notification dated Mar. 18, 2011, received in Indian Patent Appl. No. 6073/DELNP/2005.
Office Action dated Feb. 15, 2011, received in Japanese Patent Appl. No. 2006-517620.
Office Action dated Feb. 8, 2011, received in Japanese Patent Appl. No. 2006-517700.
Ghiotto et al., GenBank Acc. # AAK94829, Dec. 31, 2001.
Office Action dated Mar. 16, 2011 and English summary, received in Mexican Patent Appl. No. PA/a/2005/014152.
Office Action dated Mar. 24, 2011, received in Canadian Patent Appl. No. 2,530,285.
Office Action dated Mar. 25, 2011, received in Canadian Patent Appl. No. 2,530,172.
Rudikoff et al., "Single Amino Acid Substitution Altering Antigen Binding Specificity", Proc. Natl. Acad. Sci., 1982, Issue 79, pp. 1979-1983.
Office Action dated Mar. 8, 2013 received in Mexican Patent Application MX/a/2012/001444 (with English translation).
Office Action dated Mar. 8, 2013 received in Mexican Patent Application MX/a/2012/001445 (with English translation).
Kala et al., J. Biochem 132: 535-514, 2002.
Office Action dated May 24, 2012 in U.S. Appl. No. 12/649,179, filed Dec. 29, 2009.
Piatesi et al, ChemBio Chem 5: 460-466, 2004.
Lorimer et al. "Recombinant immunotoxins specific for a mutant epidermal growth factor receptor: Targeting with a single chain antibody variable domain isolated by phage display." Proc. Natl. Acad. Sci USA, Dec. 1996, vol. 93, pp. 14815-14820.
Office Action dated Aug. 19, 2013, received in Korean Application No. 10-2013-7014050 with English translation.
Office Action dated Sep. 12, 2013, received in U.S. Appl. No. 12/396,313.
Cochran et al. Domain-level antibody epitope mapping through yeast surface display of epidermal growth factor receptor fragments. J lmmunol Meth 2004, 287: 147-158.
Examiner Communication dated Oct. 20, 2009, received in European Appl. No. 04 777 147.2.
Henry et al. A Prostate-Specific Membrange Antigen-Targeted Monoclonal Antibody-Chemotherapeutic Conjugate Designed for the Treatment of Prostate Cancer. Cancer Res. Nov. 1, 2004. 64: 7995-8001.
Issue Notification dated May 26, 2010, received in U.S. Appl. No. 10/877,774, Issue Date Jun. 15, 2010.
Notice of Acceptance dated Jun. 10, 2010, received in Australian Application No. 2004260936.
Notice of Allowance dated Dec. 8, 2008, received in U.S. Appl. No. 10/877,773.
Notice of Allowance dated Jul. 15, 2010, received in U.S. Appl. No. 12/268,363.
Notice of Allowance dated Jul. 28, 2010, received in Mexican Application No. PA/a/2005/014155.
Notice of Allowance dated Oct. 17, 2008 received in U.S. Appl. No. 10/877,774.
Office Action dated Jul. 12, 2010, received in U.S. Appl. No. 12/396,286.
Office Action dated Jul. 12, 2010, received in U.S. Appl. No. 12/396,313.
Office Action dated Jun. 25, 2010, received in Mexican Application No. PA/a/2005/014152.
Office Action dated Mar. 17, 2010, received in Mexican Patent Appl. No. 2005/014155.
Office Action dated Mar. 25, 2010, received in Australian Application No. 2004259398.
Office Action dated May 11, 2010, received in Japanese Patent Appl. No. 2006/517620.
Office Action dated May 25, 2010, received in Japanese Patent Appl. No. 2006-517700.
Office Action dated Nov. 16, 2007, received in U.S. Appl. No. 10/877,774.
Office Action dated Oct. 12, 2009, received in Australian patent application No. 2004260936.
Office Action dated Sep. 23, 2009, received in European Patent Appl. No. 04 777 147.2.
Patent Withdrawal Notice dated Apr. 24, 2009, for U.S. Appl. No. 10/877,774.
Reimer et al. Matching of trastuzumab (Herceptin®) epitope mimics onto the surface of Her-2/neu—a new method of epitope definition. Mol Innmunol. 2005, 42: 1121-1124.
Request for Continued Examination and Petition to Withdraw from Issuance, filed on Apr. 23, 2009 in U.S. Appl. No. 10/877,774.
Request for Continued Examination filed on Oct. 11, 2010 in U.S. Appl. No. 12/268,363.
Restriction Requirement dated Aug. 19, 2010, received in U.S. Appl. No. 12/649,179.
Restriction Requirement dated Oct. 2, 2009, received in U.S. Appl. No. 12/396,286.

(56) References Cited

OTHER PUBLICATIONS

Roitt et al. page 5.8 and 5.9, in Immunology second edition, Gower Medical Publishing, New York, 1989.
Stancovski et al. Mechanistic aspects of the opposing effects of monoclonal antibodies to the ERBB2 receptor on tumor growth. Proc Natl Aced Sci USA, 1991, 88: 8691-8695.
Weber et al., Grant of U.S. Pat. No. 7,628,986, Dec. 8, 2009.
Office Action issued Aug. 26, 2011 by the Chinese Patent Office, received in Chinese Patent Application No. 200480018185.3.
Office Action dated Dec. 2, 2012, received in Korean Patent Appl. No. 10-2012-7026173 (with English translation).
Extended European Search Report dated May 4, 2012 for Application No. 11188665.1. 10 pages.
Extended European Search Report dated May 4, 2012 for Application No. 1118866.9. 11 pages.
EPO Result of Consultation dated Apr. 26, 2012 for Application No. 04 777 147.2. 3 pages.
Office Action dated Apr. 10, 2012 received in Korean Application No. 10-2011-7031662.
Office Action dated May 14, 2012 received in Canadian Application No. 2,530,172.
Office Action dated May 1, 2013 in Canadian Application No. 2,530,172.
Tamura, et al., Structural Correlates of an Anticarcinoma Antibody: Identification of Specificity-Determining Residues (SDRs) and Development of a Minimally Immunogenic Antibody Variant by Retention of SDRs Only, Journal of Immunology, 2000, vol. 164, pp. 1432-1441.
Brummell, et al., Probing the Combining Site of an Anti-Carbohydrate Antibody by Saturation-Mutagenesis: Role of the Heavy-Chain CDR3 Residues, Biochemistry, 1993, vol. 32, pp. 1180-1187.
Office Action dated Jun. 11, 2012 in Canadian Patent Application No. 2,530,285.
Office Action received in Korean Patent Application No. 10-2005-7024871, dated Jun. 29, 2012.
Thorpe et al., "An Immunotoxin Composed of Monoclonal Anti-Thy 1.1 Antibody and a Ribosome-Inactivating Protein from Saponaria Officinalis: Potent Antitumor Effects in Vitro and in Vivo", J. Natl. Cancer Inst., 75 pages, 151-159, Jul. 1985.
Office Action dated Jul. 11, 2013, received in Korean Application No. 10-2013-7011483 with English Translation.
Office Action dated Oct. 8, 2012 received in Mexican Patent Application No. MxX/a/2012/001445; (with English translation).
Office Action dated Oct. 16, 2012 received in Mexican Patent Application No. MX/a/2012/001444; (with English translation).
Office Action dated Nov. 7, 2012 received in Korean Patent Application No. 10-2012-7019601, (with English translation).
Office Action dated Aug. 27, 2013 in Japanese Patent Application 2010-252825 with English translation.
Office Action dated Aug. 27, 2013 in Japanese Patent Application 2010-262796 with English translation.
Office Action dated Jun. 9, 2013, received in Chinese Application No. 2011104605368 with English Translation.
Office Action dated Jul. 1, 2011, received in Korean Patent Appl. No. 10-2005-7024871.
Trail et al., "Monoclonal Antibody Drug Immunoconjugates for Targeted Treatment of Cancer." Cancer Immunol Immunother 52 (2003): 328-337.
Office action dated Jun. 28, 2013 received in Canadian Patent Application 2,530,285.
Advisory Action dated Jan. 9, 2013 in U.S. Appl. No. 12/649,179.
Office Action dated Jan. 15, 2013 received in Japanese Patent Application 2010-252825 (with English translation).
Office Action dated Aug. 23, 2013 in Chinese Patent Application 200480018185.3 with English translation.
Office Action dated Oct. 7, 2013 in U.S. Appl. No. 12/396,286.
Office Action dated Oct. 11, 2013 in European Application No. 11188665.1.
Office Action dated Oct. 11, 2013 in European Application No. 11188666.9.

Akers et al., "Formulation Development of Protein Dosage Forms," Pharmaceutical Biotechnology, Kluwer, Dordrecht, NL, vol. 14, Jan. 1, 2002, pp. 47-127.
Campbell, Chapter 1, Monoclonal Antibody Technology, 1984 pp. 1-32, Elsevier Science Publishers B.V., The Netherlands.
Casset et al., "A Peptide Mimetic of an Anti-CD4 Monoclonal Antibody by Rational Design," Biochemical and Biophysical Research Communications, 2003, vol. 307, pp. 198 205.
Chamow et al., "Immunoadhesins: Principles and Application," Tibtech, Feb. 1996, pp. 52-60, vol. 14.
Chen et al., "Influence of Histidine on the Stability and Physical Properties of a Fully Human Antibody in Aqueous and Solid Forms," Pharmaceutical Research, Dec. 2003, pp. 1952-1960, vol. 20 (12).
Chen et al., "Selection and Analysis of an Optimized Anti-VEGF Antibody: Crystal Structure of an Affinity Matured Fab in Complex with Antigen," J. Mol. Biol., 1999, vol. 293, pp. 865 881.
Colman, "Effects of Amino Acid Sequence Changes on Antibody-Antigen Interactions," Res. Immunol., Jan. 1994, pp. 33-36, vol. 145(1).
De Pascalis et al., "Grafting of 'Abbreviated' Complementarity Determining Regions Containing Specificity Determining Residues Essential for Ligand Contact to Engineer a Less Immunogenic Humanized Monoclonal Antibody," J. Immunol, 2002, vol. 169, pp. 3076-3084.
Ellis, et al., "Engineered Anti-CD38 Monoclonal Antibodies for Immunotherapy of Multiple Myeloma," The Journal of Immunology, 1995, pp. 925-937, Vo. 155.
Faber, et al., Three-dimensional Structure of a Human Fab with High Affinity for Tetanus Toxoid, Immunotechnology 3:253-270, 1998.
Graille, et al., Complex Between Peptostreptococcus Magnus Protein L and a Human Antibody Reveals Structural Convergence in the Interaction Modes of Fab Binding Proteins, Structure 9:679-687, Aug. 2001.
Houghten et al., "Relative Importance of Position and Individual Amino Acid Residues in Peptide Antigen-Antibody Interactions: Implications in the Mechanism of Antigenic Drift and Antigenic Shift," New Approaches to Immunization, Vaccines 86, Cold Spring Harbor Laboratory, p. 21-25, 1986.
Knappik et al., "Fully Synthetic Hyuman Combinatorial Antibody Libraries (HuCAL) Based on Modular Consensus Frameworks and CDRs Randomized with Trinucleotides," J. Mol. Biol. 2000, pp. 57-86, vol. 296.
Lamminmaki et al., "Crystal Structure of a Recombinant Anti-estradiol Fab Fragment in Complex with 17β-Estradiol," The Journal of Biological Chemistry, vol. 276 (39), Sep. 28, 2001, pp. 36687 36694.
Lederman et al., "A Single Amino Acid Substitution in a Common African Allele of the CD4 Molecule Ablates Binding of the Monoclonal Antibody, OKT4," Molecular Immunology, 1991, pp. 1171 1181, vol. 28(11).
Lescar, et al., Three-Dimensional Structure of a Fab-Peptide Complex: Structural Basis of HIV-1 protease Inhibition by a Monoclonal Antibody, J. Mo. Biol 297:1207-1222, 1997.
Li et al., "β Endorphin Omission Analogs: Dissociation of Immunoreactivity from other Biological Activities, " Proc. Natl. Acad. Sci. USA, Jun. 1980, pp. 3211 3214, vol. 77 (6).
Lonberg, Human antibodies from transgenic animals, Nature Biotechnology 23: 1117-1125, 2005.
MacCallum et al., "Antibody-Antigen Interactions: Contact Analysis and Binding Site Topography," J. Mol. Biol., 1996, pp. 732-745, vol. 262.
McNutt et al., "Antagonism of Secreted PCSK9 Increases Low Denisty Lipoprotein Receptor Expression in HepG2 Cells," The Journal of Biological Chemistry, Apr. 17, 2009, pp. 10561-10570, vol. 284(16).
Ngo et al., "Computational Complexity, Protein Structure Prediction, and the Levinthal Paradox," The Protein Folding Problem and Teritiary Structure Prediction, 1994, pp. 491-495.
Notice of Acceptance dated May 27, 2010, received in Australian Patent Application No. 2004260936.
Notice of Allowance dated Sep. 17, 2013, received in U.S. Appl. No. 12/268,363.

(56) References Cited

OTHER PUBLICATIONS

Office Action dated Apr. 8, 2011, received in Australian Patent Application No. 2010202054.
Office Action dated Apr. 8, 2011, received in Australian Patent Application No. 2010219363.
Office Action dated Apr. 27, 2011, received in Chinese Patent Application No. 200480018260.6 (with English Translation).
Office Action dated Jan. 10, 2013, received in U.S. Appl. No. 12/474,176.
Office Action dated Jul. 29, 2013, received in Chinese Patent Application No. 201110233784.9 (with English Translation).
Office Action dated Mar. 24, 2012, received in Korean Patent Application No. 10-2005-7024883 (with English Translation).
Office Action dated May 2, 2011, received in Korean Patent Application No. 10-2005-7024883 (with English Translation).
Office Action dated May 3, 2011, received in U.S. Appl. No. 12/649,179.
Oral Proceedings Summons dated Oct. 25, 2013, received in European Pat. App. No. 04777034.2.
Oral Proceedings Summons dated Oct. 25, 2013, received in European Pat. App. No. 04777147.2.
Padlan et al., "Structure of an Antibody-Antigen Complex: Crystal Structure of the HyHEL 10 Fab Lysozyme Complex," Proc. Natl. Acad. Sci., vol. 86, Aug. 1989, pp. 5938 5942.
Paul, "Fundamental Immunology," Laboratory of Immunology, National Institute of Allergy and Infectious Diseases, National Institutes of Health, Bethesda, Maryland, 1993, pp. 290-295.
Piatesi et al., "Immunological Optimization of a Generic Hydrophobic Pocket for High Affinity Hapten Binding and Diels-Alder Activity," ChemBioChem, 2004, pp. 460-466, vol. 5.
Ramsland, et al., An Unusual Human IgM Antibody with a Protruding HCDR3 and High Avidity for its Peptide Ligands, Molecular Immunology 37:295-310, 2000.
Request for Continued Examination and Petition to Withdraw from Issuance filed Apr. 29, 2009, in U.S. Appl. No. 10/877,773.
Request for Continued Examination filed Oct. 11, 2010, in U.S. Appl. No. 12/396,286.
Request for Continued Examination filed Oct. 11, 2010, in U.S. Appl. No. 12/396,313.
Strong, et al., Three-Dimensional Structure of Murine Anti-p-azophenylarsonate Fab 36-71. 1. X-ray Chrystallography, Site-Directed Mutagenesis, and Modeling of the Complex with Hapten, Biochemistry, 30:3739-3748, 1991.
Vajdos et al., "Comprehensive Functional Maps of the Antigen Binding Site of an Anti ErbB2 Antibody Obtained with Shotgun Scanning Mutagenesis," J. Mol. Biol., 2002, vol. 320, pp. 415 428.
Van Regenmortel, "Mapping Epitope Structure and Activity: From One-Dimensional Prediction to Four-Dimensional Description of Antigenic Specificity," A Comapnion to Methods in Enzymology 9, 1996, pp. 465-472, Article No. 0054.
Wells, "Additivity Of Mutational Effects in Proteins," The American Chemical Society, Sep. 18, 1990 pp. 8509-8571, vol. 29 (37).
Whitlow, et al., 1.85 A Structure of Anti-Fluorescein 4-4-20 Fab, Protein Engineering 8(8):749-761, 1995.
Wu, et al., J. Mol. Biol. 294:151-162, 1999.
Young, et al., The Three-Dimensional Structures of a Polysaccharide Binding Antibody to Cryptococcus Neoformans and its Complex with a Peptide from a Phage Display Library: Implications for the Identification of Peptide Mimotopes, J. Mol. Biol. 274:622-634, 1997.
Final Office Action dated Jan. 29, 2014 in U.S. Appl. No. 12/649,179.
Final Office Action dated Jan. 31, 2014 in U.S. Appl. No. 12/396,286.
Notice of Allowance dated Jan. 17, 2014 in U.S. Appl. No. 12/268,363.
Office Action dated Feb. 17, 2014 in Korean Application No. 10-2005-7024883 with English Translation.
EPO Notification—Invitation pursuant to Article 94(3) and Rule 71(1) EPC dated Mar. 11, 2014 in European Application No. 04 777 034.2.
EPO Notification—Invitation pursuant to Article 94(3) and Rule 71(1) EPC dated Mar. 11, 2014 in European Application No. 04 777 147.2.
Trial Decision dated Mar. 3, 2014 in Korean Application No. 10-2005-7024871 with English Translation.
Office Action dated Mar. 10, 2014 in Japanese Application No. 2010-252825 with English Translation.
Office Action dated Mar. 3, 2014 in Japanese Application No. 2010-262796 with English Translation.
Pietersz et al., "Antibody Conjugates for the Treatment of Cancer", Immunological Reviews, 1992, vol. 129, No. 29, pp. 57-80.
Office Action dated Jan. 28, 2014 in Chinese Application No. 201110460536.8 with English Translation.
Office Action dated Mar. 20, 2014, received in Korean Patent Application No. 10-2005-7024871 (with English Translation).
Notice of Allowance dated Apr. 23, 2014 in U.S. Appl. No. 12/396,286.
Babcook et al. A novel strategy for generating monoclonal antibodies from single, isolated lymphocytes producing antibodies of defined specificities. Proc Natl Acad Sci U S A.93(15):7843-8 (1996).
Barrios et al. "Length of the antibody heavy chain complementarity determining region 3 as a specificity-determining factor" J Mol Recognition 17: 332-338 (2004).
Batra et al. Epidermal growth factor ligand-independent, unregulated, cell-transforming potential of a naturally occuring human mutant EGFRvIII gene. Cell Growth Differ. 6(10):1251-9 (1995).
Bigner et al., (1988) J. Neuropathol. Exp. Neurol., 47:191-205.
Bumol et al, in Antibody Mediated Delivery Systems 55-79 (J. Rodwell, ed. 1988).
Chothia, et al. (Nature. Dec. 21-28, 1989;342(6252):877-83).
Deo et al. Immunology Today (1997) 18:127.
Diener et al, in Antibody Mediated Delivery Systems 1-23 (J. Rodwell, ed. 1988).
Dillman et al. Preclinical trials with conbinations and conjugates of T101 monoclonal antibody and doxorubicin. Cancer Res. (1986) 46:4886-4891.
Dillman et al. Superiority of an Acid-Iabile Daunorubicin-Monoclonal antibody Immunoconjugate compared to free drug. Cancer Res. (1988) 48:6097-6102.
Doronina et al. Development of potent monoclonal antibody auristatin conjugates for cancer therapy. Nature Biotechnology. (2003) 21: 778-784.
Doronnina et al. Nature Biotechnology, Jul. 2003, 21(7): 784, 941.
Downward et al. Close Similarity of Epidermal Growth Factor Receptor and v-erb B Oncogene Protein Sequence. Nature (1984) 307:521-527.
Dubowchik et al. Cathepsin B-sensitive dipeptide prodrugs. 2. Models of anticancer drugs paclitaxel (Taxol), mitomycin C and doxorubicin. Bioorg Med Chem Lett. (1998) 8(23):3347-52.
Endo et al. Cancer Res. (1980) 47:1076-1080.
Examiner's First Report on Australian Patent Application No. 2004260936, dated Aug. 25, 2008, in 2 pages.
Francisco et al. cAC10-vcMMAE, an anti-CD30-monomethyl auristatin E conjugate with potent and selective antitumor activity. Blood. (2003) Aug. 15 [Epub ahead of print]. Epub Apr. 24, 2003.
Fung et al., (1984) Activation of the Cellular Oncogene c-erb B by LTR Insertion: Molecular Basis for Induction of Erythroblastosis by Avian Leukosis Virus. Cell 33:357-368.
Gammett et al., (1986). Differences in Sequences Encoding the Carboxy-Terminal Domain of the Epidermal Growth Factor Receptor Correlate with Differences in the Disease Potential of Viral erbB Genes. Proc. Natl. Acad. Sci. USA 83:6053-6057).
Garcia de Palazzo, IE. et al. Expression of mutated epidermal growth factor receptor by non-small cell lung carcinomas. Cancer Res. 53(14):3217-20 (1993).
Garnett et al. Cancer Res. 46:2407-2412 (1986).
Ge H. et al. Evidence of high incidence of EGFRvIII expression and coexpression with EGFR in human invasive breast cancer by laser capture microdissection and immunohistochemical analysis. Int J Cancer. 98(3):357-61 (2002).
Ghose et al, in Targeted Drugs 1-22 (E. Goldberg, ed. 1983).
Gilmore et al., (1985). Protein Phosphorlytion at Tyrosine is Induced by the v-erb B Gene Product in Vivo and In Vitro. Cell 40:609-618.

(56) References Cited

OTHER PUBLICATIONS

Green and Jakobovits J. Exp. Med. 188:483-495 (1998).
Green et al. "Generation and characterization of fully human EGFRvIII antibodies suitable for immunoconjugates" American Association for Cancer Research Annual Meeting, Mar. 2004.
Humphrey et al., (1998). Amplification and Expression of the Epidermal Growth Factor Receptor Gene in Human Glioma Xenografts. Cancer Research 48:2231-2238.
Humphrey et al. "Anti-synthetic peptide antibody reacting at the fusion junction of deletion-mutant epidermal growth factor receptors in human glioblastoma" Proceedings of the National Academy of Sciences USA, Jun. 1990, 87 (11): 4207-4211.
Hurwitz et al. Appl. Biochem. 2:25-35 (1980).
International Search Report dated Aug. 1, 2005, from International Application No. PCT/US2004/020295.
International Search Report dated Aug. 14, 2006, from International Application No. PCT/US2004/20564.
Janeway et al. Immunobiology, 1994, p. 3:1-3:3
Johns et al. "Novel monoclonal antibody specific for the de2-7 epidermal growth factor receptor (EGFR) that also recognizes the EGFR expressed in cells containing amplification of the EGFR gene" Int J Cancer 98: 398-408 (2002).
Jorissen et al. "Epidermal growth factor receptor: mechanisms of activation and signaling" Experimental Cell Research 284 (2003) 31-53.
Jungbluth et al. A monoclonal antibody recognizing human cancers with amplification/overexpression of the human epidermal growth factor receptor. Proc Natl Acad Sci U S A. 100(2):639-644 (2003).
Malden et al., (1988). Selective Amplification of the Cytoplasmic Domain of the Epidermal Growth Factor Receptor Gene in Glioblastoma Multiforme. Cancer Research 4:2711-2714.
Mamot et al. Epidermal Growth Factor Receptor (EGFR)-targeted Immunoliposomes Mediate Specific and Efficient Drug Delivery to EGFR- and EGFRvIII-overexpressing Tumor Cells. Cancer Research 63:3154-3161 (2003).
Manabe et al. Biochem. Pharmacol. 34 : 289-291 (1985).
Martin, et al. J Mol Biol, Nov. 15, 1996;263(5):800-15.
Mendelsohn J., The epidermal growth factor receptor as a target for therapy with antireceptor monoclonal antibodies. Semin Cancer Biol Oct. 1990;1(5):339-344.
Mendelsohn, "Anti-epidermal growth factor receptor monoclonal antibodies as potential anti-cancer agents", J Steroid Biochem Mol Biol, Dec. 20, 1990; 37 (6):889-92.
Mendelsohn, The epidermal growth factor receptor as a target for therapy with antireceptor monoclonal antibodies. Semin Cancer Biol Oct. 1990; 1(5):339-344.
Mendelsohn, Cancer Cells 7:359 (1989).
Mendez et al. Functional transplant of megabase human immunoglobulin loci recapitulates human antibody response in mice. Nat Genet. 15(2):146-56 (1997).
Modjtahedi and Dean Int'l J. Oncology 4:277-296 (1994).
Mohammad et al. Clin Cancer Res. May 1998, 4(5): 1337-1343.
Moscatello, G. et al. Frequent expression of a mutant epidermal growth factor receptor in multiple human tumors. Cancer Res. 55(23):5536-9 (1995).
Nilsen et al., (1985). c-erbB Activation in ALV-Induced Erythroblastosis: Novel RNA Processing and Promoter Insertion Results in Expression of an Amino-Truncated EGF Receptor. Cell 41:719-726.
Notice of Allowance dated Jul. 13, 2009, received in U.S. Appl. No. 10/877,773.
Notice of Allowance dated Jun. 24, 2009, received in U.S. Appl. No. 10/877,774.
Office Action dated Dec. 4, 2007, received in U.S. Appl. No. 10/877,773.
Office Action dated Jun. 13, 2008, received in U.S. Appl. No. 10/877,773.
Office Action dated Aug. 7, 2009, received in U.S. Appl. No. 12/268,363.
Office Action dated Dec. 26, 2008, received in Indian Patent Appl. No. 6073/DELNP/2005.
First Examination Report dated Mar. 31, 2009, received in Indian Patent Application No. 6074/DELNP/2005.
Office Action dated Jul. 11, 2008, received in Chinese Appl. No. 200480018260.6.
Office Action dated Apr. 27, 2007, received in Chinese Patent Appl. No. 200480018260.6.
Ohkawa et al. Cancer Immumol. Immunother, 23:81-86 (1986).
Olapade-Olaopa, EO. et al. Evidence for the differential expression of a variant EGF receptor protein in human prostate cancer. Br J Cancer. 82(1):186-94 (2000).
Pederson et al. "The type III epidermal growth factor receptor mutation. Biological significance and potential target for anti-cancer therapy." Annals of Oncology/ESMO Jun. 2001, 12(6): 745-760.
Pelley et al., (1988). Proviral-Activated c-erbB is Leukemogenic but not Sarcomagenic: Characterization of a Replication—Competent Retrovirus Containing the Activated c-erbB. Journal of Virology 62: 1840-1844.
Pietersz et al, in Antibody Mediated Delivery Systems 25-53 (J. Rodwell, ed. 1988).
Reist et al. Astatine-211 labeling of internalizing anti-EGFRvIII monoclonal antibody using N-succinimidyl 5-[211At]astato-3-pyridinecarboxylate. Nuclear Medicine Medicine and Biology. 26(4):405-411 (1999).
Reist et al. In vitro and in vivo behavior of radiolabeled chimeric anti-EGFRvIII monoclonal antibody: comparison with its murine parent. Nuclear Medicine and Biology. 24(7):639-647 (1997).
Sampson et al. "Unarmed, tumor-specific monoclonal antibody effectively treats brain tumors" Proc Nat Acad Sci 97(13): 7503-7508, Jun. 2000.
Schlessinger et al. "Signal Transduction by Epidermal Growth Factor Receptor", Cold Spring Harb Symp Quant Biol, Jan. 1, 1988; 53: 515-519.
Schmidt et al., Expression of an Oncogenic Mutant EGF Receptor Markedly Increases The Sensitivity of Cells to an EGF-Receptor-Specific Antibody-Toxin, *Int. J. Cancer*, 75, 878-884 (Mar. 16, 1998).
Sela et al. in Immunoconjugates 189-216 (C. Vogel, ed. 1987).
Shouval et al. Proc. Natl. Acad. Sci. 85: 8276-8280 (1988).
Supplementary European Search Report dated May 4, 2009, received in European Patent Application No. 0477734.2.
Toki et al. Abstracts of Papers of the American Chemical Society, Apr. 2002, 223(2):A1113, 7-11.
Trouet et al. Proc. Natl. Acad. Sci. 79: 626-629 (1982).
Tsukada et al. Br. J. Cancer 52:111-116 (1985).
Tsukada et al. J. Natl. Canc. Inst. 73:721-729 (1984).
Ullrich et al. (1984). Human Epidermal Growth Factor Receptor cDNA Sequence and Aberrant Expression of the Amplified Gene in A431 Epidermoid Carcinoma Cells. Nature 309:418-425.
Valerius et al. Blood 90:4485-4492 (1997).
Vitetta et al. Immunotoxins: magin bullets or misguided missiles? Immunol Today 14:252 (1993).
Wells et al., (1988). Genetic Determinants of Neoplastic Transformation by the Retroviral Oncogene v-erbB. Proc. Natl. Acad. Sci. USA 85:7597-7601.
Wikstrand et al. Generation of anti-idiotypic reagents in the EGFRvIII tumor-associated antigen system. Cancer Immunology, Immunotherapy. 50(12):639-652 (2002).
Wikstrand et al. Monoclonal antibodies against EGFRvIII are tumor specific and react with breast and lung carcinomas malignant gliomas. Cancer Research. 55(14):3140-3148 (1995).
Wikstrand et al. The class III variant of the epidermal growth factor receptor (EGFRVIII): characterization and utilization as an immuno therapeutic target. J.Neurovirol. 4(2):148-158 (1998).
Wong et al. (1987). Increased Expression of the Epidermal Growth Factor Receptor Gene in Malignant Gliomas is Invariably Associated with Gene Amplification. Proc. Natl. Acad. Sci. USA 84:6899-6903.
Yamamoto et al., (1983). A New Avain Erythroblastosis Virus, AEV-H Carries erbB Gene Responsible for the Induction of Both Erythroblastosis and Sarcoma. Cell 34:225-232.

(56) References Cited

OTHER PUBLICATIONS

Yamazaki et al. (1988). Amplification of the Structurally and Functionally Altered Epidermal Growth Factor Receptor Gene (c-erbB) in Human Brain Tumors. Molecular and Cellular Biology 8:1816-1820.
Yang and Reisfeld. J. Natl. Canc. Inst. 80:1154-1159 (1988).
Yang X et al. Development of ABX-EGF, a fully human anti-EGF receptor monoclonal antibody, for cancer therapy. Crit Rev Oncol Hemato 38(1):17-23 (2001).
Yang X-D et al. Eradication of Established Tumors by a Fully Human Monoclonal Antibody to the Epidermal Growth Factor Receptor without Concomitant Chemotherapy. Cancer Research 59(6):1236-1243 (1999).
File History, U.S. Appl. No. 12/268,363, filed Nov. 10, 2008.
File History, U.S. Appl. No. 12/396,313, filed Mar. 2, 2009.
File History, U.S. Appl. No. 12/396,286, filed Mar. 2, 2009.
File History, U.S. Appl. No. 10/877,773, filed Jun. 25, 2004.
File History, U.S. Appl. No. 10/877,774, filed Jun. 25, 2004.
Office Action dated Oct. 12, 2009, received in Australian application No. 2004260936, 2 pages.
Office Action dated Sep. 23, 2009, received in EP Application No. 04 777 147.2, 6 pages.
Office Action dated Nov. 3, 2009, received in Mexican Appl. No. PA/a/2005/014152 (English translation only, original previously submitted).
Office Action dated Apr. 23, 2014 in Korean Application No. 10-2014-7004191 with English Translation.
Office Action dated Apr. 23, 2014 in Korean Application No. 10-2014-7000817 with English Translation.
Office Action dated Nov. 19, 2013, received in Mexican Patent Application No. MX/a/2012/001444 with English Translation.
Trial Decision dated Jan. 17, 2014 in Korean Patent App. No. 2005-7024882 (with English translation).
Office Action dated Apr. 30, 2014 in Chinese Application No. 200480018185.3 with English Translation.
Office Action dated Jun. 12, 2014 in Canadian Application No. 2530285.
Office Action dated Jun. 13, 2014 in Chinese Application No. 201110233784.9 with English Translation.
Office Action dated Jul. 11, 2014 in Canadian Patent App. No. 2,530,172.
Office Action dated Nov. 11, 2009, received in EP Appl. No. 04777034.2.
Office Action dated Nov. 11, 2009, received in EP Appl. No. 04777147.2.
Office Action dated Nov. 3, 2009, received in Mexican Appl. No. PA/a/2005/014152.
Notice of Allowance dated Jul. 1, 2014 in U.S. Appl. No. 12/268,363.
"Anti-c-ErbB2/c-Neu (Ab-5), clone TA-1," http://www.millipore.com/catalogue/item/mabe320, accessed May 28, 2014.
"Mertansine," Wikipedia, http://en.wikipedia.org/w/index/php?title=Metansine&oldid=45829581, accessed May 28, 2014.
"Trastuzumab," Wikipedia, http://en.wikipedia.org/wiki/Trastuzumab, accessed May 28, 2014.
Baselga, et al., "Phase II Study of Weekly Intravenous Trastuzumab (Herceptin®) in Patients With HER2/neu- Overexpressing Metastatic Breast Cancer," Semin. Oncol. 26, Suppl12:78-83 (1999).
Baselga, et al., "Recombinant humanized anti-HER2 antibody (Herceptin) enhances the antitumor activity of paclitaxel and doxorubicin against HER21neu overexpressing human breast cancer xenografts." Cancer Res., 58:2825~2831, (1998).
Batra, et al., "Recombinant anti-erbB2 immunotoxins containing Pseudomonas exotoxin." Proc. Natl. Acad. Sci. USA, 89:5867-5871 (1992).
Blythman, et al. "Immunotoxins: hybrid molecules of monoclonal antibodies and a toxin subunit specifically kill tumor cells." Nature, 290:145-146 (1981).
Caron, et al., "Supersaturating infusional humanized anti-CD33 monoclonal antibody HuM195 in myelogenous leukemia," Clin. Cancer Res., 4: 1421-1428 (Jun. 1998).

Carter, et al., "Humanization of an anti-p185 antibody for human cancer therapy." Proc. Natl. Acad. Sci., USA, 89:4285-4289 (1992).
Chari, "Targeted delivery of chemotherapeutics: tumor-activated prodrug therapy." Adv. Drug Del. Rev., 31: 89-104 (1998).
Chari, et al., "Immunoconjugates containing novel maytansinoids: promising anticancer drugs." Cancer Res., 52:127-131 (1992).
Curriculum vitae of Michael G. Rosenblum, Ph.D, last updated Mar. 12, 2014.
Declaration by Barbara Klencke, M.D., filed on Jul. 6, 2010, in U.S. Appl. No. 11/949,351.
Declaration by Mark X. Sliwokoswki, Ph.D., filed on Jul. 6, 2010, in U.S. Appl. No. 11/949,351.
Declaration of Michael G. Rosenblum, Ph.D. dated Apr. 21, 2014.
Declaration of Michael G. Rosenblum, Ph.D. dated May 29, 2014.
Declaration of Walter Blättler and Ravi Chari filed on Sep. 11, 2012, in U.S. Appl. No. 11/949,351.
Drewinko, et al., "Differential killing efficacy of twenty antitumor drugs on proliferating and non-proliferating human tumor cells." Cancer Res. 41 :2328-2333 (1981).
HERCEPTIN® Label, Sep. 1998.
Hooijberg, et al., "Eradication of Large Human B Cell Tumors in Nude Mice with Unconjugated CD20 Monoclonal Antibodies and Jun. 15, Interleukin 2," Cancer Res., 55: 2627-2634 (Jun. 15, 1995).
Hudziak, et al., "p. 185 monoclonal antibody has antiproliferative effects in vitro and sensitizes human breast tumor cells to tumor necrosis factor," Mol. Cell. Biol., 9: 1165-1172 (1989).
Knox, et al., "Yttrium-90-labeled anti-CD20 monoclonal antibody therapy of recurrent B-cell lymphoma," Clin. Cancer Res., 2: 457-470 (Mar. 1996).
Lewis et al. "Differential responses of human tumor cell lines to anti-p185 HER2 monoclonal antibodies," Cancer Immunnol. Immunother. 37:255-263 (1993).
Liu, et al. "Eradication of large colon tumor xenografts by targeted delivery of maytansinoids." Proc. Natl. Acad. Sci., USA, 93:8618-8623 (1996).
Liu, et al., "The development of antibody delivery systems to target cancer with highly potent maytansinoids." Exp. Opin. Invest. Drugs, 6: 169-172 (1997).
Louis Weiner "Monoclonal antibody therapy of cancer," Semin. Oncol. 26, Suppl. 14:43-51 (1999).
Maier, et al., "Requirements for the internalization of a murine monoclonal antibody directed against the HER-21neu gene product c-erbB-2," Cancer Res., 51: 5361-53~9 (1991).
McKenzie, et al., "Generation and characterization of monoclonal antibodies specific for the human neu oncogene product, p. 185." Oncogene, 4:543-548 (1989).
Morgan, et al., "Immunotoxins of Pseudomonasb exotoxin A (PE): effect of linkage on conjugate yield, potency, selectivity and toxicity." Mol. Immunol. 27:273-282 (1990).
Office Action of Dec. 28, 2007, in U.S. Appl. No. 11/488,545.
Office Action of Jan. 26, 2009 in U.S. Appl. No. 11/488,545.
Office Action of Jul. 9, 2008, in U.S. Appl. No. 11/488,545.
Pagliaro, et al., "Humanized M195 monoclonal antibody conjugated to recombinant gelonin: an anti-CD33 immunotoxin with antileukemic activity," Clin. Cancer Res., 4: 1971-1976 (Aug. 1998).
Paik, et al., "Pathologic Findings From the National Surgical Adjuvant Breast and Bowel Project: Prognostic Significance of erbB-2 Protein Overexpression in Primary Breast Cancer," Journal of Clin. Onc., 8(1): 103-112 (Jan. 1990).
Pegram, et al., "Inhibitory effects of combinations of HER-2/neu if antibody and chemotherapeutic agents used for treatment of human breast cancers." Oncogene, 18:2241-2251 (1999).
Phillips, et al., "Targeting HER2-positive breast cancer with trastuzumab-DM1, an antibody-cytotoxic drug conjugate." Cancer Res. 68: 9280-9290 (2008).
Petition for Inter Partes Review of U.S. Pat. No. 7,575,748 dated May 29, 2014.
Petition for Inter Partes Review of U.S. Pat. No. 8,337,856 dated Apr. 22, 2014.
Preliminary Amendment Accompanying Request for Continued Examination under 37 C.F.R. 0 1.114, filed on Oct. 24, 2008, in U.S. Appl. No. 11/488,545.

(56) References Cited

OTHER PUBLICATIONS

Press, et al., "HER-2lneu gene amplification characterized by fluorescence in situ hybridization: poor prognosis in node-negative breast carcinomas." J. Clin. Oncol. 15:2894-2904 (1997).
Response to Office Action of Dec. 28, 2007, filed on Mar. 20, 2008, in U.S. Appl. No. 11/488,545.
Response to Office Action of Jun. 8, 2010, filed on Jul. 6, 2010, in U.S. Appl. No. 11/949,351.
Ring, et al., "Identity of BCA200 and c-erbB-2 indicated by reactivity of monoclonal antibodies with recombinant c-erbB-2." Mol. Immunol., 28: 915-917 (1991).
Rosenblum, et al., "Recombinant immunotoxins directed against the c-erbB-2/HER2/neu oncogene product: in vitro cytotoxity, pharmacokinetics, and in vivo efficacy studies in xenograft models." Clin. Cancer Res., 5:865-874 (1999).
Sgouros, et al., "Pharmacokinetics and Dosimetry of an a-Particle Emitter Labeled Antibody: Bi-HuM195 (Anti-CD33) in Patients with Leukemia," 1. Nucl. Med., 40: 1935-1946 (1999).
Slamon, et al., "Studies of the HER-2/neu proto-oncogene in human breast and ovarion cancer." Science 244:707-712 (1989).
Suzuki, et al., "Immunoselective cell growth inhibition by antibody-Adriamycin conjugates targeting c-erbB2 product on human cancer cells." Biol. Pharm. Bull. 18 1279-1282 (1995).
Vitetta, et al., "Monoclonal antibodies as agonists: an expanded role for their use in cancer therapy." Cancer Res., 54:5301.5309 (1994).
Office Action dated Dec. 18, 2014 in Korean Application No. 10-2005-7024871 with English Translation.
Office Action dated Oct. 13, 2014 in Australian Application No. 2012268864.
Office Action dated Dec. 3, 2014 in Chinese Application No. 200480018185.3 with English Translation.
Notice of Allowance dated Feb. 17, 2015, received in U.S. Appl. No. 12/268,363.
Office Action dated Jan. 15, 2015, received in Korean Patent Application No. 10-2014-7029678 (with English Translation).
Notice of Allowance dated Oct. 1, 2014 in U.S. Appl. No. 12/396,313.
Notice of Allowance dated Sep. 26, 2014, received in U.S. Appl. No. 12/396,286.
Office Action dated Sep. 30, 2014 in U.S. Appl. No. 12/649,179.
Arteaga, et al. The Epidermanl Growth Factor Receptor: From Mutant Oncogene in Nonhuman Cancers to Therapeutic Target in Human Neoplasia, Journal of Clinical Oncology, 2001 (Sep. 15 Supplement), vol. 19, No. 18s: pp. 32s-40s.
Damstrup, et al., Epidermal Growth Factor Receptor Mutation Type III Transfected into a Small Lung Caner Cell Line is Predominantly Localized at the Cell Surface and Enhances the Malignant Phenotype, Int. J. Cancer, 2002, 97: pp. 7-14.
Lammering, et al., Epidermal Growth Factor Receptor as a Genetic Therapy Target for Carcinoma Cell Radiosensitization. Journal of the National Cancer Institute, Jun. 20, 2001, vol. 93, No. 12, pp. 921-929.
Reist, et al., Tumor-specific anti-epidermal growth factor receptor variant III monoclonal antibodies: use of the tyramine-cellobiose radioiodination method enhances cellular rentention and uptake in tumor xenografts. Cancer Res. Oct. 1, 1995; 55(19): 4375-82.
Office Action dated Sep. 30, 2014 in Indian Patent App. No. 8485/DELNP/2009.
Office Action dated Aug. 22, 2014, received in Chinese Application No. 201110460536.8 with English Translation.
Office Action dated Nov. 28, 2014, received in Korean Patent Application No. 10-2014-7000817 with English translation.
Notice of Allowance dated Mar. 2, 2015, received in U.S. Appl. No. 12/396,286.
Notice of Allowance dated Mar. 26, 2015, received in U.S. Appl. No. 12/396,313.
Office Action dated Jan. 13, 2015, received in Chinese Patent Application No. 201110233784.9 (with English translation).
Office Action dated Mar. 12, 2015, received in U.S. Appl. No. 12/649,179.
Office Action dated Apr. 13, 2015, received in Japanese Patent App. No. 2013-272029 (with English translation).
Office Action dated Apr. 13, 2015, received in Japanese Patent App. No. 2013-272028 (with English translation).
Issue Notification dated Jun. 3, 2015 in U.S. Appl. No. 12/268,363.

\* cited by examiner

FIG. 1

| FIG 1A |
| FIG 1B |
| FIG 1C |
| FIG 1D |
| FIG 1E |

```
EGFR wt     1  LEEKKVCQGTSNKLTQLGTFEDHFLSLQRMFNNCEVVLGNLEITYVQRNYDLSFLKTIQE  60
EGFRvIII    1  LEEKK-------------------------------------------------------  1

EGFR wt    61  VAGYVLIALNTVERIPLENLQIIRGNMYYENSYALAVLSNYDANKTGLKELPMRNLQEIL 120
EGFRvIII    1  ------------------------------------------------------------  1

EGFR wt   121  HGAVRFSNNPALCNVESIQWRDIVSSDFLSNMSMDFQNHLGSCQKCDPSCPNGSCWGAGE 180
EGFRvIII    1  ------------------------------------------------------------  1

EGFR wt   181  ENCQKLTKIICAQQCSGRCRGKSPSDCCHNQCAAGCTGPRESDCLVCRKFRDEATCKDTC 240
EGFRvIII    1  ------------------------------------------------------------  1
```

```
EGFR wt    241 PPLMLYNPTTYQMDVNPEGKYSFGATCVKKCPRNYVVTDHGSCVRACGADSYEMEEDGVR 300
EGFRvIII     1 ---------------------------------GNYVVTDHGSCVRACGADSYEMEEDGVR  33

EGFR wt    301 KCKKCEGPCRKVCNGIGIGEFKDSLSINATNIKHFKNCTSISGDLHILPVAFRGDSFTHT 360
EGFRvIII    34 KCKKCEGPCRKVCNGIGIGEFKDSLSINATNIKHFKNCTSISGDLHILPVAFRGDSFTHT  93

EGFR wt    361 PPLDPQELDILKTVKEITGFLLIQAWPENRTDLHAFENLEIIRGRTKQHGQFSLAVVSLN 420
EGFRvIII    94 PPLDPQELDILKTVKEITGFLLIQAWPENRTDLHAFENLEIIRGRTKQHGQFSLAVVSLN 153

EGFR wt    421 ITSLGLRSLKEISDGDVIISGNKNLCYANTINWKKLFGTSGQKTKIISNRGENSCKATGQ 480
EGFRvIII   154 ITSLGLRSLKEISDGDVIISGNKNLCYANTINWKKLFGTSGQKTKIISNRGENSCKATGQ 213
```

FIG. 1C

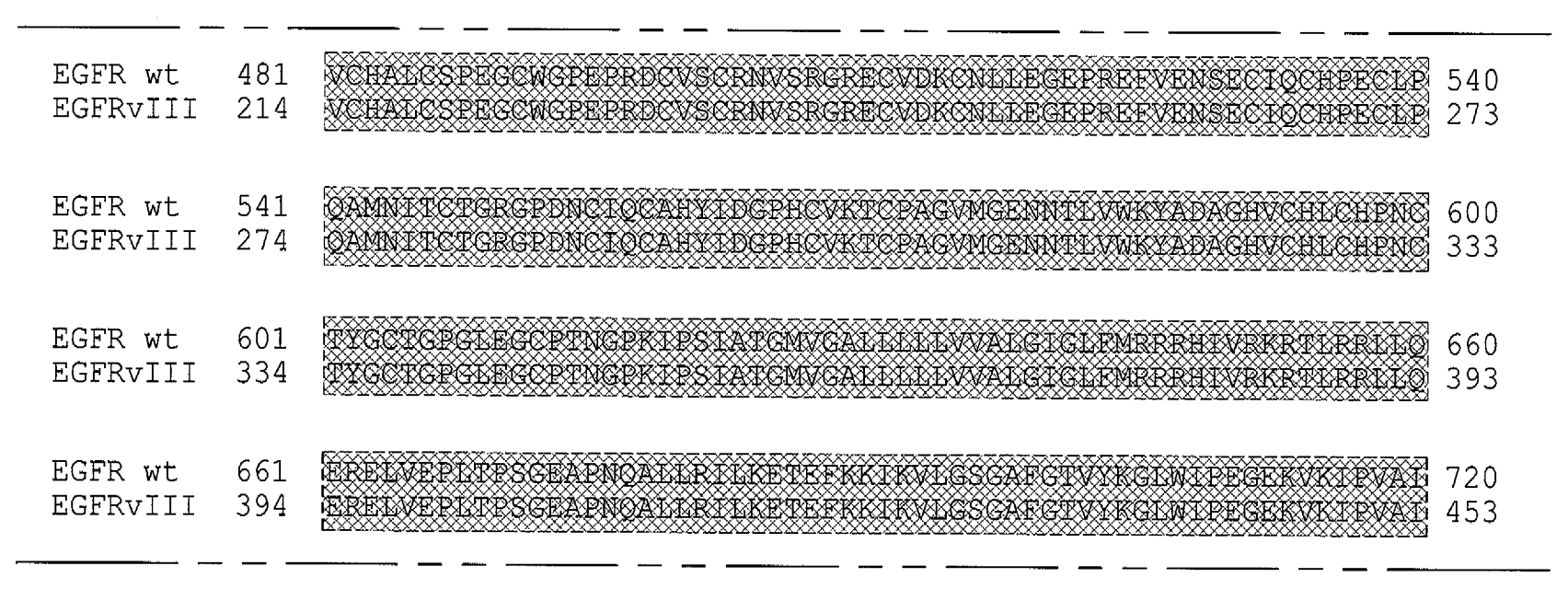

| | | | |
|---|---|---|---|
| EGFR wt | 481 | VCHALCSPEGCWGPEPRDCVSGRNVSRGRECVDKCNLLEGEPREFVEMSECIQCHPECLP | 540 |
| EGFRvIII | 214 | VCHALCSPEGCWGPEPRDCVSGRNVSRGRECVDKCNLLEGEPREFVEMSECIQCHPECLP | 273 |
| EGFR wt | 541 | QAMNITCTGRGPDNCIQCAHYIDGPHCVKTCPAGVMGENNTLVWKYADAGHVCHLCHPNC | 600 |
| EGFRvIII | 274 | QAMNITCTGRGPDNCIQCAHYIDGPHCVKTCPAGVMGENNTLVWKYADAGHVCHLCHPNC | 333 |
| EGFR wt | 601 | TYGCTGPGLEGCPTNGPKIPSIATGMVGALLLLLVVALGIGLFMRRRHIVRKRTLRRLLQ | 660 |
| EGFRvIII | 334 | TYGCTGPGLEGCPTNGPKIPSIATGMVGALLLLLVVALGIGLFMRRRHIVRKRTLRRLLQ | 393 |
| EGFR wt | 661 | ERELVEPLTPSGEAPNQALLRILKETEFKKIKVLGSGAFGTVYKGLWIPEGEKVKIPVAI | 720 |
| EGFRvIII | 394 | ERELVEPLTPSGEAPNQALLRILKETEFKKIKVLGSGAFGTVYKGLWIPEGEKVKIPVAI | 453 |

FIG. 1D

| | | | |
|---|---|---|---|
| EGFR wt | 721 | KEIREATSPKANKEILDEAYVMASVDNPHVCRLLGICLTSTVQLITQLMPFGCLLDYVRE | 780 |
| EGFRvIII | 454 | KEIREATSPKANKEILDEAYVMASVDNPHVCRLLGICLTSTVQLITQLMPFGCLLDYVRE | 513 |
| EGFR wt | 781 | HKDNIGSQYLLNWCVQIAKGMNYLEDRRLVHRDLAARNVLVKTPQHVKITDFGLAKLLGA | 840 |
| EGFRvIII | 514 | HKDNIGSQYLLNWCVQIAKGMNYLEDRRLVHRDLAARNVLVKTPQHVKITDFGLAKLLGA | 573 |
| EGFR wt | 841 | EEKEYHAEGGKVPIKWMALESILHRIYTHQSDVWSYGVTVWELMTFGSKPYDGIPASEIS | 900 |
| EGFRvIII | 574 | EEKEYHAEGGKVPIKWMALESILHRIYTHQSDVWSYGVTVWELMTFGSKPYDGIPASEIS | 633 |
| EGFR wt | 901 | SILEKGERLPQPPICTIDVYMIMVKCWMIDADSRPKFRELIIEFSKMARDPQRYLVIQGD | 960 |
| EGFRvIII | 634 | SILEKGERLPQPPICTIDVYMIMVKCWMIDADSRPKFRELIIEFSKMARDPQRYLVIQGD | 693 |

FIG. 1E

```
EGFR wt    961   ERMHLPSPTDSNFYRALMDEEDMDDVVDADEYLIPQQGFFSSPSTSRTPLLSSLSATSNN  1020
EGFRvIII   694   ERMHLPSPTDSNFYRALMDEEDMDDVVDADEYLIPQQGFFSSPSTSRTPLLSSLSATSNN  753

EGFR wt    1021  STVACIDRNGLQSCPIKEDSFLQRYSSDPTGALTEDSIDDTFLPVPEYINQSVPKRPAGS  1080
EGFRvIII   754   STVACIDRNGLQSCPIKEDSFLQRYSSDPTGALTEDSIDDTFLPVPEYINQSVPKRPAGS  813

EGFR wt    1081  VQNPVYHNQPLNPAPSRDPHYQDPHSTAVGNPEYLNTVQPTCVNSTFDSPAHWAQKGSHQ  1140
EGFRvIII   814   VQNPVYHNQPLNPAPSRDPHYQDPHSTAVGNPEYLNTVQPTCVNSTFDSPAHWAQKGSHQ  873

EGFR wt    1141  ISLDNPDYQQDFFPKEAKPNGIFKGSTAENAEYLRVAPQSSEFIGA  1186   (SEQ ID NO:134)
EGFRvIII   874   ISLDNPDYQQDFFPKEAKPNGIFKGSTAENAEYLRVAPQSSEFIGA  919    (SEQ ID NO:135)
```

FIG. 2A

```
        1 2 3 4 5 273 275 277 279
        L-E-E-K-G-N-Y-V-V-T-D-H-C    (SEQ ID NO.56)
                        278 280
```

FIG. 2B

```
  6
VCQGTSNKLTQLGTFEDHFLSLQRMFNNCEVVLGNLEITYVQRNYDLSFLKTIQEV
AGYVLIALNTVERIPLENLQIIRGNMYENSYALAVLSNYDANKTGLKELPMRNLQ
EILHGAVRFSNNPALCNVESIQWRDIVSSDFLSNMSMDFQNHLGSCQKCDPSCPNG
SCWGAGEENCQKLTKIICAQQCSGRCRGKSPSDCCHNQCAAGCTGPRESDCLVCRK
FRDEATCKDTCPPLMLYNPTTYQMDVNPEGKYSFGATCVKKCPR
                                           272
                                                    (SEQ ID NO.136)
```

XenoMax Derived Human anti- EGFRvIII Antibody Nucleotide and Amino Acid Sequences

095

Nucleotide sequence of heavy chain variable region:

5' CAGGTGCAGCTGCAGGAGTCGGGCCCAGGACTGGTGAAGCCTTCACAGACCCTGT
CCCTCACCTGCACTGTCTCTGGTGGCTCCATCAGCAGTGGTGGTTACTACTGGAGCT
GGATCCGCCAGCACCCAGGGAAGGGCCTGGAGTGGATTGGGTTCATCTATTACAGA
GGGAACACCTACTACAACCCGTCCCTCAAGAGTCGAGTTACCATATCAGTTGACACG
TCTAAGAACCAGTTCTCCCTGAAGCTGAGCTCTGTGACTGCCGCGGACACGGCCGTG
TATTACTGTGCGCGAGACGGATATTGTAGTAGAACCGGCTGCTATGGCGGCTGGTTC
GACCCCTGGGGCCAGGGAACCCTGGTCACGTCTCCT 3'  (SEQ ID NO:35)

Amino Acid sequence of heavy chain variable region:

QVQLQESGPFLVKPSQTLSLTCTVSGGSISSGGYYWSWIRQHPGKGLEWIGFIYYRGNTY
YNPSLKSRVTISVDTSKNQFSLKLSSVTAADTAVYYCARDGYCSRTGCYGGWFDPWGQ
GTLVTVSP  (SEQ ID NO:7)

Nucleotide sequence of light chain variable region:

5'GATATTGTGATGACCCAGACTCCACTCTCCTCACCTGTCACCCTTGGACAGCCGGC
CTCCATCTCCTGCAGGTCTAGTCAAAGCCTCATACACACTGATGGAAACATCTATTT
GAGTTGGCTTCAGCAGAGGCCAGGCCAGCCTCCAAGACTCCTAATTTATAAGATTTC
TAATCGGTTCTCTGGGGTCCCAGACAGATTCAGTGGCAGTGGGGCAGGGACAGATTT
CACACTGAAGATCAGCAGGGTGGAAGCTGAGGATGTGGGGGTTTATTACTGCATGC
AAGGTACACAATTTCCTATCACCTTCGGCCAAGGGACACGACTGGAGATTAAA3' (SEQ
ID NO:34)

Amino Acid sequence of light chain variable region:

DIVMTQTPLSSPVTLGQPASISCRSSQSLIHTDGNIYLSWLQQRPGQPPRLLIYKISNRFSG
VPDRFSGSGAGTDFTLKISRVEAEDVGVYYCMQGTQFPITFGQGTRLEIK  (SEQ ID
NO:23)

Nucleotide sequence of heavy chain variable region:

5' CAGGTGCAGCTGGTGGAGTCTGGGGGAGGCGTGGTCCAGCCTGGGAGGTCCCTGA
GACTCTCCTGTGCAGCCTCCGGATTCACCCTCAGTAGCTATGGCATGCACTGGGTCC
GCCAGGCTCCAGGCAAGGGGCTGGAGTGGGTGGCAGTTATGTCATATGATGGAAGT
AAAGAAGACTATGCAGACTCCGTGAAGGGCCGATTCACCATCTCTAGAGACAATTC
CGAGAACATGCTGTATCTGCAAATGAACAGCCTGAGAGCTGAGGACACGGCTGTAT
ATTACTGTGTGAGCGAAGGATATTGTAGTAGTCGTAGCTGCTATAAGTACTACTACT
ACGGCATGGACGTCTGGGGCCAAGGGACCACGGTCACCGTCTCCTCA3' (SEQ ID
NO:37)

Amino Acid sequence of heavy chain variable region:

QVQLVESGGGVVQPGRSLRLSCAASGFTLSSYGMHWVRQAPGKGLEWVAVMSYDGS
KEDYADSVKGRFTISRDNSENTLYLQMNSLRAEDTAVYYCVSEGYCSSRSCYKYYYG
MDVWGQGTTVTVSS (SEQ ID NO:13)

Nucleotide sequence of light chain variable region:

5' ATATTGTGATGACTCAGTCTCCACTCTCCCTGCCCGTCACCCCTGGAGAGCCGGCC
TCCATCTCCTGCAGGTCTAGTCAGAGCCTCCTGTATAGAAATGGAAACAACTATTTG
GATTGGTATCTGCAGAAGCCAGGGCAGTCTCCACAGCTCCTGATCTATTTGGGTTCT
AATCGGGCCTCCGGGGTCCCTGACAGGTTCAGTGGCAGTGGATCGGGCACAGATTTT
ACACTGAACATCAGCAGAGTGGAGGCTGAGGATGTTGGGCATTATTACTGCATGCA
GGCTCTACAAACTCCTCGGACGTTCGGCCAAGGGACCAAGGTGGAAATCAAA3'
(SEQ ID NO:36)

Amino Acid sequence of light chain variable region:

DIVMTQSPLSLPVTPGEPASISCRSSQSLLYRNGNNYLDWYLQKPGQSPQLLIYLGSNRA
SGVPDRFSGSGSGTDFTLNISRVEAEDVGHYYCMQALQTPRTFGQGTKVEIK (SEQ ID
NO:29)

Nucleotide sequence of heavy chain variable region:

5'CAGGTGCAGCTGGTGGAGTCTGGGGGAGGCGTGGTCCAGTCTGGGAGGTCCCTGA
GACTCTCCTGTGCAGCGTCTGGATTCACCTTCAGAAACTATGGCATGCACTGGGTCC
GCCAGGCTCCAGGCAAGGGGCTGGAGTGGGTGGCAGTTATATGGTATGATGGAAGT
GATAAATACTATGCAGACTCCGTGAGGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGATGGCTACGATATTTTGACTGGTAATCCTAGGGACTTTGACTA
CTGGGGCCAGGGAACCCTGGTCACCGTCTCCTCA3' (SEQ ID NO:39)

Amino Acid sequence of heavy chain variable region:

QVQLVESGGGVVQSGRSLRLSCAASGFTFRNYGMHWVRQAPGKGLEWVAVIWYDGS
DKYYADSVRGRFTISRDNSKNTLYLQMNSLRAEDTAVYYCARDGYDILTGNPRDFDYW
GQGTLVTVSS (SEQ ID NO:2)

Nucleotide sequence of light chain variable region:

5'GATACTGTGATGACCCAGACTCCACTCTCCTCACATGTAACCCTTGGACAGCCGGC
CTCCATCTCCTGCAGGTCTAGTCAAAGCCTCGTACACAGTGATGGAAACACCTACTT
GAGTTGGCTTCAGCAGAGGCCAGGCCAACCTCCAAGACTCCTAATTTATAGGATTTC
TAGGCGGTTCTCTGGGGTCCCAGACAGATTCAGTGGCAGTGGGGCAGGGACAGATT
TCACACTGGAAATCAGCAGGGTGGAGGCTGAGGATGTCGGGGTTTATTACTGCATG
CAATCTACACACGTTCCTCGGACGTTCGGCCAAGGGACCAAGGTGGAGATCAAA3'
(SEQ ID NO:38)

Amino Acid sequence of light chain variable region:

DTVMTQTPLSSHVTLGQPASISCRSSQSLVHSDGNTYLSWLQQRPGQPPRLLIYRISRRFS
GVPDRFSGSGAGTDFTLEISRVEAEDVGVYYCMQSTHVPRTFGQGTKVEIK (SEQ ID NO:19)

Nucleotide sequence of heavy chain variable region:

5'GAGGTGCAGGTGTTGGAGTCTGGGGGAGGCTTGGTACAGCCTGGGGGGTCCCTGA
GACTCTCCTGTGCAGCCTCTGGATTCACCTTTAGCAGCTATGCCATGAGCTGGGTCC
GCCAGGCTCCAGGGAAGGGGCTGGAGTGGGTCTCGGCTATTAGTGGTAGTGGTGGT
AGTACAAACTACGCAGACTCCGTGAAGGGCCGGTTCACCATCTCCAGAGACAATTC
CAAGAACACACTGTATCTGCAAATGAACAGCCTGAGAGCCGAGGACACGGCCGTCT
ATTACTGTGCTGGGAGCAGTGGCTGGTCCGAGTACTGGGGCCAGGGAACCCTGGTC
ACCGTCTCCTCG3' (SEQ ID NO:41)

Amino Acid sequence of heavy chain variable region:

EVQVLESGGGLVQPGGSLRLSCAASGFTFSSYAMSWVRQAPGKGLEWVSAISGSGGST
NYADSVKGRFTISRDNSKNTLYLQMNSLRAEDTAVYYCAGSSGWSEYWGQGTLVTVS
S (SEQ ID NO:10)

Nucleotide sequence of light chain variable region:

5'GACATCCAGATGACCCAGTCTCCATCCTCCCTGTCTGCATCTGTAGGAGACAGAGT
CACCATCACTTGCCGGGCTAGTCAGGGCATTAGAAATAATTTAGCCTGGTATCAGCA
GAAACCAGGGAAAGCCCCTAAGCGCCTGATCTATGCTGCCTCCAATTTGCAAAGTG
GGGTCCCATCAAGGTTCACCGGCAGTGGATCTGGGACAGAATTCACTCTCATAGTCA
GCAGCCTGCAGCCTGAAGATTTTGCGACTTATTACTGTCTACAGCATCACAGTTACC
CGCTCACTTCCGGCGGAGGGACCAAGGTGGAGATCAAA3' (SEQ ID NO:40)

Amino Acid sequence of light chain variable region:

DIQMTQSPSSLSASVGDRVTITCRASQGIRNNLAWYQQKPGKAPKRLIYAASNLQSGVPS
RFTGSGSGTEFTLIVSSLQPEDFATYYCLQHHSYPLTSGGGTKVEIK (SEQ ID NO:25)

Nucleotide sequence of heavy chain variable region:

5' CAGGTACAGCTGCAGCAGTCAGGTCCAGGACTGGTGAAGCCCTCGCAGACCCTCT
CACTCACCTGTGCCATCTCCGGGGACAGTGTCTCTAGCTACAGTTCTGCTTGGAACT
GGATCAGGCAGTCCCCATCGAGAGGCCTTGAGTGGCTGGGAAGGGCATATCACAGG
TCCAGGTGGTATTACGAGTATGCAGTATCGGTGAAAAGTCGAATAAACATCACCCC
AGACACATCCAAGAACCAGTTCTCCCTGCAGCTGAACTCTGTGACTCCCGAGGACAC
GGCTGTGTATTACTGTGCAAGAGGCAGTCGCTTTGACTACTGGGGCCAGGGAACCCT
GGTCACCGTCTCCTCA3' (SEQ ID NO:43)

Amino Acid sequence of heavy chain variable region:

QVQLQQSGPGLVKPSQTLSLTCAISGDSVSSYSSAWNWIRQSPSRGLEWLGRAYHRSRW
YYEYAVSVKSRINITPDTSKNQFSLQLNSVTPEDTAVYYCARGSRFDYWGQGTLVTVSS
(SEQ ID NO:5)

Nucleotide sequence of light chain variable region:

5' GATATTGTGATGACCCAGACTCCACTCTCCTCACCTGTCACCCTTGGACAGCCGGC
CTCCATCTCCTGCAGGTCTAGTCAAAGCCTCGTACACAGGGATGGAAATACCTACTT
GAGTTGGCTTCAGCAGAGGCCAGGCCAGCCTCCAAGACTCCTAATTTATAAGATTTC
TAACCGGTTCTCTGGGGTCCCAGACAGATTCAGTGGCAGTGGGGCAGGGACAGATT
TCACACTGAAAATTAGCAGGGTGGAAGCTGAGGATGTCGGGATTTATTTCTGCATGC
ATACTACACAATTTCCTTGGACGTTCGGCCAAGGGACCAGGGTGGAAATCAAA3'
(SEQ ID NO:42)

Amino Acid sequence of light chain variable region:

DIVMTQTPLSSPVTLGQPASISCRSSQSLVHRDGNTYLSWLQQRPGQPPRLLIYKISNRFS
GVPDRFSGSGAGTDFTLKISRVEAEDVGIYFCMHTTQFPWTFGQGTRVEIK (SEQ ID NO:21)

Nucleotide sequence of heavy chain variable region:

5' CAGGTACAGCTGCAGCAGTCAGGTCCAGGACTGGTGAAGCCCTCGCAGACCCTCT
CACTCACCTGTGCCATCTCCGGGGACAGTGTCTCTAGCAACAATGCTGCTTGGAACT
GGATCAGGCAGTCCCCAGCGAGAGGCCTTGAGTGGCTGGGAAGGACATACTACAGG
TCCAAGTGGTATAATGATTATGTAGTATCTGTGAAAAGTCGAATAACCATCAACCCA
GACACATCCAAGAACCAGTTCTCCCTGCAGCTGAACTCTGTGACTCCCGAGGACACG
GCTGTGTATTACTGTGTAAGAGGCAGTCGCTTTGACTACTGGGGCCAGGGAACCCTG
GTCACCGTCTCCTCA3' (SEQ ID NO:45)

Amino Acid sequence of heavy chain variable region:

QVQLQQSGPGLVKPSQTLSLTCAISGDSVSSNNAAWNWIRQSPARGLEWLGRTYYRSK
WYNDYVVSVKSRITINPDTSKNQFSLQLNSVTPEDTAVYYCVRATAFDYWGQGTLVTV
SS (SEQ ID NO:4)

Nucleotide sequence of light chain variable region:

5'GCTATTGTGTTGACCCAGACTCCACTCTCCTCACCTGTCACCCTTGGACAGCCGGC
CTCCATCTCCTGCAGGTCTAGTCAAAGCCTCGTTCACAGGGATGGAAACACCTACTT
GAGTTGGCTTCAGCAGAGGCCAGGCCAGCCTCCAAGACTCCTAATTTATAAGATTTC
TAACCGGTTCTCTGGGGTCCCAGACAGATTCAGTGGCAGTGGGGCAGGGACAGATT
TCACACTGAAAATCAGCAGGGTGGAACCTGACGATGTCGGGGTTTATTACTGCATGC
ATACTACACAACTTCCTTGGACGTTCGGCCAAGGGACCAAGGTGGAAATCAAA3'
(SEQ ID NO:44)

Amino Acid sequence of light chain variable region:

AIVLTQTPLSSPVTLGQPASISCRSSQSLVHRDGNTYLSWLQQRPGQPPRLLIYKISNRFSG
VPDRFSGSGAGTDFTLKISRVEPDDVGVYYCMHTTQLPWTFGQGTKVEIK (SEQ ID NO:20)

Nucleotide sequence of heavy chain variable region:

5' CAGGTGCAGCTGGTGGAGTCTGGGGGAGGCGTGGTCCAGCCTGGGAGGTCCCTGA
GACTCTCCTGTGTAGCCTCTGGATTCACCCTCAGTAGCTATGGCATGCACTGGGTCC
GCCAGGCTCCAGGCAAGGGGCTGGAGTGGGTGGCAGTGACATCATATGATGGAAGT
AAAAAAGACTATGCAGACTCCGCGAAGGGCCGATTCACCATCTCCAGAGACAATTC
CAAGAACACGCTGTATCTGCAAATGAACAGCCTGAGAGCTGAGGACACGGCTGTGT
ATTACTGTGTGAGCGAAGGATATTGTAGTAGTAGTAGCTGCTATAAGTACTACTATT
ACGGTATGGACGTCTGGGGCCAAGGGACCACGGTCACCGTCTCTTCA3' (SEQ ID
NO:47)

Amino Acid sequence of heavy chain variable region:

QVQLVESGGGVVQPGRSLRLSCVASGFTLSSYGMHWVRQAPGKGLEWVAVTSYDGSK
KDYADSAKGRFTISRDNSKNTLYLQMNSLRAEDTAVYYCVSEGYCSSSSCYKYYYYGM
DVWGQGTTVTVSS (SEQ ID NO:12)

Nucleotide sequence of light chain variable region:

5' GATATTGTGATGACTCAGTCTCCACTCTCCCTGCCCGTCACCCCTGGAGAGCCGGC
CTCCATCTCCTGCAGGTCTAGTCAGAGCCTCCTATATAGAAATGGAAACAACTATTT
GGATTGGTATCTGCAGAGGCCAGGGCAGTCTCCACAACTCCTGATCTATTTGGGTTC
TAATCGGGCCTCCGGGGTCCCTGACAGGTTCAGTGGCAGTGGATCAGGCACAGATTT
TACATTGAAAATCGGCAGAGTGGAGGCTGAGGATGTTGGGGTTTATTACTGCATGCA
GGCTCTACAAACTCCTCGGACGTTCGGCCAAGGGACCAAGGTGGAAATCAAA3'
(SEQ ID NO:46)

Amino Acid sequence of light chain variable region:

DIVMTQSPLSLPVTPGEPASISCRSSQSLLYRNGNNYLDWYLQRPGQSPQLLIYLGSNRA
SGVPDRFSGSGSGTDFTLKISRVEAEDVGVYYCMQALQTPRTFGQGTKVEIK (SEQ ID
NO:28)

Nucleotide sequence of heavy chain variable region:

5' GAGGGGCAGCTGTTGGAGTCTGGGGGAGGCTGGGTACAGCCTGGGGAGTCCCTGA
GACTCTCCTGTGCAGCCTCTGGATTCACCTTTAGCAGCTATGCCATGAGCTGGGTCC
GCCAGGCTCCAGGGAAGGGGCTGGAGTGGGTCTCGGCTATTAGTGGTAGTGGTGGT
AGCACAAATTACGCAGACTCCGTGAAGGGCCGGTTCACCATCTCCAGAGACAATTC
CAAGAACACGCTGTATCTGCAAGTGAACAGCCTGAGAGTCGAGGACACGGCCGTAT
ATTACTGTGCTGGGAGCAGTGGCTGGTCCGAGTACTGGGGCCAGGGAACCCTGGTC
ACCGTCTCCTCA3' (SEQ ID NO:49)

Amino Acid sequence of heavy chain variable region:

EGQLLESGGGWVQPGESLRLSCAASGFTFSSYAMSWVRQAPGKGLEWVSAISGSGGST
NYADSVKGRFTISRDNSKNTLYLQVNSLRVEDTAVYYCAGSSGWSEYWGQGTLVTVSS
(SEQ ID NO:9)

Nucleotide sequence of light chain variable region:

5' GACATCCAGATGACCCAGTCTCCATCCTCCCTGTCTGCATCTGTAGGAGACAGCGT
CACCATCACTTGCCGGACAAGTCAGGGCATTAGAAAAAATTTAGGCTGGTATCAGC
AGAAACCAGGGAAAGCCCCTAAGCGCCTGATCTATGCTGCATCCAGTTTACAAAGT
GGGGTCCCATCAAGGTTCAGCGGCAGTGGATCTGGGACAGAATTCACTCTCACAATC
CGCAGCCTGCAGCCTGAAGATTTTGCAACTTATTACTGTCTCCAGCATCATAGTTAC
CCGCTCACTTTCGGCGGAGGGACCAGGGTGGAGATCAGA3' (SEQ ID NO:48)

Amino Acid sequence of light chain variable region:

DIQMTQSPSSLSASVGDSVTITCRTSQGIRKNLGWYQQKPGKAPKRLIYAASSLQSGVPS
RFSGSGSGTEFTLTISRLQPEDFATYYCLQHHSYPLTFGGGTRVEIR (SEQ ID NO:26)

Nucleotide sequence of heavy chain variable region:

5' CAGGTGCAGCTGGTGGAGTCTGGGGGAGGCGTGGTCCAGCCTGGGAGGTCCCTGA
GACTCTCCTGTGTAGCCTCTGGATTCACCCTCAGTAGCTATGGCATGCACTGGGTCC
GCCAGGCTCCAGGCAAGGGGCTGGAGTGGGTGGCAGTGACATCATATGATGGAAGT
AAAAAAGACTATGCAGACTCCGTGAAGGGCCGATTCACCATCTCCAGAGACAATTC
CAAGAACACGCTGTATCTGCAAATGAACAGCCTGAGAGCTGAGGACACGGCTGTGT
ATTACTGTGTGAGCGAAGGATATTGTGATAGTAGTAGCTGCTATAAGTACTACTACT
ACGGTATGGACGTCTGGGGCCAAGGGACCACGGTCACCGTCTCTTCA3' (SEQ ID NO:51)

Amino Acid sequence of heavy chain variable region:

QVQLVESGGGVVQPGRSLRLSCVASGFTLSSYGMHWVRQAPGKGLEWVAVTSYDGSK
KDYADSVKGRFTISRDNSKNTLYLQMNSLRAEDTAVYYCVSEGYCDSSSCYKYYYYG
MDVWGQGTTVTVSS (SEQ ID NO:15)

Nucleotide sequence of light chain variable region:

5' GATATTGTGATGACTCAGTCTCCACTCTCCCTGCCCGTCACCCCTGGAGAGCCGGC
CTCCATCTCCTGCAGGTCTAGTCAGAGCCTCCTATATAGAAATGGAAACAACTATTT
GGATTGGTATCTGCAGAGGCCAGGGCAGTCTCCACAACTCCTGATCTATTTGGGTTC
TAATCGGGCCTCCGGGGTCCCTGACAGGTTCAGTGGCAGTGGATCAGGCACAGATTT
TACACTGAAAATCAGCAGAGTGGAGGCTGAGGATGTTGGGGTTTATTACTGCATGC
AGGCTCTACAAACTCCTCGGACGTTCGGCCAAGGGACCAAGGTGGAAATCAAA3'
(SEQ ID NO:50)

Amino Acid sequence of light chain variable region:

DIVMTQSPLSLPVTPGEPASISCRSSQSLLYRNGNNYLDWYLQRPGQSPQLLIYLGSNRA
SGVPDRFSGSGSGTDFTLKISRVEAEDVGVYYCMQALQTPRTFGQGTKVEIK (SEQ ID NO:33)

Nucleotide sequence of heavy chain variable region:

5' CAGGTGCAGCTGGTGGAGTCTGGGGGAGGCGTGGTCCAGCCTGGGAGGTCCCTGA
GACTCTCCTGTGTAGCCTCTGGATTCACCCTCAGTAGCTATGGCATGCACTGGGTCC
GCCAGGCTCTAGGCAAGGGGCTGGAGTGGGTGGCAGTGACATCATATGATGGAAGT
AAAAAAGACTATGCAGACTCCGTGAAGGGCCGATTCACCATCTCCAGAGACAATTC
CAAGAACACGCTGTATCTGCAAATGAACAGCCTGAGAGCTGAGGACACGGCTGTGT
ATTACTGTGTGAGCGAAGGATATTGTGATAGTACTAGTTGCTATAAGTACTACTACT
ACGGTATGGACGTCTGGGGCCAAGGGACCACGGTCACCGTCTCTTCA3' (SEQ ID NO:53)

Amino Acid sequence of heavy chain variable region:

QVQLVESGGGVVQPGRSLRLSCVASGFTLSSYGMHWVRQALGKGLEWVAVTSYDGSK
KDYADSVKGRFTISRDNSKNTLYLQMNSLRAEDTAVYYCVSEGYCDSTSCYKYYYYG
MDVWGQGTTVTVSS (SEQ ID NO:17)

Nucleotide sequence of light chain variable region:

5' GATATTGTGATGACTCAGTCTCCACTCTCCCTGCCCGTCACCCCTGGAGAGCCGGC
CTCCATCTCCTGCAGGTCTAGTCAGAGCCTCCTATATAGAAATGGAAACAACTATTT
GGATTGGTATCTGCAGAGGCCAGGGCAGTCTCCACAACTCCTGATCTATTTGGGTTC
TAATCGGGCCTCCGGGGTCCCTGACAGGTTCAGTGGCAGTGGATCAGGCACAGATTT
TACACTGAAAATCAGCAGAGTGGAGGCTGAGGATGTGGGGTTTATTACTGCATGC
AGGCTCTACAAACTCCTCGGACGTTCGGCCAAGGGACCAAGGTGGAAATCAAA3'
(SEQ ID NO:52)

Amino Acid sequence of light chain variable region:

DIVMTQSPLSLPVTPGEPASISCRSSQSLLYRNGNNYLDWYLQRPGQSPQLLIYLGSNRA
SGVPDRFSGSGSGTDFTLKISRVEAEDVGVYYCMQALQTPRTFGQGTKVEIK (SEQ ID NO:32)

Nucleotide sequence of heavy chain variable region:

5' CAGGTGCAGCTGGTGGAGTCTGGGGGAGGCGTGGTCCAGCCTGGGAGGTCCCTGA
GACTCTCCTGTGTAGCCTCTGGATTCACCCTCAGTAGCTATGGCATGCACTGGGTCC
GCCAGGCTCCAGGCAAGGGGCTGGAGTGGGTGGCAGTGACATCATATGATGGAAGT
AAAAAAGACTATGCAGACTCCGTGAAGGGCCGATTCACCATCTCCAGAGACAATTC
CAAGAACACGCTGTATCTGCAAATGAACAGCCTGAGAGCTGAGGACACGGCTGTGT
ATTACTGTGTGAGCGAAGGATATTGTGATAGTACTAGCTGCTATAAGTACTACTACT
ACGGTATGGACGTCTGGGGCCAAGGGACCACGGTCACCGTCTCTTCA3' (SEQ ID NO:55)

Amino Acid sequence of heavy chain variable region:

QVQLVESGGGVVQPGRSLRLSCVASGFTLSSYGMHWVRQAPGKGLEWVAVTSYDGSK
KDYADSVKGRFTISRDNSKNTLYLQMNSLRAEDTAVYYCVSEGYCDSTSCYKYYYYG
MDVWGQGTTVTVSS (SEQ ID NO:16)

Nucleotide sequence of light chain variable region:

5'GATATTGTGATGACTCAGTCTCCACTCTCCCTGCCCGTCACCCCTGGAGAGCCGGC
CTCCATCTCCTGCAGGTCTAGTCAGAGCCTCCTATATAGAAATGGAAACAACTATTT
GGATTGGTATCTGCAGAGGCCAGGGCAGTCTCCACAACTCCTGATCTATTTGGGTTC
TAATCGGGCCTCCGGGGTCCCTGACAGGTTCAGTGGCAGTGGATCAGGCACAGATTT
TACACTGAAAATCAGCAGAGTGGAGGCTGAGGATGTTGGGGTTTATTACTGCATGC
AGGCTCTACAAACTCCTCGGACGTTCGGCCAAGGGACCAAGGTGGAAATCAAA3'
(SEQ ID NO:54)

Amino Acid sequence of light chain variable region:

DIVMTQSPLSLPVTPGEPASISCRSSQSLLYRNGNNYLDWYLQRPGQSPQLLIYLGSNRA
SGVPDRFSGSGSGTDFTLKISRVEAEDVGVYYCMQALQTPRTFGQGTKVEIK (SEQ ID NO:31)

Nucleotide sequence of heavy chain variable region:
CAGGTGCAGCTGGTGGAGTCTGGGGGAGGCGTGGTCCAGC
CTGGGAGGTCCCTGAGACTCTCCTGTGCAGCGTCTGGATT
CACCTTCAGTAGCTATGGCATGCACTGGGTCCGCCAGGCT
CCAGGCAAGGGGCTGGAGTGGGTGGCAGTTATATGGTATG
ATGGAAGTAATAAATACTATGTAGACTCCGTGAAGGGCCG
ATTCACCATCTCCAGAGACAATTCCAAGAACACGCTGTAT
CTGCAAATGAACAGCCTGAGAGCCGAGGACACGGCTGTGT
TGACTACTGGGGCCAGGGAACCCTGGTCACCGTCTCCTCA
GCCTCCACCAAGGGCCCATCGGTCTTCCCCCTGGCACCCT
CTAGCAAGAGCACCTCTGGGGGCACAGCGGCCCTGGGCTG
CCTGGTCAAGGACTACTTCCCCGAACCGGTGACGGTGTCG
TGGAACTCAGGCGCCCTGACCAGCGGCGTGCA (SEQ ID NO: 137)

Amino Acid sequence of heavy chain variable region:
QVQLVESGGGVVQPGRSLRLSCAASGFTFS
SYGMHWVRQAPGKGLEWVAVIWYDGSNKYY
VDSVKGRFTISRDNSKNTLYLQMNSLRAED
TAVYYCARDGWQQLAPFDYWGQGTLVTVSS
ASTKGPSVFPLAPSSKSTSGGTAALGCLVK
DYFPEPVTVSWNSGALTSGV (SEQ ID NO: 138)

Nucleotide sequence of light chain variable region:
GATATTGTGATGACCCAGACTCCACTCTCCTCACCTGTCA
CCCTTGGACAGCCGGCCTCCATCTCCTGCAGGTCTAGTCA
AAGCCTCGTGCATAGTGATGGAAACACCTACTTGAGTTGG
CTTCACCAGAGGCCAGGCCAGCCTCCAAGACTCCTAATTT
ATAAGATTTCTAACCGGTTCTCTGGGGTCCCAGACAGATT
CAGTGGCAGTGGGGCAGGGACAGCTTTCACACTGAAAATC
AGCAGGGTGGAAGCTGAGGATGTCGGGGTTTATTACTGCA
TGCAAGCTACACAACTTCCTCGGACGTTCGGCCAAGGGAC
CAAGGTGGAAATCAAACGAACTGTGGCTGCACCATCTGTC
TTCATCTTCCCGCCATCTGATGAGCAGTTGAAATCTGGAA
CTGCTAGCGTTGTGTGCCTGCTGAATAACTTCTATCCCAG
AGAGGCCAAAGTACAGTGGAAGGTGGATAACGCCCTCCAA
TCGGGTAACTCCCAGG (SEQ ID NO: 139)

Amino Acid sequence of light chain variable region:
DIVMTQTPLSSPVTLGQPASISCRSSQSLV
HSDGNTYLSWLHQRPGQPPRLLIYKISNRF
SGVPDRFSGSGAGTAFTLKISRVEAEDVGV
YYCMQATQLPRTFGQGTKVEIKRTVAAPSV
FIFPPSDEQLKSGTASVVCLLNNFYPREAK
VQWKVDNALQSGNSQ (SEQ ID NO: 140)

| HeavyChain Chain Name | V | D | J | SEQ ID NO |
|---|---|---|---|---|
| | | Germline | | |
| 13_1_2 | VH3-33 | D6-13 | JH4B | |

| | CDR1 | FR2 | CDR2 | SEQ ID NO |
|---|---|---|---|---|
| | GFTFSSYGMH | WVRQAPGKGLEWVA | VIWYDGSNKYYADSVKG | SEQ ID NO 141 |
| 13_1_2 | ---------- | -------------- | --------V------- | SEQ ID NO 142 |

| | FR1 | | | SEQ ID NO |
|---|---|---|---|---|
| | QVQLVESGGGVVQPGRSLRLSCAAS | | | SEQ ID NO 141 |
| 13_1_2 | ------------------------- | | | SEQ ID NO 142 |

| | FR3 | CDR3 | J | SEQ ID NO |
|---|---|---|---|---|
| | RFTISRDNSKNTLYLQMNSLRAEDTAVYYCAR | DGWQQLAPFDY | WGQGTLVTVSSA | SEQ ID NO 141 |
| 13_1_2 | -------------------------------- | ----------- | ------------ | SEQ ID NO 142 |

FIG. 5

| LightChain Chain Name | V | J | Germline | FR1 | SEQ ID NO |
|---|---|---|---|---|---|
| | | | | | |
| 13_1_2 | A23 | JK1 | | DIVMTQTPLSSPVTLGQPASISC | SEQ ID NO 143 |
| | | | | -------- | SEQ ID NO 144 |

| | CDR1 | FR2 | CDR2 | SEQ ID NO |
|---|---|---|---|---|
| 13_1_2 | RSSQSLVHSDGNTYLS | WLQQRPGQPPRLLIY | KISNRFS | SEQ ID NO 143 |
| | -------- | --H-------- | -------- | SEQ ID NO 144 |

| | FR3 | CDR3 | J | SEQ ID NO |
|---|---|---|---|---|
| 13_1_2 | GVPDRFSGSGAGTDFTLKISRVEAEDVGVYYC | MQATQFPRT | FGQGTKVEIKR | SEQ ID NO 143 |
| | --------A-------- | ---L--- | -------- | SEQ ID NO 144 |

| Well | Single Cell | V Heavy/D/J | FR1 |
|---|---|---|---|
| - | - | Germline | QVQLVESGGGVVQPGRSLRLSCAASGFTFS |
| 174F1 | 131 | VH-33/D3-9/JH4b | ----------S------------------R |
| - | - | Germline | QVQLQQSGPGLVKPSQTLSLTCAISGDSVS |
| 125D10 | 170 | VH6-01/D2-21/JH4b | ------------------------------ |
| 182D5 | 150 | | ------------------------------ |
| - | - | Germline | QVQLQESGPFLVKPSQTLSLTCTVSGGSIS |
| 172B12 | 095 | VH4-31/D4/JH5b | ------------------------------ |
| - | - | Germline | EVQLLESGGGLVQPGGSLRLSCAASGFTFS |
| 138D2 | 250 | VH3-23/D6-19/JH5b | -G----W---------------------- |
| 182A5 | 139 | | ---V------------------------- |
| - | - | Germline | QVQLVESGGGVVQPGRSLRLSCAASGFTFS |
| 190D7 | 211 | VH3-30/D2-15/JH6b | -----------------V-------L--- |
| 129A7 | 124 | | -------------------------L--- |
| - | - | Germline | QVQLVESGGGVVQPGRSLRLSCAASGFTFS |
| 141A10 | 318 | VH3-30/D2-2/JH6b | -----------------V-------L--- |
| 124D4 | 342 | | -----------------V-------L--- |
| 132D8 | 333 | | -----------------V-------L--- |

| FIG 6A₁ | FIG 6A₂ |
|---|---|
| FIG 6A₃ | FIG 6A₄ |

| CDR1 | FR2 | SEQ ID NO. |
|---|---|---|
| SYGMH | WVRQAPGKGLEWVA | 1 |
| -N--- | -------------- | 2 |
| SNSAAWN | WIRQSPSRGLEWLG | 3 |
| --N---- | ------A------- | 4 |
| -Y-S--- | -------------- | 5 |
| SGGYYWS | WIRQHPGKGLEWIG | 6 |
| ------- | -------------- | 7 |
| SYAMS | WVRQAPGKGLEWVS | 8 |
| ----- | -------------- | 9 |
| ----- | -------------- | 10 |
| SYGMH | WVRQAPGKGLEWVA | 11 |
| ----- | -------------- | 12 |
| ----- | -------------- | 13 |
| SYGMH | WVRQAPGKGLEWVA | 14 |
| ----- | -------------- | 15 |
| ----- | -------------- | 16 |
| ----- | -------L------ | 17 |

| Well | Single Cell | CDR2 | FR3 |
|---|---|---|---|
| - | - | VIWYDGSNKYYADSVKG | RFTISRDNSKNTLYLQMNSLRAEDTAVYYCAR |
| 174F1 | 131 | ------D-R-------- | -------------------------------- |
| - | - | RTYYRSKWYNDYAVSVKS | RITINPDTSKNQFSLQLNSVTPEDTAVYYCAR |
| 125D10 | 170 | ---------V------- | -------------------------------- |
| 182D5 | 150 | -A-H--R--YE------ | ---N-T-------------------------- |
| - | - | YIYYSGSTYYNPSLKS | RVTISVDTSKNQFSLKLSSVTAADTAVYYCAR |
| 172B12 | 095 | F---R-N--------- | -------------------------------- |
| - | - | AISGSGGSTYYADSVKG | RFTISRDNSKNTLYLQMNSLRAEDTAVYYCAK |
| 138D2 | 250 | --------N------- | --------------V----------------G |
| 182A5 | 139 | --------N------- | --------------V----------------G |
| - | - | VISYDGSNKYYADSVKG | RFTISRDNSKNTLYLQMNSLRAEDTAVYYCAK |
| 190D7 | 211 | -T------K-D------ | -------------------------------VS |
| 129A7 | 124 | -M-----KED------- | ------------E------------------VS |
| - | - | VISYDGSNKYYADSVKG | RFTISRDNSKNTLYLQMNSLRAEDTAVYYCAK |
| 141A10 | 318 | -T------K-D------ | -------------------------------VS |
| 124D4 | 342 | -T------K-D------ | -------------------------------VS |
| 132D8 | 333 | -T------K-D------ | -------------------------------VS |

| CDR3 | FR4 | SEQ ID NO. |
|---|---|---|
| DGYDILTGNPRDFDY | WGQGTLVTVSS | 1 |
| --------------- | ----------- | 2 |
| ATAFDY | WGQGTLVTVSS | 3 |
| ------ | ----------- | 4 |
| GSR--- | ----------- | 5 |
| DGYCSRTGCYGGWFDP | WGQGTLVTVSS | 6 |
| ---------------- | ----------- | 7 |
| SSGWSEY | WGQGTLVTVSS | 8 |
| ------- | ----------- | 9 |
| ------- | ----------- | 10 |
| EGYCSSSSCYKYYYYGMDV | WGQGTLVTVSS | 11 |
| ------------------- | ----------- | 12 |
| ----R-------------- | ----------- | 13 |
| EGYCDSSSCYKYYYYGMDV | WGQGTLVTVSS | 14 |
| ------------------- | ----------- | 15 |
| ------T------------ | ----------- | 16 |
| ------T------------ | ----------- | 17 |

| FIG 7A₁ | FIG 7A₂ |
|---------|---------|
| FIG 7A₃ | FIG 7A₄ |

FIG. 7

| Well | Single Cell | V Kappa/J | FR1 |
|------|-------------|-----------|-----|
| - | - | Germline | DIVMTQTPLSSPVTLGQPASISC |
| 174F1 | 131 | | -T------------------- |
| 125D10 | 170 | A23 (VK2)/JK1 | A--L----------------- |
| 182D5 | 150 | | --------------------- |
| - | - | Germline | DIVMTQTPLSSPVTLGQPASISC |
| 172B12 | 095 | A23 (Vk2)/JK5 | --------------------- |
| - | - | Germline | DIQMTQSPSSLSASVGDRVTITC |
| 182A5 | 139 | A30 (VK1)/JK4 | --------------------- |
| 138D2 | 250 | | ------S-------------- |
| - | - | Germline | DIVMTQSPLSLPVTPGEPASISC |
| 190D7 | 211 | A3 (Vk2)/JK1 | --------------------- |
| 129A7 | 123 | | --------------------- |
| - | - | Germline | DIVMTQSPLSLPVTPGEPASISC |
| 124D4 | 342 | | --------------------- |
| 132D8 | 333 | A3 (Vk2)/JK1 | --------------------- |
| 141A10 | 318 | | --------------------- |

| CDR1 | FR2 | SEQ ID NO. |
|---|---|---|
| RSSQSLVHSDGNTYLS | WLQQRPGQPPRLLIY | 18 |
| ---------------- | --------------- | 19 |
| -------R-------- | --------------- | 20 |
| -------R-------- | --------------- | 21 |
| RSSQSLVHSDGNTYLS | WLQQRPGQPPRLLIY | 22 |
| ----I-T----I---- | --------------- | 23 |
| RASQGIRNDLG | WYQQKPGKAPKRLIY | 24 |
| -------N-A | --------------- | 25 |
| --T----KN- | --------------- | 26 |
| RSSQSLLHSNGYNYLD | WYLQKPGQSPQLLIY | 27 |
| ----YR---N----- | ----R---------- | 28 |
| ----YR---N----- | --------------- | 29 |
| RSSQSLLHSNGYNYLD | WYLQKPGQSPQLLIY | 30 |
| ----YR---N----- | ----R---------- | 31 |
| ----YR---N----- | ----R---------- | 32 |
| ----YR---N----- | ----R---------- | 33 |

| Well | Single Cell | CDR2 | FR3 |
|---|---|---|---|
| - | - | KISNRFS | GVPDRFSGSGSGAGTDFTLKISRVEAEDVGVYYC |
| 174F1 | 131 | R--R--- | ---------------------E---------- |
| 125D10 | 170 | ------- | ------------------------PD------ |
| 182D5 | 150 | ------- | ------------------------------I-F- |
| - | - | KISNRFS | GVPDRFSGSGSGAGTDFTLKISRVEAEDVGVYYC |
| 172B12 | 095 | ------- | -------------------------------- |
| - | - | AASSLQS | GVPSRFSGSGSGTEFTLTISSLQPEDFATYYC |
| 182A5 | 139 | ---N--- | ---------T---------------------- |
| 138D2 | 250 | ------- | ------------------IV------------ |
| - | - | LGSNRAS | GVPDRFSGSGSGTDFTLKISRVEAEDVGVYYC |
| 190D7 | 211 | ------- | -----------------------R-------- |
| 129A4 | 123 | ------- | ---------------N---------------- |
| - | - | LGSNRAS | GVPDRFSGSGSGTDFTLKISRVEAEDVGVYYC |
| 124D4 | 342 | ------- | ----------------------H--------- |
| 132D8 | 333 | ------- | -------------------------------- |
| 141A10 | 318 | ------- | -------------------------------- |

| CDR3 | FR4 | SEQ ID NO. |
|---|---|---|
| MQATQFPWT | FGQGTKVEIK | 18 |
| --S-HV-R- | ---------- | 19 |
| -HT--L--- | ---------- | 20 |
| -HT-----R- | -----R---- | 21 |
| MQATQFPIT | FGQGTRLEIK | 22 |
| --G------ | ---------- | 23 |
| LQHNSYPLT | FGGGTKVEIK | 24 |
| --H------ | S--------- | 25 |
| --H------ | ----R---R- | 26 |
| MQALQTPWT | FGQGTKVEIK | 27 |
| ------R-- | ---------- | 28 |
| --------R- | ---------- | 29 |
| MQALQTPWT | FGQGTKVEIK | 30 |
| ------R-- | ---------- | 31 |
| ------R-- | ---------- | 32 |
| ------R-- | ---------- | 33 |

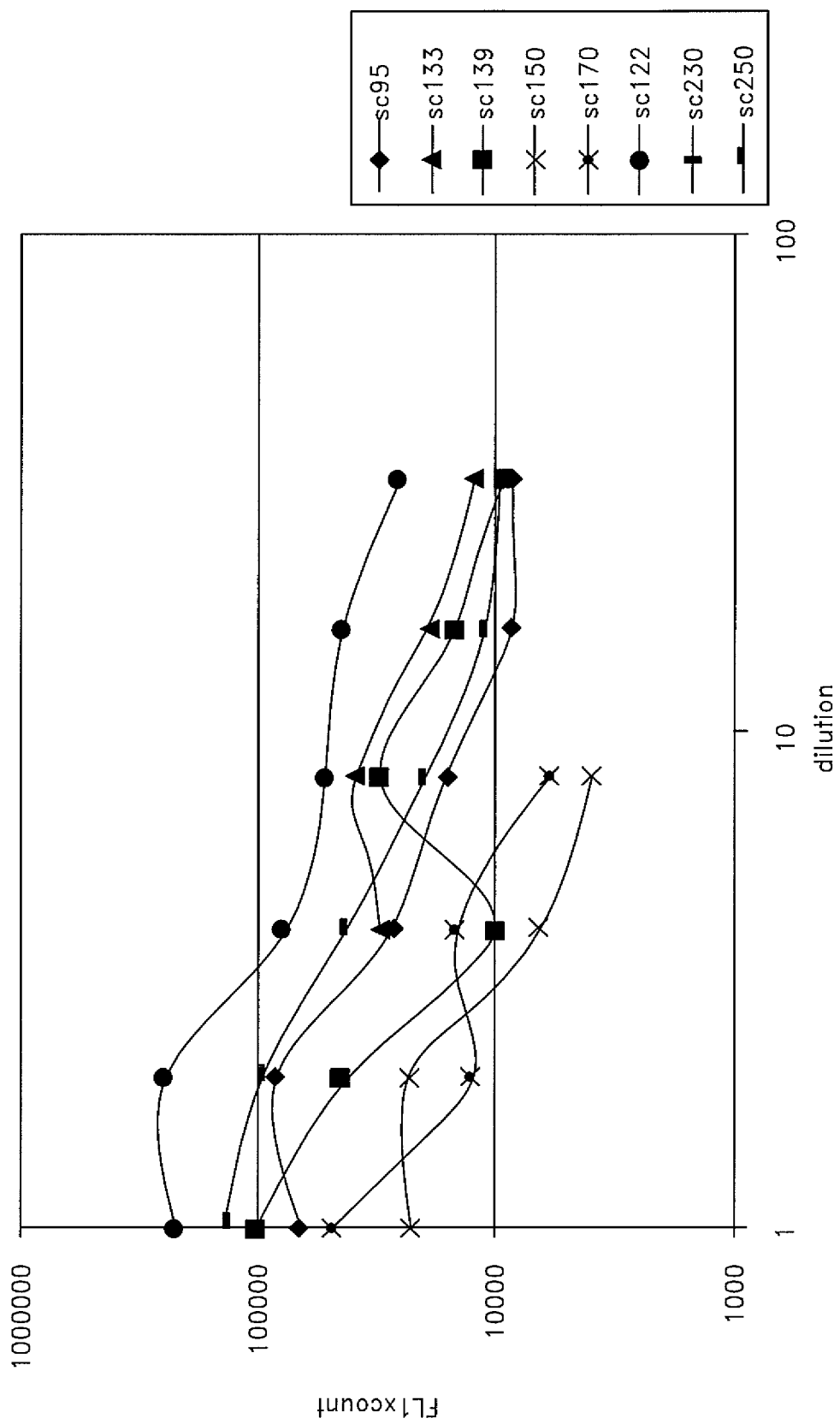

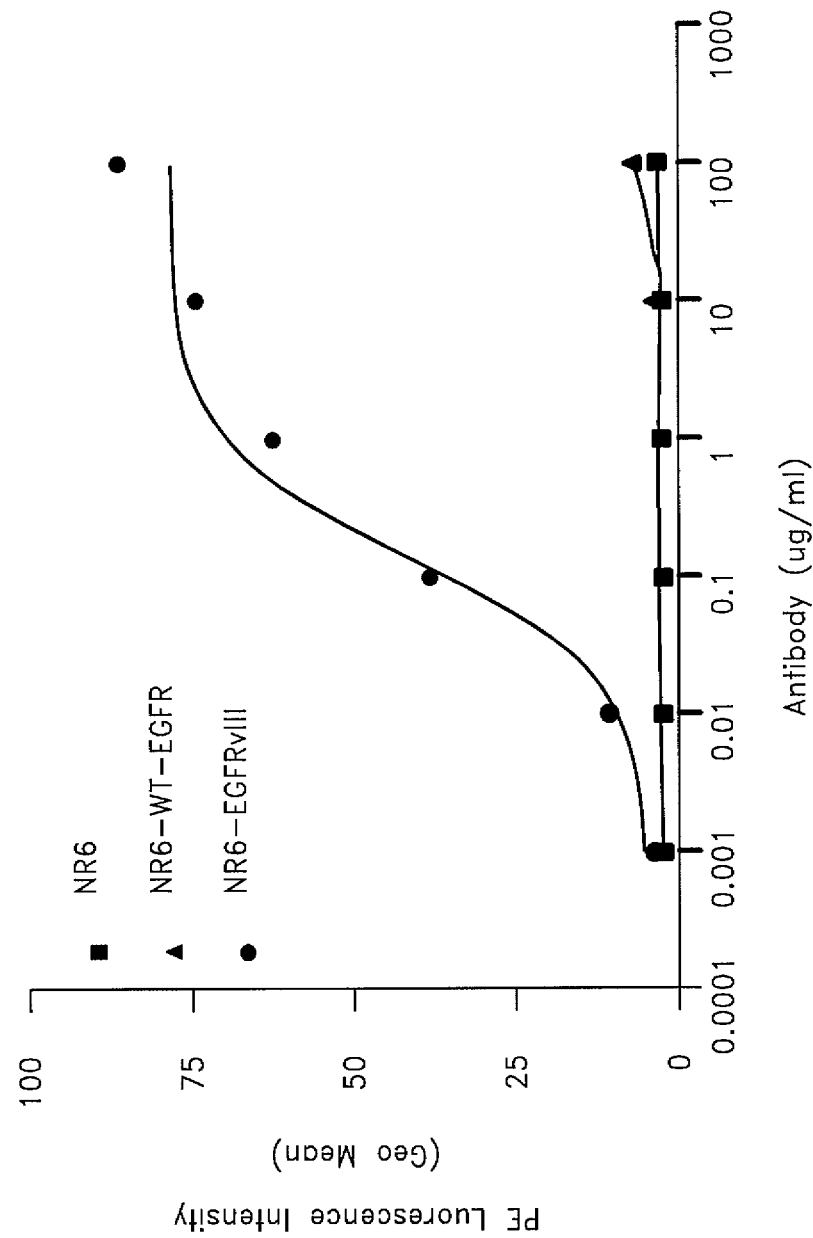

ANTIBODIES DIRECTED TO THE DELETION MUTANTS OF EPIDERMAL GROWTH FACTOR RECEPTOR AND USES THEREOF

This Application is a divisional of U.S. patent application Ser. No. 10/877,774, filed Jun. 25, 2004, which claims priority to U.S. Provisional Applications Ser. No. 60/562,453 filed Apr. 15, 2004, Ser. No. 60/525,570, filed Nov. 26, 2003, and Ser. No. 60/483,145, filed Jun. 27, 2003, hereby incorporated by reference in their entireties.

SEQUENCE LISTING

The present application is being filed along with a Sequence Listing in electronic format. The Sequence Listing is provided as a file entitled ABGENIX087A2DVSEQSub.TXT created Feb. 27, 2009, which is 91,100 bytes in size. The information in the electronic format of the Sequence Listing is incorporated herein by reference in its entirety.

FIELD OF THE INVENTION

The present embodiments relate to novel antibodies, particularly antibodies directed against deletion mutants of epidermal growth factor receptor and particularly to the type III deletion mutant, EGFRvIII. The embodiments also relate to human monoclonal antibodies directed against deletion mutants of epidermal growth factor receptor and particularly to EGFRvIII. The embodiments also relate to variants of such antibodies. Diagnostic and therapeutic formulations of such antibodies, and immunoconjugates thereof, are also provided.

BACKGROUND OF THE INVENTION

Tumor specific molecules to aid in better diagnosis and treatment of human and animal cancer have been sought since the last century. Hard evidence of tumor-specific substances, based on molecular structural data, has been difficult to provide in most types of human cancer except those based on virally-induced cancer and involving molecular structures specified by the virus genome. There have been extremely few examples of tumor-specific molecules based on novel molecular structures. In the case of malignant human gliomas and other tumors potentially associated with amplification or changes in the epidermal growth factor receptor molecule, such as carcinoma of the breast and other human carcinomas, there have been no unequivocal demonstrations of structurally altered molecules with unique sequences.

The epidermal growth factor receptor (EGFR) is the 170 kilodalton membrane glycoprotein product of the proto-oncogene c-erb B. The sequence of the EGFR gene is known (Ullrich et al. (1984). Human Epidermal Growth Factor Receptor cDNA Sequence and Aberrant Expression of the Amplified Gene in A431 Epidermoid Carcinoma Cells. Nature 309:418-425). The EGFR gene is the cellular homolog of the erb B oncogene originally identified in avian erythroblastosis viruses (Downward et al. (1984). Close Similarity of Epidermal Growth Factor Receptor and v-erb B Oncogene Protein Sequence. Nature 307:521-527, Ullrich, et al. (1984)). Activation of this oncogene by gene amplification has been observed in a variety of human tumors (Haley et al. (1987A). The Epidermal Growth Factor Receptor Gene in: Oncogenes, Genes, and Growth Factors Edited by: Guroff, G. 12th Edition. Chapter 2. pp. 40-76. Wiley, N.Y.), and in particular, those of glial origin (Libermann et al. (1985). Amplification, Enhanced Expression and Possible Rearrangement of EGF Receptor Gene in Primary Human Brain Tumours of Glial Origin. Nature 313:144-147; Wong et al. (1987). Increased Expression of the Epidermal Growth Factor Receptor Gene in Malignant Gliomas is Invariably Associated with Gene Amplification. Proc. Natl. Acad. Sci. USA 84:6899-6903; Yamazaki et al. (1988). Amplification of the Structurally and Functionally Altered Epidermal Growth Factor Receptor Gene (c-erbB) in Human Brain Tumors. Molecular and Cellular Biology 8:1816-1820; Malden et al., (1988). Selective Amplification of the Cytoplasmic Domain of the Epidermal Growth Factor Receptor Gene in Glioblastoma Multiforme. Cancer Research 4:2711-2714).

EGF-r has been demonstrated to be overexpressed on many types of human solid tumors. Mendelsohn Cancer Cells 7:359 (1989), Mendelsohn Cancer Biology 1:339-344 (1990), Modjtahedi and Dean Int'l J. Oncology 4:277-296 (1994). For example, EGFR overexpression has been observed in certain lung, breast, colon, gastric, brain, bladder, head and neck, ovarian, kidney and prostate carcinomas. Modjtahedi and Dean Int'l J. Oncology 4:277-296 (1994). Both epidermal growth factor (EGF) and transforming growth factor-alpha (TGF-alpha.) have been demonstrated to bind to EGF-r and to lead to cellular proliferation and tumor growth.

One major difference between v-erb B oncogenes and the normal EGFR gene is that the viral oncogenes are amino-truncated versions of the normal receptor; they lack most of the extracytoplasmic domain but retain the transmembrane and tyrosine kinase domains (Fung et al., (1984) Activation of the Cellular Oncogene c-erb B by LTR Insertion: Molecular Basis for Induction of Erythroblastosis by Avian Leukosis Virus. Cell 33:357-368; Yamamoto et al., (1983). A New Avain Erythroblastosis Virus, AEV-H Carries erbB Gene Responsible for the Induction of Both Erythroblastosis and Sarcoma. Cell 34:225-232, Nilsen et al., (1985). c-erbB Activation in ALV-Induced Erythroblastosis: Novel RNA Processing and Promoter Insertion Results in Expression of an Amino-Truncated EGF Receptor. Cell 41:719-726; Gammett et al., (1986). Differences in Sequences Encoding the Carboxy-Terminal Domain of the Epidermal Growth Factor Receptor Correlate with Differences in the Disease Potential of Viral erbB Genes. Proc. Natl. Acad. Sci. USA 83:6053-6057). This results in a protein that is unable to bind epidermal growth factor (EGF) but can still phosphorylate other substrates (Gilmore et al., (1985). Protein Phosphorlytion at Tyrosine is Induced by the v-erb B Gene Product in Vivo and In Vitro. Cell 40:609-618; Kris et al., (1985). Antibodies Against a Synthetic Peptide as a Probe for the Kinase Activity of the Avian EGF Receptor and v-erB Protein. Cell 40:619-625), and has led to speculation that the v-erb B proteins are oncogenic because the kinase domain is unregulated and constitutively active (Downward et al., 1984).

A variety of genetic alterations can occur in viral erb B oncogenes, e.g. amino acid substitutions and deletions in the carboxy terminus of the gene. Available evidence, however, argues that the amino truncation is critical to carcinogenesis. Amino truncations are a feature of all v-erb B oncogenes, including those that arise by promoter insertion or retroviral transduction (Nilsen et al., (1985). c-erbB Activation in ALV-Induced Erythroblastosis: Novel RNA Processing and Promoter Insertion Results in Expression of an Amino-Truncated EGF Receptor. Cell 41:719-726; Gammett et al., (1986). Differences in Sequences Encoding the Carboxy-Terminal Domain of the Epidermal Growth Factor Receptor Correlate with Differences in the Disease Potential of Viral erbB Genes. Proc. Natl. Acad. Sci. USA 83:6053-6057).

In contrast, carboxy-terminal deletions appear to be associated only with tumors that arise through retroviral transduction and seem to determine host range and tumor type specificity (Gammett et al., 1986; Raines et al., (1985). c-erbB Activation in Avian Leukosis Virus-Induced Erythroblastosis: Clustered Integration Sites and the Arrangement of Provirus in the c-erbB Alleles. Proc. Natl. Acad. Sci. USA 82:2287-2291). Transfection experiments with amino-truncated avian c-erb B genes or chimeric viral oncogene-human EGF receptors demonstrates that this deletion is sufficient alone to create a transforming protein (Pelley et al., (1988). Proviral-Activated c-erbB is Leukemogenic but not Sarcomagenic: Characterization of a Replication—Competent Retrovirus Containing the Activated c-erbB. Journal of Virology 62: 1840-1844; Wells et al., (1988). Genetic Determinants of Neoplastic Transformation by the Retroviral Oncogene v-erbB. Proc. Natl. Acad. Sci. USA 85:7597-7601).

Amplification of the EGFR gene occurs in 40% of malignant human gliomas (Libermann et al., (1985) Amplification, Enhanced Expression and Possible Rearrangement of EGF Receptor Gene in Primary Human Brain Tumours of Glial Origin. Nature 313:144-147; Wong et al., (1987). Increased Expression of the Epidermal Growth Factor Receptor Gene in Malignant Gliomas is Invariably Associated with Gene Amplification. Proc. Natl. Acad. Sci. USA 84:6899-6903), Rearrangement of the receptor gene is evident in many of the tumors with gene amplification. The structural alterations seem to preferentially affect the amino terminal half of the gene (Yamazaki et al., (1985). Amplification, Enhanced Expression and Possible Rearrangement of EGF Receptor Gene in Primary Human Brain Tumours of Glial Origin. Nature 313:144-147; Malden et al., (1988). Selective Amplification of the Cytoplasmic Domain of the Epidermal Growth Factor Receptor Gene in Glioblastoma Multiforme. Cancer Research 4:2711-2714), but the nature of the rearrangements had not at that time been precisely characterized in any tumor.

Size variant EGFR genes and amplification have been reported in several human cancers. (Humphrey et al., (1988). Amplification and Expression of the Epidermal Growth Factor Receptor Gene in Human Glioma Xenografts. Cancer Research 48:2231-2238; Bigner et al., (1988) J. Neuropathol. Exp. Neurol., 47:191-205; Wong et al., (1987). Increased Expression of the Epidermal Growth Factor Receptor Gene in Malignant Gliomas is Invariably Associated with Gene Amplification. Proc. Natl. Acad. Sci. USA 84:6899-6903; and Humphrey et al. Amplification and expression of the epidermal growth factor receptor gene in human glioma xenografts. Cancer Res. 48(8):2231-8 (1988). There had been no determination, however, of the molecular basis for the altered EGFR molecules in cells.

In 1989, work of Drs. Bigner and Vogelstein elucidated the sequence of a EGF receptor mutant that has become known as the type III mutant (also referred to as delta-EGFr or EGFrvIII). This work is described in U.S. Pat. Nos. 6,455,498, 6,127,126, 5,981,725, 5,814,317, 5,710,010, 5,401,828, and 5,212,290, the disclosures of which are hereby incorporated by reference.

EGFR variants are caused by gene rearrangement accompanied by EGFR gene amplification. There are eight major variants of EGFr that are known: (i) EGFRvI lacks a majority of the extracellular domain of EGFR, (ii) EGFRvII consists of an 83 aa in-frame deletion in the extracellular domain of EGFR, (iii) EGFRvIII consists of a 267 aa in-frame deletion in the extracellular domain of EGFR, (iv) EGFRvIV contains deletions in the cytoplasmic domain of EGFR, (v) EGFRvV contains deletions in cytoplasmic domain of EGFR, (vi) EGFR.TDM/2-7 contains a duplication of exons 2-7 in the extracellular domain of EGFR, (vii) EGFR.TDM/18-25 contains a duplication of exons 18-26 in the tyrosine kinase domain of EGFR, and (viii) EGFR.TDM/18-26 contains a duplication of exons 18-26 in the tyrosine kinase domain of EGFR (Kuan et al. EGF mutant receptor vIII as a molecular target in cancer therapy. Endocr Relat Cancer. 8(2):83-96 (2001)). In addition, there is a second, more rare, EGFRvIII mutant (EGFRvIII/Δ12-13) that possesses a second deletion that introduces a novel histidine residue at the junction of exons 11 and 14 (Kuan et al. EGF mutant receptor vIII as a molecular target in cancer therapy. Endocr Relat Cancer. 8(2): 83-96 (2001)).

EGFRvIII is the most commonly occurring variant of the epidermal growth factor (EGF) receptor in human cancers (Kuan et al. EGF mutant receptor vIII as a molecular target in cancer therapy. Endocr Relat Cancer. 8(2):83-96 (2001)). During the process of gene amplification, a 267 amino acid deletion occurs in the extracellular domain creating a novel junction to which tumor specific monoclonal antibodies can be directed. This variant of the EGF receptor contributes to tumor progression through constitutive signaling in a ligand independent manner. EGFrVIII is not know to be expressed on any normal tissues (Wikstrand, C J. et al. Monoclonal antibodies against EGFRv III are tumor specific and react with breast and lung carcinomas malignant gliomas. Cancer Research 55(14): 3140-3148 (1995); Olapade-Olaopa, E O. et al. Evidence for the differential expression of a variant EGF receptor protein in human prostate cancer. Br J Cancer. 82(1): 186-94 (2000)). Yet, EGFRvIII shows significant expression in tumor cells, e.g., 27~76% breast cancer biopsies express EGFRvIII (Wikstrand, C J. et al. Monoclonal antibodies against EGFRvIII are tumor specific and react with breast and lung carcinomas malignant gliomas. Cancer Research 55(14): 3140-3148 (1995); Ge H. et al. Evidence of high incidence of EGFRvIII expression and coexpression with EGFR in human invasive breast cancer by laser capture microdissection and immunohistochemical analysis. Int J Cancer. 98(3):357-61 (2002)), 50~70% gliomas express EGFRvIII (Wikstrand, C J. et al. Monoclonal antibodies against EGFRvIII are tumor specific and react with breast and lung carcinomas malignant gliomas. Cancer Research 55(14): 3140-3148 (1995); Moscatello, G. et al. Frequent expression of a mutant epidermal growth factor receptor in multiple human tumors. Cancer Res. 55(23):5536-9 (1995)), 16% NSCL cancers express EGFRvIII (Garcia de Palazzo, I E. et al. Expression of mutated epidermal growth factor receptor by non-small cell lung carcinomas. Cancer Res. 53(14):3217-20 (1993)), 75% ovarian cancers express EGFRvIII (Moscatello, G. et al. Frequent expression of a mutant epidermal growth factor receptor in multiple human tumors. Cancer Res. 55(23):5536-9 (1995)), and 68% prostate cancers express EGFRvIII (Olapade-Olaopa, E O. et al. Evidence for the differential expression of a variant EGF receptor protein in human prostate cancer. Br J Cancer. 82(1): 186-94 (2000)).

The deletion of 267 amino acids with a Glycine substitution creates a unique junction that may be capable of antibody targeting. Further, in view of EGFRvIII's expression in certain tumors and its lack of expression in normal tissues, EGFRvIII may be an ideal target for drug targeting in tumor therapy. In particular, EGFRvIII would appear to be an ideal candidate for immunoconjugate therapy of tumors (e.g., an antibody conjugated to an antineoplastic agent or toxin). Another method of treatment of cancers which over-express EGFRvIII involved the use of a tumor-specific ribozyme targeted specifically to the variant receptor which did not cleave normal EGFR. The ribozyme was found to significantly inhibit breast cancer growth in athymic nude mice (Luo et al. Int. J. Cancer. 104(6):716-21 (2003)).

General antibodies for the entire EGFRvIII protein have been described. See International Patent Application No. WO 01/62931 and Kuan et al. EGF mutant receptor vIII as a molecular target in cancer therapy. Endocr Relat Cancer. 8(2): 83-96 (2001), Kuan et al. EGFRvIII as a promising target for antibody-based brain tumor therapy. Brain Tumor Pathol. 17(2):71-78 (2000), Kuan et al. Increased binding affinity enhances targeting of glioma xenografts by EGFRvIII-specific scFv. International Journal of Cancer. 88(6):962-969 (2000), Landry et al. Antibody recognition of a conformational epitope in a peptide antigen: Fv-peptide complex of an antibody fragment specific for the mutant EGF receptor, EGFRvIII. Journal of Molecular Biology. 308(5):883-893 (2001), Reist et al. Astatine-211 labeling of internalizing anti-EGFRvIII monoclonal antibody using N-succinimidyl 5-[211At]astato-3-pyridinecarboxylate. Nuclear Medicine and Biology. 26(4):405-411 (1999), Reist et al. In vitro and in vivo behavior of radiolabeled chimeric anti-EGFRvIII monoclonal antibody: comparison with its murine parent. Nuclear Medicine and Biology. 24(7):639-647 (1997), Wikstrand et al. Generation of anti-idiotypic reagents in the EGFRvIII tumor-associated antigen system. Cancer Immunology, Immunotherapy. 50(12):639-652 (2002), Wikstrand et al. Monoclonal antibodies against EGFRvIII are tumor specific and react with breast and lung carcinomas malignant gliomas. Cancer Research. 55(14):3140-3148 (1995), Wikstrand et al. The class III variant of the epidermal growth factor receptor (EGFRvIII): characterization and utilization as an immunotherapeutic target. J. Neurovirol. 4(2):148-158 (1998), Wikstrand et al. The class III variant of the epidermal growth factor receptor (EGFRvIII): characterization and utilization as an immunotherapeutic target. J. Neurovirol. 4(2):148-158 (1998), Jungbluth et al. A monoclonal antibody recognizing human cancers with amplification/overexpression of the human epidermal growth factor receptor. Proc Natl Acad Sci USA. 100(2):639-44 (2003), Mamot et al. Epidermal Growth Factor Receptor (EGFR)-targeted Immunoliposomes Mediate Specific and Efficient Drug Delivery to EGFR- and EGFRvIII-overexpressing Tumor Cells. Cancer Research 63:3154-3161 (2003)). Each of these above-mentioned antibodies, however, possess or contain murine sequences in either the variable and/or constant regions. The presence of such murine derived proteins can lead to the rapid clearance of the antibodies or can lead to the generation of an immune response against the antibody in a patient. In addition, such antibodies are relatively low affinity, on the order of $2.2 \times 10^{-8}$ through $1.5 \times 10^{-9}$, even after affinity maturation. (Kuan et al. EGF mutant receptor vIII as a molecular target in cancer therapy. Endocr Relat Cancer. 8(2):83-96 (2001)).

In order to avoid the utilization of murine or rat derived antibodies, researchers have introduced human antibody function into rodents so that the rodents can produce fully human antibodies. See e.g., Mendez et al. Functional transplant of megabase human immunoglobulin loci recapitulates human antibody response in mice. Nat. Genet. 15(2):146-56 (1997). This approach has been used in connection with the generation of successful antibodies directed against wild type EGFR. See e.g., Yang X et al. Development of ABX-EGF, a fully human anti-EGF receptor monoclonal antibody, for cancer therapy. Crit. Rev Oncol Hemato 38(1):17-23 (2001); Yang X-D et al. Eradication of Established Tumors by a Fully Human Monoclonal Antibody to the Epidermal Growth Factor Receptor without Concomitant Chemotherapy. Cancer Research 59(6):1236-1243 (1999); and U.S. Pat. No. 6,235,883.

SUMMARY OF THE INVENTION

In one embodiment, the invention comprises an isolated human monoclonal antibody that specifically binds to EGFRvIII and a peptide that comprises the sequence L E E K K G N Y V V T D H C (SEQ ID NO: 56). In one embodiment, a therapeutic agent may be conjugated to the antibody. In one embodiment, a toxin is used. In another embodiment, the invention comprises an isolated human monoclonal antibody that specifically binds to an epitope contained within a sequence comprising L E E K K G N Y V V T D H C (SEQ ID NO: 56), wherein the residues required for binding, as determined by Alanine scanning in a SPOTs array, are selected from the group consisting of EEK, KKNYV, LEK, EKNY and EEKGN.

Further embodiments include an isolated human monoclonal antibody that comprises a heavy chain variable region amino sequence that is encoded by a VH3-33 gene. The heavy chain variable region amino sequence can include an amino acid sequence that is encoded by a JH4b gene, or an amino acid sequence that is encoded by a D gene that is selected from the group consisting of D6-13 and D3-9.

Other embodiments include an isolated human monoclonal antibody that comprises a light chain variable region amino sequence that is encoded by a A23(VK2) gene. The light chain variable region amino sequence can include an amino acid sequence that is encoded by a JK1 gene.

Other embodiments include an isolated antibody, or fragment thereof, that binds to EGFRvIII and that comprises a heavy chain amino acid sequence selected from the group consisting of the heavy chain amino acid sequence of antibody 13.1.2, 131, 170, 150, 095, 250, 139, 211, 124, 318, 342 and 333 as identified in (SEQ ID NO: 138, 2, 4, 5, 7, 9, 10, 12, 13, 15, 16, and 17). The antibody can be a monoclonal antibody, a chimeric antibody, a humanized antibody or a human antibody. The antibody or fragment can be associated with a pharmaceutically acceptable carrier or diluent, and can be conjugated to a therapeutic agent. The therapeutic agent can be a toxin. The therapeutic agent can be a toxin such as DM-1, AEFP, AURISTATIN E, or ZAP. The agent can be associated with the antibody via a linker. The toxin can be associated with the antibody via a secondary antibody. Further embodiments include a hybridoma cell line producing the antibody, and a transformed cell comprising a gene encoding the antibody. The cell can be, for example, a Chinese hamster ovary cell.

Further embodiments include a method of, inhibiting cell proliferation associated with the expression of EGFRvIII, comprising treating cells expressing EGFRvIII with an effective amount of the antibody or fragment. In one embodiment, the antibody comprises a heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17). The method can be performed in vivo, and performed on a mammal, such as a human, who suffers from a cancer involving epithelial cell proliferation, such as a lung, colon, gastric, renal, prostate, breast, glioblastoma or ovarian carcinoma.

Further embodiments include a method of killing a targeted cell. This is achieved by contacting the targeted cell with an antibody associated with a toxin. The antibody binds to a peptide LEEKKGNY (SEQ ID NO: 133). In one embodiment, the antibody has a binding affinity greater than $1.3 \times 10^{-9}$ M to the peptide. In one embodiment the toxin is selected from AEFP, DM-1, and ZAP. In one embodiment, the antibody toxin compound is 10 fold more toxic to targeted cells than to cells without the peptide. In one embodiment, the antibody comprises a heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17). In another embodiment, the antibody is associated with a toxin via a peptide linker or a second antibody.

Further embodiments of the invention include an isolated antibody that binds to EGFRvIII and that comprises a heavy chain amino acid sequence comprising the following complementarity determining regions (CDRs):
  (a) CDR1 consisting of a sequence selected from the group consisting of the amino acid sequences for the CDR1 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17;
  (b) CDR2 consisting of a sequence selected from the group consisting of the amino acid sequences for the CDR2 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17; and
  (c) CDR3 consisting of a sequence selected from the group consisting of the amino acid sequences for the CDR3 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17. In one embodiment, the antibody is a monoclonal antibody, a chimeric antibody, human, or a humanized antibody. In one embodiment, the antibody is associated with a pharmaceutically acceptable carrier, diluent, and/or therapeutic agent. In one embodiment, the therapeutic agent is a toxin. In one embodiment, the toxin is DM-1 or Auristatin E.

Also included is an isolated antibody, or fragment thereof, that binds to EGFRvIII and that comprises a light chain amino acid sequence selected from the group consisting of the light chain amino acid sequence of antibody 13.1.2, 131, 170, 150, 123, 095, 139, 250, 211, 318, 342, and 333 as identified in SEQ ID NO: 140, 19, 20, 21, 29, 23, 25, 26, 28, 33, 31 and 32. The antibody can be a monoclonal antibody, a chimeric antibody, a humanized antibody, or a human antibody. It can be associated with a pharmaceutically acceptable carrier or diluent, or conjugated to a therapeutic agent, such as a toxin, for example DM1 or AURISTATIN E. In one embodiment a hybridoma cell line or a transformed cell producing an antibody comprising a light chain amino acid sequence selected from the group consisting of the light chain amino acid sequence of antibody 13.1.2, 131, 170, 150, 123, 095, 139, 250, 211, 318, 342, and 333 as identified in SEQ ID NO: 140, 19, 20, 21, 29, 23, 25, 26, 28, 33, 31 and 32 is contemplated.

Further embodiments include a hybridoma cell line producing such an antibody, and a transformed cell, such as a Chinese hamster ovary cell, comprising a gene encoding the antibody.

Yet another embodiment includes a method of inhibiting cell proliferation associated with the expression of EGFRvIII, comprising treating cells expressing EGFRvIII with an effective amount of the antibodies or fragments described above. The method can be performed in vivo and on a mammal, such as a human, who suffers from a cancer involving epithelial cell proliferation such as lung, colon, gastric, renal, prostate, breast, glioblastoma or ovarian carcinoma.

Yet another embodiment includes an isolated antibody that binds to EGFRvIII and that comprises a light chain amino acid sequence comprising the following complementarity determining regions (CDRs):
  (a) CDR1 consisting of a sequence selected from the group consisting of the amino acid sequences for the CDR1 region of antibodies 13.1.2, 131, 170, 150, 123, 095, 139, 250, 211, 318, 342, and 333 as identified in SEQ ID NO: 140, 19, 20, 21, 29, 23, 25, 26, 28, 33, 31 and 32;
  (b) CDR2 consisting of a sequence selected from the group consisting of amino acid sequences for the CDR1 region of antibodies 13.1.2, 131, 170, 150, 123, 095, 139, 250, 211, 318, 342, and 333 as identified in SEQ ID NO: 140, 19, 20, 21, 29, 23, 25, 26, 28, 33, 31 and 32; and
  (c) CDR3 consisting of a sequence selected from the group consisting of amino acid sequences for the CDR1 region of antibodies 13.1.2, 131, 170, 150, 123, 095, 139, 250, 211, 318, 342, and 333 as identified in SEQ ID NO: 140, 19, 20, 21, 29, 23, 25, 26, 28, 33, 31 and 32.

The antibody described in the paragraph above can also include a heavy chain amino acid sequence comprising the following complementarity determining regions (CDRs):
  (a) CDR1 consisting of a sequence selected from the group consisting of the amino acid sequences for the CDR1 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17;
  (b) CDR2 consisting of a sequence selected from the group consisting of the amino acid sequences for the CDR2 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17; and
  (c) CDR3 consisting of a sequence selected from the group consisting of the amino acid sequences for the CDR3 region of antibodies 13.1.2, 131, 170, 150, 095, 250, 139, 211, 124, 318, 342 and 333 as identified in SEQ ID NO: 138, 2, 4, 5, 7, 9, 10, 12, 13, 15, 16, and 17.

Further embodiments include a method of inhibiting cell proliferation associated with the expression of EGFRvIII, comprising treating cells expressing EGFRvIII with an effective amount of the antibody or fragment described above. The method can be performed in vivo, on a mammal, such as a human, suffering from a cancer involving epithelial cell proliferation, such as lung carcinoma, breast carcinoma, head & neck cancer, prostate carcinoma or glioblastoma.

Further embodiments include an isolated polynucleotide molecule comprising a nucleotide sequence encoding a heavy chain amino acid sequence, or a fragment thereof, selected from the group consisting of the heavy chain amino acid sequence of antibodies 13.1.2, 131, 170, 150, 095, 250, 139, 211, 124, 318, 342, and 333 as identified in SEQ ID NO: 138, 2, 4, 5, 7, 9, 10, 12, 13, 15, 16, and 17, or an isolated polynucleotide molecule comprising a nucleotide sequence encoding a light chain amino acid sequence, or a fragment thereof, selected from the group consisting of the light chain amino acid sequence of antibodies 13.1.2, 131, 170, 150, 123, 095, 139, 250, 211, 318, 342, and 333, as identified in SEQ ID NO: 140, 19, 20, 21, 29, 23, 25, 26, 28, 33, 31 and 32.

Further embodiments include an article of manufacture comprising a container, a composition contained therein, and a package insert or label indicating that the composition can be used to treat cancer characterized by the expression of EGFRvIII, wherein the composition comprises an antibody as described above. Such cancers include a lung carcinoma, breast carcinoma, head & neck cancer, prostate carcinoma or glioblastoma. Also included is an assay kit for the detection of EGFRvIII in mammalian tissues or cells in order to screen for lung, colon, gastric, renal, prostate or ovarian carcinomas, the EGFRvIII being an antigen expressed by epithelial cancers, the kit comprising an antibody that binds the antigen protein and means for indicating the reaction of the antibody with the antigen, if present. The antibody can be a labeled monoclonal antibody, or the antibody can be an unlabeled first antibody and the means for indicating the reaction comprises a labeled second antibody that is anti-immunoglobulin. The antibody that binds the antigen can be labeled with a marker selected from the group consisting of a fluorochrome, an enzyme, a Radionuclide and a radiopaque material. The antibody that binds the antigen can also bind to over-expressed wtEGFR. The kit can be used clinically for patient selection.

A further embodiment includes an antibody which specifically recognizes the epitope of EGFRvIII containing the novel Gly residue.

A further embodiment includes a protein variant of EGFRvIII. The variant may have a pFLAG insert, may consist of the amino acids in SEQ ID NO: 56, and can exist in silico.

Another embodiment includes an antibody, or variant thereof, which binds to the recognition sequence EEKKGNYVVT (SEQ ID NO: 57).

Another embodiment includes an antibody variant that specifically binds to EGFRvIII. The antibody variant can further bind to a peptide that comprises SEQ ID NO: 57. The EGFRvIII antibody variant can have residues that interact with residues EKNY or EEKGN in the peptide. In one embodiment, the antibody variant binds to the peptide sequence ten fold more tightly than it does to a wild-type EGFR protein. In one embodiment, the antibody binds specifically binds to EGFRvIII and the peptide of SEQ ID NO: 56. In one embodiment, the isolated antibody or variant has a complementarity determining region comprising a deep cavity, wherein the cavity is created by CDR2 and CDR3 of the heavy chain, CDR3 of the light chain, and a small portion from CDR1 of the light chain. In one embodiment, the isolated antibody or variant has residues 31, 37, 95-101, 143-147, 159, 162-166, 169-171, 211-219, 221, and 223 within 5 angstroms of a binding cavity. In one embodiment, the isolated antibody or variant has a complementarity determining region comprising a narrow groove, wherein the groove is created by heavy chain CDR2 and CDR3, and light chain CDR1, CDR2, and CDR3. In one embodiment, the isolated antibody or variant has residues 31, 33, 35-39, 51, 54-56, 58-61, 94-101, 144-148, 160, 163-166, 172, and 211-221 within 5 angstroms of a binding groove. In one embodiment, the isolated antibody or variant has residues 31-33, 35, 37, 55, 96-101, 148, 163, 165, 170, 172, 178, 217, and 218 within 5 angstroms of a binding groove. In one embodiment, the isolated antibody or variant has a paratope configured so that when the epitope of peptide EEKKGN (SEQ ID NO 127) binds to the paratope of the antibody, at least one bond is formed between two residues selected from the group consisting of E2 and Y172, K3 and H31, K4 and H31, N6 and D33, N6 and Y37, and N6 and K55. In one embodiment, the isolated antibody or variant has a paratope configured so that when the epitope of peptide EEKKGNY (SEQ ID 131) binds to the paratope of the antibody, at least one bond is formed between two residues selected from the group consisting of K4 and Q95, K4 and Q95, N6 and Q98, G5 and H31, Y7 and H31, Y7 and W165. In one embodiment, the antibody has a structure or interaction with a structure that is determined in silico.

Another embodiment provides a method for selecting variants that bind to EGFRvIII with particular binding characteristics, the method comprising the use of a molecular structure to create a paratope, the use of a molecular structure to create an epitope, calculating the interaction energy between the two and comparing that energy level to the energy level of the epitope and a second paratope of a mAb variant, and selecting a variant based on the differences in the energy levels. The method can further include using an interaction energy between a second variant of the paratope and the epitope to determine a third interaction energy and comparing the third interaction energy and the second interaction energy to determine which variant to select. In one embodiment, the variant is created and tested for binding.

Another embodiment provides a method for selecting variants that bind to EGFRvIII with particular binding characteristics, the method comprising examining residues of an epitope which interact with a paratope, selecting important residues to create a recognition sequence, using this sequence to create a EGFRvIII variant, and using the EGFRvIII variant to select the mAb variant.

Another embodiment provides a method for making antibody variants to EGFRvIII, said method comprising analyzing the residues of an epitope which interact with a paratope, selecting the more important residues of an epitope to create a recognition sequence, using the recognition sequence to create an EGFRvIII variant, and using the EGFRvIII variant to select antibody variants. In one embodiment, the selection of the antibodies is achieved in silico. In one embodiment, the selection of the antibodies through the use of the EGFRvIII variant is achieved by raising antibodies against EGFRvIII variant.

In the embodiment where the isolated antibody variant binds to EGFRvIII and the peptide of SEQ ID NO: 57, the antibody can further comprise a point mutation of the following: Tyr172Arg, Leu99Glu, Arg101Glu, Leu217Glu, Leu99Asn, Leu99His, L99T, Arg101Asp, or some combination thereof. In one embodiment, the antibody is a monoclonal antibody, a chimeric antibody, a humanized antibody, or a human antibody.

In one embodiment, the antibody or variant thereof binds to the sequence EEKKGNYVVT (SEQ ID NO: 57), and the antibody or variant has subnanomolar binding ability.

In a further embodiment, the antibody binds to EGFRvIII and the antibody has a paratope that binds to an epitope, and the epitope has a set of residues that interact with the paratope that include E, K, N, and Y. In one embodiment, the antibody is antibody 131.

In a further embodiment, the antibody binds to EGFRvIII and the antibody has a paratope that binds to an epitope that has a set of residues that interact with the paratope comprising: E, E, K, G, and N. In one embodiment, the primary structure of the epitope is EEKKGNY (SEQ ID NO: 131). In one embodiment, the antibody is 13.1.2.

In a further embodiment, the antibody that binds to EGFRvIII and has a $K_D$ of less than $1.3 \times 10^{-9}$ M, less than $1.0 \times 10^{-9}$ M, or less than 500 pM. In one embodiment, the antibody is specific for SEQ ID NO: 56 compared to a wild type EGFR peptide. In one embodiment, the nonspecific binding of the antibody to the wild type EGFR peptide (SEQ ID NO: 134) is less than 10% of that of the specific binding of the antibody to EGFRVIII (SEQ ID NO: 135). In one embodiment, the antibody is selected from the group consisting of 131, 139, and 13.1.2. In one embodiment, the antibody is internalized. In one embodiment, the internalization occurs for at least about 70% or at least about 80% of the antibody.

In one embodiment, the variant human monoclonal antibody preferentially binds to an epitope that is substantially unique to an EGFRvIII protein compared to a wild-type EGFR protein or variant thereof (SEQ ID NO: 134). In one embodiment, the variant comprises a heavy chain complementarity determining region (CDR1) corresponding to canonical class 1. In one embodiment, the variant comprises a heavy chain complementarity determining region (CDR2) corresponding to canonical class 3. In one embodiment, the variant comprises a light chain complementarity determining region (CDR1) corresponding to canonical class 4. In one embodiment, the variant comprises a light chain complementarity determining region (CDR2) corresponding to canonical class 1. In one embodiment, the variant comprises a light chain complementarity determining region (CDR3) corresponding to canonical class 1. In one embodiment, the variant comprises a first heavy chain complementarity determining region (CDR1) corresponding to canonical class 1, a second heavy chain complementarity determining region (CDR2) corresponding to canonical class 3, a first light chain complementarity determining region (CDR1) corresponding to canonical class 4, a second light chain complementarity determining region (CDR2) corresponding to canonical class 1; and a third light chain complementarity determining region (CDR3) corresponding to canonical class 1, wherein the complementarity determining regions are configured to allow the variant to bind to an epitope that is substantially unique to an EGFRvIII protein as compared to a EGFR protein.

BRIEF DESCRIPTION OF THE DRAWINGS

FIG. 1 is an alignment between wild type EGFR and EGFRvIII showing the 267 amino acid deletion and G substitution. FIG. 1 is divided into 5 parts (FIG. 1A-1E) for display purposes.

FIG. 2 is a diagram of the design of the EGFRvIII PEP3 14-mer peptide. In FIG. 2A, the N-terminal sequence of EGFRvIII with amino acids LEEKK (SEQ ID NO: 58) (1-5) that are identical to the N-terminal sequence of EGFR, followed by the unique Glysine residue, followed by amino acids that are identical to residues 273 through 280 in EGFR. FIG. 2B represents the amino acids of EGFR that are deleted in EGFRvIII (6-272).

FIGS. 3A-L provide sequences of antibodies of the invention. For each antibody provided, a nucleotide and amino acid sequence is provided for both a heavy chain and a light chain variable region. Accordingly, four sequences are provided for every antibody listed.

FIG. 4 is a table comparing the 13.1.2 antibody heavy chain regions to a particular germ line heavy chain region. "–"s indicate that the amino acid residue of the hybridoma heavy chain region is the same as the germ line for that particular position. Deviation from the germline is indicated by the appropriate amino acid residue.

FIG. 5 is a table comparing the 13.1.2 antibody light chain regions to a particular germ line light chain region. "–"s indicate that the amino acid residue of the hybridoma light chain region is the same as the germ line for that particular position. Deviation from the germline is indicated by the appropriate amino acid residue.

FIG. 6 is a table comparing various hybridoma derived antibody heavy chain regions to a particular germ line heavy chain region. "–"s indicate that the amino acid residue of the hybridoma heavy chain region is the same as the germ line for that particular position. Deviation from the germline is indicated by the appropriate amino acid residue. FIG. 6 is divided into 4 parts (FIG. 6A₁-6A₄) for display purposes.

FIG. 7 is a table comparing various hybridoma derived antibody light chain regions to a particular germ line light chain region. "–"s indicate that the amino acid residue of the hybridoma light chain region is the same as the germ line for that particular position. Deviation from the germline is indicated by the appropriate amino acid residue. FIG. 7 is divided into 4 parts (FIG. 7A₁-7A₄) for display purposes.

FIG. 8 is a representative figure showing binding of recombinant EGFRvIII mAbs to cells expressing EGFRvIII (NR6 cells). Diamonds represent 95, triangles represent 133, squares represent 139, "x" represent 150, asterixes represent 170, circles represent 221, lines 230, and rectangles represent 250.

FIG. 9O is a graph displaying the binding of antibody 13.1.2 to NR6 murine fibroblast cell lines. The squares represent NR6. The triangles represent NR6 with wild type EDFR. The circles represent NR6 with EGFRvIII.

DETAILED DESCRIPTION OF THE PREFERRED EMBODIMENTS

Figure 9A:
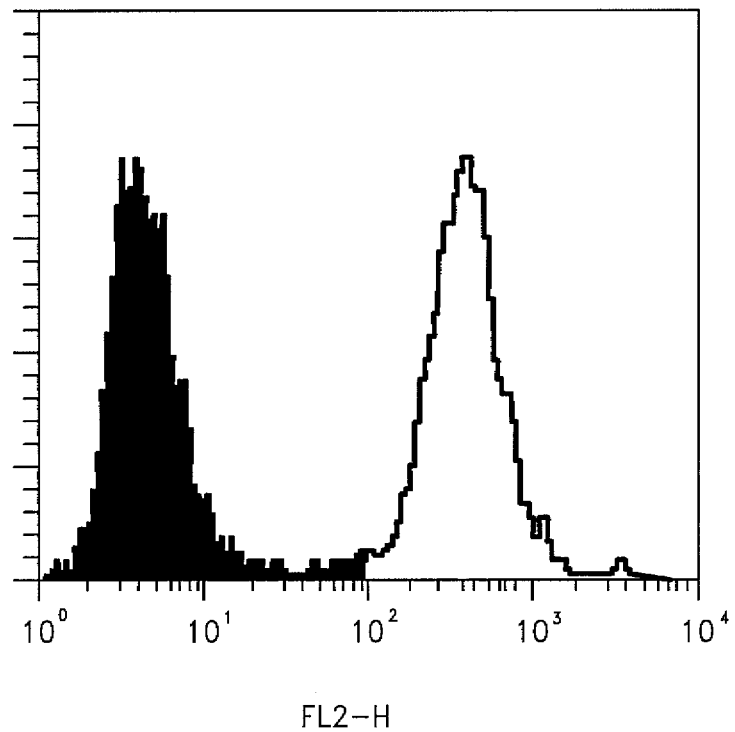
FIG. 9A shows FACS staining analysis for a human anti-EGFR antibody (ABX-EGF) to H80.
Figure 9B:
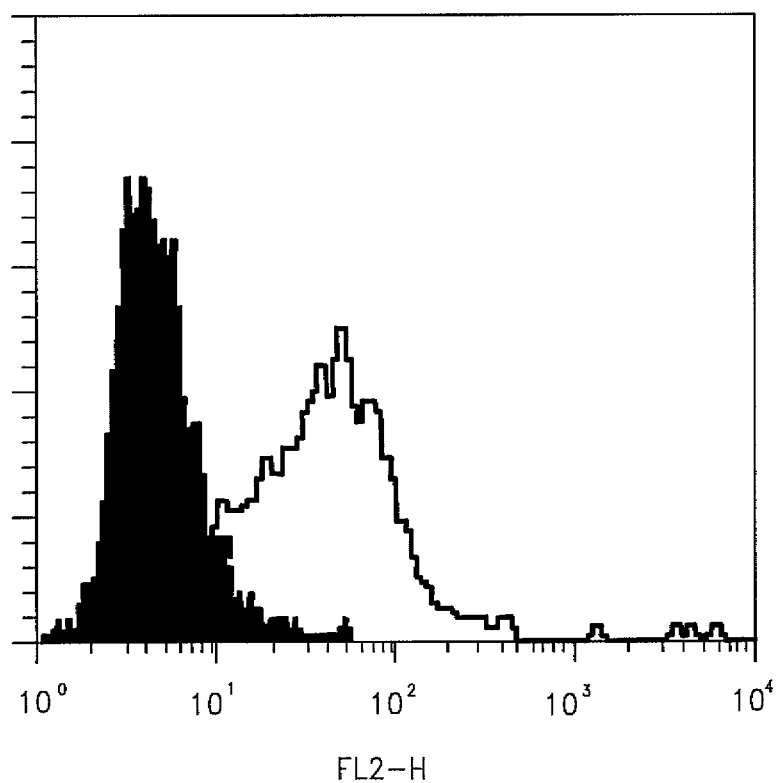
FIG. 9B shows FACS staining analysis for antibody 131 to H80.
Figure 9C:
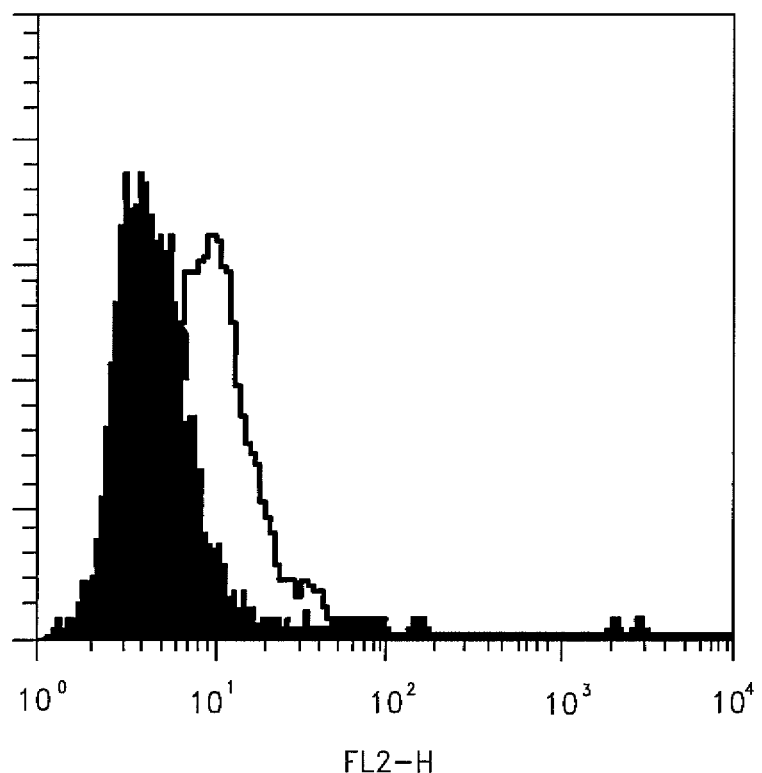
FIG. 9C shows FACS staining analysis for antibody 139 to H80.
Figure 9D:
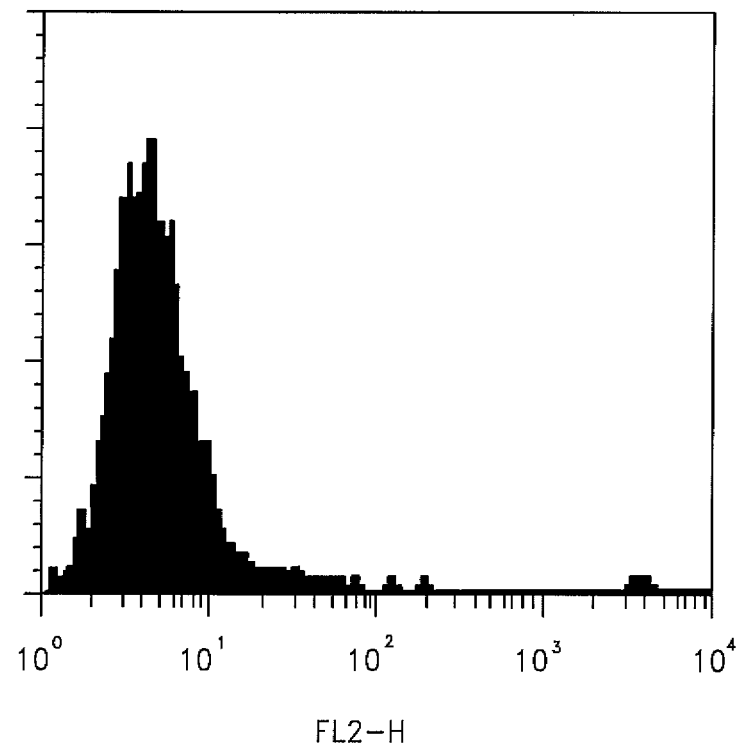
FIG. 9D shows FACS staining analysis for antibody 13.1.2 to H80.
Figure 9E:
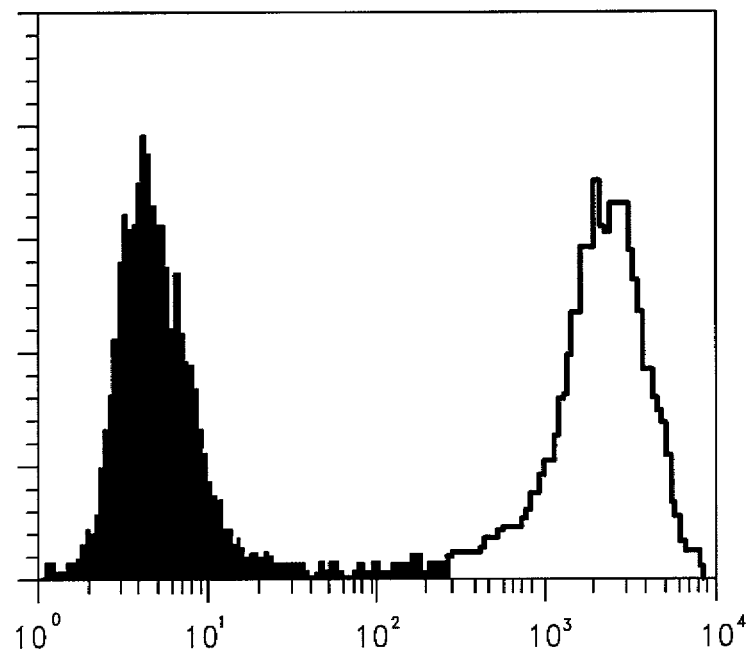
FIG. 9E shows FACS staining analysis for ABX-EGF to H1477.
Figure 9F:
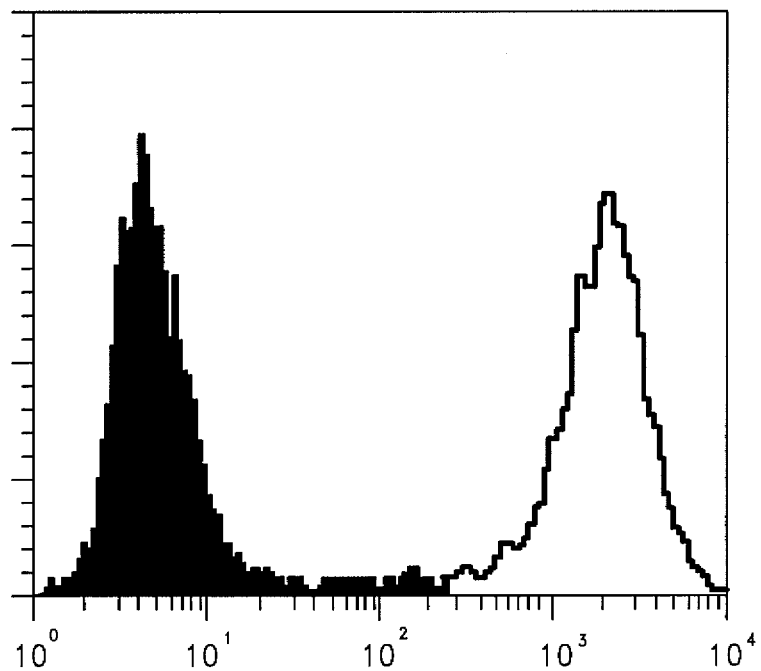
FIG. 9F shows FACS staining analysis for antibody 131 to H1477.
Figure 9G:
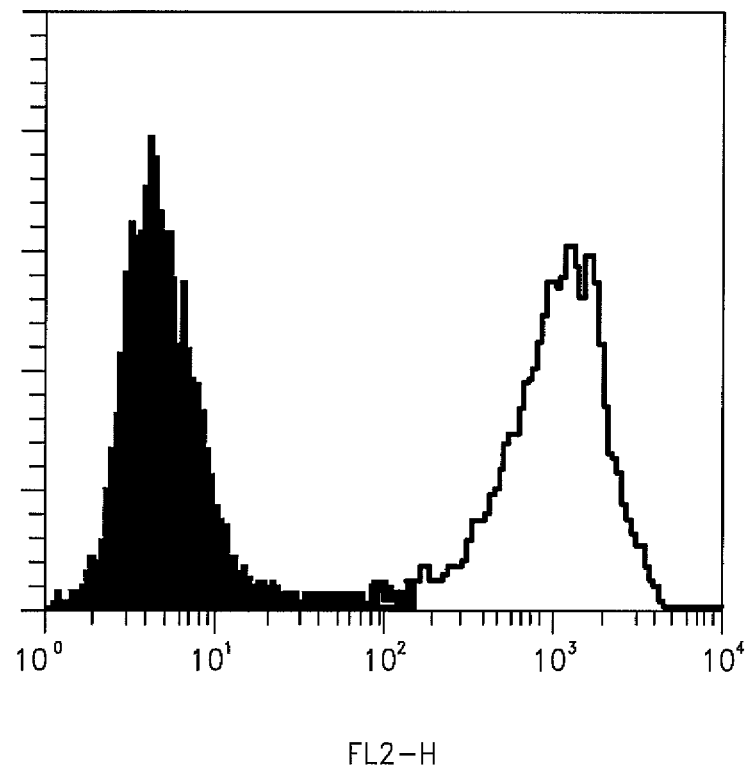
FIG. 9G shows FACS staining analysis for antibody 139 to H1477.
Figure 9H:
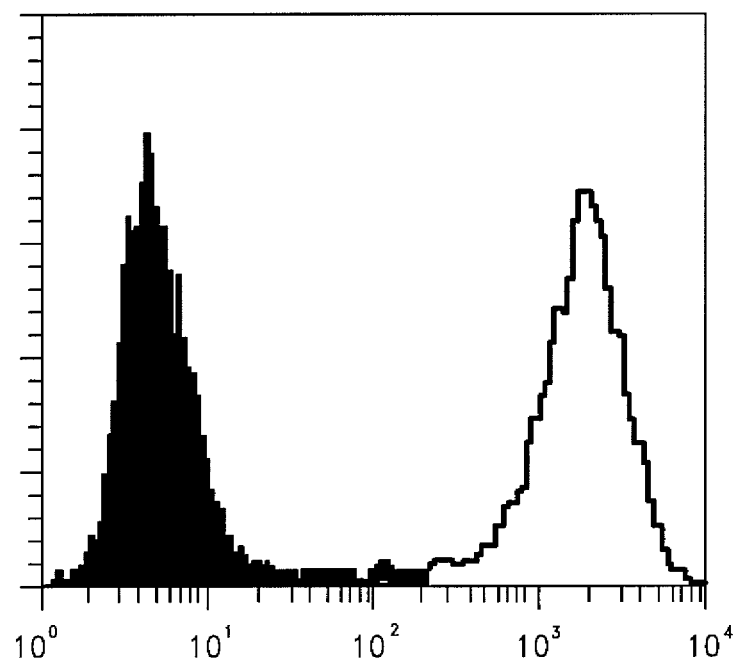
FIG. 9H shows FACS staining analysis for antibody 13.1.2 to H1477.
Figure 9I:
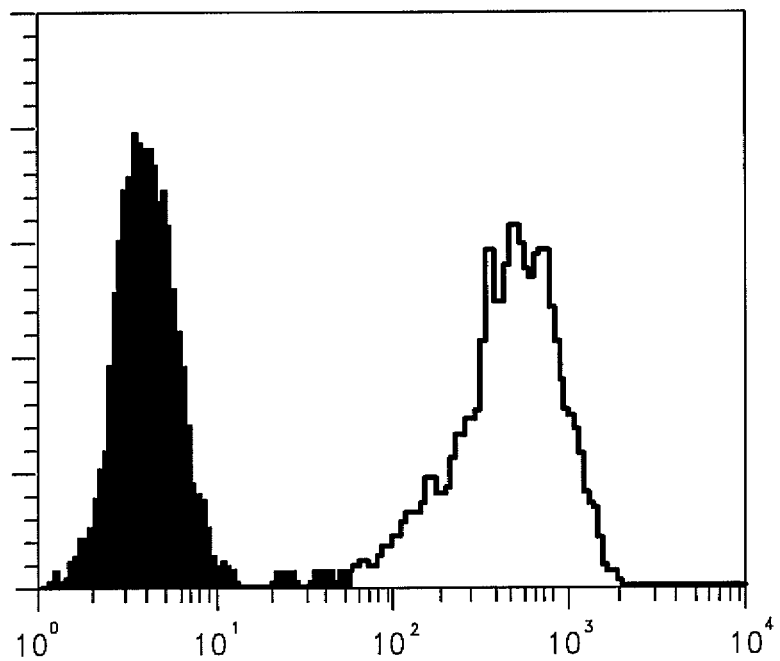
FIG. 9I shows FACS staining analysis for ABX-EGF to A549.
Figure 9J:
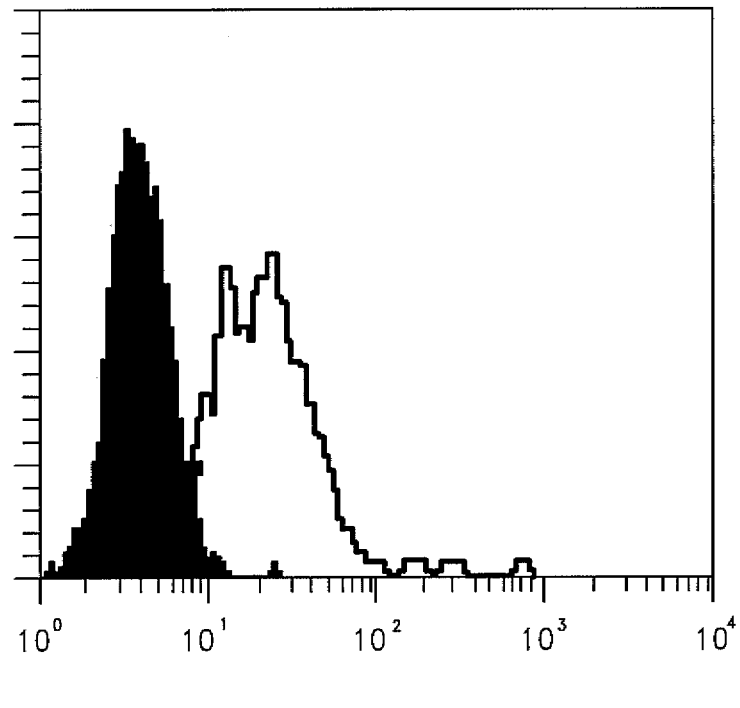
FIG. 9J shows FACS staining analysis for antibody 131 to A549.
Figure 9K:
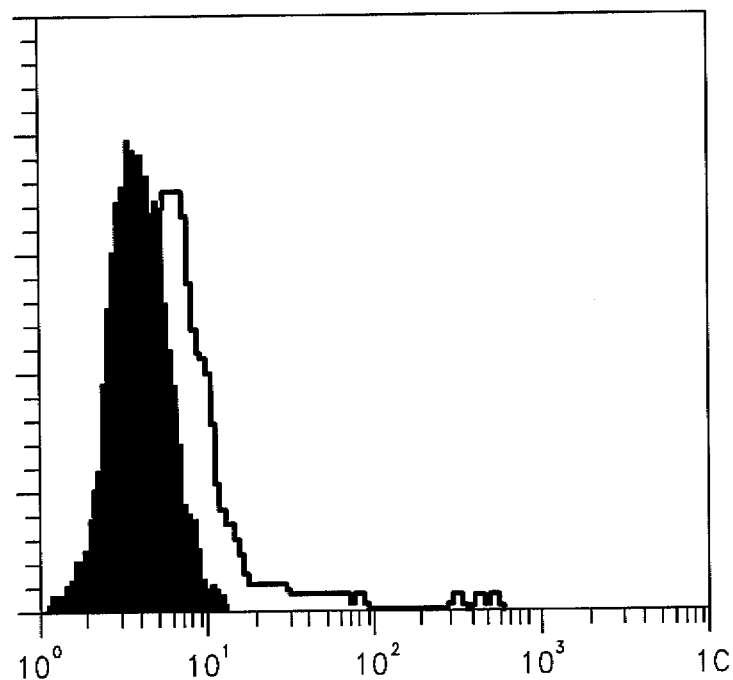
FIG. 9K shows FACS staining analysis for antibody 139 to A549.
Figure 9L:
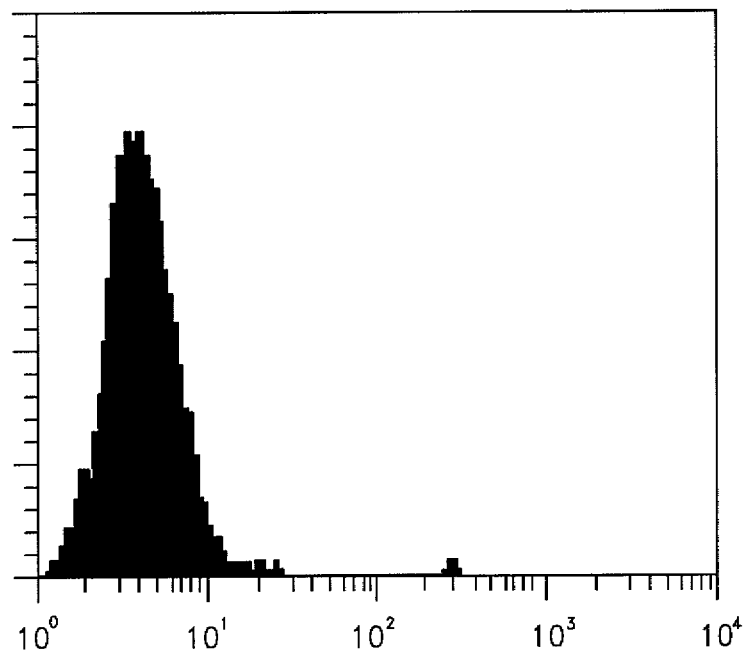
FIG. 9L shows FACS staining analysis for antibody 13.1.2 to A549.
Figure 9M:
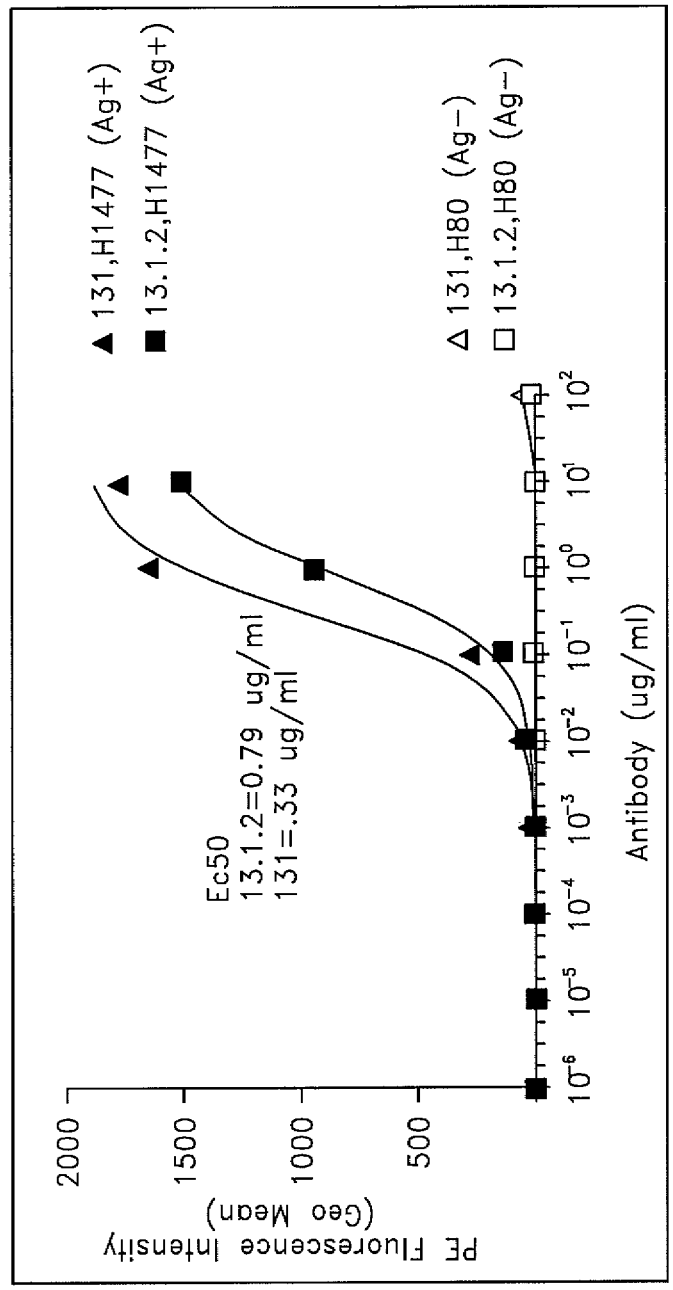
FIG. 9M is a graph displaying binding of EGFRvIII mAbs to glioblastoma cells. Filled triangles represent antibody 131 binding to H1477. Filled squares represent antibody 13.1.2 binding to H1477. Empty triangles represent antibody 131 binding to H80. Empty squares represent antibody 13.1.2 binding to H80.
Figure 9N:
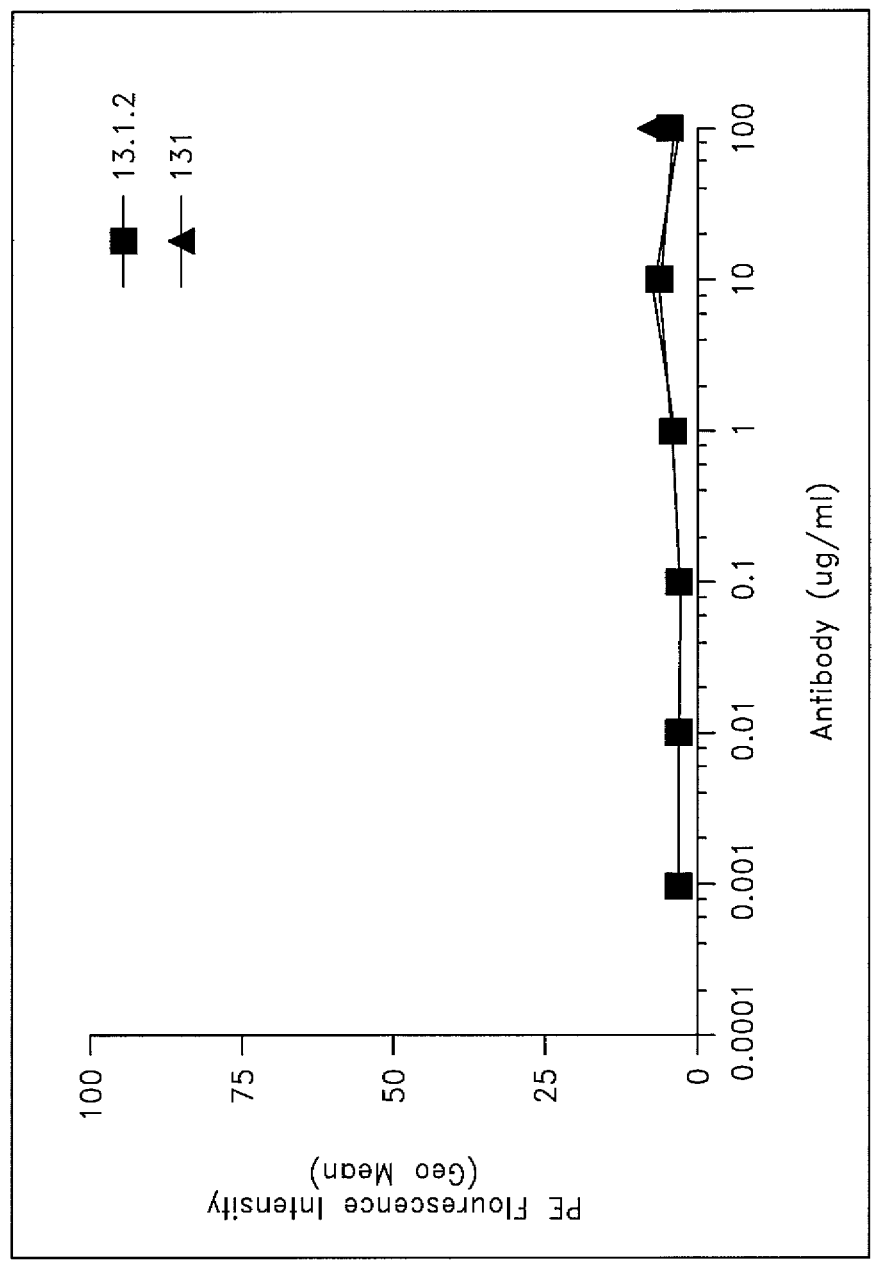
FIG. 9N is a graph displaying the binding of EGFRvIII mAbs to human epidermoid carcinoma cell line A431. The filled squares represent antibody 13.1.2. The filled triangles represent antibody 131.
Figure 9P:
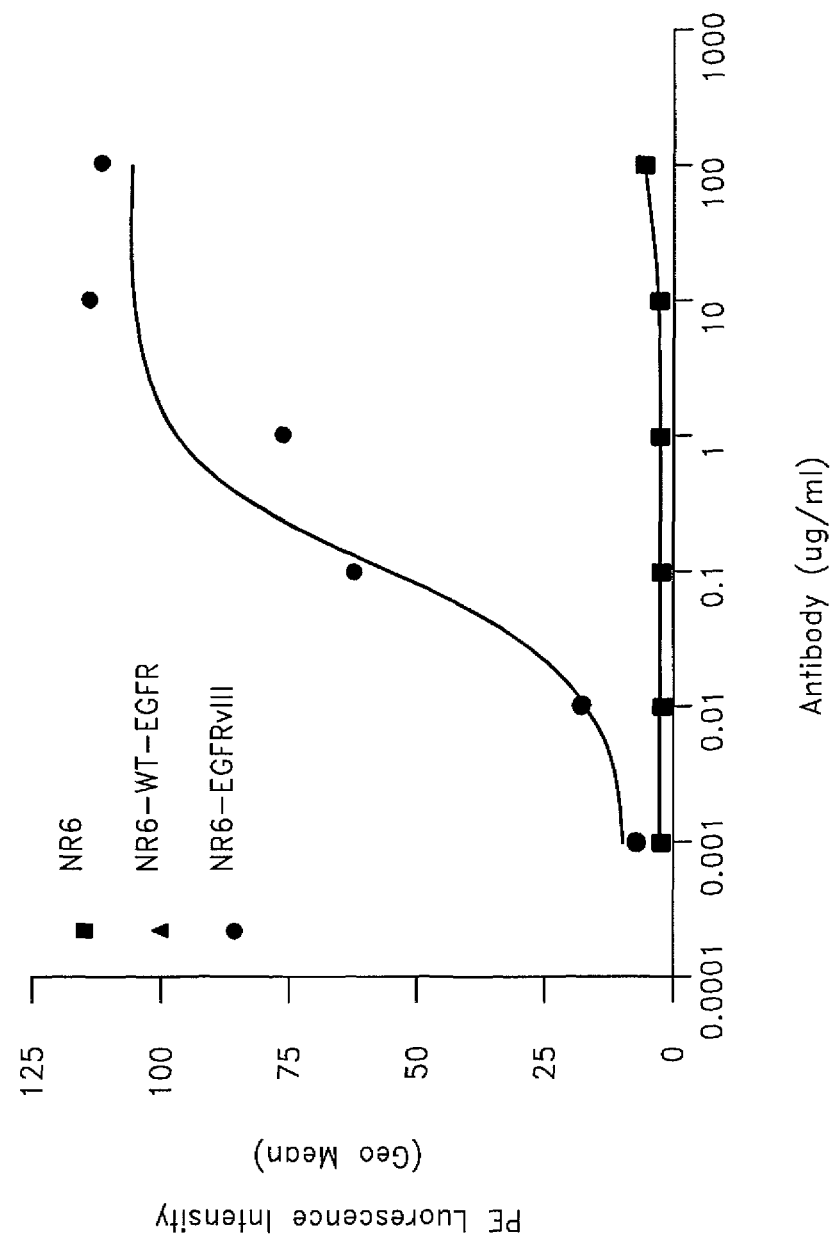
FIG. 9P is a graph displaying the binding of antibody 131 to murine fibroblast cell lines. The squares represent NR6. The triangles represent NR6 with wild type EGFR. The circles represent NR6 with EGFRvIII.

As discussed above, EGFRvIII is a deletion mutant of EGFR in which 267 amino acids in the extracellular domain of EGFr are deleted with a single amino-acid substitution of Glycine at the junction. These features are shown in a sequence alignment between wild type EGFR and EGFRvIII in FIG. 1. In view of the amino acid substitution of Glycine at the junction of the deletion, it becomes theoretically possible to generate antibodies to the novel epitope present in EGFRvIII that is not present in wild type EGFR. Thus, a peptide for immunization and screening was designed, termed PEP3, as shown in FIG. 2 (Kuan et al. EGF mutant receptor vIII as a molecular target in cancer therapy. Endocr Relat Cancer. 8(2):83-96 (2001)). Such 14-mer peptide possesses the 5 n-terminal amino acids common to EGFRvIII and wild type EGFR, the unique Glycine junction site, and 8 amino acid residues contained in the conserved sequences between wild type EGFR (corresponding to residues 273-280) and EGFRvIII (corresponding to residues 7-14). In addition, glioblastoma cell and cells (B300.19 cells) transfected with the gene encoding EGFRvIII were also utilized for immunization and screening (sometimes referred to herein as B300.19/EGFRvIII transfectants).

In order to generate human antibodies against EGFRvIII, transgenic. XenoMouse® mice were immunized with combinations of glioblastoma cells/EGFRvIII, B300.19/EGFRvIII cells, and peptides (PEP3) directed to the junction region in the novel extracellular domain represented in EGFRvIII as compared to wild type EGFR. B cells from immunized mice were isolated and either used to produce hybridomas followed by screening for binding to EGFRvIII or used directly in screening for binding to EGFRvIII using XenoMax™/SLAM™ technologies (Babcook et al. A novel strategy for generating monoclonal antibodies from single, isolated lymphocytes producing antibodies of defined specificities. Proc Natl Acad Sci USA. 93(15):7843-8 (1996), and U.S. Pat. No. 5,627,052). Antibodies identified that bound to EGFRvIII were screened in a series of assays to ascertain specific recognition of EGFRvIII. Through this process, panels of human monoclonal antibodies that bound to and were specific for EGFRvIII were generated, isolated, and characterized. Subsequent epitope mapping demonstrated unique but overlapping specificities. All antibodies were further evaluated in vitro for their ability to be internalized by cells for the purpose of delivering cytotoxic drugs to cells. Antibodies demonstrating efficient drug delivery were directly conjugated with a cytotoxic drug and examined for their ability to kill tumor cells expressing EGFRvIII in vitro and in vivo. These studies provide the basis for the next generation of antibody drug conjugates for treating cancer in patients whose tumor harbor specific genetic lesions.

Through the processes described above, panels of fully human anti-EGFRvIII antibodies were generated. Using the hybridoma approach, several antibodies, including antibody 13.1, 13.2, 13.3, and 13.4 that were positive on ELISA for binding with the PEP3, were generated with limited cross-reactivity with wild type EGFR. Out of these, antibody 13.1 (and, particularly, its subclone 13.1.2) was selected for further research and development. Using the XenoMax approach a panel of antibodies, including antibody 131, 139, 250, and 095, were generated that were highly specific for binding with the pep3 oligonucleotide and had limited cross-reactivity with wild type EGFR. Of these, the 131 antibody has very interesting properties. The sequences for each of the antibodies are displayed in FIGS. 4-7 (SEQ ID NO: 1-33 and 141-144). A comparison of the sequences and binding abilities of the various antibodies was made and the results are displayed in FIGS. 4-10. As can be seen in FIGS. 9A-9L, and FIGS. 10A-10D antibodies 131, 139, and 13.1.2 all demonstrated superior selectivity for EGFRvIII expressing cells (H1477) as compared to ABX-EGF. Some of the results are shown in graph form in FIGS. 9M-9P, which demonstrates that at least two of the antibodies, 13.1.2 and 131 demonstrated superior specificity for EGFRvIII expressing cells compared to simply EGFRvIII cells. Finally, based on predicted structural models, variants of the antibodies were made in order to obtain antibodies with altered binding characteristics.

Further, antibodies of the invention are highly useful for the screening of other antibodies that bind to the same or similar epitopes. Antibodies of the invention can be utilized in cross competition studies for the elucidation of other antibodies that are expected to have the same or improved effects with respect to characteristics of the antigen-antibody complex that is formed.

Each of the 131 antibody and the 13.1.2 possessed very high affinities for EGFRvIII, were internalized well by cells, and appeared highly effective in cell killing when conjugated to toxins. Intriguingly, both of the antibodies, despite having been generated in different immunizations of XenoMouse mice, and utilizing different technologies, were derived from very similar germline genes. Based upon epitope mapping work, however, each of the antibodies appears to bind to slightly different epitopes on the EGFRvIII molecule and have slightly different residues on EGFRvIII that are essential for binding. These results indicate that the germline gene utilization is of importance to the generation of antibody therapeutics targeting EGFRvIII and that small changes can modify the binding and effects of the antibody in ways that allow for the further design of antibodies and other therapeutics based upon these structural findings.

Antibodies that bind to the same epitope as, or compete for binding with, the 13.1.2 and 131 antibodies are highly desirable. As discussed in more detail below, through Alanine scanning on SPOTs arrays important residues for binding of certain antibodies have been elucidated. Accordingly, antibodies that share critical binding residues are also highly desirable.

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y., 1989), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa light chain immunoglobulin molecules or lambda light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or anti-sense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et ai. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "variant" as used herein, is a polypeptide, polynucleotide, or molecule that differs from the recited polypeptide or polynucleotide, but only such that the activity of the protein is not detrimentally altered. There may be variants of epitopes. There may be variants of antibodies. In a preferred embodiment, the ability of a protein variant to bind to the epitope is not detrimentally altered. In one embodiment, the protein variant can bind with 10-500% of the ability of the wild type mAb. For example, the protein variant can bind with 10%, 50%, 110%, 500%, or greater than 500% of the ability of the wild type mAb. In one embodiment, the range of binding abilities between 10-500% is included. Binding ability may be reflected in many ways, including, but not limited to the $k_a$, $k_d$, or $K_D$ of the variant to an epitope. In one preferred embodiment, the epitope is one described in the present specification.

Figure 11:
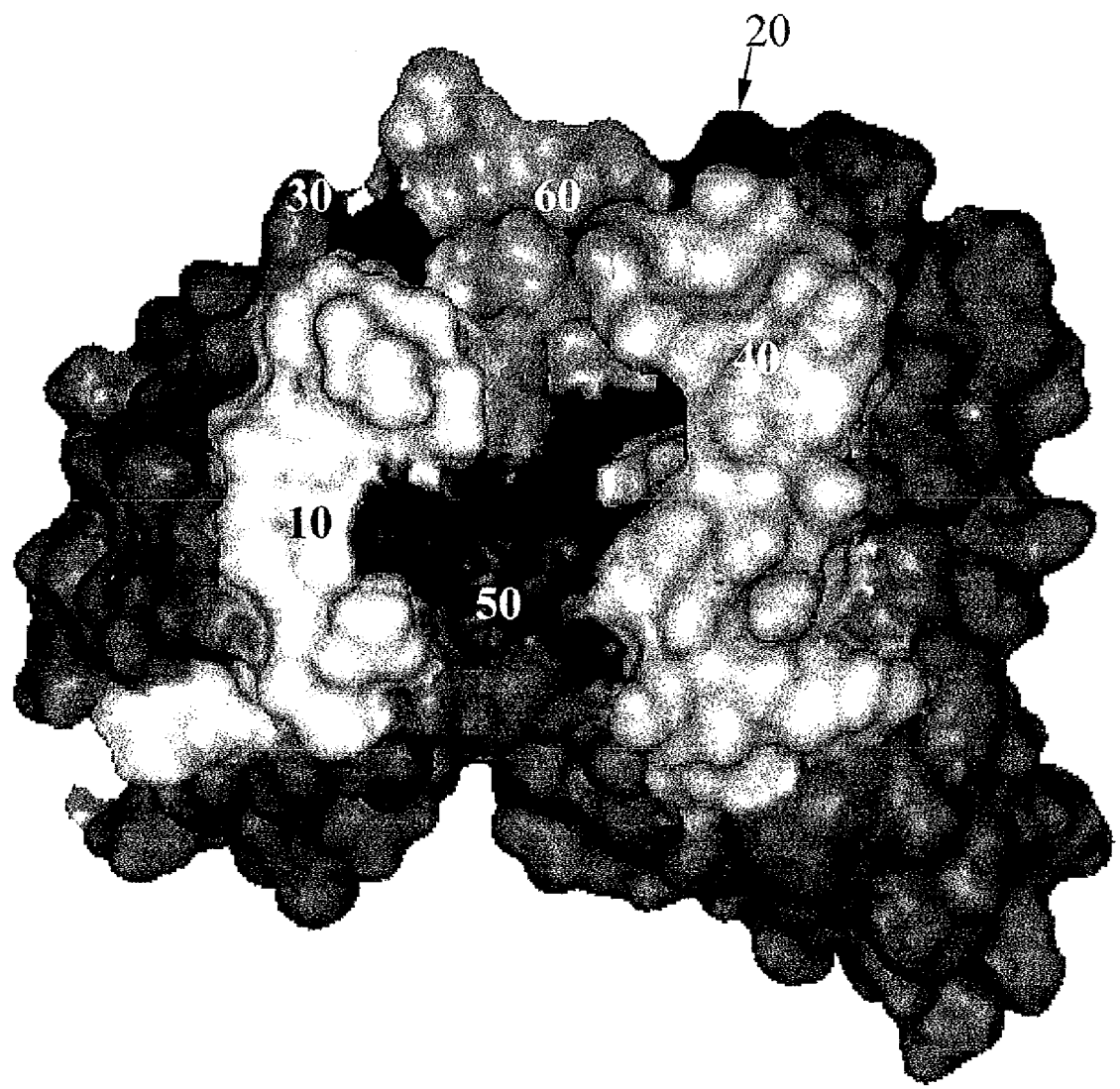
FIG. 11 shows the molecular surface of antibody 131 structure model. The six CDRs are shaded different shades to mark their boundries. The binding cavity is located close to the center.
Figure 12:
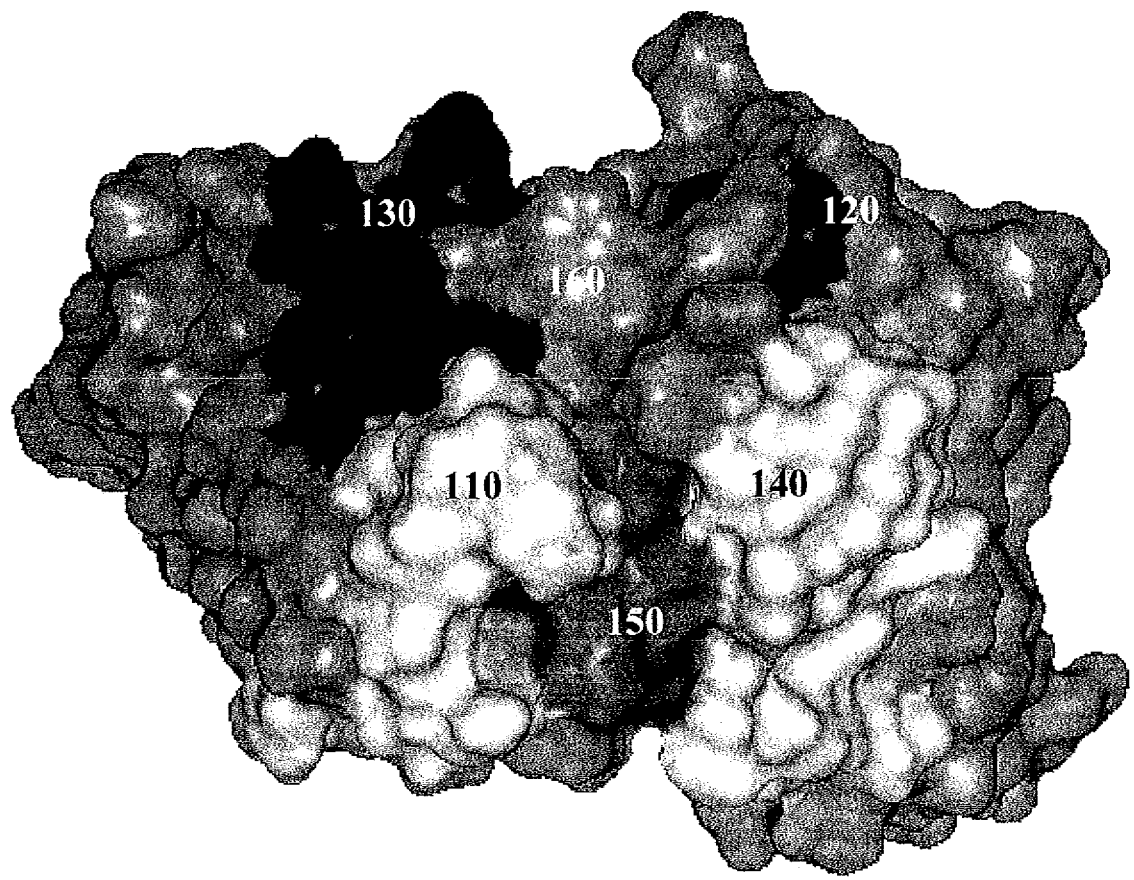
FIG. 12 shows a structural model of the molecular surface of antibody 13.1.2. The six CDR regions are shaded and identified by number. The long groove is located approximately along the vertical centerline.
Figure 13A:
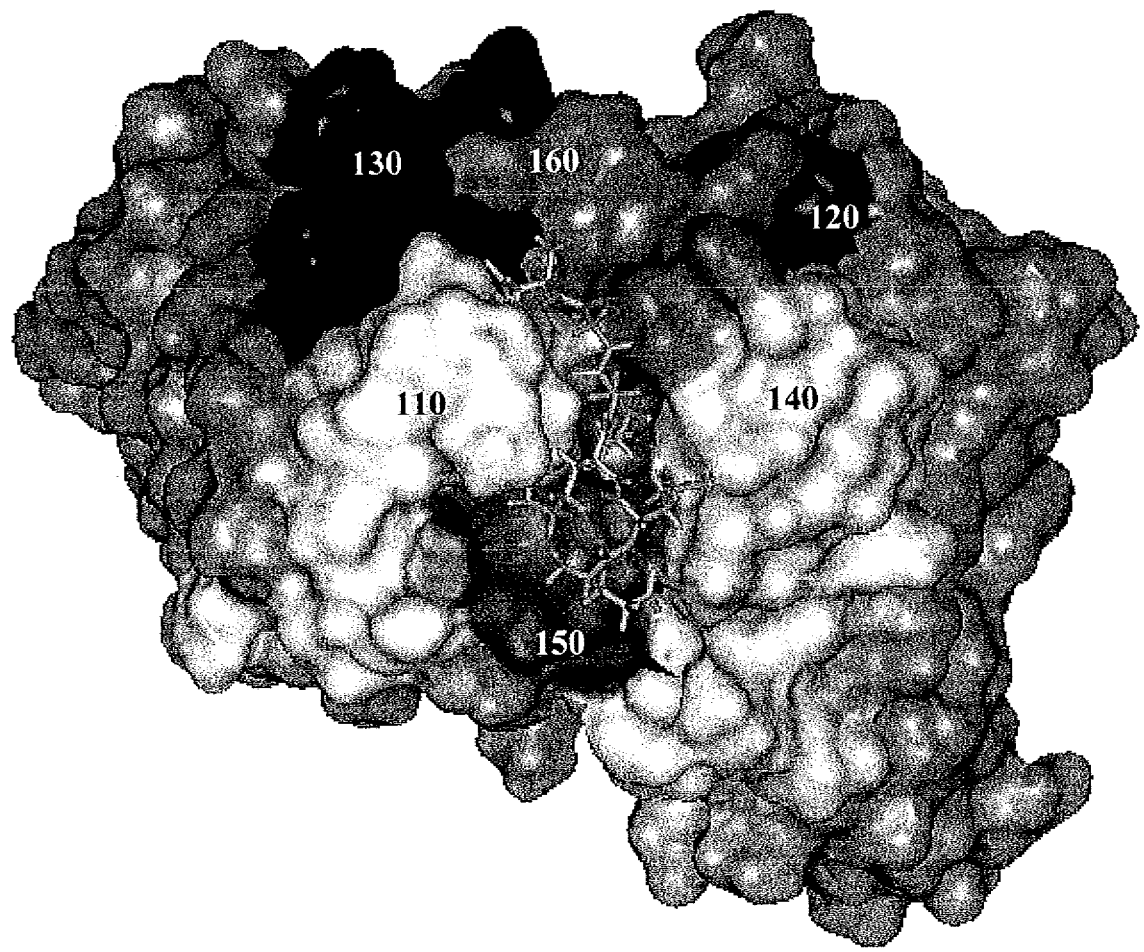
FIG. 13A is a possible docking model of the 13.1.2 antibody and peptide EEKKGN (SEQ ID NO: 127) complex. The CDR regions are shaded to denote boundries.
Figure 13B:
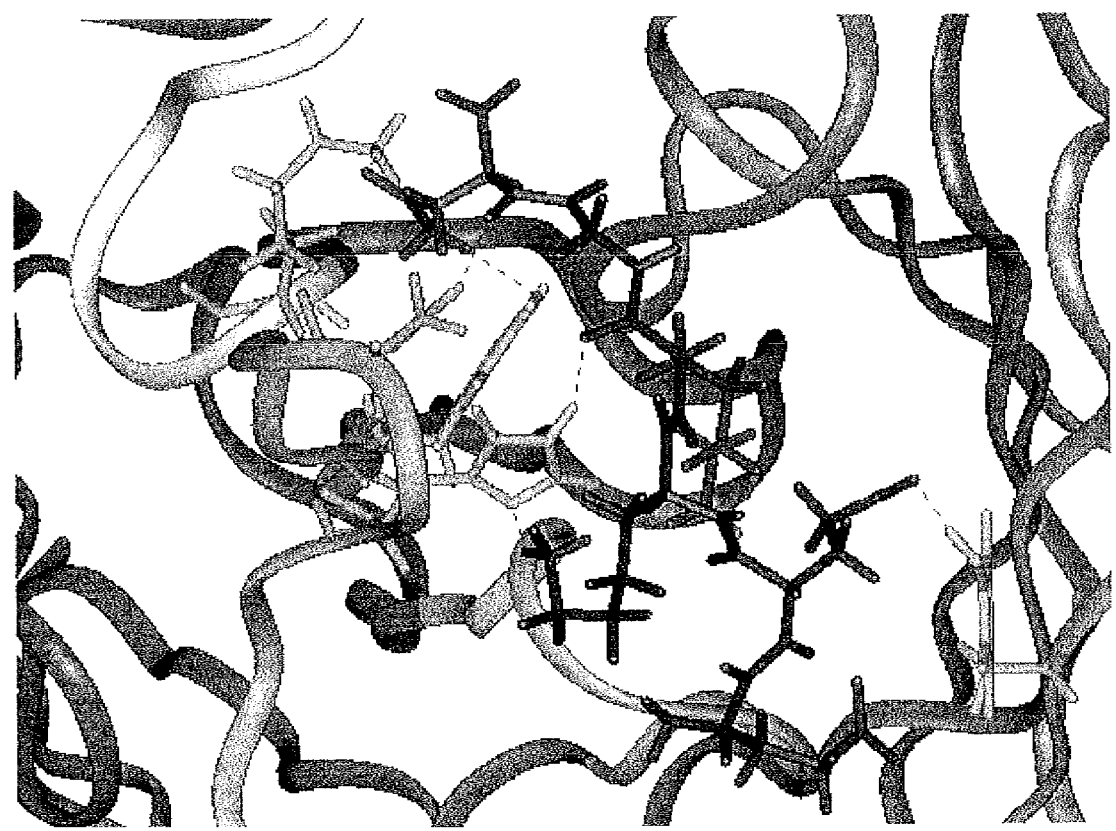
FIG. 13B shows the hydrogen bonds in the docking model of the 13.1.2 antibody and peptide EEKKGN (SEQ ID NO: 127) complex. Shading of the CDR loops and residues is the same as in FIG. 12. The peptide residue is numbered from the N-terminus, at the top of the figure, to the C-terminus as 1 through 6. Six hydrogen bonds are indicated by dashed lines. The six pairs of amino acids forming hydrogen bonds are: E2 ... Y172, K3 ... H31, K4 ... H31, N6 ... D33, N6 ... Y37, and N6 ... K55.
Figure 14:
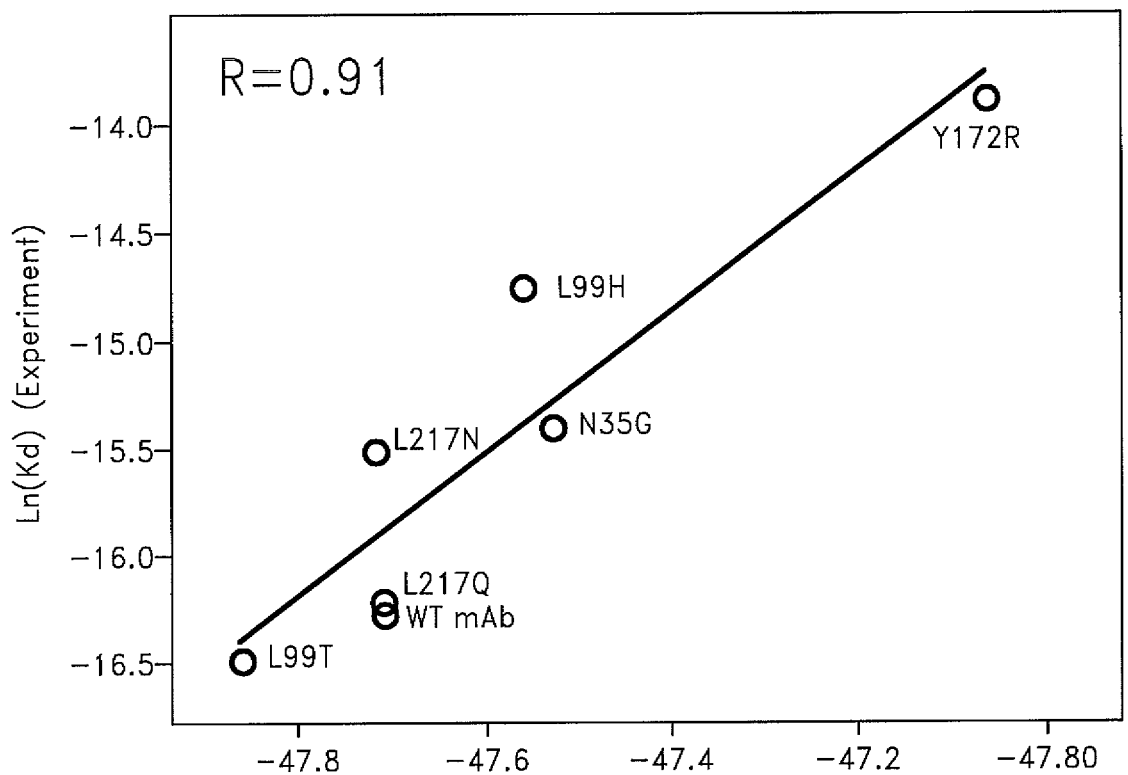
FIG. 14 is a graph demonstrating a correlation between the epitope-antibody binding energy and the logarithm of Kd for one of the docking models selected.
Figure 15:
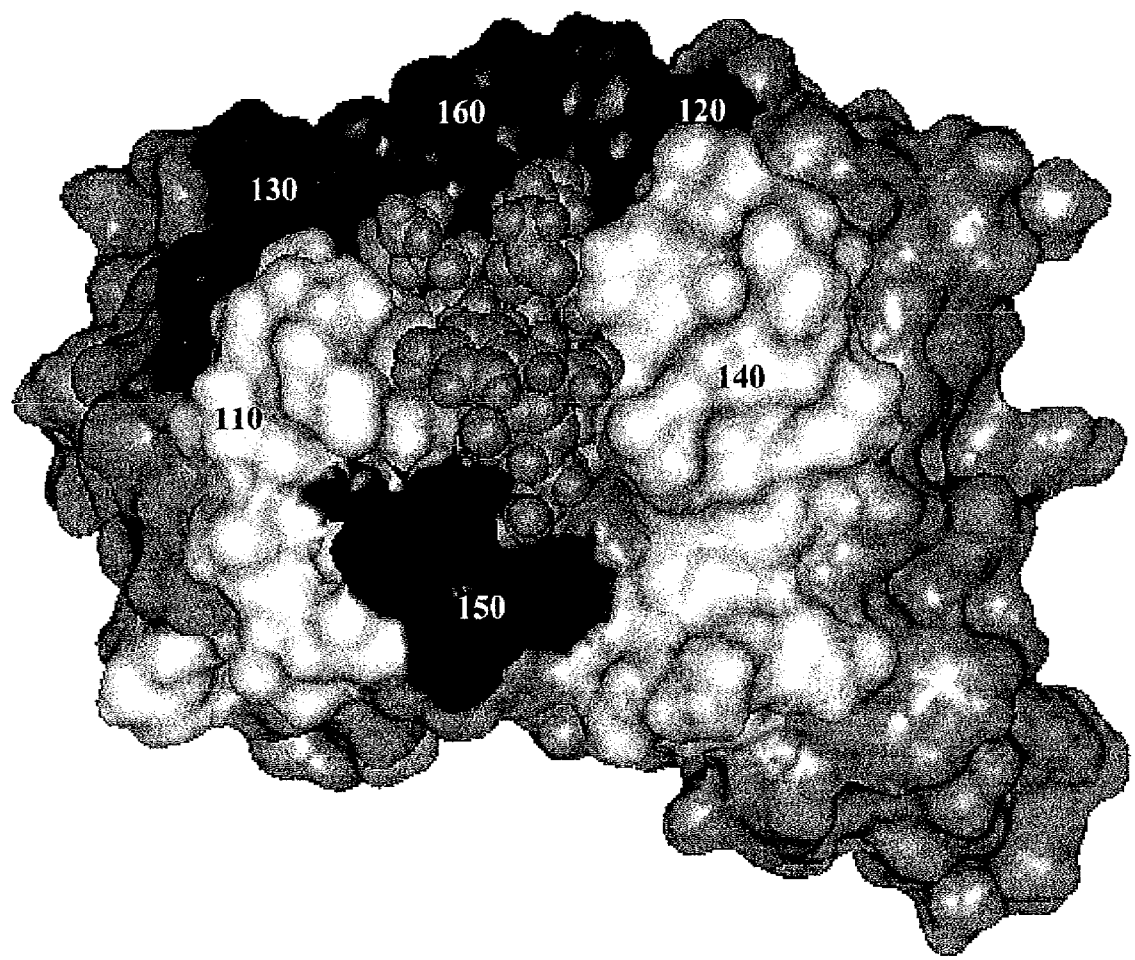
FIG. 15 is a depiction of a refined docking model for the peptide-13.1.2 antibody complex. The peptide is rendered in a space-filling manner.
Figure 16:
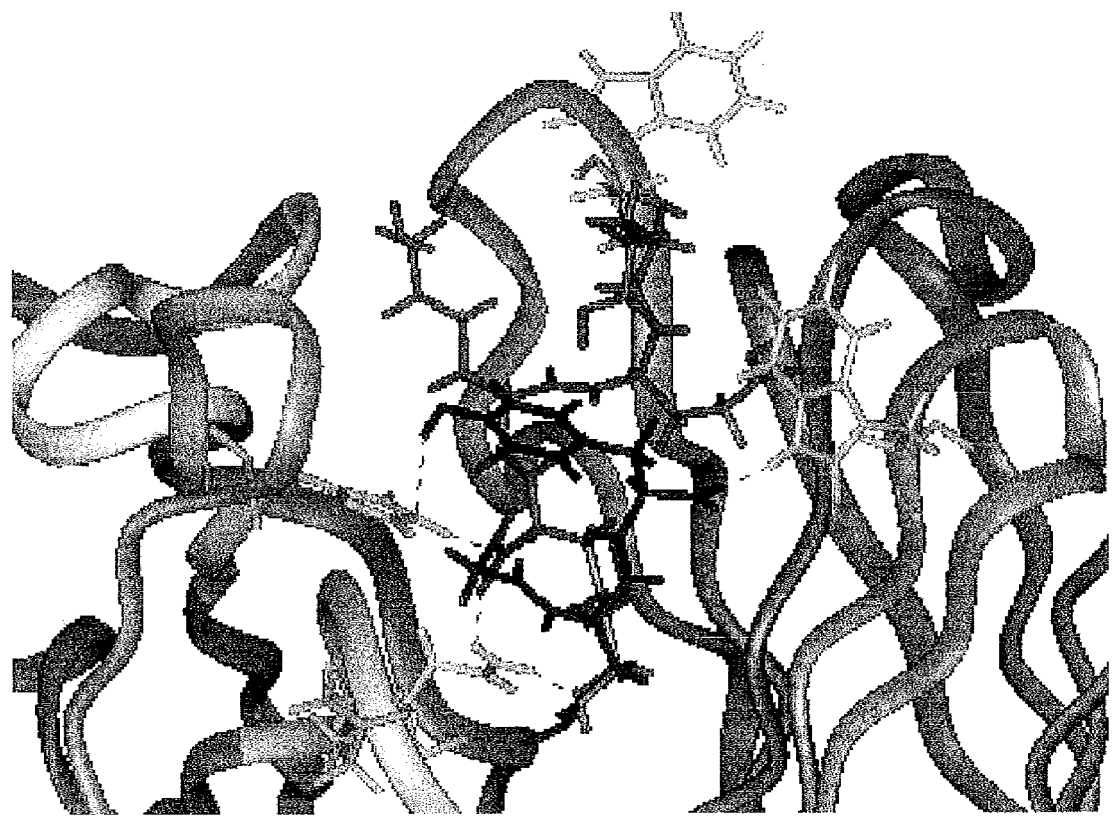
FIG. 16 is a depiction representing the hydrogen bonds in the refined docking model.

In one embodiment, variant antibodies can differ from the wild-type sequence by substitution, deletion or addition of five amino acids or fewer. Such variants may generally be identified by modifying one of the disclosed polypeptide sequences, and evaluating the binding properties of the modified polypeptide using, for example, the representative procedures described herein. In another embodiment, polypeptide variants preferably exhibit at least about 70%, more preferably at least about 90% and most preferably at least about 95% identity to the identified polypeptides. Preferably, the variant differs only in conservative substitutions and/or modifications. Variant proteins include those that are structurally similar and those that are functionally equivalent to the protein structures described in the present specification. In another embodiment, the protein is a variant if it is functionally equivalent to the proteins described in this specification, so long as the paratope of variant is similar to the paratopes described in the specification. In one embodiment, any substance with a shape that is similar to the paratope described in FIG. 11 is a variant. In one embodiment, any substance with a shape that is similar to the paratope described in FIG. 12 is a variant. In one embodiment, any substance that has a shape that is similar to the interaction surface described in FIGS. 13A and 13B is a variant.

In one embodiment, the antibody is a variant if the nucleic acid sequence can selectively hybridize to wild-type sequence under stringent conditions. In one embodiment, suitable moderately stringent conditions include prewashing in a solution of 5×SSC; 0.5% SDS, 1.0 mM EDTA (pH 8:0); hybridizing at 50° C.-65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an antibody polypeptide that is encoded by a hybridizing DNA sequence. The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to non-specific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementarity to" is used herein to mean that the complementarity sequence is homologous to all or a portion of a reference polynucleotide sequence. For illustration, the nucleotide sequence "TATAC" corresponds to a reference sequence "TATAC" and is complementarity to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. Amino acids or nucleic acids with substantial identity to the wild-type protein or nucleic acid are examples of variants of the wild-type protein or nucleic acid.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ∈-N,N,N-trimethyllysine, ∈-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine. Polypeptides with substantial identity can be variants.

Variant proteins also include proteins with minor variations. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated.

Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence. Analogs typically are at least 20 amino acids long, preferably at least 50 amino acids long or longer, and can often be as long as a full-length naturally-occurring polypeptide. Both fragments and analogs are forms of variants Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —$CH(OH)CH_2$—, and $CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide. Peptide mimetics and peptidomimetics are both forms of variants.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. An antibody is said to specifically bind an antigen when the dissociation constant is ≤1 µM, preferably ≤100 nM and more preferably ≤10 nM, and even more preferably ≤1 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competively bind with one another, e.g., the antibodies compete for binding to the antigen. A high throughput process for "binning" antibodies based upon their cross-competition is described in International Patent Application No. WO 03/48731. As will be appreciated by one of skill in the art, practically anything to which an antibody can specifically bind could be an epitope. An epitope can comprises those residues to which the antibody binds. In one embodiment, the epitope is the EGFRvIII epitope. In a more preferred embodiment, the epitope is that described in Example 4 of this specification. In one embodiment, the epitope is the epitope described in Example 14. In one embodiment, the epitope comprises the sequence LEEKKGNYVVTD (SEQ ID NO: 59). In one embodiment, the epitope comprises the sequence EEKKGNYVVT (SEQ ID NO: 57). In one embodiment, the epitope comprises the sequence EKNY (SEQ ID NO: 60). In one embodiment, the epitope comprises the sequence EEKGN (SEQ ID NO: 61). One of skill in the art will appreciate that these need not be actually assembled in this order on a single peptide, rather, these are the residues that form the eptiope which interacts with the paratope. As will be appreciated by one of skill in the art, the space that is occupied by a residue or side chain that creates the shape of a molecule helps to determine what an epitope is. Likewise, any functional groups associated with the epitope, van der Waals interactions, degree of mobility of side chains, etc. can all determine what an epitope actually is. Thus an epitope may also include energetic interactions.

The term "paratope" is meant to describe the general structure of a binding region that determines binding to an epitope. This structure influences whether or not and in what manner the binding region might bind to an epitope. Paratope can refer to an antigenic site of an antibody that is responsible for an antibody or fragment thereof, to bind to an antigenic determinant. Paratope also refers to the idiotype of the antibody, and the complementarity determining region (CDR) region that binds to the epitope. In one embodiment, the paratope is the region of the antibody that is L1 10, L2 30, L3 50, H1 20, H2 40, and H3 60 in FIG. 11. In one embodiment, the paratope is the region of the antibody that comprises the CDR sequences in Example 16 for L1, L2, L3, H1, H2, and H3. In one embodiment, the paratope is the region of the antibody that is L1 110, L2 130, L3 150, H1 120, H2 140, and H3 160 in FIG. 12. In one embodiment, the paratope is the region of the antibody that comprises the CDR sequences in Example 18 for L1, L2, L3, H1, H2, and H3. In one embodiment, the paratope comprises the sequences listed in Example 18. In one embodiment, the paratope comprises the residues that interact with the epitope, as shown in FIG. 13A and FIG. 13B. The solid black structure is the peptide structure. In one embodiment, the paratope comprises residue Tyr172Arg of the 13.1.2 mAb. In one embodiment, the paratope of the 13.1.2 mAb comprises at least one residue selected from the group consisting of: Tyr 172Arg, Arg101Glu, Leu99Asn, Leu99His, Arg101Asp, Leu217Gln, Leu99Thr, Leu217Asn, Arg101Gln, and Asn35Gly. As will be appreciated by one of skill in the art, the paratope of any antibody, or variant thereof, can be determined in the manner set forth by the present application. Residues are considered "important" if they are predicted to contribute 10% of the binding energy. In one embodiment, residues are considered "important" if they are predicted to contribute 2% of the binding energy. In one embodiment, residues are considered "important" if they are predicted to contribute 50% of the binding energy. In one embodiment, residues are considered "important" if they are predicted to interact with the surface of the epitope, or the surface of the paratope. In one embodiment, residues are considered "important" if changing the residue results in a loss in binding.

The terms "specifically" or "preferentially" binds to, or similar phrases are not meant to denote that the antibody exclusively binds to that epitope. Rather, what is meant is that the antibody, or variant thereof, can bind to that epitope, to a higher degree than the antibody binds to at least one other substance to which the antibody is exposed to. In one embodiment, the specifically binding antibody will bind to the EGFRvIII protein with an affinity greater than (more tightly, or lower $K_D$) it will to the EGFR protein. For example, the specifically binding antibody will bind more tightly by at least a minimal increase to 1, 1-2, 2-5, 5-10, 10-20, 20-30, 30-50, 50-70, 70-90, 90-120, 120-150, 150-200, 200-300, 300-500, 500-1000 percent or more.

The shorthand of amino acid, number, amino acid, e.g., Leu217Gln, denotes a mutation at the numbered amino acid, from the first amino acid, to the second amino acid. Thus, Tyr172Arg would mean that while the wild type protein has a tyrosine at position 172, the mutant has an arginine at position 172.

The term "agent" is used herein to denote a chemical compound, a mixture of chemical compounds, a biological macromolecule, or an extract made from biological materials.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. These fragments can also be considered variants of the antibody.

"Fab" when used herein refers to a fragment of an antibody which comprises the constant domain of the light chain and the CH1 domain of the heavy chain.

The term "mAb" refers to monoclonal antibody.

The description of XenoMax method generated antibody sequences is coded as follows: "AB"-referring to antibody, "EGFRvIII"-referring to antibody's binding specificity, "X" referring to XenoMouse mouse derived, "G1"-referring to IgG1 isotype or "G2" referring to IgG2 isotype, the last three digits refer to the single cell number from which the antibody was derived, for example: AB-EGFRvIII-XG1-095 would be an antibody with binding specificity to EGFRvIII from XenoMouse mouse of a IgG1 isotype and cell number 95.

The term "SC" refers to single cell and a particular XenoMax method derived antibody may be referred to as SC followed by three digits, or just three digits, referring to the single cell number from which the antibody was derived herein.

The description of hybridoma derived antibody sequences is coded as follows: "AB"-referring to antibody, "EGFRvIII"-refers to the antibody's binding specificity, "X" refers to XenoMouse mouse derived, "G1"-refers to IgG1 isotype or "G2" refers to IgG2 isotype, "K" refers to kappa, "L" refers to lambda. The last three digits referring to the clone from which the antibody was derived, for example: AB-EGFRvIII-XG1K-13.1.2

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, 99%, and 99.9%. Most preferably, the object species is purified to essential homogeneity (contaminant species cannot be detected in the composition by conventional detection methods) wherein the composition consists essentially of a single macromolecular species.

The term "patient" includes human and veterinary subjects.

The term "SLAM®" Technology" refers to the "Selected Lymphocyte Antibody Method" (Babcook et al., *Proc. Natl. Acad. Sci. USA*, i93:7843-7848 (1996), and Schrader, U.S. Pat. No. 5,627,052, both of which are incorporated by reference in their entirety).

The term "XenoMax™" refers to the use of SLAM Technology with XenoMouse® mice (as described below).

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental *Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

In addition to the general structural aspects of antibodies, the more specific interaction between the paratope and the epitope may be examined through structural approaches. In one embodiment, the structure of the CDRs form a paratope, through which an antibody is able to bind to an epitope. The structure of such a paratope may be determined in a number of ways. Traditional structural examination approaches may be used, such as NMR or x-ray crystalography. These approaches may examine the structure of the paratope alone, or while it is bound to the epitope. Alternatively, molecular models may be generated in silico. A structure can be generated through homology modeling, aided with a commercial package, such as InsightII modeling package from Accelrys (San Diego, Calif.). Briefly, one can use the sequence of the antibody to be examined to search against a database of proteins of known structures, such as the Protein Data Bank. After one identifies homologous proteins with known structures, these homologous proteins are used as modeling templates. Each of the possible templates can be aligned, thus producing structure based sequence alignments among the templates. The sequence of the antibody with the unknown structure can then be aligned with these templates to generate a molecular model for the antibody with the unknown structure. As will be appreciated by one of skill in the art, there are many alternative methods for generating such structures in silico, any of which may be used. For instance, a process similar to the one described in Hardman et al., issued U.S. Pat. No. 5,958,708 employing QUANTA (Polygen Corp., Waltham, Mass.) and CHARM (Brooks, B. R., Bruccoleri, R. E., Olafson, B. D., States, D. J., Swaminathan, S. and Karplus, M., 1983, J. Comp. Chem., 4:187) may be used (hereby incorporated in its entirety by reference).

Not only is the shape of the paratope important in determining whether and how well a possible paratope will bind to an epitope, but the interaction itself, between the epitope and the paratope is a source of great information in the design of variant antibodies. As appreciated by one of skill in the art, there are a variety of ways in which this interaction can be studied. One way is to use the structural model generated, perhaps as described above, and then to use a program such as InsightII (Accelrys, San Diego, Calif.), which has a docking module, which, among other things, is capable of performing a Monte Carlo search on the conformational and orientational spaces between the paratope and its epitope. The result is that one is able to estimate where and how the epitope interacts with the paratope. In one embodiment, only a fragment, or variant, of the epitope is used to assist in determining the relevant interactions. In one embodiment, the entire epitope is used in the modeling of the interaction between the paratope and the epitope. As will be appreciated by one of skill in the art, these two different approaches have different advantages and disadvantages. For instance, using only a fragment of the epitope allows for a more detailed examination of the possible variations of each side chain, without taking huge amounts of time. On the other hand, by using only a fragment of the epitope, or simply the epitope instead of the entire protein, it is possible that the characteristics of the epitope fragment may not be the same as the characteristics for the whole epitope, thus possibly increasing the risk of being mislead during the computational modeling. In one embodiment, both approaches are used to a limited extent, in order to cross check the results. In a preferred embodiment, if a variant of an epitope is used, it will be optimized so that the variant of the epitope comprises the most important residues of the epitope. The identity of the most important residues can be determined in any number of ways, for instance as described in Examples 4 and 14 of the present specification.

Through the use of these generated structures, one is able to determine which residues are the most important in the interaction between the epitope and the paratope. Thus, in one embodiment, one is able to readily select which residues to change in order to alter the binding characteristics of the antibody. For instance, it may be apparent from the docking models that the side chains of certain residues in the paratope may sterically hinder the binding of the epitope, thus altering these residues to residues with smaller side chains may be beneficial. One can determine this in many ways. For example, one may simply look at the two models and estimate interactions based on functional groups and proximity. Alternatively, one may perform repeated pairings of epitope and paratope, as described above, in order to obtain more favorable energy interactions. One can also determine these interactions for a variety of variants of the antibody to determine alternative ways in which the antibody may bind to the epitope. One can also combine the various models to determine how one should alter the structure of the antibodies in order to obtain an antibody with the particular characteristics that are desired.

The models determined above can be tested through various techniques. For example, the interaction energy can determined with the programs discussed above in order to determine which of the variants to further examine. Also, columbic and van der Waals interactions are used to determine the interaction energies of the epitope and the variant paratopes. Also site directed mutagenesis is used to see if predicted changes in antibody structure actually result in the desired changes in binding characteristics. Alternatively, changes may be made to the epitope to verify that the models are correct or to determine general binding themes that may be occurring between the paratope and the epitope.

The above methods for modeling structures can be used to determine what changes in protein structure will result in particular desired characteristics of an antibody. These methods can be used to determine what changes in protein structure will not result in the desired characteristics.

As will be appreciated by one of skill in the art, while these models will provide the guidance necessary to make the antibodies and variants thereof of the present embodiments, it may still be desirable to perform routine testing of the in silico models, perhaps through in vitro studies. In addition, as will be apparent to one of skill in the art, any modification may also have additional side effects on the activity of the antibody. For instance, while any alteration predicted to result in greater binding, may induce greater binding, it may also cause other structural changes which might reduce or alter the activity of the antibody. The determination of whether or not this is the case is routine in the art and can be achieved in many ways. For Example, the activity can be tested through an ELISA test, as in Example 21. Alternatively, the samples can be tested through the use of a surface plasmon resonance device.

Antibodies Binding, and Variant Antibodies for Superior Binding

In one embodiment, the models described above are used to increase the binding ability of the antibody to its epitope. The antibody can bind to the epitope more readily, and thus have a higher association constant ($k_a$). Alternatively, the antibody may dissociate from the epitope slower, and thus have a lower dissociation constant ($k_d$), or the $K_D$ of the epitope-paratope interaction can be smaller in value, thus making the extent of the binding between the epitope and paratope higher.

In some embodiments, the variant antibodies are designed to bind with the opposite characteristics. That is, the antibodies do not bind as tightly or perhaps as quickly.

In other embodiments, the variant antibodies are not different in their $K_D$ from the wild-type antibodies, but the variant antibodies are more specific for a particular epitope. This may mean that the paratopes of the designed antibodies have a lower risk of binding to other epitopes. The antibodies can have other characteristics that have been altered. For example, a variant may be more immune to nonspecific antibody binding or may stay solvated in solution even when the antibody is present in high concentrations. Such a variant may be present in the discussed antibodies. For instance, while the higher concentrations of some variant antibodies examined below resulted in slower binding components in Biacore experiments, for instance 13.1.2 mAb, certain variants did not exhibit this slower component, even at the same concentrations, L217N-2.1, for example.

The variants predicted by the models determined above can be created and then tested to determine if they actually bind with the desired characteristics. Mutants with a greater total interaction energy with the epitope can be selected for further testing. The interaction energy can be determined in a number of ways, one of which is described above.

These variants can be tested in a number of ways. Exemplary options include and are not limited to KinExA (e.g., Lackie, Issued U.S. Pat. No. 5,372,783, Dec. 13, 1994, herein incorporated in its entirety by reference) (Sapidyne Instruments Inc., ID, Boise), surface plasmon resonance (SPR) (e.g., BIACORE™ Biacore, Inc., Pistcataway, N.J.), stopped-flow fluorescence, resonant mirror, and fluorescence polarization. Many of these options are able to not only record the data, but also provide ready means for fitting the data to various theoretical curves and thus determine the $k_a$, $k_d$, and $K_D$, as well as other properties. It is important to note that the fitting of these curves to the resulting data is not without the possibility for some variation. Because of this, the relevant association, dissociation, and equilibrium constants can be looked at, not only through these curve fitting mechanisms, but also in direct comparison with each other, and in light of the knowledge of one of skill in the art.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies are expected to minimize the immunogenic and allergic responses intrinsic to mouse or mouse-derivatized mAbs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with our generation of the first XenoMouse mouse strains, as published in 1994. (See Green et al. Nature Genetics 7:13-21 (1994)) The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620, filed Dec. 3, 1996, the disclosures of which are hereby incorporated by reference.

The production of the XenoMouse mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000, WO 03/47336. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996, 5,698,767, and 5,958,765.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against EGFRvIII in order to vitiate concerns and/or effects of HAMA or HACA response.

Antibody Therapeutics

As discussed herein, the function of the EGFRvIII antibody appears important to at least a portion of its mode of operation. By function, it is meant, by way of example, the activity of the EGFRvIII antibody in operation with EGFRvIII. Accordingly, in certain respects, it may be desirable in connection with the generation of antibodies as therapeutic candidates against EGFRvIII that the antibodies be capable of fixing complement and recruiting cytotoxic lymphocytes thus participating in CDC and ADCC. There are a number of isotypes of antibodies that are capable of the same, including, without limitation, the following: murine IgM, murine IgG2a, murine IgG2b, murine IgG3, human IgM, human IgG1, human IgG3, and human IgA. Also, it may be desirable in connection with the generation of antibodies as therapeutic candidates against EGFRvIII that the antibodies be capable of activating antibody-dependent cellular cytotoxicity (ADCC), through engagement of Fc receptors on effectors cells such as natural killer (NK) cells. There are a number of isotypes of antibodies that are capable of ADCC, including, without limitation, the following: murine IgG2a, murine IgG2b, murine IgG3, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397) and cell-cell fusion techniques (see e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, certain anti-EGFRvIII antibodies discussed herein are human anti-EGFRvIII IgG1 antibodies. If such antibody possessed desired binding to the EGFRvIII molecule, it could be readily isotype switched to generate a human IgM, human IgG3, or human IgGA while still possessing the same variable region (which defines the antibody's specificity and some of its affinity). Such molecules, including IgG1, would then be capable of fixing complement and participating in CDC, and, if comprising and IgG1 or IgG3 constant region, such molecules would also be capable of participating in antibody-dependent cellular cytotoxicity (ADCC) through recruiting cytotoxic lymphocytes.

Accordingly, as antibody candidates are generated that meet desired "structural" attributes as discussed above, they can generally be provided with at least certain of the desired "functional" attributes through isotype switching.

Design and Generation of Other Therapeutics

Based on the activity of the antibodies that are produced and characterized herein with respect to EGFRvIII, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation and recruitment of cytoxic lymphocytes is a desirable attribute, it is possible to enhance cell killing through the use of bispecifics, immunotoxins, or radiolabels, for example.

For example, in connection with bispecific antibodies, bispecific antibodies can be generated that comprise (i) two antibodies one with a specificity to EGFRvIII and another to a second molecule that are conjugated together, (ii) a single antibody that has one chain specific to EGFRvIII and a second chain specific to a second molecule, or (iii) a single chain antibody that has specificity to EGFRvIII and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the Fc chain activation receptors, including, without limitation, CD16 or CD64 (see e.g., Deo et al. 18:127 (1997)) CD3 (Micromet's BiTE technology) or CD89 (see e.g., Valerius et al. *Blood* 90:4485-4492 (1997)). Bispecific antibodies prepared in accordance with the foregoing would be likely to kill cells expressing EGFRvIII, and particularly those cells in which the EGFRvIII antibodies of the invention are effective.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing EGFRvIII, and particularly those cells in which the antibodies described herein are effective.

The antibodies can be designed to bind more quickly, or to dissociate more slowly from the epitope, and thus the antibodies themselves can be designed therapeutics. The altered characterisitics of the antibodies can be used, for example, in the administration of a therapeutic to a patient.

Therapeutic Immunoconjugates

As will be appreciated, antibodies conjugated to drugs, toxins, or other molecules (immunoconjugates or immunotoxins) are highly useful in the targeted killing of cells that express a molecule that can be specifically bound by a specific binding molecule, such as an antibody. As discussed above, EGFRvIII is not known to be expressed on any normal tissues. Further, EGFRvIII shows significant expression in numerous human tumors. Accordingly, EGFRvIII is a highly attractive molecule for targeting with an immunotoxin.

Many reports have appeared on the attempted specific targeting of tumor cells with monoclonal antibody-drug conjugates (Sela et al. in Immunoconjugates 189-216 (C. Vogel, ed. 1987); Ghose et al, in Targeted Drugs 1-22 (E. Goldberg, ed. 1983); Diener et al, in Antibody Mediated Delivery Systems 1-23 (J. Rodwell, ed. 1988); Pietersz et al, in Antibody Mediated Delivery Systems 25-53 (J. Rodwell, ed. 1988); Bumol et al, in Antibody Mediated Delivery Systems 55-79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al. Cancer Res. 46:2407-2412 (1986); Ohkawa et al. Cancer Immumol. Immunother. 23:81-86 (1986); Endo et al. Cancer Res. 47:1076-1080 (1980)), dextran (Hurwitz et al. Appl. Biochem. 2:25-35 (1980); Manabi et al. Biochem. Pharmacol. 34:289-291 (1985); Dillman et al. Cancer Res. 46:4886-4891 (1986); Shoval et al. Proc. Natl. Acad. Sci. 85: 8276-8280 (1988)), or polyglutamic acid (Tsukada et al. J. Natl. Canc. Inst. 73:721-729 (1984); Kato et al. J. Med. Chem. 27:1602-1607 (1984); Tsukada et al. Br. J. Cancer 52:111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (Biochem. Biophys. Res. Commun. 102:1048-1054 (1981)). Yang and Reisfeld used the same technique to conjugate daunorubicin to an anti-melanoma antibody (J. Natl. Canc. Inst. 80:1154-1159 (1988)). Recently, Dillman et al. also used an acid-labile linker in a similar fashion to prepare conjugates of daunorubicin with an anti-T cell antibody (Cancer Res. 48:6097-6102 (1988)).

An alternative approach, explored by Trouet et al. involved linking daunorubicin to an antibody via a peptide spacer arm (Proc. Natl. Acad. Sci. 79:626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al. J. Biol. Chem. 260:12035-12041 (1985); Lambert et al. in Immunotoxins 175-209 (A. Frankel, ed. 1988); Ghetie et al. Cancer Res. 48:2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al. described the conversion of methotrexate into a mercaptoethylamide derivative followed by conjugation with poly-D-lysine via a disulfide bond (J. Biol. Chem. 260:10905-10908 (1985)). In addition, a report described the preparation of a conjugate of the trisulfide-containing toxic drug calicheamycin with an antibody (Menendez et al. Fourth International Conference on Monoclonal Antibody Immunoconjugates for Cancer, San Diego, Abstract 81 (1989)). Another report described the preparation of a conjugate of the trisulfide-containing toxic drug calicheamycin with an antibody (Hinman et al, 53 Cancer Res. 3336-3342 (1993)).

One reason for the lack of disulfide linked antibody-drug conjugates is the unavailability of cytotoxic drugs that bear a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

Maytansinoids are highly cytotoxic drugs. Maytansine was first isolated by Kupchan et al. from the east African shrub Maytenus serrata and shown to be 100 to 1000 fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al. J. Med. Chem. 21:31-37 (1978); Higashide et al. Nature 270:721-722 (1977); Kawai et al. Chem. Pharm. Bull. 32:3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:
(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and
(b) C-3 esters with derivatives of N-methyl-L-alanine (U.S. Pat. Nos. 4,137,230; 4,260,608; 5,208,020; and Chem. Pharm. Bull. 12:3441 (1984)).

Esters of group (b) were found to be much more cytotoxic than esters of group (a).

Maytansine is a mitotic inhibitor. Treatment of L1210 cells in vivo with maytansine has been reported to result in 67% of the cells accumulating in mitosis. Untreated control cells were reported to demonstrate a mitotic index ranging from between 3.2 to 5.8% (Sieber et al. 43 Comparative Leukemia Research 1975, Bibl. Haemat. 495-500 (1976)). Experiments with sea urchin eggs and clam eggs have suggested that maytansine inhibits mitosis by interfering with the formation of microtubules through the inhibition of the polymerization of the microtubule protein, tubulin (Remillard et al. Science 189:1002-1005 (1975)).

In vitro, P388, L1210, and LY5178 murine leukemic cell suspensions have been found to be inhibited by maytansine at doses of $10^{-3}$ to $10^{-1}$.mu.g/.mu.l with the P388 line being the most sensitive. Maytansine has also been shown to be an active inhibitor of in vitro growth of human nasopharyngeal carcinoma cells, and the human acute lymphoblastic leukemia line CEM was reported inhibited by concentrations as low as $10^{-7}$ mg/ml (Wolpert-DeFillippes et al. Biochem. Pharmacol. 24:1735-1738 (1975)).

In vivo, maytansine has also been shown to be active. Tumor growth in the P388 lymphocytic leukemia system was shown to be inhibited over a 50- to 100-fold dosage range which suggested a high therapeutic index; also significant inhibitory activity could be demonstrated with the L1210 mouse leukemia system, the human Lewis lung carcinoma system and the human B-16 melanocarcinoma system (Kupchan, Ped. Proc. 33:2288-2295 (1974)).

Current methods of conjugation of maytansinoids with cell binding agents (such as antibodies) involve two reaction steps. A cell binding agent, for example an antibody, is first modified with a cross-linking reagent such as N-succinimidyl pyridyldithiopropionate (SPDP) to introduce dithiopyridyl groups into the antibody (Carlsson et al. Biochem. J. 173:723-737 (1978); U.S. Pat. No. 5,208,020). In a second step, a reactive maytansinoid having a thiol group, such as DM1 (formally termed $N^{2'}$-deacetyl-$N^{2'}$-(3-mercapto-1-oxopropyl)-maytansine, as the starting reagent., is added to the modified antibody, resulting in the displacement of the thiopyridyl groups in the modified antibodies, and the production of disulfide-linked cytotoxic maytansinoid/antibody conjugates (U.S. Pat. No. 5,208,020). A one-step process for conjugation of maytansinoids is described in U.S. Pat. No. 6,441,163. Maytansinoid-based immunotoxin technology is available from Immunogen Corporation (Cambridge, Mass.).

Another important toxin technology is based upon auristatin toxins. Auristatins are derived from Dolastatin 10 that was obtained from the Indian Ocean sea hare Dolabella, as a potent cell growth inhibitory substance. See U.S. Pat. Nos. 4,816,444 and 4,978,744. With respect to other Dolastatins, see also U.S. Pat. No. 4,414,205 (Dolastatin-1,2, and 3), U.S. Pat. No. 5,076,973 (Dolastatin-3), U.S. Pat. No. 4,486,414 (Dolastatin-A and B); U.S. Pat. No. 4,986,988 (Dolastatin-13), U.S. Pat. No. 5,138,036 (Dolastatin-14), and U.S. Pat. No. 4,879,278 (dolastatin-15). Isolated and synthesized by Dr. Pettit and colleagues at the University of Arizona, a variety of auristatine derivatives have been tested and shown to be highly toxic to cells. See Pettit et al. Antineoplastic agents 337. Synthesis of dolastatin 10 structural modifications. Anticancer Drug Des. 10(7):529-44 (1995), Woyke et al. In vitro activities and postantifungal effects of the potent dolastatin 10 structural modification auristatin PHE. Antimicrobial Agents and Chemotherapy. 45:3580-3584 (2001), Pettit et al. Specific activities of dolastatin 10 and peptide derivatives against *Cryptococcus neoformans*. Antimicrobial Agents and Chemotherapy. 42:2961-2965 (1998), Woyke Three-dimensional visualization of microtubules during the *Cryptococcus neoformans* cell cycle and the effects of auristatin PHE on microtubule integrity and nuclear localization. Submitted, Antimicrobial Agents and Chemotherapy.

Recently, additional auristatin derivatives have been developed that appear quite effective when delivered as payloads on antibodies. For example monomethyl auristatin E (MMAE) has been shown as a potent toxin for tumor cells when conjugated to tumor specific antibodies. Doronina et al. Development of potent monoclonal antibody auristatin conjugates for cancer therapy. Nature Biotechnology. (2003) (available online), Francisco et al. cAC10-vcMMAE, an anti-CD30-monomethyl auristatin E conjugate with potent and selective antitumor activity. Blood. (2003) May 8 [Epub ahead of print]. Epub 2003 Apr. 24 (available online). In addition to the toxicity of the auristatin molecule, research has shown that peptide-linked conjugates are more stable, and, thus, more specific and less toxic to normal tissues than other linker technologies in buffers and plasma. Doronina et al. Development of potent monoclonal antibody auristatin conjugates for cancer therapy. Nature Biotechnology. (2003) (available online), Francisco et al. cAC10-vcMMAE, an anti-CD30-monomethyl auristatin E conjugate with potent and selective antitumor activity. Blood. (2003) May 8 [Epub ahead of print]. Epub 2003 Apr. 24 (available online). Such linkers are based on a branched peptide design and include, for example, mAb-valine-citrulline-MMAE and mAb-phenylalanine-lysine-MMAE conjugates. Doronina et al. Development of potent monoclonal antibody auristatin conjugates for cancer therapy. Nature Biotechnology. (2003) (available online), Francisco et al. cAC10-vcMMAE, an anti-CD30-monomethyl auristatin E conjugate with potent and selective antitumor activity. Blood. (2003) May 8 [Epub ahead of print]. Epub 2003 Apr. 24 (available online). Such designs and conjugation techniques are described, for example, by King et al. Monoclonal antibody conjugates of doxorubicin prepared with branched peptide linkers: inhibition of aggregation by methoxytriethyleneglycol chains. J Med. Chem. 45(19):4336-43 (2002) and Dubowchik et al. Cathepsin B-sensitive dipeptide prodrugs. 2. Models of anticancer drugs paclitaxel (Taxol), mitomycin C and doxorubicin. Bioorg Med Chem. Lett. 8(23):3347-52 (1998). Auristatin E-based immunotoxin technology based upon the foregoing is available from Seattle Genetics Corporation (Seattle, Wash.).

There are a large number of novel microtubule effecting compounds obtained from natural sources-extracts, and semisynthetic and synthetic analogs that appear to possess potential as toxins for the generation of immunoconjugates. (see the website at newmedinc "dot" com). Such molecules and examples of drug products utilizing them, include the following: Colchicine-site Binders (Curacin), Combretastatins (AVE806, Combretastatin A-4 prodrug (CA4P), Oxi-4503), Cryptophycins (LY355703), Discodermolide, Dolastatin and Analogs (Auristatin PHE, Dolastatin 10, ILX-651, Symplostatin 1, TZT-1027), Epothilones (BMS-247550, BMS-310705, EP0906, KOS-862, ZK-EPO), Eleutherobin, FR182877, Halichondrin B (E7389), Halimide (NPI-2352 and NPI-2358), Hemiasterlins (HTI-286), Laulimalide, Maytansinoids ("DM1") (Bivatuzumab mertansine, Cantuzumab mertansine, huN901-DM1/BB-10901TAP, MLN591DM1, My9-6-DM1, Trastuzumab-DM1), PC-SPES, Peloruside A, Resveratrol, S-allylmercaptocysteine (SAMC), Spongistatins, Vitilevuamide, Molecular Motor-Kinesins (SB-715992), Designed Colchicine-Site Binders (A-289099, A-293620/A-318315, ABT-751/E7010, D-24851/D-64131, ZD6126), Other Novel Spindle Poisons (2-Methoxyestradiol (2-ME2), Bezimidazole Carbamates (ANG 600 series, Mebendazole), CP248/CP461, HMN-214, R440, SDX-103, T67/T607). Further, additional marine derived toxins are reviewed in Mayer, A. M. S. Marine Pharmacology in 1998: Antitumor and Cytotoxic Compounds. The Pharmacologist. 41(4):159-164 (1999).

Therapeutic Administration and Formulations

A prolonged duration of action will allow for less frequent and more convenient dosing schedules by alternate parenteral routes such as intravenous, subcutaneous or intramuscular injection.

When used for in vivo administration, antibody formulations described herein should be sterile. This is readily accomplished, for example, by filtration through sterile filtration membranes, prior to or following lyophilization and reconstitution. Antibodies ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. Antibodies are preferably administered continuously by infusion or by bolus injection.

An effective amount of antibody to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies as described herein can be prepared in a mixture with a pharmaceutically acceptable carrier. Therapeutic compositions can be administered intravenously or through the nose or lung, preferably as a liquid or powder aerosol (lyophilized). Composition can also be administered parenterally or subcutaneously as desired. When administered systemically, therapeutic compositions should be sterile, pyrogen-free and in a parenterally acceptable solution having due regard for pH, isotonicity, and stability. These conditions are known to those skilled in the art. Briefly, dosage formulations of the compounds are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington's Pharmaceutical Sciences* (18$^{th}$ ed, Mack Publishing Company, Easton, Pa., 1990). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustain release effect. Other compositions also include liposomally entrapped antibodies. Liposomes containing such antibodies are prepared by methods known per se: U.S. Pat. No. DE 3,218,121; Epstein et al., Proc. Natl. Acad. Sci. USA, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (18$^{th}$ ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci* 0.89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Preparation of Antibodies

Antibodies, as described herein, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein. In particular, however, a one embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through use of such technology, fully human monoclonal antibodies to a variety of antigens can be produced. In one embodiment, XenoMouse® lines of mice are immunized with an antigen of interest (e.g. EGFRvIII), lymphatic cells are recovered (such as B-cells) from the mice that expressed antibodies, and such cells are fused with a myeloid-type cell line to prepare immortal hybridoma cell lines, and such hybridoma cell lines are screened and selected to identify hybridoma cell lines that produce antibodies specific to the antigen of interest. Provided herein are methods for the production of multiple hybridoma cell lines that produce antibodies specific to EGFRvIII. Further, provided herein are characterization of the antibodies produced by such cell lines, including nucleotide and amino acid sequences of the heavy and light chains of such antibodies.

Alternatively, instead of being fused to myeloma cells to generate hybridomas, the antibody produced by recovered cells, isolated from immunized XenoMouse® lines of mice, are screened further for reactivity against the initial antigen, preferably EGFRvIII protein. Such screening includes ELISA with EGFRvIII protein, in vitro binding to NR6 M cells stably expressing full length EGFRvIII and internalization of EGFRvIII receptor by the antibodies in NR6 M cells. Single B cells secreting antibodies of interest are then isolated using a EGFRvIII-specific hemolytic plaque assay (Babcook et al., *Proc. Natl. Acad. Sci. USA*, i93:7843-7848 (1996)). Cells targeted for lysis are preferably sheep red blood cells (SRBCs) coated with the EGFRvIII antigen. In the presence of a B cell culture secreting the immunoglobulin of interest and complement, the formation of a plaque indicates specific EGFRvIII-mediated lysis of the target cells. The single antigen-specific plasma cell in the center of the plaque can be isolated and the genetic information that encodes the specificity of the antibody is isolated from the single plasma cell. Using reverse-transcriptase PCR, the DNA encoding the variable region of the antibody secreted can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences. Herein, we describe the isolation of multiple single plasma cells that produce antibodies specific to EGFRvIII. Further, the genetic material that encodes the specificity of the anti-EGFRvIII antibody is isolated, introduced into a suitable expression vector that is then transfected into host cells.

B cells from XenoMouse mice may be also be used as a source of genetic material from which antibody display libraries may be generated. Such libraries may be made in bacteriophage, yeast or in vitro via ribosome display using ordinary skills in the art. Hyperimmunized XenoMouse mice may be a rich source from which high-affinity, antigen-reactive antibodies may be isolated. Accordingly, XenoMouse mice hyperimmunized against EGFRvIII may be used to generate antibody display libraries from which high-affinity antibodies against EGFRvIII may be isolated. Such libraries could be screened against the pep3 oligopeptide and the resultingly derived antibodies screening against cells expressing EGFRvIII to confirm specificity for the natively display antigen. Full IgG antibody may then be expressed using recombinant DNA technology. See e.g., WO 99/53049.

In general, antibodies produced by the above-mentioned cell lines possessed fully human IgG1 or IgG2 heavy chains with human kappa light chains. In one embodiment, the antibodies possessed high affinities, typically possessing Kd's of from about $10^{-9}$ through about $10^{-13}$ M, when measured by either solid phase and solution phase. In other embodiments the antibodies possessed lower affinities, from about $10^{-6}$ through about $10^{-8}$ M.

As appreciated by one of skill in the art, antibodies in accordance with the present embodiments can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive EGFRvIII binding properties.

EXAMPLES

The following examples, including the experiments conducted and the results achieved are provided for illustrative purposes only and are not to be construed as limiting upon the present invention.

The strategy for generating EGFRvIII-specific antibodies initially involved immunization of XenoMouse mice with combinations of antigens (peptide, various soluble proteins, antigen-expressing cells) followed by isolation of antibody producing cells, either as through fusions to produce hybridomas or isolation of B cell cells through the XenoMax™/SLAM™ technology. Antibody producing cells were subjected to a primary screen for specificity by ELISA and a secondary screen for cell surface binding by FMAT and/or FACS. Internalization assays were then conducted to identify antibodies that would be useful for drug delivery. Affinities of the antibodies were measured. Certain antibodies were selected for epitope mapping. In addition, certain antibodies were selected for in vitro and in vivo tests to analyze the efficacy of such antibodies for treatment of cancers.

Example 1

Antigen Preparation

A. EGFRvIII PEP3-KLH Antigen Preparation

In connection with Example 2, the 14-mer human EGFRvIII PEP3 (L E E K K G N Y V V T D H C (SEQ ID NO: 56)) peptide was custom synthesized by R&D Systems. The PEP3 peptide was then conjugated to keyhole limpet hemocyanin (KLH), as follows: EGFRvIII PEP3 (200 mcg) (R&D) was mixed with 50 mcg of keyhole limpet hemocyanin (KLH; Pierce, Rockford, Ill.) to a final volume of 165 mcl using distilled water. 250 mcl of conjugation buffer (0.1M MES, 0.9M NaCl, pH 4.7) was added and EGFRvIII PEP3 and KLH were crosslinked by the addition of 25 mcl of 10 mg/ml stock solution of 1-ethyl-3-[3-dimethylaminopropyl] carbodiimide hydrochloride (EDC, Pierce, Rockford, Ill.). Conjugate was incubated for 2 hours at room temperature and the unreacted EDC was removed by centrifugation through a 1 kDa filter (Centrifugal filter; Millipore, Bedford, Mass.) using PBS pH 7.4.

In connection with Example 3, the 14-mer human EGFRvIII PEP3 (L E E K K G N Y V V T D H C (SEQ ID NO: 56)) peptide was custom synthesized. The PEP3 peptide was then conjugated to KLH, as follows: human EGFRvIII PEP3 (200 mcg) was mixed with 50 mcg of keyhole limpet hemocyanin (KLH; Pierce, Rockford, Ill.) to a final volume of 165 mcl using distilled water. 250 mcl of conjugation buffer (0.1M MES, 0.9M NaCl, pH 4.7) was added and EGFRvIII PEP3 and KLH were crosslinked by the addition of 25 mcl of 10 mg/ml stock solution of 1-ethyl-3-[3-dimethylaminopropyl]carbodiimide hydrochloride (EDC, Pierce, Rockford, Ill.). Conjugate was incubated for 2 hours at room temperature and the unreacted EDC was removed by centrifugation through a 1 kDa filter (Centrifugal filter; Millipore, Bedford, Mass.) using PBS pH 7.4.

B. B300.19/EGFRvIII Transfectants

In order to prepare the B300.19/EGFRvIII transfectants, wild type EGFR was initially cloned from A431 cells and EGFR gene was modified to code for EGFRvIII to delete the codons encoding residues 6-273, with a codon encoding a Glycine residue created at the junction of the deletion. The deletion occurs within the codons surrounding the deletion GTT (Valine) and CGT (Arginine), such that the resulting codon after the deletion is GGT (Glycine). (Wikstrand et al. J Neurovirol. 4(2):148-58 (1998))

1. Cloning of Wild Type EGFR Construct:

PolyA+ mRNA was extracted from A431 (ATCC) cells using Micro-fast RNA kit (Invitrogen, Burlington, ON). Total cDNA was synthesized from polyA+ mRNA with random pdN6 primers and M-MuLV reverse transcriptase (NEB, New England Biolabs, Beverly, Mass.). A 2.3 kb PCR product was amplified from A431 cDNA with the following primers:

```
sense
                                        (SEQ ID NO: 62)
5'-GGATCTCGAGCCAGACCGGAACGACAGGCCACCTC-3';

anti-sense
                                        (SEQ ID NO: 63)
5'-CGGATCTCGAGCCGGAGCCCAGCACTTTGATCTT-3'
``` using Pfu DNA polymerase.

The PCR product was digested with XhoI, gel purified and ligated into plasmid pWBFNP (see International Patent Application No. WO 99/45031, the disclosure of which is hereby incorporated by reference) linearized with XhoI to yield plasmid Wt-EGFR/pWBFNP.

2. Generation of EGFRvIII Construct:

PCR products amplified from plasmid Wt-EGFR/pWBFNP template with primer pairs C13659/C29538 and C29539/C14288 (BioSource International), in which the C29538 and C29539 were phosphorylated with T4 Polynucleotide kinase (NEB, New England Biolabs, Beverly, Mass.):

```
C13659:
                                        (SEQ ID NO: 64)
5'-CGGATGAATTCCCAGACCGGACGACAGGCCACCTC-3'
(Sense);

C29538:
                                        (SEQ ID NO: 65)
5'-CTTTCTTTTCCTCCAGAGCC-3'
(Anti-Sense);

C29539:
                                        (SEQ ID NO: 66)
5'-GTAATTATGTGGTGACAGATC-3'
(Sense);

C14288:
                                        (SEQ ID NO: 67)
5'-CGGATCTCGAGCTCAAGAGAGCTTGGTTGGGAGCT-3'
(Anti-Sense).
``` were ligated to introduce a deletion in the sequence encoding amino acids 6 through 273 of the EGFR extracellular domain and subcloned into expression vector pWBDHFR2 (see International Patent Application No. WO 99/45031, the disclosure of which is hereby incorporated by reference).

A 232 bp fragment representing the 5' end of the deletion was generated with primer pair C13659/C29538 from Wt- EGFR/pWBFNP template amplified with Pfu polymerase (NEB, New England Biolabs, Beverly, Mass.). The PCR product was digested with EcoR1 (NEB, New England Biolabs, Beverly, Mass.) and gel purified. A 1273 bp fragment representing the 3' end of the deletion was generated with primer pair C29539/C14288 from Wt-EGFR/pWBFNP and the template amplified with Pfu polymerase. The PCR product was digested with XhoI (NEB, New England Biolabs, Beverly, Mass.) and gel purified. Fragments were ligated into EcoRI/XhoI digested pWBDHFR2 with T4 DNA ligase (NEB, New England Biolabs, Beverly, Mass.) to yield construct EGFRvIII/pWBDHFR The intracellular domain of EGFR was introduced into the resulting construct as follows: A 1566 bp DraIII/XhoI fragment was isolated from plasmid Wt-EGFR/pWBFNP and ligated into DraIII/XhoI digested EGFRvIII/pWBDHFR to yield EGFRvIII-FL/pWBDHFR.

3. Transfection of B300.19 Cells with EGFRvIII-FL/pWBDHFR:

B300.19 cells ($8 \times 10^6$) were used per transfection in 700 µl DMEM/HI medium. 20 µg EGFRvIII-FL/pWBDHFR and 2 µg CMV-Puro plasmid DNA were added. Cells were electroporated at 300 volts/960 uF with Bio-Rad Gene Pulser. Following electroporation, cells were cooled on ice for 10 minutes and, thereafter, 10 ml non-selection medium (DMEM/HI Glucose, 10% FBS, 50 µM BME, 2 mM L-Glutamine, 100 units Penicillin-G/ml, 100 units MCG Streptomycin/ml) was added. Cells were incubated for 48 hrs at 37° C. 7.5% $CO_2$.

Following incubation, cells were split into selection medium (DMEM/HI Glucose, 10% FBS, 2 mM L-Glutamine, 50 µM BME, 100 units Penicillin-G/ml, 100 units MCG Streptomycin/ml, 2 ug/ml puromycin) at $2 \times 10^4$, $0.4 \times 10^4$ and $0.08 \times 10^4$ cells/well in 96 well plate and were selected in selection medium for 14 days to generate stable clones. Puro resistant clones were stained with E752 mAb (an anti-EGFR antibody, described in Yang et al. Crit. Rev Oncol Hematol., 38(1):17-23 (2001)) and goat anti-human IgG PE then analyzed on FACS Vantage (Becton Dickinson).

C. Construction of EGFRvIII-RbFc Expression Constructs.

In order to generate the EGFRvIII rabbit Fc fusion, protein, we first constructed a vector containing DNA encoding rabbit Fc. This was ligated with DNA encoding EGFRvIII. This approach is described in more detail below:

1. Construction of RbFc/pcDNA3.1 Hygro:

Primers 1322/867 (below) were used to amplify a 721 bp fragment encoding the Hinge-CH2-CH3 dormain of rabbit IgG.

```
#1322 (sense):
                                    (SEQ ID NO: 68)
5'-GGTGGCGGTACCTGGACAAGACCGTTGCG-3'

#867 (antisense):
                                    (SEQ ID NO: 69)
5'-ATAAGAATGCGGCCGCTCATTTACCCGGAGAGCGGGA-3'
```

The resulting PCR product was digested with KpnI and NotI, gel purified and ligated into KpnI/NotI digested pcDNA3.1(+)/Hygro (Invitrogen, Burlington, ON) to yield plasmid RbFc/pcDNA3.1 Hygro.

2. Construction of EGFRvIII-RbFc/pCEP4:

Primers 1290/1293 (below) were used to amplify an 1165 bp product from EGFRvIII-FL/pWBDHFR plasmid template with Pfu polymerase

```
#1290 (sense):
                                    (SEQ ID NO: 70)
5'-CTACTAGCTAGCCACCATGCGACCCTCCGGGA-3'

#1293 (anti-sense):
                                    (SEQ ID NO: 71)
5'-CGGGGTACCCGGCGATGGACGGGATC-3'
```

The PCR product was digested with NheI and KpnI, gel purified and ligated into NheI/KpnI digested RbFc/pcDNA3.1 Hygro to yield plasmid EGFRvIII-RbFc/pcDNA3.1Hygro.

A 2170 bp SnaBI/XhoI fragment was isolated from EGFRvIII-RbFc/pcDNA3.1Hygro and subcloned into SnaBI/XhoI digested pCEP4 (Invitrogen, Burlington, ON) to yield plasmid EGFRvIII-RbFc/pCEP4.

3. Generation of 293F EGFRvIII-RbFc Stable Cell Lines:

Plasmid EGFRvIII-RbFc/pCEP4 was introduced into 293F cells (Gibco, Grand Island, N.Y.) by Calcium Phosphate transfection, as follows: one day prior to transfection, $1 \times 10^6$ 293F cells were plated on a gelatin coated 100 mm tissue culture petridish and incubated at 5% CO2, 37° C. Cells were fed with 10 ml of fresh non-selective media (DMEM/F12, 10% FBS, 2 mM L-Glutamine, 100 U/ml Penicillin G, 100 U/ml MCG Streptomycin) 2-3 hours before transfection. Transfection reagents were prepared in a microfuge tube, as follow: 10 µg of DNA (EGFRvIII-RbFc/pCEP4) was mixed with 62 µl of 2M Calcium Phosphate and deionized water to make the final volume 500 µl. In another tube pipette 500 µl of 2×HBS is drawn and used to transfer the transfection reagents.

The solution in the tube pipette was added to the cells drop by drop, while maintaining proper pH by leaving cells in a 5% CO2 incubator until transfection was performed. 15-20 hours after transfection, cells were washed with PBS and feed with 10 ml of fresh 293F non-selective media. Expressing cells were harvested with trypsin 48-72 post-transfection and cells were plated at $0.08 \times 10^4$ cells/well in a 96 well plate in 293F selective media (DMEM/F12, 10% FBS, 2 mM L-Glutamine, 100 U/ml Penicillin G, 100 U/ml MCG Streptomycin, 250 ug/ml Hygromycin) for 14 days.

Hygromycin resistent clones were screened by ELISA using anti-EGFR antibody E763 (U.S. Pat. No. 6,235,883) as the capture antibody at 1 ug/ml and detecting with a goat anti-rabbit IgG HRPO (CalTag) at 1:100 dilution.

Example 2

Production of Anti-EGFRvIII Antibodies Through Hybridoma Generation

Eight XenoMouse mice that produce antibodies with a gamma-1 constant region (XenoMouse G1 mice) were immunized on day 0 and boosted on days 11, 21, 32, 44 and 54 for this protocol and fusions were performed on day 58. All immunizations were conducted via subcutaneous administration at the base of tail plus intraperitoneal administration for all injections. The day 0 immunization was done with $1.5 \times 10^7$ B300.19/EGFRvIII transfected cells (Example 1A) suspended in pyrogen free DPBS admixed 1:1 v/v with complete Freunds adjuvant (CFA) (Sigma, St. Louis, Mo.). Boosts on days 11, 21, and 32 were done with $1.5 \times 10^7$ B300.19/EGFRvIII transfected cells in DPBS-admixed 1:1 v/v with incomplete Freunds adjuvant (IFA) (Sigma, St. Louis, Mo.). The boosts on day 44 was done with 5 µg of the PEP3 (EGFRvIII peptide)—KLH conjugate (Example 1) in DPBS admixed 1:1 v/v with IFA and final boost, on day 54, was done with 5 ug PEP3 (EGFRvIII peptide)—KLH conjugate in DPBS without adjuvant.

On day 58, mice were euthanized, and then inguinal and Lumbar lymph nodes were recovered. Lymphocytes were released by mechanical disruption of the lymph nodes using a tissue grinder then depleted of T cells by CD90 negative selection. The fusion was performed by mixing washed enriched B cells and non-secretory myeloma P3X63Ag8.653 cells purchased from ATCC, cat. #CRL 1580 (Kearney et al, J. Immunol. 123:1548-1550 (1979)) at a ratio of 1:1. The cell mixture was gently pelleted by centrifugation at 800 g. After complete removal of the supernatant, the cells were treated with 2-4 mL of Pronase solution (CalBiochem, cat. #53702; 0.5 mg/ml in PBS) for no more than 2 minutes. Then, 3-5 ml of FBS was added to stop the enzyme activity and the suspension was adjusted to 40 ml total volume using electro cell fusion solution, ECFS (0.3M Sucrose, Sigma, Cat# S7903, 0.1 mM Magnesium Acetate, Sigma, Cat# M2545, 0.1 mM Calcium Acetate, Sigma, Cat# C4705 (St. Louis, Mo.)).

The supernatant was removed after centrifugation and the cells washed by resuspension in 40 ml ECFS. This wash step was repeated and the cells again were resuspended in ECFS to a concentration of $2 \times 10^6$ cells/ml. Electro-cell fusion was performed using a fusion generator, model ECM2001, Genetronic, Inc., San Diego, Calif. The fusion chamber size used was 2.0 ml, and using the following instrument settings: Alignment condition: voltage: 50 v, time: 50 s, Membrane breaking at: voltage: 3000 v, time: 30 µs, Post-fusion holding time: 3 s. After fusion, the cells were re-suspended in DMEM (JRH Biosciences), 15% FCS (Hyclone), containing HAT, and supplemented with L-glutamine, pen/strep, OPI (oxaloacetate, pyruvate, bovine insulin) (all from Sigma, St. Louis, Mo.) and IL-6 (Boehringer Mannheim) for culture at 37° C. and 10% $CO^2$ in air.

Cells were plated in flat bottomed 96-well tissue culture plates at $4 \times 10^4$ cells per well. Cultures were maintained in HAT (hypoxanthine, aminopterin and thymidine) supplemented media for 2 weeks before transfer to HT (hypoxanthine and thymidine) supplemented media. Hybridomas were selected for by survival in HAT medium and supernatants were screened for antigen reactivity by ELISA. The ELISA format entailed incubating supernatants on antigen coated plates (EGFRvIII peptide-OVA coated plates and wild type EGFr peptide-OVA coated plates as a counter screen) and detecting EGFRvIII-specific binding using horseradish peroxidase (HRP) labeled mouse anti-human IgG (see Table 2.1).

TABLE 2.1

| Plate.Well | Hybridoma | 1$^{st}$ OD fusion plate | 2nd OD muEGFr | EGFr |
|---|---|---|---|---|
| 13.2 D10 | 13.1 | 4.034 | 2.653 | 0.051 |
| 13.3 C12 | 13.2 | 3.829 | 2.443 | 0.049 |
| 13.3 F11 | 13.3 | 3.874 | 1.081 | 0.049 |
| 13.6 B11 | 13.4 | 3.322 | 1.311 | 0.052 |

| Clones | Plate | OD #1 cloning plate | OD #2 muEGFr | EGFr |
|---|---|---|---|---|
| 13.1.1 | 0.5 c/w D2 | 2.614 | 2.586 | 0.042 |
| 13.1.2 | 0.5 c/w F5 | 2.248 | 1.272 | 0.041 |

As will be observed, at least four antigen specific hybridomas were detected: 13.1, 13.2, 13.3, and 13.4. These hybridomas that were positive in the ELISA assay EGFRvIII specificity were confirmed by FACS on stably transfected 300.19 cells expressing EGFRvIII versus 300.19 untransfected parental cells.

Cloning was performed on selected antigen-positive wells using limited dilution plating. Plates were visually inspected for the presence of single colony growth and supernatants from single colony wells then screened by antigen-specific ELISAs and FACS confirmation as described above. Highly reactive clones were assayed to verify purity of human gamma and kappa chain by multiplex ELISA using a Luminex instrument. Based on EGFRvIII specificity in the ELISA and FACS assay, Clone 13.1.2 was selected as the most promising candidate for further screening and analysis. The nucleotide and amino acid sequences of the heavy and light chains of 13.1.2 antibody are shown in FIG. 3L and SEQ ID NO: 137 and 139 for heavy and light chain nucleic acids and 138 and 140 for heavy and light chain amino acid sequences. In addition, a comparison of the 13.1.2 heavy chain and light chain sequences with the germline sequence from which they were derived as shown in FIGS. 4 and 5.

Example 3

Antibody Generation Through Use of Xenomax Technology

Immunization of XenoMouse Animals

Human monoclonal antibodies against human EGFRvIII were developed by sequentially immunizing XenoMouse mice that produce antibodies with a gamma-1 constant region (XenoMouse G1 mice), XenoMouse mice that produce antibodies with gamma-2 constant regions (XenoMouse XMG2 mice), and XenoMouse mice that produce antibodies with a gamma-4 constant region (XenoMouse G4 mice).

To generate mAbs by through XenoMax technology, cohorts of XenoMouse G1 and XMG2 mice were immunized with EGFRvIII PEP3 (Example 1A) and EGFRvIII-expressing 300.19 cells (Example 1B) or with bacterially expressed extracellular domain of EGFRvIII protein (EGFRvIII-ECD) (Dr. Bigner, Duke University) and EGFRvIII-expressing 300.19 cells or with EGFRvIII-Rabbit Fc fusion protein (EGFRvIII-RbFc) (Example 1C) and EGFRvIII-expressing 300.19 cells or with EGFRvIII-RbFc only via foot pad (FP), or via base of the tail by subcutaneous injection and intraperitoneum (BIP).

For footpad immunizations, the initial immunization was with or without $10 \times 10^6$ EGFRvIII-expressing 300.19 cells and with or without 10 µg of EGFRvIII PEP3 or EGFRvIII-ECD or EGFRvIII-RbFc mixed 1:1 v/v with Titermax gold (Sigma, Oakville, ON) per mouse. The subsequent boosts were performed with half of the amount of immunogen used in the initial immunization. The first four boosts were done by taking the immunogen mixed with alum (Sigma, Oakville, ON), adsorbed overnight, per mouse as shown in the Table 3.1 below. This was followed by one injection with the respective immunogen in Titermax gold, one injection with alum and then a final boost of the immunogen in PBS as shown in Table 3.1. In particular, animals were immunized on days 0, 3, 7, 10, 14, 17, 21 and 24. The animals were bled on day 19 to obtain sera and determine the titer for harvest selection. The animals were harvested on Day 28.

TABLE 3.1

Footpad immunization schedule

| | | Group # | | | | | | | |
|---|---|---|---|---|---|---|---|---|---|
| | | 1 | 2 | 3 | 4 | 5 | 6 | 7 | 8 |
| | | # of animals | | | | | | | |
| | | 5 | 5 | 5 | 5 | 5 | 5 | 5 | 5 |
| | | Mouse strain | | | | | | | |
| Boost # | Adjuvant | XMG2 Immunogen | XM3C-3 Immunogen | XMG2 Immunogen | XM3C-3 Immunogen | XMG2 Immunogen | XM3C-3 Immunogen | XMG2 Immunogen | XM3C-3 Immunogen |
| 1st | Titermax gold | EGFRvIII-300.19 cells + PEP3-KLH | | EGFRvIII-300.19 cells + EGFRvIII-ECD | | EGFRvIII-300.19 cells + EGFRvIII-RbFc | | EGFRvIII-RbFc | |
| 2nd | Alum | EGFRvIII-300.19 cells | | EGFRvIII-300.19 cells | | EGFRvIII-300.19 cells | | EGFRvIII-RbFc | |
| 3rd | Alum | PEP3-KLH | | EGFRvIII-ECD | | EGFRvIII-ECD | | EGFRvIII-RbFc | |
| 4th | Alum | EGFRvIII-300.19 cells | | EGFRvIII-300.19 cells | | EGFRvIII-300.19 cells | | EGFRvIII-RbFc | |
| 5th | Alum | PEP3-KLH | | EGFRvIII-ECD | | EGFRvIII-ECD | | EGFRvIII-RbFc | |
| 6th | Titermax gold | EGFRvIII-300.19 cells | | EGFRvIII-300.19 cells | | EGFRvIII-300.19 cells | | EGFRvIII-RbFc | |
| 7th | Alum | PEP3-KLH | | EGFRvIII-ECD | | EGFRvIII-ECD | | EGFRvIII-RbFc | |
| 8th | PBS | EGFRvIII-300.19 cells + PEP3-KLH | | EGFRvIII-300.19 cells + EGFRvIII-ECD | | EGFRvIII-300.19 cells + EGFRvIII-RbFc | | EGFRvIII-RbFc | |
| | Harvest | | | | | | | | |

The initial BIP immunization with the respective immunogen, as described for the footpad immunization, was mixed 1:1 v/v with Complete Freund's Adjuvant (CFA, Sigma, Oakville, ON) per mouse. Subsequent boosts were made first with the immunogen respectively, mixed 1:1 v/v with Incomplete Freund's Adjuvant (IFA, Sigma, Oakville, ON) per mouse, followed by a final boost in PBS per mouse. The animals were immunized on days 0, 14, 28, 42, 56, and day 75 (final boost) as shown in Table 3.2 below. The animals were bled on day 63 to obtain sera and determine the titer for harvest selection. The animals were harvested on Day 78.

Selection of Animals for Harvest by Titer Determination

Anti-hEGFRvIII antibody titers were determined by ELISA. EGFRvII-RbFc (2.5 μg/ml) or a control RbFc (2 μg/ml) or EGFRvIIIpeptide-OVA (2 μg/ml) (Example 1) or control OVA (4 μg/ml) were coated onto Costar Labcoat Universal Binding Polystyrene 96-well plates (Corning, Acton, Mass.) overnight at four degrees. The solution containing unbound antigen was removed and the plates were treated with UV light (365 nm) for 4 minutes (4000 microjoules). The plates were washed five times with dH$_2$O, Sera from the EGFRvIII immunized XenoMouse® animals, or

TABLE 3.2

Bip Immunization schedule

| | | Group | | | | | | | |
|---|---|---|---|---|---|---|---|---|---|
| | | 9 | 10 | 11 | 12 | 13 | 14 | 15 | 16 |
| | | # of animals | | | | | | | |
| | | 5 | 5 | 5 | 5 | 5 | 5 | 5 | 5 |
| | | Mouse strain | | | | | | | |
| Boost # | Adjuvant | XMG2 Immunogen | XM3C-3 Immunogen | XMG2 Immunogen | XM3C-3 Immunogen | XMG2 Immunogen | XM3C-3 Immunogen | XMG2 Immunogen | XM3C-3 Immunogen |
| 1st | CFA | EGFRvIII-300.19 cells + PEP3-KLH | | EGFRvIII-300.19 cells + EGFRvIII-ECD | | EGFRvIII-300.19 cells + EGFRvIII-RbFc | | EGFRvIII-RbFc | |
| 2nd | IFA | EGFRvIII-300.19 cells | | EGFRvIII-300.19 cells | | EGFRvIII-300.19 cells | | EGFRvIII-RbFc | |
| 3rd | IFA | PEP3-KLH | | EGFRvIII-ECD | | EGFRvIII-ECD | | EGFRvIII-RbFc | |
| 4th | IFA | EGFRvIII-300.19 cells | | EGFRvIII-300.19 cells | | EGFRvIII-300.19 cells | | EGFRvIII-RbFc | |
| 5th | IFA | PEP3-KLH | | EGFRvIII-ECD | | EGFRvIII-ECD | | EGFRvIII-RbFc | |
| 6th | PBS | EGFRvIII-300.19 cells + PEP3-KLH | | EGFRvIII-300.19 cells + EGFRvIII-ECD | | EGFRvIII-300.19 cells + EGFRvIII-RbFc | | EGFRvIII-RbFc | |
| | Harvest | | | | | | | | | naïve XenoMouse® animals, were titrated in 2% milk/PBS at 1:2 dilutions in duplicate from a 1:100 initial dilution. The last well was left blank. The plates were washed five times with dH$_2$O. A goat anti-human IgG Fc-specific horseradish peroxidase (HRP, Pierce, Rockford, Ill.) conjugated antibody was added at a final concentration of 1 μg/mL for 1 hour at room temperature. The plates were washed five times with dH$_2$O. The plates were developed with the addition of TMB chromogenic substrate (Gaithersburg, Md.) for 30 minutes and the ELISA was stopped by the addition of 1 M phosphoric acid. The specific titer of individual XenoMouse® animals was determined from the optical density at 450 nm and is shown in Tables 3.3 and 3.4. The titer represents the reciprocal dilution of the serum and therefore the higher the number the greater the humoral immune response to hEGFRvIII.

For the mice immunized via base of the tail by subcutaneous injection and intraperitoneum, the titre was determined exactly as above except the plates were coated with EGFRvIII-RbFc (2.0 μg/ml) or a control RbFc (2.5 μg/ml).

TABLE 3.3

| Group # | Immunization (site and Immunogen) | Mouse Strain and sex | Mouse I.Ds | EGFRvIII-RbFc @ 2.5 ug/ml. | Control RbFc @ 2.0 ug/ml. | EGFRvIII peptide-OVA coated at 2.0 μg/ml | OVA coated at 4.0 μg/ml |
|---|---|---|---|---|---|---|---|
| 1 | FP EGFRvIII-300.19 cells + EGFRvIII PEP3-KLH (see Imm. Sched.) | XMG2 | 0748-1 | 330 | | 13549 | <100 |
| | | | 0748-2 | 237 | | 7635 | <100 |
| | | | 0748-3 | 109 | | 9824 | <100 |
| | | | 0748-4 | 714 | | 8014 | <100 |
| | | | 0748-5 | 165 | | 9421 | <100 |
| | | | Naïve | <100 | | n/a | n/a |
| 2 | FP EGFRvIII-300.19 cells + EGFRvIII PEP3-KLH (see Imm. Sched.) | XM3C-3 | 0741-1 | 388 | | 347 | <100 |
| | | | 0741-2 | 327 | | 240 | <100 |
| | | | 0741-3 | 385 | | 330 | <100 |
| | | | 0741-4 | 589 | | 227 | <100 |
| | | | 0741-5 | 273 | | 626 | <100 |
| | | | Naïve | <100 | | n/a | n/a |
| 3 | FP EGFRvIII-300.19 cells + EGFRvIII-ECD (see Imm. Sched.) | XMG2 | 0749-1 | 552 | | <100 | <100 |
| | | | 0749-2 | 477 | | <100 | <100 |
| | | | 0749-3 | 100 | | <100 | <100 |
| | | | 0749-4 | 100 | | <100 | <100 |
| | | | 0749-5 | 1631 | | <100 | <100 |
| | | | Naïve | 100 | | n/a | n/a |
| 4 | FP EGFRvIII-300.19 cells + EGFRvIII-ECD (see Imm. Sched.) | XM3C-3 | 0742-1 | 372 | | <100 | <100 |
| | | | 0742-2 | 745 | | <100 | <100 |
| | | | 0742-3 | 484 | | <100 | <100 |
| | | | 0742-4 | 530 | | <100 | <100 |
| | | | 0742-5 | 270 | | <100 | <100 |
| | | | Naïve | 100 | | n/a | n/a |
| 5 | FP EGFRvIII-300.19 cells + EGFRvIII-RbFc (see Imm. Sched.) | XMG2 | 0750-1 | 5399 | 175 | <100 | <100 |
| | | | 0750-2 | 3072 | 151 | <100 | <100 |
| | | | 0750-3 | >6400 | 358 | <100 | <100 |
| | | | 0750-4 | 5845 | 196 | <100 | <100 |
| | | | 0750-5 | 5770 | 196 | <100 | <100 |
| | | | Naïve | 100 | 100 | n/a | n/a |
| 6 | FP EGFRvIII-300.19 Cells + EGFRvIII-RbFc (see Imm. Sched.) | XM3C-3 | 0743-1 | 1220 | <100 | <100 | <100 |
| | | | 0743-2 | 1183 | <100 | <100 | <100 |
| | | | 0743-3 | 645 | <100 | <100 | <100 |
| | | | 0743-4 | 759 | <100 | <100 | <100 |
| | | | 0743-5 | 1260 | <100 | <100 | <100 |
| | | | Naïve | 100 | <100 | n/a | n/a |
| 7 | FP EGFRvIII-RbFc (see Imm. Sched.) | XMG2 | 0745-1 | 1897 | <100 | <100 | <100 |
| | | | 0745-2 | >6400 | 323 | <100 | <100 |
| | | | 0745-3 | 1225 | <100 | <100 | <100 |
| | | | 0745-4 | 4047 | <100 | <100 | <100 |
| | | | 0745-5 | 852 | <100 | <100 | <100 |
| | | | Naïve | 100 | <100 | n/a | n/a |
| 8 | FP EGFRvIII-RbFc (see Imm. Sched.) | XM3C-3 | 0744-1 | 362 | <100 | <100 | <100 |
| | | | 0744-2 | 807 | <100 | <100 | <100 |
| | | | 0744-3 | 479 | <100 | <100 | <100 |
| | | | 0744-4 | 631 | <100 | <100 | <100 |
| | | | 0744-5 | 1112 | <100 | <100 | <100 |
| | | | Naïve | 100 | <100 | n/a | n/a |

All the XenoMouse animals from group 5 and XenoMouse animals 0743-5 from group 6 from Table 3.3 were selected for XenoMax harvests based on the serology.

*Natl. Acad. Sci. USA,* 93:7843-7848 (1996). ELISA was used to identify primary EGFRvIII-peptide-OVA-specific wells. About 5 million B-cells were cultured from XenoMouse animals in 245 96 well plates at 500 or 150 or 50 cells/well, and were screened on EGFRvIII-peptide-OVA to identify the antigen-specific wells. About 515 wells showed ODs significantly over background, a representative sample of which are shown in Table 3.5.

TABLE 3.4

| Group # | Immunization (site and Immunogen) | Mouse Strain and sex | Mouse I.Ds | EGFRvIII-RbFc @ 2.0 ug/ml. | Control RbFc @ 2.5 ug/ml. | EGFRvIII peptide-OVA coated at 2.0 μg/ml | OVA coated at 4.0 μg/ml |
|---|---|---|---|---|---|---|---|
| 9 | BIP EGFRvIII-300.19 cells + EGFRvIII PEP3-KLH (see Imm. Sched.) | XMG2 | O695-1 | 2921 | | >128000 | 472 |
| | | | O695-2 | 2219 | | 30504 | 379 |
| | | | O695-3 | 4609 | | >128000 | 608 |
| | | | O695-4 | >6400 | | >128000 | 368 |
| | | | O695-5 | 1580 | | 19757 | 269 |
| | | | Naïve | <100 | | n/a | 242 |
| 10 | BIP EGFRvIII-300.19 cells + EGFRvIII PEP3-KLH (see Imm. Sched.) | XM3C-3 | O700-1 | <100 | | | |
| | | | O700-2 | <100 | | | |
| | | | O700-3 | >6400 | | | |
| | | | O700-4 | 5342 | | | |
| | | | O700-5 | >6400 | | | |
| | | | Naïve | <100 | | | |
| 11 | BIP EGFRvIII-300.19 cells + EGFRvIII-ECD (see Imm. Sched.) | XMG2 | O696-1 | <100 | | 561 | 240 |
| | | | O696-2 | <100 | | 788 | 326 |
| | | | O696-3 | <100 | | 604 | 266 |
| | | | O696-4 | 143 | | 444 | 263 |
| | | | O696-5 | <100 | | 303 | 254 |
| | | | Naïve | <100 | | | 242 |
| 12 | BIP EGFRvIII-300.19 cells + EGFRvIII-ECD (see Imm. Sched.) | XM3C-3 | O702-1 | 358 | | | |
| | | | O702-2 | 469 | | | |
| | | | O702-3 | 401 | | | |
| | | | O702-4 | >6400 | | | |
| | | | O702-5 | >6400 | | | |
| | | | Naïve | <100 | | | |
| 13 | BIP EGFRvIII-300.19 cells + EGFRvIII-RbFc (see Imm. Sched.) | XMG2 | O694-1 | >6400 | >6400 | 250 | 243 |
| | | | O694-2 | >6400 | >6400 | 296 | 309 |
| | | | O694-3 | >6400 | >6400 | 736 | 605 |
| | | | O694-4 | >6400 | >6400 | 739 | 1111 |
| | | | O694-5 | 3710 | >6400 | 517 | 465 |
| | | | Naïve | <100 | >6400 | | 242 |
| 14 | BIP EGFRvIII-300.19 cells + EGFRvIII-RbFc (see Imm. Sched.) | XM3C-3 | O703-1 | 2740 | >6400 | | |
| | | | O703-2 | 408 | >6400 | | |
| | | | O703-3 | 1406 | >6400 | | |
| | | | O703-4 | 1017 | >6400 | | |
| | | | O703-5 | 403 | >6400 | | |
| | | | Naïve | <100 | >6400 | | |
| 15 | BIP EGFRvIII-RbFc (see Imm. Sched.) | XMG2 | O697-1 | >6400 | >6400 | 340 | 348 |
| | | | O697-2 | >6400 | >6400 | 642 | 1793 |
| | | | O697-3 | 6242 | >6400 | 319 | 246 |
| | | | O697-4 | 1766 | >6400 | 133 | <100 |
| | | | O697-5 | >6400 | >6400 | 685 | 448 |
| | | | Naïve | <100 | >6400 | 243 | 242 |
| 16 | BIP EGFRvIII-RbFc (see Imm. Sched.) | XM3C-3 | O701-1 | 592 | >6400 | | |
| | | | O701-2 | 1118 | >6400 | | |
| | | | O701-3 | >6400 | >6400 | | |
| | | | O701-4 | <100 | <100 | | |
| | | | O701-5 | n/a | n/a | | |
| | | | Naïve | <100 | >6400 | | |

XenoMouse animals (0695-1, 0695-3 and 0695-4) were selected for harvests based on the serology data in Table 3.4.

Selection of B Cells.

B-cells from the above-discussed animals were harvested and cultured. Those secreting EGFRvIII-peptide specific antibodies were isolated as described in Babcook et al., *Proc.*

TABLE 3.5

| | Total # of plates | Positives above cutoff OD of: | | | | | | | | | | | | | | | |
|---|---|---|---|---|---|---|---|---|---|---|---|---|---|---|---|---|---|
| | | 0.0 | 0.1 | 0.2 | 0.3 | 0.4 | 0.5 | 0.6 | 0.7 | 0.8 | 0.9 | 1.0 | 1.5 | 2.0 | 2.5 | 3.0 | 3.5 |
| Cansera 500 cells/well | 12 | 1152 | 634 | 81 | 56 | 49 | 45 | 38 | 32 | 29 | 26 | 25 | 18 | 11 | 4 | 1 | 0 |
| Sigma 500 cells/well | 13 | 1248 | 773 | 195 | 139 | 117 | 99 | 80 | 73 | 58 | 53 | 49 | 21 | 9 | 5 | 1 | 0 |
| Sigma 150 cells/well | 20 | 1920 | 1304 | 478 | 178 | 91 | 67 | 55 | 47 | 45 | 36 | 33 | 19 | 9 | 5 | 2 | 0 |
| Total | 45 | 4320 | 2711 | 754 | 373 | 257 | 211 | 173 | 152 | 132 | 115 | 107 | 58 | 29 | 14 | 4 | 0 |

244 of EGFRvIII-peptide-OVA-Elisa positive wells of OD>0.5 were screened again on EGFRvIII-peptide-OVA and on OVA to confirm that they were EGFRvIII-peptide specific. A representative example of these results is shown in Table 3.6.

TABLE 3.6

| Plate | Well | | 1' EGFRvIII peptide-OVA OD | 2' EGFRvIII peptide-OVA OD | OVA OD |
|---|---|---|---|---|---|
| 121 | G | 1 | 0.7534 | 1.4065 | 0.1355 |
| 121 | A | 7 | 1.3472 | 2.1491 | 0.1268 |
| 121 | D | 8 | 0.6743 | 0.4179 | 0.1531 |
| 121 | E | 8 | 2.0415 | 2.6965 | 0.1498 |
| 121 | H | 10 | 0.8611 | 0.4288 | 0.1595 |
| 121 | C | 12 | 2.1455 | 2.6443 | 0.1404 |
| 122 | H | 1 | 1.8890 | 2.5987 | 0.1164 |
| 122 | H | 5 | 0.5943 | 0.8321 | 0.1572 |
| 122 | F | 8 | 0.6834 | 0.7715 | 0.1450 |

Limited Antigen Assay and Analysis

The limited antigen analysis is a method that affinity-ranks the antigen-specific antibodies present in B-cell culture supernatants relative to all other antigen-specific antibodies. In the presence of a very low coating of antigen, only the highest affinity antibodies should be able to bind to any detectable level at equilibrium. (See, e.g., International Patent Application No. WO 03/48730)

EGFRvIII peptide-OVA was coated to plates at three concentrations; 7.5 ng/ml, 1.5 ng/ml and 0.03 ng/ml for overnight at 4° C. on 96-well Elisa plates. Each plate was washed 5 times with dH$_2$O, before 50 ul of 1% milk in PBS with 0.05% sodium azide were added to the plate, followed by 4 µl of B cell supernatant added to each well. After 18 hours at room temperature on a shaker, the plates were again washed 5 times with dH$_2$O. To each well was added 50 ul of Gt anti-Human (Fc)-HRP at 1 µg/ml. After 1 hour at room temperature, the plates were again washed 5 times with dH$_2$O and 50 µl of TMB substrate were added to each well. The reaction was stopped by the addition of 50 uL of 1M phosphoric acid to each well and the plates were read at wavelength 450 nm and the results shown in Table 3.7.

TABLE 3.7

| Culture | | | Limited Ag | | | | | High Antigen |
|---|---|---|---|---|---|---|---|---|
| | | | 0.03 ng/ml | | 1.5 ng/ml | | 7.5 ng/ml | (1.0 µg/ |
| Plate | Well | | OD | Rank | OD | Rank | OD | Rank | ml) |
| 133 | B | 2 | 0.7670 | 1 | 1.189 | 54 | 1.871 | 95 | 2.050 |
| 124 | G | 12 | 0.7400 | 2 | 1.895 | 1 | 3.101 | 1 | 3.463 |
| 145 | C | 1 | 0.715 | 3 | 1.552 | 7 | 2.671 | 10 | 3.194 |
| 129 | G | 10 | 0.6720 | 4 | 1.367 | 22 | 2.692 | 8 | 2.977 |
| 186 | B | 6 | 0.657 | 5 | 1.842 | 2 | 2.859 | 3 | 3.411 |
| 143 | F | 12 | 0.653 | 6 | 1.677 | 3 | 2.741 | 6 | 3.156 |
| 136 | E | 3 | 0.6340 | 7 | 1.468 | 15 | 2.683 | 9 | 3.280 |
| 137 | C | 11 | 0.595 | 8 | 1.582 | 5 | 2.94 | 2 | 3.444 |
| 139 | A | 11 | 0.582 | 9 | 1.374 | 19 | 2.282 | 47 | 2.255 |
| 174 | F | 1 | 0.573 | 10 | 1.577 | 6 | 2.775 | 4 | 2.364 |

The results generated from limited antigen analysis were compared to the total OD obtained in high antigen assay. A relative ranking of affinity was done by taking the ratio of the OD obtained in limited antigen assay Vs that obtained in high antigen assay. Antibodies with higher ratio will have the highest affinity. Table 3.7 shows the sample of B-cell culture supernatants that were ranked based on limited antigen assay OD (for the lowest antigen plating concentration of 0.03 ng/ml) Vs the high antigen assay OD.

Native Cell Binding Assay by FMAT

EGFRvIII peptide-OVA-Elisa positive well supernatants were analyzed for their ability to bind to the native form of EGFRvIII stably expressed on NR6 cells (NR6 M cells) (See, Batra et al. Epidermal growth factor ligand-independent, unregulated, cell-transforming potential of a naturally occurring human mutant EGFRvIII gene. Cell Growth Differ. 6(10):1251-9 (1995)). NR 6 M cells were seeded at 8000 cells per well and incubated over night in 96 well FMAT plates. Media was then removed leaving 15 µl in the well. 15 µl B-cell culture supernatants were added and 15 µl anti-human IgG Fc Cy5 at 1 µg/ml final concentration added to wells. It is then left incubated at 4° C. for 2 hours. The cells were washed with 150 µl PBS, and fixed before reading on FMAT. The results were expressed as total fluorescent intensity (Table 3.8). Human anti-EGFRvIII mAb 13.1.2 was used as a positive control starting at 1 µg/ml final concentration and negative control was PK 16.3.1 at the same concentration. 134 of the 244 samples tested bound to NR6M cells of which 62 had a total fluorescence of greater than 8000. 6 of these 134 binders were false positives.

The same type of native binding assay was done on NTR6 Wt cells (NR6 cells expressing EGF receptor) (See Batra et al. Epidermal growth factor ligand-independent, unregulated, cell-transforming potential of a naturally occurring human mutant EGFRvIII gene. Cell Growth Differ. 6(10):1251-9 (1995)) to eliminate the binding is due to binding to Wt receptor (Table 3.8). ABX-EGF was used as a positive control and PK 16.3.1 at the same concentration was used as a negative control antibody. 3 out the 134 NR6 M binders were binding strongly to NR6 Wt cells. 190 of the 244 wells bound EGFRvIII peptide in Elisa were also bound to the native form on cells. Examples are given in Table 3.8.

TABLE 3.8

| Plate | | | 1' VIII-pep-OVA OD | 2' VIII-pep-OVA OD | OVA OD | FMAT native binding to NR6 M cells | FMAT native binding to NR6 Wt cells |
|---|---|---|---|---|---|---|---|
| 174 | F | 1 | 2.4945 | 3.0308 | 0.1900 | 138373 | 1668 |
| 187 | A | 4 | 1.5337 | 1.2085 | 0.1920 | 128626 | 202459.8 |
| 132 | D | 8 | 0.8555 | 1.2070 | 0.1649 | 109379 | 0 |
| 142 | C | 11 | 2.2889 | 2.8194 | 0.2239 | 94944 | 0 |
| 129 | A | 7 | 2.1501 | 2.8208 | 0.1515 | 84024 | 0 |
| 127 | E | 1 | 2.6923 | 3.1986 | 0.1219 | 82031 | 0 |
| 124 | G | 12 | 3.2929 | 3.5634 | 0.1455 | 73080 | 0 |
| 141 | C | 6 | 0.7512 | 1.2567 | 0.1547 | 60816 | 814.5 |
| 173 | C | 1 | 2.5728 | 2.5714 | 0.2134 | 58702 | 2523.4 |
| 128 | G | 9 | 0.6293 | 0.7483 | 0.1520 | 49631 | 0 |
| 129 | H | 6 | 2.9370 | 3.0952 | 0.2582 | 0 | 0 |
| 183 | E | 11 | 2.3450 | 2.7717 | 0.1050 | 0 | 0 |

In Table 3.8, supernatant from well 187A4 is identified as a Wt binder and 141C6 was a false positive for NR6 M cells binding. Wells 129H6 and 183E11 are strong peptide binders with no native binding.

Internalization Assay

The top 60 native binding B cell culture supernatants were further assayed for their ability to internalize the receptor. NR6 M cells were seeded at 8000 cells/well into 96 well FMAT plates and incubated overnight. Media was removed and 10-15 μl B-Cell culture supernatant in a total volume of 30 μl media, in duplicate was added. Next, 15 μl of secondary antibody (SS Alexa 647 anti-human IgG Fab at 1.5 μg/ml final concentration) was added and the mixture was incubated on ice for 1 hr. An irrelevant B-Cell Culture supernatant was used to see the effect of the culture media. Human anti-EGFRvIII mAb 13.2.1 was used as a positive control starting at 1 μg/ml (final concentration) and negative control was PK 16.3.1 (human anti-KLH IgG2 antibody) at the same concentration. After incubation, the cells were washed with cold PBS, 50 μl media was added to all of the wells, one of the duplicates were incubated at 37° C. for 30 mins while the other duplicate remained on ice. After the incubations media was removed, 100 μl of cold 50 mM glutathione was added to the set incubated at 37° C. and 100 μl of cold media added to the other set, both sets were then left on ice for 1 hr. The cells were then washed with 100 μl cold PBS and then fixed with 1% paraformaldehyde and read in FMAT. The results were expressed as % internalized, calculated as total fluorescence in the presence of glutathione/total fluorescence in the absence of glutathione×100. Representative information is given in Table 3.9.

TABLE 3.9

| Well no. | No glutathione FL1xcount | With glutathione FL1xcount | % internalized, (glut+/glut−) × 100 |
|---|---|---|---|
| 124 C9 | 1877 | 1394 | 74.3% |
| 124 G12 | 26465 | 9959 | 37.6% |
| 125 H1 | 14608 | 3686 | 25.2% |
| 125 D10 | 2342 | 1236 | 52.8% |
| 127 E1 | 15059 | 1318 | 8.7% |
| 127 B9 | 12444 | 7109 | 57.1% |
| 127 E11 | 6623 | 0 | 0.0% |
| 128 G9 | 10071 | 1851 | 18.4% |
| 129 A7 | 27648 | 8708 | 31.5% |
| 130 B4 | 4558 | 4354 | 95.5% |
| 131 H5 | 9258 | 2656 | 28.7% |
| 132 D8 | 35820 | 13293 | 37.1% |
| 133 F9 | 9773 | 3621 | 37.0% |
| 136 F10 | 2392 | 0 | 0.0% |
| 137 G6 | 5104 | 1021 | 20.0% |
| 137 G10 | 3451 | 0 | 0.0% |

EGFRvIII-Specific Hemolytic Plaque Assay.

A number of specialized reagents were needed to conduct this assay. These reagents were prepared as follows.
1. Biotinylation of Sheep red blood cells (SRBC). SRBCs were stored in RPMI media as a 25% stock. A 250 μl SRBC packed-cell pellet was obtained by aliquoting 1.0 ml of SRBC to a fresh eppendorf tube. The SRBC were pelleted with a pulse spin at 8000 rpm (6800 rcf) in microfuge, the supernatant drawn off, the pellet re-suspended in 1.0 ml PBS at pH 8.6, and the centrifugation repeated. The wash cycle was repeated 2 times, then the SRBC pellet was transferred to a 15-ml falcon tube and made to 5 ml with PBS pH 8.6. In a separate 50 ml falcon tube, 2.5 mg of Sulfo-NHS biotin was added to 45 ml of PBS pH 8.6. Once the biotin had completely dissolved, the 5 ml of SRBCs were added and the tube rotated at RT for 1 hour. The SRBCs were centrifuged at 300 rpm for 5 min and the supernatant drawn off. The biotinylated SRBCs were transferred to an eppendorf tube and washed 3 times as above but with PBS pH 7.4 and then made up to 5 ml with immune cell media (RPMI 1640) in a 15 ml falcon tube (5% B-SRBC stock). Stock was stored at 4° C. until needed.
2. Streptavidin (SA) coating of B-SRBC. 1 ml of the 5% B-SRBC stock was transferred into a fresh eppendorf tube. The B-SRBC cells were washed 3 times as above and resuspended in 1.0 ml of PBS at pH 7.4 to give a final concentration of 5% (v/v). 10 μl of a 10 mg/ml streptavidin (CalBiochem, San Diego, Calif.) stock solution was added and the tube mixed and rotated at RT for 20 min. The washing steps were repeated and the SA-SRBC were re-suspended in 1 ml PBS pH 7.4 (5% (v/v)).
3. EGFRvIII coating of SA-SRBC. The SA-SRBCs were coated with biotinylated-EGFRvIIIpeptide-OVA at 10 μg/ml, mixed and rotated at RT for 20 min. The SRBC were washed twice with 1.0 ml of PBS at pH 7.4 as above. The EGFRvIII-coated SRBC were re-suspended in RPMI (+10% FCS) to a final concentration of 5% (v/v).
4. Determination of the quality of EGFRvIIIpeptide-SRBC by immunofluorescence (IF). 10 μl of 5% SA-SRBC and 10 μl of 5% EGFRvII peptide-coated SRBC were each added to a separate fresh 1.5 ml eppendorf tube containing 40 ul of PBS. A control human anti-EGFRvIII antibody was added to each sample of SRBCs at 45 μg/ml. The tubes were rotated at RT for 25 min, and the cells were then washed three times with 100 µl of PBS. The cells were re-suspended in 50 µl of PBS and incubated with 40 mcg/mL Gt-anti Human IgG Fc antibody conjugated to Alexa488 (Molecular Probes, Eugene, Oreg.). The tubes were rotated at RT for 25 min. and then washed with 100 µl PBS and the cells re-suspended in 10 µl PBS. 10 µl of the stained cells were spotted onto a clean glass microscope slide, covered with a glass coverslip, observed under fluorescent light, and scored on an arbitrary scale of 0-4.

5. Preparation of plasma cells. The contents of a single microculture well previously identified by various assays as containing a B cell clone secreting the immunoglobulin of interest were harvested. Using a 100-1000 µl pipetman, the contents of the well were recovered by adding 37C RPMI (10% FCS). The cells were re-suspended by pipetting and then transferred to a fresh 1.5 ml eppendorf tube (final vol. approx 500-700 µl). The cells were centrifuged in a microfuge at 2500 rpm (660 rcf) for 1 minute at room temperature, and then the tube was rotated 180 degrees and spun again for 1 minute at 2500 rpm. The freeze media was drawn off and the immune cells resuspended in 100 µl RPMI (10% FCS), then centrifuged. This washing with RPMI (10% FCS) was repeated and the cells re-suspended in 60 µl RPMI (10% FCS) and stored on ice until ready to use.

6. Micromanipulation of plasma cells. Glass slides (2×3 inch) were prepared in advance with silicone edges and allowed to cure overnight at RT. Before use, the slides were treated with approx. 5 ul of SigmaCoat (Sigma, Oakville, ON) wiped evenly over glass surface, allowed to dry and then wiped vigorously. To a 60 µl sample of cells was added 60 µl each of EGFRvIIIpeptide-coated SRBC (5% v/v stock), 4× guinea pig complement (Sigma, Oakville, ON) stock prepared in RPMI (10% FCS), and 4× enhancing sera stock (1:150 in RPMI with 10% FCS). The mixture was spotted (10-15 µl) onto the prepared slides and the spots covered with undiluted paraffin oil. The slides were incubated at 37° C. for a minimum of 45 minutes. The EGFRvIII-specific plasma cells were identified from plaques and rescued by micromanipulation (see Table 3.10).

TABLE 3.10

| Well ID | | Single Cell Number | Total number of Single cells picked |
|---|---|---|---|
| 124 | G | 12 EGFRvIII-SCX-105-116 (LL) | 12 |
| 129 | A | 7 EGFRvIII-SCX-117-128 (DM) | 12 |
| 174 | F | 1 EGFRvIII-SCX-129-137 (DM) | 9 |
| 182 | A | 5 EGFRvIII-SCX-138-149 (LL); 162-169 (OP) | 20 |
| 125 | D | 10 EGFRvIII-SCX-170-181 (DM); 194-201 (LL) | 20 |
| 127 | B | 9 EGFRvIII-SCX-182-193 (LL); 202-209 (OP) | 20 |
| 190 | D | 7 EGFRvIII-SCX-210-229 (LL) | 20 |
| 130 | B | 4 EGFRvIII-SCX-230-249 (LL) | 20 |
| 138 | D | 2 EGFRvIII-SCX-250-269 (LL) | 20 |
| 145 | C | 1 EGFRvIII-SCX-80-92 (DM) | 13 |
| 172 | B | 12 EGFRvIII-SCX-93-104 (LL) | 12 |
| 187 | A | 4 EGFRvIII-SCX-270-281 (LL) | 12 |
| 173 | C | 1 EGFRvIII-SCX-282-293 (BC) | 12 |
| 127 | E | 1 EGFRvIII-SCX-294-305 (LL) | 12 |
| 142 | C | 11 EGFRvIII-SCX-306-317 (LL) | 12 |
| 141 | A | 10 EGFRvIII-SCX-318-329 (BC) | 12 |
| 132 | D | 8 EGFRvIII-SCX-330-341 (LL) | 12 |
| 124 | D | 4 EGFRvIII-SCX-342-349 (BC) | 8 |

Single cell PCR, Cloning, Expression, Purification and Characterization of Recombinant anti-EGFRvIII Antibodies.

The genes encoding the variable regions were rescued by RT-PCR on the single micromanipulated plasma cells. mRNA was extracted and reverse transcriptase PCR was conducted to generate cDNA. The cDNA encoding the variable heavy and light chains was specifically amplified using polymerase chain reaction. The human variable heavy chain region was cloned into an IgG1 expression vector. This vector was generated by cloning the constant domain of human IgG1 into the multiple cloning site of pcDNA3.1+/Hygro (Invitrogen, Burlington, ON). The human variable light chain region was cloned into an IgK expression vector. These vectors were generated by cloning the constant domain of human IgK into the multiple cloning site of pcDNA3.14+/Neo (Invitrogen, Burlington, ON). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24-72 hours. The supernatant (3 mL) was harvested from the HEK 293 cells and the secretion of an intact antibody was demonstrated with a sandwich ELISA to specifically detect human IgG (Table 3.11). Specificity was assessed through binding of the recombinant antibody to EGFRvIII using ELISA (Table 3.11).

TABLE 3.11

| | | Titer | |
|---|---|---|---|
| mAb ID | Cell # | Total antibody | Antigen binding |
| 129A7 | SC-EGFRvIII-XG1-123/124 | >1:64 | >1:64 |
| 138D2 | SC-EGFRvIII-XG1-250 | >1:64 | >1:64 |
| 174F1 | SC-EGFRvIII-XG1-131 | >1:64 | >1:64 |
| 182A5 | SC-EGFRvIII-XG1-139 | >1:64 | >1:64 |
| 190D7 | SC-EGFRvIII-XG1-211 | >1:64 | >1:64 |
| 125D10 | SC-EGFRvIII-XG2-170 | >1:64 | >1:64 |
| 182D5 | SC-EGFRvIII-XG2-150 | >1:64 | >1:64 |
| 141A10 | SC-EGFRvIII-XG1-318 | 1:64 | 1:64 |
| 132D8 | SC-EGFRvIII-XG1-333 | >1:64 | >1:64 |
| 124D4 | SC-EGFRvIII-XG1-342 | >1:64 | >1:64 |

The secretion ELISA tests were performed as follows. For Ab secretion, 2 µg/mL of Goat anti-human IgG H+L and for antigen binding, 1.5 µg/ml of EGFRvIII-Rab Ig Fc fusion protein was coated onto Costar Labcoat Universal Binding Polystyrene 96 swell plates and held overnight at four degrees. The plates were washed five times with dH$_2$O. Recombinant antibodies were titrated 1:2 for 7 wells from the undiluted minilipofection supernatant. The plates were washed five times with dH$_2$O. A goat anti-human IgG Fc-specific HRP-conjugated antibody was added at a final concentration of 1 µg/mL for 1 hour at RT for the secretion plates and binding plates detected with 1 µg/ml Rb anti Hu Fc for 1 hour at room temperature. The plates were washed five times with dH$_2$O. The plates were developed with the addition of TMB for 30 minutes and the ELISA was stopped by the addition of 1 M phosphoric acid. Each ELISA plate was analyzed to determine the optical density of each well at 450 nm.

Sequencing and Sequence Analysis

The cloned heavy and light chain cDNAs were sequenced in both directions and analyzed to determine the germline sequence derivation of the antibodies and identify changes from germline sequence. Such sequences are provided in FIGS. 3A-3K and (SEQ ID NO: 34-55). A comparison of each of the heavy and light chain sequences and the germline sequences from which they are derived is provided in FIGS. 4-7. In addition, the sequence of the hybridoma derived 13.1.2 antibody is compared to its germline sequence in FIGS. 4 and 5.

As will be appreciated from the discussion herein, each of the 131 antibody and the 13.1.2 antibody possess very high affinities for EGFRvIII, are internalized well by cells, and appear highly effective in cell killing when conjugated to toxins. Intriguingly, each of the antibodies, despite having been generated in different immunizations of XenoMouse mice, and utilizing different technologies, each are derived from very similar germline genes. Based upon epitope mapping work (described herein), each of the antibodies, however, appear to bind to slightly different epitopes on the EGFRvIII molecule and have slightly different residues on EGFRvIII that are essential for binding. These results indicate that the germline gene utilization is of importance to generation of antibody therapeutics targeting EGFRvIII and that small changes can modify the binding and effects of the antibody in ways that allow further design of antibody and other therapeutics based upon these structural findings.

Binding of Anti-EGFRvIII mAbs to Native EGFRvIII Expressed on Cells

In this example, binding of anti-EGFRvIII antibodies to NR6 M cells was measured. Specifically, unquantitated supernatants of XenoMax derived IgG1 recombinant antibodies were assayed for their ability to bind to NR6 M and NR6 WT cells. Cells were seeded at 10000/well and incubated overnight at 37 C in FMAT 96 well plates. Media was removed and 40 µl mini lipo supernatant (titrated down) was added, the cells were incubated on ice for 1 hr. The human 13.1.2 EGFRvIII antibodies and ABX EGF (E7.6.3, U.S. Pat. No. 6,235,883) antibodies were added as positive controls. The PK 16.3.1 antibody was used as a negative control. The cells were washed with Cold PBS, secondary antibody was added (SS Alexa antihuman IgG Fc) at 1 µg/ml, 40 µl/well and incubated on ice for 1 hr. The cells were then washed with Cold PBS and fixed and read by FMAT. All antibodies were tested for specificity for binding by counter screening against NR6 WT cells.

Purification of Recombinant Anti-EGFRvIII Antibodies

For larger scale production, heavy and light chain expression vectors (2.5 µg of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). Each antibody was purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialyzed in PBS, pH 7.4 and filter-sterilized. The antibody was analyzed by non-reducing SDS-PAGE to assess purity and yield. Concentration was also measured by UV analysis at OD 250.

Internalization of EGFRvIII Receptor by Recombinant Anti-EGFRvIII mAbs

XenoMax derived IgG1 recombinant antibodies were expressed, purified and quantitated as described previously. Antibodies were further assayed for their ability to internalize the EGFRvIII receptor in NR6 M cells. 250,000 NR6 M cells were incubated with primary antibody (SC95, SC131, SC133, SC139, SC150, SC170, SC211, SC230, SC250 and human 13.1.2 as a control) at 0.25 µg/ml, 7 mins on ice in 96 well v-bottomed plate in triplicate. The cells were washed with cold 10% FCS in PBS and secondary antibody (SS Alexa antihuman IgG Fab) at 3 µg/ml Fab was added and incubated for 7 mins on ice. The cells were washed with cold 10% FCS in PBS once and then resuspended in cold media. Next, two sets of the triplicate were incubated at 37° C. and the remaining set was incubated at 4° C. for 1 hr. After that the cells incubated at 4° C. and one set of the cells incubated at 37° C. were treated with glutathione (as previously mentioned) for 1 hr on ice. Then the cells were washed and resuspended in 100 µl of cold 1% FCS in PBS and analyzed by FACS. The % internalization was calculated from the geometric mean obtained from the FACS analysis [(mean at 37° C. with glutathione–mean at 4° C. with glutathione)/(mean at 37° C. without glutathione–mean at 4 C with glutathione)]. NA means that a FACS analysis was performed but the data was not provided in Table 3.12.

TABLE 3.12

| | FACS Geometric mean | | | |
|---|---|---|---|---|
| mAb | Without glutathione 37° C. | With glutathione 37° C. | With glutathione 4° C. | % internalization |
| 13.1.2 | 22.12 | 19.19 | 5.38 | 82.5% |
| sc95 | 22.56 | 17.75 | 5.13 | 72.4% |
| sc131 | NA | NA | NA | 72% |
| sc133 | 23.39 | 18.63 | 6.24 | 72.2% |
| sc139 | 22.64 | 19.23 | 4.88 | 80.8% |
| sc150 | 20.29 | 7.78 | 4.66 | 20.0% |
| sc170 | 19.97 | 7.75 | 4.67 | 20.1% |
| sc211 | 20.76 | 8.23 | 4.78 | 21.6% |
| sc230 | 20.68 | 7.97 | 5.02 | 18.8% |
| sc250 | 24.13 | 8.07 | 4.84 | 16.7% |

13.1.2 is an antibody that was generated through hybridoma generation (Example 2) that was directed against the EGFRvIII epitope previously and was used as a positive control in this experiment. These results in Table 3.12 demonstrate the presence of two subsets of antibodies, those that are efficiently internalized (70-80%) and those that are not (22% or less).

Example 4

Epitope Mapping of Human Anti EGFRvIII Antibodies

In order to determine the epitopes to which certain of the antibodies of the present invention bound, the epitopes of 6 human and 3 murine monoclonal antibodies (mabs) against EGFRvIII were mapped using synthetic peptides derived from the specific EGFRvIII peptide sequence. The antibodies mapped were the human hybridoma derived anti-EGFRvIII 13.1.2 antibody, the human XenoMax derived anti-EGFRvIII 131, 139, 250, 095, and 211 antibodies and the murine anti-EGFRvIII H10, Y10, and B9 antibodies (from Dr. D. Bigner, Duke University).

The approach that was used was a custom SPOTs peptide array (Sigma Genosys) to study the molecular interaction of the human anti-EGFrVIII antibodies with their peptide epitope. SPOTs technology is based on the solid-phase synthesis of peptides in a format suitable for the systematic analysis of antibody epitopes. Synthesis of custom arrayed oligopeptides is commerically available from Sigma-Genosys. A peptide array of overlapping oligopeptides derived from the amino-acid sequence of the EGFr VIII variant was ordered from Sigma-Genosys.

A series of nine 12-mer peptides were synthesized as spots on polypropylene membrane sheets. The peptide array spanned residues 1-20 of the EGFrVIII sequence, representing the deletion of amino acids 6-273 in the extracellular domain of wtEGFr, and the generation of a glycine (G) residue at the junction point. Each consecutive peptide was offset by 1 residue from the previous one, yielding a nested, overlapping library of arrayed oligopeptides. The membrane carrying the 9 peptides was reacted with 9 different anti EGFrVIII antibodies (1 µg/ml). The binding of the mAbs to the membrane-bound peptides was assessed by an enzyme-linked immunosorbent assay using HRP-conjugated secondary antibody followed by enhanced chemiluminescence (ECL). The array utilized is shown in Table 4.1.

TABLE 4.1

Spot Array Sequence:

| | | |
|---|---|---|
| 1. | ALEEKKGNYVVT | (SEQ ID NO: 72) |
| 2. | LEEKKGNYVVTD | (SEQ ID NO: 59) |
| 3. | EEKKGNYVVTDH | (SEQ ID NO: 73) |
| 4. | EKKGNYVVTDHG | (SEQ ID NO: 74) |
| 5. | KKGNYVVTDHGS | (SEQ ID NO: 75) |
| 6. | KGNYVVTDHGSC | (SEQ ID NO: 76) |
| 7. | GNYVVTDHGSCV | (SEQ ID NO: 77) |
| 8. | NYVVTDHGSCVR | (SEQ ID NO: 78) |
| 9. | YVVTDHGSCVRA | (SEQ ID NO: 79) |

In addition, functional epitopes were mapped by combinatorial Alanine scanning. In this process, a combinatorial Alanine-scanning strategy was used to identify amino acids in the EGFrVIII peptide necessary for interaction with anti-EGFrVIII mAbs. To accomplish this, a second set of SPOTs arrays was ordered for Alanine scanning. A panel of variants peptides with alanine substitutions in each of the 12 residues was scanned as above. Spot #1, the unmutated sequence, is a positive control for antibody binding. The array utilized is shown in Table 4.2.

TABLE 4.2

Alanine Scanning Array:

| | | |
|---|---|---|
| 1. | LEEKKGNYVVTD | (SEQ ID NO: -59) |
| 2. | AEEKKGNYVVTD | (SEQ ID NO: 80) |
| 3. | LAEKKGNYVVTD | (SEQ ID NO: 81) |
| 4. | LEAKKGNYVVTD | (SEQ ID NO: 82) |
| 5. | LEEAKGNYVVTD | (SEQ ID NO: 83) |
| 6. | LEEKAGNYVVTD | (SEQ ID NO: 84) |
| 7. | LEEKKANYVVTD | (SEQ ID NO: 85) |
| 8. | LEEKKGAYVVTD | (SEQ ID NO: 86) |
| 9. | LEEKKGNAVVTD | (SEQ ID NO: 87) |
| 10. | LEEKKGNYAVTD | (SEQ ID NO: 88) |
| 11. | LEEKKGNYVATD | (SEQ ID NO: 89) |
| 12. | LEEKKGNYVVAD | (SEQ ID NO: 90) |
| 13. | LEEKKGNYVVTA | (SEQ ID NO: 91) |

Epitopes of all 9 mAbs to the human EGFrVIII were mapped and identified by SPOTs procedure. All 9 antibodies were reactive with the peptides. The results obtained with 3 murine antibodies and 6 XenoMouse mouse derived human antibodies are presented in Table 4.3. Highlighted residues are those which we mutated to alanine and abrogated binding by the test antibody. These are therefore relevant residues for binding to the antibody.

TABLE 4.3

| | | |
|---|---|---|
| EGFR | A T C V K K C P R N Y V V T D H G S C V R A | SEQ ID NO: 92 |
| EGFRvIII | L E E K K G N Y V V T D H G S C V R A | (SEQ ID NO: 93) |
| 13.1.2 | E E K K G N Y V V T | (SEQ ID NO: 94) |
| 131 | E E K K G N Y V V T | (SEQ ID NO: 94) |
| 139 | L E E K K G N Y V V T D | (SEQ ID NO: 95) |
| 50 | L E E K K G N Y V V T D | (SEQ ID NO: 95) |
| 095 | Y V V T D H | (SEQ ID NO: 96) |
| 211 | Y V V T D | (SEQ ID NO: 97) |
| H10 | Y V V T D | (SEQ ID NO: 97) |
| Y10 | E E K K G N Y V V T | (SEQ ID NO: 98) |
| B9 | G N Y V V T | (SEQ ID NO: 99) |

The shaded amino acids shown in Table 4.3 are the most relevant residues in the epitope for antibody recognition. The minimal lengths of epitopes of all ten of the mAbs were precisely mapped using peptides of overlapping sequences, and the tolerance for mAb binding to mutated epitopes was determined by systematically replacing each residue in the epitope with Alanine.

In Table 4.4, additional characteristics of the antibodies are summarized. Specifically, a subset of the antibodies were tested for their binding of to lysates of tumor cell lines in Western plates of polyacrylamide gel electrophoresis under either non-reducing or reducing conditions. Purified recombinant protein is also included. Antibodies binding in both reducing and non-reducing conditions suggest that the epitope is linear. Sample identifications:

EGFRvIII—the rabbit Fc fusion protein

H1477—H80 human tumor cell line transfected with EGFRvIII expression construct. These cells express both EGFR and EGFRvIII.

EGFR—purified wild-type EGFR protein

A431—human tumor cell line expressing only wild-type EGFR

A549—human tumor cell line expressing only wild-type EGFR

H80—human tumor cell line expressing only wild-type EGFR

EGFR Biacore—mAbs were tested in Biacore for binding to purified EGFR as a highly sensitive test for specificity variant of EGFR expressed on the cell surface of some human tumor cell lines. This variant would be sensitive to denaturation.

Example 5

Characterization of Specificity of Anti-EGFRvIII Antibodies In Vitro

The specificity of the purified antibodies was ascertained by performing FACS analysis on NR6 cells that were transfected with either wild type or mutant EGFR. Cells were incubated on ice with 5 µg/ml of the respective antibody for 1 hr, washed in FACs buffer and subsequently incubated with PE-conjugated goat anti-human IgG.

Example 6

Cross-Reactivity with Amplified EGFR

Antibodies directed to variant EGF receptors have been shown to cross-react with subsets of wild type EGF receptors

TABLE 4.4

| mAb | EGFRvIII Western (native) | rEGFRvIII Western (reduced) | EGFRvIII FACS | H1477 Western (native) | H1477 Western (reduced) | pep3 KinExA | EGFR Western (native) | EGFR Western (reduced) |
|---|---|---|---|---|---|---|---|---|
| 13.1.2 | + | + | + | + | + | 25 pM | – | – |
| 131 | + | + | + | + | + | 0.05 pM | – | – |
| 139 | ? | + | + | ND | ND | ND | ND | ND |
| 095 | + | + | + | ND | ND | ND | ND | ND |
| 211 | + | + | + | ND | ND | ND | ND | ND |
| 250 | + | + | + | ND | ND | ND | ND | ND |

| MAb | EGFR Biacore | A431 FACS | A431 Western (native) | A431 Western (reduced) | A549 FACS | A549 Western (native) | A549 Western (reduced) | H80 FACS | H80 Western (native) | H80 Western (reduced) |
|---|---|---|---|---|---|---|---|---|---|---|
| 13.1.2 | – | – | – | – | – | – | – | – | – | – |
| 131 | – | ++ | – | – | + | – | – | – | – | – |
| 139 | N.D. | ND | ND | ND | ND | ND | ND | ND | ND | ND |
| 095 | – | ND | ND | ND | ND | ND | ND | ND | ND | ND |
| 211 | – | ND | ND | ND | ND | ND | ND | ND | ND | ND |
| 250 | – | ND | ND | ND | ND | ND | ND | ND | ND | ND |

The results showed that most of these mAbs have essentially the same binding specificity, seven of the mAbs were shown to bind specifically to the EGFrVIII variant, while 2 mAbs cross reacted with wildtype EGFr (murine H10 and human 211) in Western blots of purified protein and in lysate of A431 cells. Note, however, that while antibody 211 binds to both native and reduced purified EGFRvIII in Western blots, it binds slightly more strongly to the non-reduced protein. In tests against a lysate of A431 cells, antibody 211 binds strongly to a band of the size of wild-type EGFR in the non-reduced sample but there is no signal in the reduced sample. This suggests that the binding of antibody 211 is due to a conformational epitope present in wild-type EGFR and represented differently in the EGFRvIII variant. The epitopes of 5 of the mAbs are within residues 2-12 spanning the EGFRvIII variant specific Glycine residue, whereas the epitope of 4 of the mAbs (including H10 and 211) spans residues 7-16 which are common to the EGFRvIII and wild-type EGFr. Antibody 131 binds to A431 and A549 cells in FACS. These cells are apparently negative for expression of EGFRvIII while positive for EGFR expression. Antibody 131 does not bind to non-reduced or non-reduced purified EGFR or to reduced or non-reduced lysates of A43 and A549 cells in Westerns suggesting that antibody 131 may be binding to a on cells in which gene amplification has occurred (Johns et al., Int. J. Cancer. 98: 398, 2002). To determine whether the human EGFRvIII antibodies identified had similar properties, they were tested for their ability to recognize wild type EGF receptors on a variety of cells in culture. Antibodies were incubated with the indicated cell lines at 4° C. After washing in FACS buffer, a secondary antibody conjugated with phyoerythrin was added and the incubation was continued. All cell lines analyzed expressed wild type EGFR. A subset of wild type EGFRs was recognized by the antibody XG1-131 on both A431 and SF-539 cells but not on A498 or SKRC-52 cells. Another antibody to EGFRvIII, 13.1.2, did not recognize this subset of wild type EGFRs. When considered together these data indicate that only a subset of antibodies directed to the mutant EGFRvIII are able to recognize wild type EGFRs on the surface of cells. The ability of certain antibodies directed to mutant EGFRvIII to recognize a subpopulation of wild type EGF receptors is not dependent on total EGFR density but likely represents a novel conformational epitope that is unique to tumor cells. The ability of antibodies directed to EGFRvIII to cross-react with subpopulations of wild type receptors may be determined by both the specific epitope within the junction of the mutant receptor and the affinity of the antibody for this unique epitope (See the results of the epitope mapping and affinity determination section herein).

Example 7

Characterization of Specificity of Anti-EGFRvIII Antibodies In Vitro

Binding of the Antibodies to Cell Lines

The specificity of the purified antibodies was ascertained by performing FACS analysis on a panel of cell lines. H80, a human glioblastoma line, and H1477 (H80-EGFRvIII) that expresses high levels of EGFRvIII, A431, a human epidermoid carcinoma line, and A549, a human lung carcinoma cell line were used as the cell lines. All cell lines were from Dr. Bigner except A431 and A549, which were from ATCC (Rockville, Md., U.S.A.). Cells were incubated on ice with 10 µg/ml of the respective antibody for 30 min., washed in FACS buffer and subsequently incubated with PE-conjugated goat anti-human IgG from Jackson ImmunoResearch (West Grove, Pa., U.S.A.). In FIGS. 9A-9L and 10A-10D, the darkened histogram indicates cells stained with an irrelevant IgG, the outlined, or white histogram, represents the staining of the relevant antibodies. The anti-EGFRvIII antibodies 13.1.2, 131 and 139 bind to the EGFRvIII protein on the transfected cell lines. A graph summarizing some of the results is displayed in FIGS. 9M-9P.

Figure 10A:
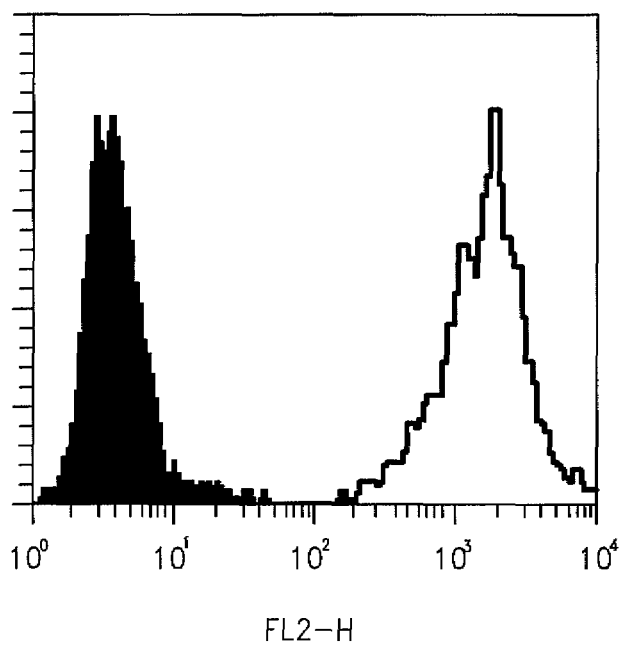
FIG. 10A shows FACS staining analysis for a human anti-EGFR antibody (ABX-EGF) binding to cells expressing EGFR (A431).
Figure 10B:
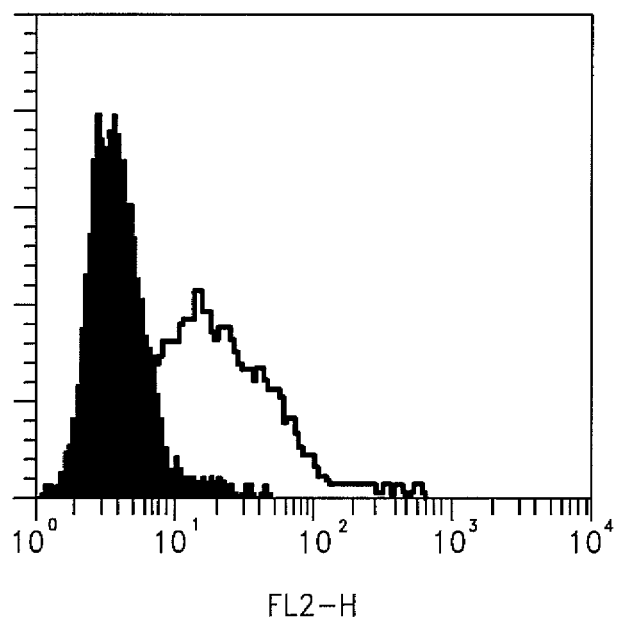
FIG. 10B shows FACS staining analysis for antibody 131 to cells expressing EGFR (A431).
Figure 10C:
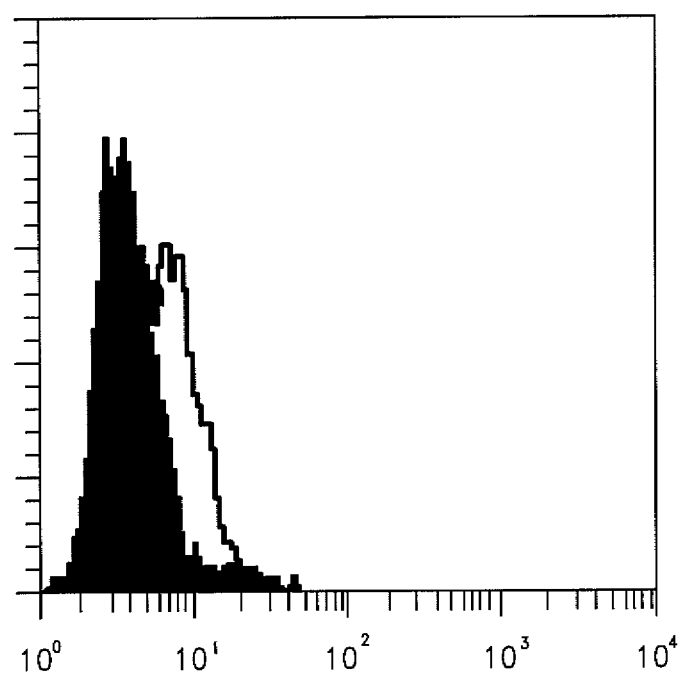
FIG. 10C shows FACS staining analysis for antibody 139 to cells expressing EGFR (A431).
Figure 10D:
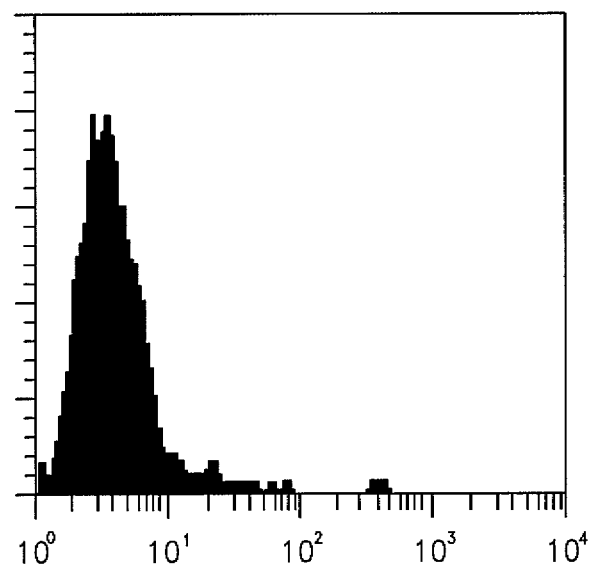
FIG. 10D shows FACS staining analysis for antibody 13.1.2 to cells expressing EGFR (A431).

Antibodies directed to variant EGF receptors have been shown to cross-react with subsets of wild type EGF receptors on cells in which gene amplification has occurred (Johns et al., Int. J. Cancer. 98: 398, 2002). In this example, A431 and A549 stained by XG1-131 and XG1-139. FIG. 10B and FIG. 10 C show that 131 and 139 have certain cross reactivity with the wild type EGFR instead of just recognizing a subset of population in H80, A431 and A549 line. However, this cross reactivity is only at 10% of the level of ABX-EGF (E7.6.3) staining on these cell lines. The results are provided in FIGS. 9A-9P and 10A-10D.

Antibodies directed to cell surface antigens can be used as delivery vehicles that specifically transport drugs or toxins into cells. If the antibody stimulates internalization of antigen, the drug or toxin can result in death of the cell, perhaps after the drug or toxin is cleaved from the antibody. Such a mechanism can be utilized to specifically kill tumor cells in animals and in patients. One way to select antibodies that can deliver drugs to cells is through secondary cytotoxicity assays. In these assays the primary antibody binds to the cell surface and a secondary antibody that is conjugated with a drug or toxin is added. If the primary antibody stimulates antigen internalization, the secondary antibody will be co-internalized and upon cleavage of the drug or toxin result in cell killing.

Example 8

Secondary Cytotoxicity Assays

This example demonstrates how the antibodies could be used to direct toxins conjugated via secondary antibodies to cells expressing the target epitope (target cell). Antibodies conjugated to a toxin are administered to cells expressing the target peptide. The death of those cells indicates the effectiveness of the antibody toxin combination.

The amount of specific killing required can vary depending upon the particular use. In one embodiment, any reduction in possibly cancerous cells is sufficient. For example, a reduction of 0-1, 1-5, 5-10, 10-20, 20-30, 30-40, 40-50, 50-60, 60-70, 70-80, 80-90, 90-95, 95-99, or 100% of the target cells will be sufficient. In another embodiment, the desired reduction in target cell number is also a function of the nonspecific lethality of the antibody combination. For example, antibody/toxin combinations that only have a 10% decrease in target cell number may be sufficient, if there is very little nonspecific targeting and lethality by the antibody. For example, the antibody toxin combination kills less than 10% of a non-target population. Again, the particular amount will depend on the particular need and situation. Particularly useful are antibodies that are highly selective for a target cell and bind well to the target cell, or proteins associated with the cell. In one embodiment, the target is the EGFRvIII protein, or a fragment thereof. In one embodiment, antibodies that are human, or humanized, efficient at being internalized, specific to the EGFRvIII protein or fragments thereof, associate tightly with the EGFRvIII protein or fragment, and are associated with an effective toxin, are taught from these examples.

Example 9

Secondary Cytotoxicity Clonogenic Assays

In addition to the secondary Cytotoxicity assays, EGFRvIII-specific antibodies can also be used for clonogenic assays. As above, antibodies associated with toxin are administered to cells. The ability of the cells to proliferate is monitored. A decrease in proliferation indicates that the antibody toxin combination is effective.

Example 10

Anti-EGFRvIII Antibody (13.1.2) Direct Conjugates in the Cytotoxicity Assays In addition to the indirectly conjugated examples above, these tests can also be performed with antibodies that are directly conjugated to the toxins. An antibody that is directly conjugated to a toxin is used in the same manner as described for the antibody toxin conjugate in Example 8.

Example 11

In Vivo Anti-EGFRvIII Antibodies Characterization

The antibody toxin conjugates can also be tested in vivo. An antibody toxin conjugate is administered to a test organism that has target cells that are expressing the target peptide. A decrease in the number of target cells in the test organism indicates the ability of the antibody conjugated toxin to work in an in vivo setting.

Example 12

Expression of EGFRvIII in Cancer Patients/Human Tumors

The expression of EGFRvIII on human tumors was determined by staining frozen tissue sections from a variety of cancer patients with a combination of 2 murine monoclonal antibodies (B9, IgG1 and Y10, IgG2 (Dr. Bigner, Duke University)) known to bind specifically to EGFRvIII. The same sections were stained with isotype matched control antibodies. A summary of the staining results obtained from all patient samples is presented in Table 12.1.

TABLE 12.1

Summary Of Staining Results From Patient Samples

| Tumor type | Sample Size (N) | EGFRvIII>+ | EGFRvIII>++ |
|---|---|---|---|
| Glioblastoma | 8 | 100% | 100% |
| Breast Cancer | 100 | 31% | 24% |
| NSCL cancer | 51 | 47% | 39% |
| Head & neck Cancer | 21 | 42% | 38% |
| Prostate Cancer | 22 | 4.5% | 4.5% |

EGFRvIII>+: include all tumors that express EGFRvIII
EGFRvIII>++: include only those tumors that express at least 10% or more EGFRvIII The expression was found primarily on the cell membrane and/or cytoplasm. Significant numbers of breast (31%), NSCL (47%), and head & neck (42%) cancer specimens stained positively for EGFRvIII. In certain instances, in order to obtain high quality IHC staining, the use of two antibodies can be better than the use of one antibody. Frozen tissue specimens were superior over fixed tissues.

As appreciated by one of skill in the art, it may be advantageous to test patients before using therapeutic antibodies to ensure that the tumor which is being treated expresses EGFRvIII.

Example 13

In Vivo Anti-EGFRvIII Antibodies Characterization

The method of Example 11 will be used to treat lung cancer and gliomas. This will be broadly examined by producing animal models. Animal models for glioblastoma and lung cancer are developed as follows: lung cancer cells that express wt-EGFR are transfected with EGFRvIII. The cells are injected into the lungs of nu/nu mice and tumors allowed to progress to a comparable stage to that above. Anti-EGFRvIII conjugates will then be injected intravenously as above every 1 to 10 days as needed. The size and prevention or suppression of continued growth of these cancer cells will then be monitored, to determine the effectiveness of these Anti-EGFRvIII antibodies and antibody-toxins combinations. As appreciated by one of skill in the art, this can be done for any of the antibodies disclosed herein.

Example 14

Functional Characterization of Epitopes by Substitional Analyses

In order to further resolve the identity of those amino acid residues that are indispensable for binding within the EGFRvIII epitope, substitutional analyses of the amino acids in the epitope peptides were performed. The starting point was the sequence that was derived from Example 4, LEEKKGNYVVTD (SEQ ID NO 59). In this example each amino acid of the mapped epitope was substituted one-at-a-time by all 20 L-amino acids, thus, all possible single site substitution analogs were synthesized and screened to provide detailed information on the mode of peptide binding. Discrete substitution patterns were identified for mAbs 131 and 13.1.2. The results from the substitutions are summarized in Table 14.1.

TABLE 14.1

| Abs | Recognition sequence | |
|---|---|---|
| 131 | E E K K G N Y V V T | (SEQ ID NO: 57) |
| 13.1.2 | E E K K G N Y V V T | (SEQ ID NO: 57) |

It appears that for mAb 13.1.2, 5 residues are important for binding (bold), while only 4 residues are essential for the binding of mAb 131. The rest of the residues were replaced by various amino acids without significant loss of binding. Although the 131 and 13.1.2 epitopes are identical by sequence and length, the binding pattern for each appears different. Binding of mAb 131 is strongly dependent on the residues EKNY (SEQ ID NO: 60). On the other hand, the data revealed that residues EEKGN (SEQ ID NO: 61) are involved in binding of mAb 13.1.2.

Example 15 mABS Chain Shuffling

Heavy and light chains of mAbs 131 and 13.1.2 were shuffled and transiently transfected into 293T cells. Seventy-two hours later supernatants were collected and assayed for secretion and binding to EGFrVIII antigen by ELISA.

The results demonstrated that antibodies derived from expression of 131 heavy chain with 13.1.2 kappa chain, and vice versa were expressed well but binding activity was reduced by 75% probably due to the different binding pattern of these two mAbs to EGFrVIII antigen. (data not shown). This demonstrates the difference between the two paratopes of the 131 and 13.1.2 mAbs, again suggesting that the structural characteristics of the epitope selected for between the two mAbs are different.

Example 16

Molecular Modeling of 131 and its Paratope

This example demonstrates how three-dimensional structures can be generated for the proteins of the embodiments. The three-dimensional structure model of the variable region of antibody 131 was generated through a homology modeling approach using the InsightII modeling package from Accelrys (San Diego, Calif.). The model was built from the variable region sequences described below, Table 16.1. The residue numbering starts with the light chain amino acids, and continues to heavy chain amino acids.

TABLE 16.1

| Light chain variable region | |
|---|---|
| DTVMTQTPLSSHVTLGQPASISC | (SEQ ID NO: 100) |
| RSSQSLVHSDGNTYLS (CDR1) | (SEQ ID NO: 101) |
| WLQQRPGPPRLLIY | (SEQ ID NO: 102) |
| RISRRFS (CDR2) | (SEQ ID NO: 103) |
| GVPDRFSGSGAGTDFTLEISRVEAEDVGVYYC | (SEQ ID NO: 104) |
| MQSTHVPRT (CDR3) | (SEQ ID NO: 105) |
| FGQTKVEIK | (SEQ ID NO: 106) |

TABLE 16.1-continued

Heavy chain variable region

| | |
|---|---|
| QVQLVESGGGVVQSGRSLRLSCAASGFTFR | (SEQ ID NO: 107) |
| NYGMH (CDR1) | (SEQ ID NO: 108) |
| WVRQAPGKGLEWVA | (SEQ ID NO: 109) |
| VIWYDGSDKYYADSVRG (CDR2) | (SEQ ID NO: 110) |
| RFTISRDNSKNTLYLQMNSLRAEDTAVYYCAR | (SEQ ID NO: 111) |
| DGYDILTGNPRDFDY (CDR3) | (SEQ ID NO: 112) |
| WGQGTLVTVSS | (SEQ ID NO: 113) |

Antibody 131 sequences were used to search against the Protein Data Bank to identify homologous antibodies and their structures. Based on the homologous antibodies' sequence similarity to the 131 antibody, several structures were selected. The structures selected for modeling samples from the Protein Data Bank had the Protein Data. Bank identifications of 1HEZ, 2H1P, 1AQK, 1DQL, 1MF2 and 1FLR. These template structures were then aligned by superposition and used to generate structure-based sequence alignments among the templates. The sequences of antibody 131's variable region were then aligned to the template sequences. The structure and sequence alignments were used to generate the molecular model for the variable region of the 131 antibody. The sequence for CDR1, light chain was: RSSQSLVHS-DGNTYLS (SEQ ID NO 101) The sequence for CDR2, light chain was: RISRRFS (SEQ ID NO 103). The sequence for CDR3, light chain was: MQSTHVPRT (SEQ ID NO 105). The sequence for CDR1, heavy chain was: NYGMH (SEQ ID NO 108). The sequence for CDR2, heavy chain was: VIW-YDGSDKYYADSVRG (SEQ ID NO 110). The sequence for CDR3, heavy chain was: DGYDILTGNPRDFDY (SEQ ID NO 112).

The interaction surface for antibody 131 was calculated from the structure model and shown in FIG. 11. The various CDRs are identified as follows: L1 (light CDR1) 10, H1 (heavy CDR1) 20, L2 30, H2 40, L3 50 and H3 60. A prominent feature on the predicted antibody 131 interaction surface is a deep cavity. The cavity is mainly surrounded by heavy chain CDR2, CDR3 and light chain CDR3, with a small portion contributed by light chain CDR1. The cavity is probably the binding pocket. Within 5 Angstroms of the binding cavity are residues 31, 37, 95-101, 143-147, 159, 162-166, 169-171, 211-219, 221 and 223. These residues are likely to comprise the paratope and make key contacts in the binding of EGFRvIII epitope. It is also likely that the residues provide important structural features to the binding site in general.

Example 17

Site-Directed Mutagenesis Confirming the Model for Antibody 131

This example demonstrates one method by which models that suggest residues that are important in binding may be tested. The Example also results in several antibody variants. Antibody variants of the 131 clone were generated by single residue mutations introduced to the heavy and the light chain of mAb 131. These variants were then analyzed to determine how the altered side chains from the point mutation contributed to antigen binding.

Changes were made in the heavy and light chains of mAb 131. On the heavy chain L216 was changed by site directed mutagenesis to R. On the light chain, V99 was changed to F. Both mutations affected the expression and secretion of the variant antibodies compared to the wildtype sequence. Both mutations resulted in a loss of binding of the mAb variant to the EGFRvIII antigen. This demonstrates L216 and V99 probably have significant contacts with the EGFRvIII antigen since substitutions of these residues to R and F respectively resulted in reduced activity. Of course, it is always an option that these substitutions are disruptive to the antibody's general structure.

Example 18

Molecular Modeling of 13.1.2 and its Paratope

The three-dimensional structure model of the variable region of the 13.1.2 antibody was generated through homology modeling approach with the InsightII modeling package from Accelrys (San Diego, Calif.). The model was built from the variable region sequences, shown below in Table 18.1, using the published x-ray crystal structures as templates.

TABLE 18.1

Light chain variable region (1-113)

| | |
|---|---|
| DIVMTQTPLSSPVTLGQPASISC | (SEQ ID NO: 114) |
| RSSQSLVHSDGNTYLS (CDR1) | (SEQ ID NO: 101) |
| WLHQRPGQPPRLLIY | (SEQ ID NO: 115) |
| KISNRFS (CDR2). | (SEQ ID NO: 116) |
| GVPDRFSGSGAGTAFTLKISRVEAEDVGVYYC | (SEQ ID NO: 117) |
| MQATQLPRT (CDR3) | (SEQ ID NO: 118) |
| FGQGTKVEIKR | (SEQ ID NO: 119) |

Heavy chain variable region (114-234)

| | |
|---|---|
| QVQLVESGGGVVQPGRSLRLSCAASGFTFS | (SEQ ID NO: 120) |
| SYGMH (CDR1) | (SEQ ID NO: 121) |
| WVRQAPGKGLEWVA | (SEQ ID NO: 122) |
| VIWYDGSNKYYVDSVKG (CDR2) | (SEQ ID NO: 123) |
| RFTISRDNSKNTLYLQMNSLRAEDTAVYYCAR | (SEQ ID NO: 124) |
| DGWQQLAPFDY (CDR3) | (SEQ ID NO: 125) |
| WGQGTLVTVSSA | (SEQ ID NO: 126) |

The sequence for CDR1, light chain was: RSSQSLVHS-DGNTYLS (SEQ ID NO: 101). The sequence for CDR2, light chain was: KISNRFS (SEQ ID NO: 116). The sequence for CDR3, light chain was: MQATQLPRT (SEQ ID NO: 118). The sequence for CDR1, heavy chain was: SYGMH (SEQ ID NO: 121). The sequence for CDR2, heavy chain was: VIWYDGSNKYYVDSVKG (SEQ ID NO: 123). The sequence for CDR3, heavy chain was: DGWQQLAPFDY (SEQ ID NO: 125).

Antibody 13.1.2 sequences were used to search the Protein Data Bank to identify homologous antibodies. The structures with the Protein Data Bank identifications of 1HEZ, 2H1P, 8FAB and 1AQK were selected as modeling templates, based on their sequence similarity to antibody 13.1.2. The template structures were aligned by superposition and used to generate structure-based sequence alignments among the templates. The sequences of the variable regions of the 13.1.2 antibody were then aligned to the template sequences. The structure and sequence alignments were used to generate the molecular model for antibody 13.1.2 variable region.

The interaction surface was calculated for the model and is shown in FIG. 12. A major feature of the 13.1.2 model is a long and narrow groove on the surface of the CDR region. The groove is outlined by heavy chain CDR2 140, CDR3 160, and light chain CDR1 110, CDR2 130 and CDR3 150. One end of the groove touches the rest of light chain CDR3 150, and the other end opens to the wider area of heavy chain CDR3 160 near the heavy chain-light chain interface. The groove is probably the binding pocket for the antigen. Within 5 Angstroms of the binding groove are residues 31, 33, 35-39, 51, 54-56, 58-61, 94-101, 144-148, 160, 163-166, 172, and 211-221. These residues are likely to comprise the paratope for the binding of EGFRvIII epitope. It is also likely that the residues provide important structural features to the binding site in general.

Example 19

Docking Models of a Peptide to an Antibody

The epitope mapping studies in Example 14 revealed that the relevant amino acids required for binding of the epitope to the paratope of 13.2.1 mAb reside in the six-residue peptide EEKKGN (SEQ ID NO: 127). Therefore, docking models of this six-residue peptide complexed to the CDR region of 13.1.2 structure model were generated, First, a model of the peptide EEKKGN (SEQ ID NO: 127) was produced. This was done, similarly as described before, except this time using the x-ray crystal structure of 1I8I, as identified in the Protein Data Bank, as the template. Next, this peptide structure was manually placed into the long groove to form an initial assembly complex. A Monte Carlo search in the conformational and orientational spaces were then automatically performed with the Docking module in InsightII. The peptide conformation was allowed to be flexible by giving each of the Phi, Psi and Chi angles full rotational freedom. During the docking process, the residues within 5 Angstroms of the binding groove were allowed to move while the other residues of the antibody were fixed. The plausible configurations found by Monte Carlo search were subjected to simulated annealing and energy minimization to reach the final complex structure models. For each docking model obtained, the interaction energy between the antibody and the peptide was calculated with the Discover_3 module of InsightII package. The interaction energies for all docking models were assessed and the model with the strongest overall antibody-peptide interaction was examined and is shown in FIGS. 13A and 13B.

In this docking model, there are six hydrogen bonds between peptide EEKKGN (SEQ ID NO: 127) and antibody 13.1.2, as shown in FIG. 13B. The peptide residue number is labeled from N-terminus to the C-terminus as 1 through 6. Six hydrogen bonds are indicated by green dashed lines. The six pairs of amino acids forming hydrogen bonds are: E2 . . . Y172, K3 . . . H31, K4 . . . H31, N6 . . . D33, N6 . . . Y37, and N6 . . . K55. In this docking model, the peptide is bound to the groove in an extended β-strand conformation. Residues in the peptide alternately face the solvent and the antibody surface. The residues facing the binding groove with the most significant contacts to the antibody are E2, K4 and N6. This indicates that these three residues may be important to peptide binding, consistent with the epitope mapping results. The interaction energies for each of the six peptide residues with the 13.1.2 paratope was calculated with the Discover_3 module and the results are shown in Table 19.1. Table 19.1 shows the interaction energies for each of the six peptide residues with the 13.1.2 paratope. All energies are in the unit of kcal/mol.

The residues with the strongest interaction energies are in the order of N6, K4 and E2, confirming that these residues are key contributors on the antigen side in the antibody-antigen interaction, again consistent with experimental data. These data provided strong evidence to support the docking model. In this embodiment, the paratope is defined as the residues within 5 Angstroms of the docked peptide. The 20 residues comprising the paratope as so defined are residues 31-33, 35, 37, 55, 96-101, 148, 163, 165, 170, 172, 178 and 217-218. To evaluate, on an individual residue basis, the contribution of each of these residues of the antibody in the antibody-antigen interaction, the interaction energy between the paratope residues and the peptide EEKKGN (SEQ ID NO: 127) was calculated for each of the above 20 residues. The results are listed in Table 19.2. Table 19.2 shows the interaction energies for each of the 20 paratope residues with the peptide EEKKGN (SEQ ID NO:127). All energies are in the unit of kcal/mol. The residues with the strongest interaction energies with the peptide are Lys55 and His31, followed by Tyr172, Ala96, Asp33, Tyr37, Leu99, Thr97, Gln98, Lys178 and Asn170.

TABLE 19.1

| Peptide Residue | Coulumbic | VdW | Total |
|---|---|---|---|
| E1 | −2.013 | −3.738 | −5.751 |
| E2 | −10.661 | −0.617 | −11.278 |
| K3 | −9.816 | −0.493 | −10.309 |
| K4 | −11.123 | −0.968 | −12.091 |
| G5 | −1.241 | −1.468 | −2.709 |
| N6 | −16.504 | −0.181 | −16.685 |

TABLE 19.2

| 13.1.2 Residue | Coulumbic | VdW | Total |
|---|---|---|---|
| His31 | −12.835 | 3.033 | −9.801 |
| Ser32 | 2.857 | −1.062 | 1.794 |
| Asp33 | −4.181 | −0.698 | −4.879 |
| Asn35 | 0.253 | −1.009 | −0.756 |
| Tyr37 | −2.058 | −2.463 | −4.521 |
| Lys55 | −14.363 | 1.568 | −12.794 |
| Ala96 | −6.077 | 0.896 | −5.182 |
| Thr97 | −2.739 | −1.431 | −4.171 |
| Gln98 | −2.542 | −1.548 | −4.09 |
| Leu99 | −1.507 | −2.779 | −4.286 |
| Pro100 | 0.439 | −0.379 | 0.061 |
| Arg101 | 3.992 | −0.549 | 3.443 |
| His148 | 0.101 | −0.083 | 0.018 |
| Val163 | −0.104 | −0.237 | −0.342 |
| Trp165 | 1.358 | −1.122 | 0.236 |
| Asn170 | −2.102 | −0.487 | −2.589 |
| Tyr172 | −8.7 | 0.896 | −7.804 |
| Lys178 | −3.614 | −0.03 | −3.644 |
| Leu217 | 0.761 | −1.426 | −0.664 |
| Ala218 | −0.071 | −0.281 | −0.352 |

Example 20

Rational Design for Affinity-Improved Antibodies

This Example demonstrates how the docking model can be used as the basis of rational design for affinity-improved antibodies by site-directed mutagenesis. Each of the 13.1.2 paratope residues was mutated to all 19 other amino acids in silico, resulting in a total of 19×20 or 380 virtual mutants. The mutation was done by residue replacement followed by 50 steps of energy minimization to account for any local conformational changes that could be induced by the side chain change. The interaction energy between the whole peptide and the whole paratope was calculated for each mutant. Mutants with a total interaction energy stronger than the wild type 13.1.2 could potentially have a higher affinity for the peptide EEKKGN (SEQ ID NO: 127), and perhaps even the whole EGFRvIII protein. These mutants mostly have stronger coulumbic interactions than the wild type 13.1.2, but some of them have weaker van der Waals (VdW) interactions than the wild type antibody. Considering that in the wild type 13.1.2 antibody, the VdW interacting energy is −9.689 kcal/mol, mutants with VdW interaction energy weaker than −8.5 kcal/mol were filtered out. The rest of the mutants that have stronger, total interaction energy, than the wild type 13.1.2 are listed in Table 20.1. The wild type data are listed at the bottom for comparison. All energies are in the units of kcal/mol. The numbering in Table 20.1 starts with light chain amino acids and continues to heavy chain amino acids.

TABLE 20.1

| Mutant | Coulumbic | VdW | Total |
|---|---|---|---|
| Tyr172Arg | −93.004 | −8.702 | −101.706 |
| Leu99Glu | −79.897 | −8.506 | −88.403 |
| Arg101Glu | −77.984 | −8.833 | −86.817 |
| Leu217Glu | −75.124 | −8.998 | −84.123 |
| Leu99Asn | −73.337 | −9.894 | −83.231 |
| Leu99His | −73.631 | −9.008 | −82.639 |
| Arg101Asp | −71.983 | −9.877 | −81.861 |
| Leu217Gln | −70.263 | −9.795 | −80.058 |
| Leu99Thr | −69.882 | −10.153 | −80.035 |
| Gln98Glu | −70.651 | −9.257 | −79.908 |
| Leu217Asn | −70.989 | −8.769 | −79.758 |
| Arg101Gln | −69.432 | −10.164 | −79.596 |
| Leu217Asp | −69.934 | −9.643 | −79.578 |
| Asn35Gly | −69.016 | −10.191 | −79.207 |
| Tyr172His | −69.312 | −9.509 | −78.820 |
| Val163Asn | −68.841 | −9.944 | −78.784 |
| Tyr172Asn | −68.896 | −9.871 | −78.767 |
| Ala218Lys | −70.024 | −8.570 | −78.594 |
| Asn35Arg | −68.989 | −9.604 | −78.593 |
| Trp165Lys | −69.578 | −8.766 | −78.344 |
| Trp165Arg | −68.814 | −9.216 | −78.030 |
| Leu99Tyr | −67.052 | −10.464 | −77.517 |
| Tyr172Thr | −68.146 | −9.225 | −77.371 |
| Ala96Thr | −67.534 | −9.623 | −77.158 |
| Ala96Ser | −67.222 | −9.822 | −77.045 |
| Pro100Trp | −67.399 | −9.496 | −76.894 |
| Leu217Ser | −66.676 | −10.133 | −76.810 |
| Ser32Ile | −66.700 | −10.077 | −76.777 |
| Tyr172Ser | −67.588 | −9.146 | −76.734 |
| His31Glu | −67.070 | −9.461 | −76.531 |
| Leu217Tyr | −65.605 | −10.726 | −76.331 |
| Val163His | −67.236 | −9.064 | −76.300 |
| His148Ser | −66.780 | −9.495 | −76.274 |
| His148Val | −66.634 | −9.629 | −76.263 |
| His148Ala | −66.770 | −9.473 | −76.243 |
| His148Gly | −66.762 | −9.456 | −76.217 |
| His148Thr | −66.700 | −9.508 | −76.209 |
| Leu99Ser | −66.126 | −10.006 | −76.132 |
| Pro100Asp | −66.153 | −9.787 | −75.940 |
| Trp165Glu | −66.665 | −9.267 | −75.932 |
| His148Asn | −66.010 | −9.889 | −75.899 |
| Pro100Gln | −65.873 | −9.871 | −75.745 |
| Leu217Thr | −66.045 | −9.672 | −75.717 |
| Ser32Val | −65.845 | −9.854 | −75.699 |
| Ser32Pro | −65.807 | −9.813 | −75.620 |
| Pro100Gly | −65.841 | −9.774 | −75.615 |
| Pro100Ala | −65.889 | −9.712 | −75.601 |
| Ser32Ala | −65.497 | −10.089 | −75.586 |

TABLE 20.1-continued

| Mutant | Coulumbic | VdW | Total |
|---|---|---|---|
| Ser32Thr | −65.723 | −9.861 | −75.584 |
| Ala218Thr | −66.054 | −9.505 | −75.560 |
| Pro100Ser | −65.831 | −9.699 | −75.530 |
| Val163Gly | −65.993 | −9.536 | −75.529 |
| Gln98Thr | −66.162 | −9.277 | −75.438 |
| Pro100Met | −65.811 | −9.602 | −75.412 |
| Ser32Met | −66.252 | −9.153 | −75.406 |
| Ser32Gly | −65.509 | −9.891 | −75.399 |
| Pro100Asn | −65.729 | −9.655 | −75.384 |
| Tyr37Phe | −66.253 | −9.020 | −75.272 |
| Val163Ala | −65.713 | −9.543 | −75.255 |
| Leu217Ile | −65.479 | −9.759 | −75.238 |
| Wild type 13.1.2 | −65.517 | −9.689 | −75.205 |

The mutants listed in Table 20.1 could be candidates for engineering of affinity-improved antibodies. For the top 14 candidates in the list, per residue contributions on the antigen side and on the antibody side were further analyzed to examine the impact of the proposed modifications. The 10 mutants selected for in vitro site-directed mutagenesis were Tyr172Arg, Arg101Glu, Leu99Asn, Leu99His, Arg101Asp, Leu217Gln, Leu99Thr, Leu217Asn, Arg101Gln and Asn35Gly. The results can be seen in Example 21.

Example 21

Site-Directed Mutagenesis Confirming the Model for 13.1.2

This example demonstrates one method by which the above models, which suggest residues that are important in binding, can be tested. The Example also results in several antibody variants. Antibody variants of 13.1.2 were generated by single residue mutations introduced into the heavy and the light chains of the 13.1.2 mAb. The variants were analyzed to determine the contribution that the various side chains had in antigen binding. A list of the mutations introduced by site directed mutagenesis are summarized in Table 21.1.

TABLE 21.1

|   | Chain | Mutation |
|---|---|---|
| 1 | Light chain (CDR3) | Arg101Asp |
| 2 | Light chain (CDR3) | Arg101Gln |
| 3 | Light chain (CDR3) | Arg101Glu |
| 4 | Light chain (CDR1) | Asn35Gly |
| 5 | Heavy chain (CDR3) | Leu217Asn |
| 6 | Heavy chain (CDR3) | Leu217Gln |
| 7 | Light chain (CDR3) | Leu99Asn |
| 8 | Light chain (CDR3) | Leu99His |
| 9 | Light chain (CDR3) | leu99Thr |
| 10 | heavy chain (CDR2) | Tyr172Arg |

Each of the 10 mutations in Table 21.1 was introduced into the heavy or light chain of the 13.1.2 mAb. Each mutated chain was then transfected with the complementarity wild-type chain in 293 cells. Supernatants were then tested for expression and secretion of human IgG antibodies, and for binding to EGFrVIII antigen. The results, as determined by an ELISA, are summarized in Table 21.2.

TABLE 21.2

|   | Mutation | Binding Energy | Expression | Binding |
|---|---|---|---|---|
| 1 | Arg101Asp | −81.861 | Yes | No |
| 2 | Arg101Gln | −79.596 | Yes | No |

TABLE 21.2-continued

|   | Mutation | Binding Energy | Expression | Binding |
|---|----------|----------------|------------|---------|
| 3 | Arg101Glu | −86.817 | Yes | No |
| 4 | Asn35Gly | −79.207 | Yes | Yes |
| 5 | Leu217Asn | −79.758 | Yes | Yes |
| 6 | Leu217Gln | −80.058 | Yes | Yes |
| 7 | Leu99Asn | −83.231 | Yes | Yes |
| 8 | Leu99His | −82.639 | Yes | Yes |
| 9 | Leu99Thr | −80.035 | Yes | Yes |
| 10 | Tyr172Arg | −101.706 | Yes | Yes |
| 11 | WT | −75.205 | Yes | Yes |

Example 22

Preparation Of EGFRvIII/pFLAG Variant Construct

This example demonstrates how a variant to EGFRvIII can be made. A 1092 bp fragment encoding the extracellular domain of EGFRvIII was generated with primer pairs 9712 and 9713 (Qiagen, Valencia, Calif.):

```
Primer # 9712:
                                  (SEQ ID NO 128)
5'-ataaaagcttctggaggaaaagaaaggtaatta-3'
(sense)

Primer # 9713:
                                  (SEQ ID NO 129)
5'-TTATTGGTACCTCAGGCGATGGACGGGATCTTA-3'
(antisense)
``` from plasmid template EGFRvIII-rbIgG/pCEP4 (as described above) amplified using Pfu DNA polymerase enzyme (Stratagene, La Jolle, Calif.). Primer #9712 introduced a HindIII site and primer #9713 introduced a KpnI site. The PCR product was column purified (Qiagen column purification kit, Valencia, Calif.) digested with HindIII and KpnI (NEB, New England Biolabs, Beverly, Mass.) and gel purified (Qiagen gel purification kit, Valencia, Calif.). Fragments were ligated with T4 DNA Ligase (NEB, New England Biolabs, Beverly, Mass.) into pFLAG-CMV-1 (Sigma, St. Louis, Mo.) linearized with HindIII and KpnI (NEB, New England Biolabs, Beverly, Mass.). The resulting vector was designated EGFRvIII/pFLAG-CMV-1#1.

Example 23

Preparation of EGFRvIIIpFLAG/Recombinant Protein

This example demonstrates how a variant EGFRvIII protein can be made. First, 500 µg of EGFRvIII/pFLAG-CMV-1#1 plasmid DNA was resuspended in 25 ml of Opti-MEMI (Invitrogen, Burlington, ON) and combined with 500 µl of 293fectin (Invitrogen, Burlington, ON) resuspended in 25 ml of Opti-MEMI. The mixture was incubated for 20 min at room temperature then mixed with 293T cells (1×10$^9$) prepared in 1 L 293 FreeStyle media (Invitrogen, Burlington, ON), supplemented with 2% FBS and 50 µg/ml G418 (Invitrogen, Burlington, ON). Cells are grown for 7 days at 37° C. in 8% $CO_2$ with shaking at 125 rpm.

EGFRvIII-FLAG fusion protein purification was carried out with Anti-FLAG M2 Affinity Chromatography kit (Sigma, St. Louis, Mo.) according to the manufacture's protocol.

Monomeric fusion protein was produced as follows. First, purified protein (1508 µg), was reduced with DTT in a final concentration of 10 mM for 30 minutes at 55° C. Then IAA (iodoacetic acid) (Sigma, St. Louis, Mo.) was added to 22 mM and incubated 15 minutes at room temperature in the dark then dialyzed against PBS at 4° C. in 7k MWCO dialysis cassettes (Pierce, Rockford, Ill.).

Examples 24-30

Binding Studies of Antibody Variants

The following examples involve Biacore experiments (surface plasmon resonance) and KinExA experiments. These examples demonstrate how one can test the various antibodies and variants thereof produced by the above examples to determine if they have the desired binding characteristics. All of the variants examined were variants in the 13.1.2 background.

Instrumentation

All surface plasmon resonance experiments were performed using Biacore 2000 optical biosensors (Biacore, Inc., Piscataway, N.J.). All Kinetic Exclusion Assays were performed using a KinExA 3000 instrument (Sapidyne Instruments, Inc., Boise, Id.).

Reagents

Pep-3, $NH_2$-LEEKKGNYVVTDHG-OH (MW=1590 Da) (SEQ ID NO: 130), was custom synthesized and purchased from Anatech, Inc. (San Jose, Calif.). All mAbs were prepared in-house. The antigen EGFRvIIIpflag (iodoacetic acid reacted in order to block aggregation through free sulfhydryl groups), MW 39,907, was prepared in-house. Bovine serum albumin (BSA) fraction V (#BP1605-100) was purchased from Fisher Scientific (Pittsburgh, Pa.). All other general reagents were purchased from Sigma-Aldrich, Inc (St. Louis, Mo.).

All antigen and mAb samples for Biacore and KinExA analysis were prepared in vacuum-degassed HBS-P buffer (0.01 M HEPES, 0.15 M NaCl, 0.005% surfactant P-20, Biacore Inc., Uppsala, Sweden) containing 100 µg/mL BSA. Biacore amine-coupling reagents, 1-ethyl-3-(3-dimethylaminopropyl) carbodiimide (EDC), N-hydroxysuccinimide (NHS), and ethanolamine were purchased from Biacore, Inc. Biacore surface regeneration was with a 12 second pulse of 26 mM NaOH for the pep-3/mAb 131 experiment. All other mAbs dissociated to baseline within 20 minutes. Research grade CM5 biosensor chips were purchased from Biacore, Inc.

The KinExA detection antibody was Cy5-labeled goat anti-human IgG, Fcγ specific (Jackson ImmunoResearch Laboratories, Inc., West Grove, Pa., #109-175-008) and was diluted 1000-fold in HEPES buffer (0.01 M HEPES, 0.15 M NaCl, pH 7.2) from a 0.5 mg/mL stock (1×PBS, pH 7.4). The solid phase particles used for the KinExA experiments were NHS-activated Sepharose 4 Fast Flow beads (Pharmacia Biotech AB, Uppsala, Sweden, #17-0906-01). Prior to reacting the sepharose beads with antigen, a bead stock aliquot of 1.5 mL in a microcentrifuge tube was spun down and washed at least six times with cold deionized $H_2O$. After rinsing the beads once with sodium carbonate buffer (0.05 M, pH 9.3), antigen (~40 µg) in sodium carbonate buffer was added to the sepharose beads. The sepharose/antigen tube was rocked overnight at 4° C. After rocking, the sepharose was spun and rinsed twice with 1 M Tris buffer, pH 8.3. The antigen-coated beads were then rocked for 1 hour at room temperature in 1 M Tris buffer with 2% BSA.

Biacore Measurements

Standard EDC/NHS and carbohydrate coupling was used to covalently immobilize mAbs to a CM5 sensor chip. To minimize mass transport and crowding mAbs were immobilized at levels that gave a maximum antigen binding response ($R_{max}$) of no more than 50-100 RU. A reference flow cell on each chip was activated and blocked with no mAb immobilization to serve as a control.

All Biacore kinetic experiments were conducted at 23° C. For each experiment, a series of six to eight antigen concentrations (starting with 1.01 µM pep-3) was prepared using 2-fold dilutions. Antigen samples were randomly injected over the biosensor surface in triplicate at 100 µL/min. Several buffer blanks were injected intermittently over the course of an experiment for double referencing. Each pep-3 concentration and blank were injected for 90 seconds. Dissociation was followed for 13 to 180 minutes. Dissociation data for pep-3 binding to mAb 131 were acquired by alternating three additional injections of 251 nM pep-3 with three additional blank injections and following the dissociation phase for 3-4 hours.

All Biacore sensorgrams were processed using Scrubber software (Version 1.1f, BioLogic Software, Australia). Sensorgrams were first zeroed on the y-axis and then x-aligned at the beginning of the injection. Bulk refractive index changes were removed by subtracting the reference flow cell responses. The average response of all blank injections was subtracted from all analyte and blank sensorgrams to remove systematic artifacts between the experimental and reference flow cells. CLAMP biosensor data analysis software (Version 3.40, BioLogic Software, Australia) was used to determine $k_a$ and $k_d$ from the processed data sets. Data from all flow cells were globally fit to a 1:1 bimolecular binding model that included a mass transport term. For several of the mAbs the injections corresponding to the first or second concentration of the pep-3 series were excluded in the nonlinear kinetic fit where it was obvious that the sensorgrams were not described well by a 1:1 interaction model. The $K_D$ was calculated from the quotient $k_d/k_a$.

KinExA Equilibrium Measurements

All KinExA experiments were conducted at room temperature (~23° C.). For all equilibrium experiments, antigen was serially diluted into solutions having a constant mAb binding site concentration. For the first 10 titration points the dilutions were 2-fold and the $11^{th}$ and $12^{th}$ serial dilutions were 10-fold. The sample flow rate for all experiments was 0.25 mL/min and the labeling antibody flow rate was 0.5 mL/min. Antigen/antibody samples were then allowed to reach equilibrium, which took ~48-72 hr to reach. For the pep-3/mAb 131 KinExA experiment the starting concentration of pep-3 in the $K_D$-controlled titration was 352 nM and the constant [mAb binding site]=219 pM; for the mAb-controlled titration the starting [pep-3]=251 nM and the [mAb binding site]=11 nM. During the $K_D$-controlled experiment with pep-3/mAb 131, 1.25 mL of each sample was drawn through the flow cell. A sample volume of 250 µL was analyzed for the antibody-controlled experiment. Two or three replicates of each sample were measured for all equilibrium experiments. The equilibrium titration data were fit in a dual curve analysis to a 1:1 binding model using KinExA software (Version 2.4, Sapidyne Instruments).

The EGFRvIIIpflag/mAb 131 complex was studied with KinExA under $K_D$-controlled conditions only. The starting [EGFRvIIIpflag] was 198 nM and the [mAb binding site] was 150 pM. A sample volume of 1 mL was drawn through the flow cell. Duplicate measurements were collected for all samples. The equilibrium titration data were fit in a dual curve analysis to a 1:1 binding model using KinExA software (Version 2.4, Sapidyne Instruments). See Example 28 below for results and predicted equilibrium constant.

For the KinExA titrations of the EGFRvIIIpflag/mAb 13.1.2 complex the starting concentration of EGFRvIII was 5.26 µM (mAb-controlled), 230.1 nM ($K_D$-controlled) and [mAb binding site]=9.59 nM (mAb-controlled), 498 pM ($K_D$-controlled). During the $K_D$-controlled experiment, 1.30 mL of each sample was drawn through the flow cell. A sample volume of 250 µL was analyzed for the antibody-controlled experiment. Two or three replicates of each sample were measured for all equilibrium experiments. The equilibrium titration data were fit in a dual curve analysis to a 1:1 binding model using KinExA software (Version 2.4, Sapidyne Instruments).

Example 24

In Vitro Determination of Binding Constants for Antibodies

The binding kinetics of the wild type mAb 131 was observed by using a Surface Plasmon Resonance (SPR) instrument from Biacore. The $K_D$ was very low, 380 pM, owing to the very slow $k_d$ and a rapid $k_a$. Estimates for the other kinetic parameters, derived from curve fitting, were $k_a=2.246\times10^6$ and $k_d=8.502\times10^{-4}$.

In one embodiment, improved or variant antibodies with improved kinetics are taught. By improved kinetics, it is meant that one of the kinetic elements of antibody binding to an epitope is superior to the same element in previously known antibodies for the same epitope. For example, an antibody that binds to pep-3 with a $K_D$ of greater (in binding ability) than $1.3\times10^{-9}$ M would be an improved antibody. As such, antibodies with a $K_D$ of less than 500 nM, 500-300 nM, 300-100nM, 100-1nM, 1.3 nM, 1.3 nM to 1000 pM, 1000 pM to 900 pM, 900-500pM, 500-400 pM, 400-300 pM, 300-100 pM, 100-50 pM, 50-1 pM, or smaller $K_D$ are contemplated.

Example 25

In Vitro Determination of Binding Constants for Antibodies

Similar to Example 24, the binding kinetics of mAb13.1.2 to Pep-3 (EGFRvIII epitope) were examined. The estimated $K_D$ was 67 nM, but varied slightly between experiments. Estimates, for the other kinetic parameters, derived from curve fitting, were $k_a=2.835\times10^5$ and $k_d=0.01922$.

Example 26

In Vitro Determination of Binding Constants for Antibodies

Similar to Example 24, the binding kinetics of mAb 095 to Pep-3 (EGFRvIII epitope) were examined. The estimated $K_D$ was 66 nM. Estimates, for the kinetic parameters, derived from curve fitting, were $k_a=1.491\times10^5$ and $k_d=9.927=10^{-3}$.

Example 27

In Vitro Determination of Binding Constants for Antibodies

Similar to Example 24, the binding kinetics of mAb 139 to Pep-3 (EGFRvIII epitope) were examined. The estimated $K_D$ was 290 nM. Estimates, for the kinetic parameters, derived from curve fitting, were $k_a=10328$ and $k_d=2.981\times10^{-3}$.

Example 28

In Vitro Determination of Binding Constants for Antibodies

In order to more fully analyze the binding characteristics of the antibodies, KinExA experiments were performed to determine the binding characteristics of the mAb 131. The $K_D$ determined from a dual curve analysis was $1.74 \times 10^{10}$. In a KinExA experiment, the $K_D$ for EGFRvIIIpflag to mAb 131 was $6.266 \times 10^{-11}$.

Example 29

In Vitro Determination of Binding Constants for Variant Antibodies

In order to more fully analyze the binding characterisitics of the 13.1.2 antibodies, a KinExA experiment was performed to determine the binding characteristics of the mAb 13.1.2. The $K_D$ determined from a dual curve analysis was $7.538 \times 10^{-10}$. Additionally, the antigen in this example was the EGFRvIIIpflag variant and was reacted with iodoacetic acid (IAA).

Example 30

Comparison of Biacore Results and Kinexa Results

The results of the previous Examples and the KinExA tests are presented in Table 30.1 below. Numbers in parentheses in Table 30.1 are 95% confidence intervals. "ND," means not determined and "*" denotes binding to EGFRvIIIpflag (iodoacetic acid reacted), instead of pep-3.

As is evidenced by the rate constants, mAb 131 appears to have the greatest association constant and the lowest dissociation constant, thus giving mAb 131 the lowest $K_D$.

TABLE 30.1

| MAb | $K_a$ (M$^{-1}$s$^{-1}$) | $K_d$ (s$^{-1}$) | $K_D$ (nM) | KinExA $K_D$ (nM) |
|---|---|---|---|---|
| 131 | $2.25 \times 10^6$ | $8.50 \times 10^{-4}$ | 0.380 | 0.174 (0.0627 on EGFRvIIIpflag) |
| 13.1.2 | $2.10 (0.58) \times 10^5$ | 0.016 (0.003) | 75 (14) | 0.75 (on EGFRvIIIpflag (IAA reacted)) |
| 095 | $1.49 \times 10^5$ | $9.90 \times 10^{-3}$ | 66 | ND |
| 139 | $1.03 \times 10^4$ | $2.98 \times 10^{-3}$ | 290 | ND |

Example 31

In Vitro Determination of Binding Constants for L99T-5.3 Variant Antibodies

The binding kinetics of mAb L99T-5.3 to Pep-3 (EGFRvIII epitope) were examined. The first step was to immobilize 5,600 resonance units (RU) to 8,000 RU of mAb L99T-5.3 to two flow cells (Fc) of a CM5 sensor chip and 5,600 resonance units (RU) to 8,000 RU of mAb 13.1.2 to one Fc using standard EDC/NHS coupling chemistry. This surface density yielded a binding signal with pep-3 of less than 100 RU. Two CM5 sensor chips were used in total to immobilize both mAbs. With the previously collected data, this produced a total of 5 independent experiments for both antibodies that allows the 95% confidence intervals to be calculated. Biacore 2000 optical biosensors were used for all studies.

Next, pep-3 was flowed across the mAb immobilized biosensor surfaces. The starting concentration of pep-3 was 1.25 µM, which was followed with eight two-fold serial dilutions in randomized triplicate injections. Blank injections were run every sixth sample throughout the injection series for double referencing purposes.

Finally, the biosensor data was processed with Scrubber and the data was fit to curves utilizing Clamp with a 1:1 interaction model with a term included for mass transport. The high concentration injections, 1.25 µM, were excluded from the kinetic fits because it was apparent that the data was not consistent with a 1:1 interaction model. Most likely, this deviation is caused by non-specific interactions occurring at high concentrations of pep-3. All the kinetic data fit a 1:1 interaction model satisfactorily.

The estimated $K_D$ varied from 54-70 nM. Estimates, for the other kinetic parameters, which also varied slightly between runs, were $-k_a = 2.238 \times 10^5$ and $k_d = 0.01217$.

Examples 32-38

Examples 32-38 further examined the binding kinetics of the variant mAbs through the use of a Biacore device. The first step in these examples involved the immobilization of 5,600 resonance units (RU) to 8,000 RU of each mAb tested to one flow cell (Fc) of a CM5 sensor chip using standard EDC/NHS coupling chemistry. This surface density yielded a binding signal with pep-3 of less than 100 RU. Three CM5 sensor chips were used in total to immobilize all mutant mAbs with a unique mAb immobilized to each flow cell. MAb 13.1.2 was included on one flow cell for two out of the three CM5 sensor chips. Biacore 2000 optical biosensors were used for all studies.

Next, pep-3 was run across the mAb immobilized biosensor surfaces. The starting concentration of pep-3 was 4.98 µM, followed by eight to eleven two-fold serial dilutions in randomized duplicate or triplicate injections. Blank injections were run every sixth sample throughout the injection series for double referencing purposes.

Finally, the biosensor data was processed with Scrubber and fitted utilizing Clamp with a 1:1 interaction model with a term included for mass transport. Some high concentration injections (4.98-1.25 µM), depending upon the mAb and its affinity, were excluded from the kinetic fits when it was apparent that the data was not consistent with a 1:1 interaction model. Most likely, this deviation is caused by non-specific interactions occurring at high concentrations of pep-3. All the kinetic data fit a 1:1 interaction model.

Example 32

In Vitro Determination of Binding Constants for L217Q-10.1 Variant Antibodies The binding kinetics of mAb L217Q-10.1 to Pep-3 (EGFRvIII epitope) were examined. The estimated $K_D$ was 92 nM. Estimates, for the other kinetic parameters, derived from curve fitting, were $-k_a = 2.04 \times 10^5$ and $k_d = 0.01885$.

Example 33

In Vitro Determination of Binding Constants for L217N-2.1 Variant Antibodies Similar to Example 32, the binding kinetics of mAb L217N-2.1 to Pep-3 (EGFRvIII epitope) were examined. The estimated $K_D$ was 185 nM. Estimates, for the other kinetic parameters, derived from curve fitting, were $k_a=2.198\times10^5$ and $k_d=0.04069$.

Example 34

In Vitro Determination of Binding Constants for N35G-3.1 Variant Antibodies

Similar to Example 32, the binding kinetics of mAb N35G-3.1 to Pep-3(EGFRvIII epitope) were examined. The estimated $K_D$ was 204 nM. Estimates, for the other kinetic parameters, derived from curve fitting, were $-k_a=1.497\times10^5$ and $k_d=0.03057$.

Example 35

In Vitro Determination of Binding Constants for Variant Antibodies

Similar to Example 32, the binding kinetics of mAb L99H-9.2 to Pep-3 (EGFRvIII epitope) were examined. The estimated $K_D$ was 395 nM. Estimates, for the other kinetic parameters, derived from curve fitting, were $k_a=83390$ and $k_d=0.03293$.

Example 36

In Vitro Determination of Binding Constants for Variant Antibodies

Similar to Example 32, the binding kinetics of mAb Y172R-1.2 to Pep-3 (EGFRvIII epitope) were examined. The estimated $K_D$ was 927 nM. Estimates, for the other kinetic parameters, derived from curve fitting, were $k_a=82237$ and $k_d=0.07622$.

Example 37

In Vitro Determination of Binding Constants for Variant Antibodies

Similar to Example 32, the binding kinetics of mAb L99N-4.1 to Pep-3 (EGFRvIII epitope) were examined. The estimated $K_D$ was 1.4 µM. MAb L99N-4.1 was fit using a steady-state (equilibrium) binding model in order to determine the $K_D$ because the kinetics were too fast to be fitted.

Example 38

Comparison of 13.1.2 with Designed Variants

As can be seen in Table 38.1 a mAb with improved binding characteristics was developed. The 95% confidence intervals are shown in parentheses. L99T-5.3 exhibited an enhanced $k_a$, a decreased $k_d$, and thus a slower $K_D$ overall. While statistically there appears to be little if any significant difference in the equilibrium dissociation constants and kinetic rate constants of Pep-3 binding to mAbs 13.1.2 and L99T-5.3 (at the 95% confidence interval), there still seems to be an intuitive bias for a marginal increase in affinity for Pep-3 binding to L99T-5.3. Moreover, when the same biosensor chip was used, L99T-5.3 seemed to always have a higher affinity than 13.1.2.

TABLE 38.1

| MAb | $k_a$ (M$^{-1}$s$^{-1}$) | $k_d$ (s$^{-1}$) | $K_D$ (nM) |
|---|---|---|---|
| 13.1.2 | 2.10 (0.58) × 10$^5$ | 0.016 (0.003) | 75 (14) |
| L99T-5.3 | 2.16 (0.12) × 10$^5$ | 0.013 (0.001) | 60 (10) |
| L217Q-10.1 | 2.04 × 10$^5$ | 0.019 | 92 |
| L217N-2.1 | 2.20 × 10$^5$ | 0.040 | 185 |
| N35G-3.1 | 1.50 × 10$^5$ | 0.030 | 204 |
| L99H-9.2 | 8.34 × 10$^4$ | 0.033 | 395 |
| Y172R-1.2 | 8.22 × 10$^4$ | 0.076 | 927 |
| L99N-4.1 | ND | ND | 1,400* |

Additional Docking Models and Methods of Selecting Models and Predicting Binding Affinity In other embodiments, the examples described above can be performed with various length peptides rather than just peptides that are 6 amino acids in length, as long as the key binding residues are included in the peptide. For example, instead of the six amino acid peptide, EEKKGN (SEQ ID NO: 127), a seven amino acid peptide, EEKKGNY (SEQ ID NO: 131) can be used. Any size peptide for the epitope can be used. In other embodiments, the peptide is selected from the following peptides: LEEKKGNYVVTDHC (SEQ ID NO: 56), LEEKKGNYVVTD (SEQ ID NO: 59), LEEKKGNYVVT (SEQ ID NO:132), and EEKKGNYVVT (SEQ ID NO:57). Any sized peptide between the short fragments disclosed herein, to the full length peptide, or variants thereof, can be used.

As appreciated by one of skill in the art, the presence of additional amino acids can alter the manner in which the peptide binds to the antibody. Not only does the presence of the additional amino acid allow for alternative and additional bonds to be formed between the peptide and the antibody, but the additional amino acid can change the structure of the peptide and the structure of the antibody upon binding of the peptide with the antibody. Thus, in one embodiment, various lengths of the epitope peptide, e.g. EEKKGN (SEQ ID NO: 127) and EEKKGNY (SEQ ID NO: 131), can be examined for binding properties and binding optimization. Not only will the longer fragments of the peptide provide an accurate depiction of the peptide-antibody interaction for longer segments of the peptide, but an examination of the changes in binding strength and the residues involved in binding will allow additional information concerning longer peptides to be extrapolated from the data.

In addition, and perhaps complementary to the testing of longer peptide fragments, additional filtering steps can be performed on the various docking models in order to select a refined docking model. An additional filtering step can allow one to filter through numerous docking models to find those that are consistent with available experimental data.

In one embodiment, the filter is based on fine-resolution epitope mapping data, e.g., the experimentally characterized individual residue binding profile, which could be correlated with the computed binding energy profile for each amino acid in the peptide. The binding energy profile of a seven amino acid peptide, for example, can be used to select docking models that contain similar binding energy profiles. A binding energy profile is an assignment of the binding energy of each amino acid in a peptide to the particular amino acid to create a profile of the peptide in terms of each amino acid's binding energy in that model. For example, in one docking model, given a peptide comprising amino acids A and B, where A has a binding energy of −5 and B has a binding energy of −20, one would have a profile of A1 (at −5) and B2 (at −20). This profile could be used as a filter to select other docking models. For example, the use of this binding energy profile as a filter or "template" would result in other docking models being selected if the peptide in the candidate model had a relatively low value attributed to position A, and a relatively high (larger negative, higher absolute value) value attributed to position B. In an alternative embodiment, the template requires additional limitations; for example, that the value at position B is four fold higher than the value at position A.

One can compare the binding energy profile template with the profiles of the peptide in the other docking models in a variety of ways. If the binding energy profile template is similar to the desired binding energy profile, then the filter can be used to pick out favorable docking models for further examination. If the binding energy profile template is dissimilar to the desired binding energy profile, then the filter can be used to eliminate unfavorable docking models. In one embodiment, the filtering process includes a template with both favorable and unfavorable binding energies and the filter is used to both select and exclude docking models. As appreciated by one of skill in the art, there are many possible different binding energy profiles, and thus many different binding energy profile templates that can be used depending upon the situation.

In one embodiment, one can define a binding energy profile template as a template that has a series of relatively high binding energies at particular positions in the peptide. In a preferred embodiment, the binding energy profile template, and the binding energy profile selected by the template, will have relatively high binding energy at position 2, 4, or 6 of the peptide, EEKKGNY (SEQ ID NO: 131). In another embodiment, the binding energy profile template will have a relatively high binding energy at positions 2, 4, and 6 of the peptide EEKKGNY (SEQ ID NO: 131). In another embodiment, the binding energy profile template will have a relatively low binding energy attributed to position 3 of the peptide EEKKGNY (SEQ ID NO: 131). In the above discussion, the positions are assigned as follows: E1, E2, K3, K4 G5, N6, Y7.

In one embodiment, the filtering process first involves a comparison of the binding energies at K3 and K4. Docking models that result in a relatively higher binding energy for K4 compared to K3 are selected, while docking models that result in a lower binding energy for K4 compared to K3 are filtered out. Thus, by "relatively high," it is meant that the binding energy for K4 is greater (more negative value, larger absolute value) than K3. Next, the docking models are again filtered through the binding energy profile template, this time, those binding models with relatively higher energies at positions 2, 4, and 6 are selected for, while the other models can be removed. Thus, by "relatively high," it is meant that the binding energy at positions 2, 4, and 6 are higher (more negative value, larger absolute value) than the lowest binding energy in the peptide. Thus, in this embodiment, the binding energy profile template could be summarized as follows: E1 can be any value, E2 should be greater than the lowest value, K3 should be less than K4, K4 should be greater than the lowest value, G5 can be any value, N6 should be greater than the lowest value, Y7 can be any value. Thus, E1, G5, and Y7 could be any value, as long as at least one (or K3) is lower than at least one of E2, K4, and N6. In another embodiment, "relatively high" can be set to a standard value as determined through modeling or experimentation. In one embodiment, that the docking models pass the first filter is more important than the docking model pass the second filtering step. As appreciated by one of skill in the art, one need not perform these two steps sequentially and they can be performed simultaneously.

Additionally, these profile templates for filtering through results will vary depending upon the peptide, the antibody, and the binding conditions. One of skill in the art, given the present disclosure, especially with reference to Example 14, could determine the appropriate binding energy profile template. For example, as shown in Table 14.1, there are several possible important residues for peptide binding both in the 131 and in the 13.1.2 antibody. In the 131 mAb, positions E2, K4, N6, and Y7 are important for the particular peptide tested. In the 13.1.2 mAb, positions E1, E2, K4, G5, and N6 are important for the particular peptide tested. Those residues that are important can be residues involved in the creation of a binding energy profile template. As clear from the discussion below, the binding energy profile template in Example 39 appears to be different from that suggested by an analysis of Example 14. Example 39 is a less stringent version of the template that allows more models to pass through the screening step. If one wanted to reduce the number of models that made it through the screening step, one could further add requirements concerning E1 and G5.

The following example demonstrates both the use of a longer peptide, how it can alter the results demonstrated above, what such changes can mean, as well as demonstrating the use of one of the above filters for selecting particular docking models.

Example 39

Epitope-Antibody Docking Model for a Seven Amino Acid Peptide

This example demonstrates the generation of a set of docking models for a seven-residue peptide complexed to the CDR region of 13.1.2 structure model. Additionally, this example demonstrates methods for selecting one docking model over another docking model.

First, a structural model for the seven-residue peptide EEKKGNY (SEQ ID NO: 131) was built in an extended conformation and energy minimized with Discover_3 module in InsightII modeling package. Next, the peptide structure was manually placed into the combining site to form an initial assembly. A Monte Carlo search in the translational and rotational spaces was then automatically performed with relaxed energy constraints in the Docking module in InsightII. During the docking process, the residues within 5 Angstroms of the binding groove were allowed to move while other antibody residues were fixed. The peptide was constrained to within 5 Angstroms of the starting position. The plausible configurations found by the Monte Carlo search were followed by simulated annealing and energy minimization to reach the final complex structure models. A total of 63 docking models were obtained.

For each docking model, the interaction energy between the antibody and the individual residue in the peptide was calculated with Discover_3. The profile of individual residue contribution in epitope-antibody binding was inspected to select the docking models that are consistent with the fine-resolution epitope mapping data, i.e., "the binding energy profile template." 19 out of 63 docking models passed this check. A typical individual residue binding energy profile is shown in Table 39.1. Consistent with the epitope mapping data, in Example 14, the binding energy for K4 is prominent, and those for N6 and E2 are large. This binding energy profile template placed particular emphasis on the fact that K4 is greater than K3. This binding energy profile also placed an emphasis on the requirement that E2, K4, and N6 are relatively large. In other words, the binding energies of E2, K4, and N6 were not the lowest (least negative or smallest absolute value) binding energies in the peptide.

TABLE 39.1

Binding Energy Profile For Individual Residue In The Seven-Residue Peptide To Antibody 13.1.2 Is Consistent With Epitope Mapping Data In Example 14.

| E1 | E2 | K3 | K4 | G5 | N6 | Y7 | Total |
|---|---|---|---|---|---|---|---|
| −10.97 | −19.34 | −13.46 | −24.26 | −10.1 | −18.19 | −15.15 | −111.45 |

For the 19 models that passed the filter based on the binding energy profile, epitope-antibody binding energetics simulations were performed on each of the seven mutants with affinity data (Tyr172Arg, Example 36; Leu217Asn, Example 33; Leu217Gln, Example 32; Asn35Gly, Example 34; Leu99Asn, Example 37; Leu99His, Example 35; and Leu99Thr, Example 31). Since the extent of electrostatic interaction in this complex had to be approximated, a number of different dielectric constants were used in a series of calculations. The mutation was done with residue replacement followed by 30-100 steps of energy minimization to account for any local conformational changes that are induced by the side chain change. For each docking model, the interaction energy between the seven-residue peptide and the whole antibody was calculated for each mutant for the selected parameters. For each set of 8 binding energies (7 mutants plus the wild type), a linear fitting procedure was done on each set of the binding data, in comparison with the logarithm of Kd. A correlation coefficient was calculated for each linear fitting. The best correlation was obtained for one model, the model with the data described in Table 39.1, with a dielectric constant 1*r and 50 steps of energy minimization. The epitope-antibody binding energies for this model are shown in Table 39.2. The correlation coefficient was 0.80 with all the data. As the $K_D$ for Leu99Asn was not measured with high degree of accuracy, see Example 37 above, a separate linear fitting was performed excluding the data for Leu99Asn. An excellent correlation coefficient of 0.91 was obtained, as shown in FIG. 14. The refined docking model is thus well represented by the above selected model. The model with space-filling peptide is shown in FIG. 15, and the hydrogen bonds are shown in FIG. 16. L3 150 is the lower section and H3 160 is the upper section on FIG. 16. H2 140 is to the right of the peptide binding area. The peptide itself is placed into the binding site with E1 being positioned at the top of the page in a light shade, down through K3, K4, G5, N6, and Y7, progressively getting darker. The antibody residues involved in hydrogen bonding are shown in FIG. 16. The model produced from this example demonstrates that there are seven hydrogen bonds: K4 . . . Q95, K4 . . . Q95, N6 . . . Q98, G5 . . . H31, Y7 . . . H31, and Y7 . . . W165.

TABLE 39.2

Simulation Of Epitope-Antibody Binding Energetics, In Comparison With Logarithm Of Kd.

| mutant | coulumbic | vdw | total | Ln(Kd) |
|---|---|---|---|---|
| 172Arg | −19.103 | −27.962 | −47.065 | −13.891 |
| 217Asn | −19.003 | −28.715 | −47.718 | −15.503 |
| 217Gln | −18.977 | −28.73 | −47.707 | −16.201 |
| 35Gly | −19.095 | −28.431 | −47.526 | −15.405 |
| 99Asn | −18.719 | −28.778 | −47.497 | (−13.479) |
| 99His | −18.837 | −28.719 | −47.556 | −14.744 |
| 99Thr | −19.155 | −28.704 | −47.859 | −16.475 |
| WT | −18.981 | −28.728 | −47.708 | −16.269 |

As can be seen from the model selected in Example 39, which is represented in FIG. 15, the docking model revealed some unexpected results. One interesting result is that while residues E2, K4, and N6 are important residues in the binding of the peptide as a whole, not all of these amino acids are modeled as involved in forming H-bonds with the antibody. It appears that K4 is involved in the formation of two H-bonds, both with Q95, which is consistent with K4's importance in the binding energy profile and profile template. It also appears that N6 is modeled to bond to Q98; however, in this particular model, E2 does not appear to form H-bonds in the model. One interesting trend that is consistent is that each of the key residues from the binding energy profile template (e.g., E2, K4, and N6) are mostly buried and thus in close contact with the antibody binding groove. Thus, this docking model selection can account for the fact that these key residues are important because of their close interaction with the antibody. Additionally, it is possible that E1 is involved in a hydrogen bond with W214.

Example 39 also demonstrates that the above described method results in a strong correlation between binding energy and $K_D$, suggesting that models created by this method will also allow optimization or at least a prediction of the $K_D$ of the antibody-peptide complex.

As can be seen from a comparison of Example 39 and Example 19, there are some residues that are important between the two models, some residues that appear only in the seven amino acid docking model, as well as some residues that do not appear to be as important in the seven amino acid docking model. For example, the seven peptide epitope appears to create H bonds between K4 . . . Q95, K4 . . . Q95, N6 . . . Q98, G5 . . . H31, Y7 . . . H131, and Y7 . . . W165. On the other hand, the six peptide epitope appears to create H bonds between E2 . . . Y172, K3 . . . H31, K4 . . . H31, N6 . . . D33, N6 . . . Y37, and N6 . . . K55. As can be seen from the above data, both the six and the seven amino acid peptide models emphasize the importance of H31, as both models involve H31 forming two hydrogen bonds with the peptide. While there are other possible trends between the two data sets, it also appears that many of the binding interactions have changed from the six amino acid model to the seven amino acid model. However, these examples demonstrate that variations due to epitope size can be detected with these models and thus the scaling up from shorter to longer epitope peptides should not be problematic in light of the present disclosure. The presence of amino acids that consistently demonstrate their importance in various binding models allows one to bias the importance of the various interactions accordingly so that shorter peptide models can be more representative of longer peptide interactions.

As appreciated by one of skill in the art, any of the above discussion or examples concerning the six amino acid peptide, EEKKGN (SEQ ID NO: 127), can also be applied towards the seven amino acid peptide, EEKKGNY (SEQ ID NO: 131), or any longer peptide. For instance, Example 20 can be repeated with the information from Example 39 for rational design for affinity-improved antibodies by site-directed mutagenesis. Furthermore, Example 21 can be repeated, using the results of Example 39, following an attempt of rational design for affinity-improved antibodies by site-directed mutagenesis to test any new antibodies derived from Example 20.

In one embodiment, the results from Example 39 are used to redefine the interaction area between the antibody and the peptide. For example, the paratope, for EEKKGNY (SEQ ID NO: 131), can be defined as including the other residues on the antibody that are predicted to interact with the peptide, for example, residue 95. Alternatively, as in Example 19, the paratope can be defined as all residues within 5 Angstroms of the docked peptide.

In Silico Affinity Maturation in Different Proteins

Antibody affinity maturation has been successfully done in vitro in a number of different studies. Typically, randomized mutant libraries need to be constructed by molecular biology methods and selection/screening assays need to be developed to enrich the clones with good binding capability. Selected variants then need to be purified to determine affinities. This process requires a series of lengthy and laborious experiments. The following example demonstrates that it is possible to accurately predict affinity maturation through in silico selection utilizing an antibody-antigen complex structure alone.

Example 40

In Silico Affinity Maturation Through Antibody-Antigen Binding Energetics Simulations This Example demonstrates that in silico antibody-antigen binding energetics simulations can be used for affinity maturation. In particular, this example demonstrates that the binding kinetics of a Fab-12 (IgG form known as rhuMAb VEGF) to VEGF (vascular endothelial growth factor) can be predicted through the above described in silico process.

Figure 17:
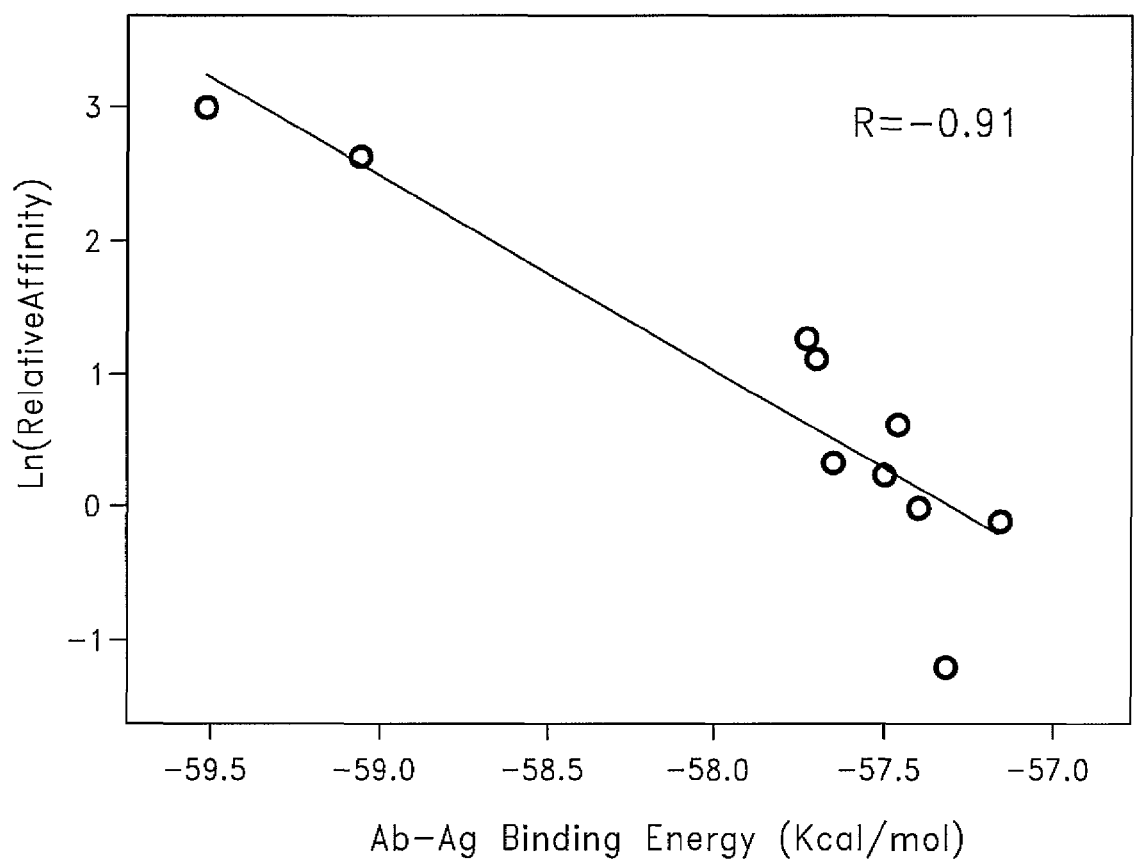
FIG. 17 is a graph that depicts the linear fitting of antibody-antigen binding energy versus the logarithm of relative affinities.

The crystal structure of the VEGF-Fab complex used was located in the PDB database with the accession number 1BJ1, at a resolution of 2.4 angstroms. Published experimental affinity data for a series of mutants of an anti-VEGF Fab were used to test the concept. The 3-D coordinates of the VEGF-Fab structure were used for carrying out in silico mutation for the following mutants: H97Y, S100aT, T28D, 28D31H, 28D31H97Y100aT, N31H, Y53W, 71I73K, 71V73V. The affinity data were obtained from the paper by Chen, Y et al., (J Mol Biol., 293(4):865-81 (1999)). The energetics simulations were carried out between the various VEGF-Fab mutants, as described in Example 39. The results are listed in Table 40.1. The results from this example demonstrate that a significant correlation between the binding energy and affinity ranking was obtained through this process. The linear fitting of the binding energy versus logarithm of the relative affinity is shown in FIG. 17. The correlation coefficient of −0.91 indicates that the in silico simulation accurately captures the detailed interaction at the atomic level.

TABLE 40.1

Antibody-Antigen Binding Energy Simulation Compared With Affinity

| Kabat Number | Sequence Number | Relative Affinity | Ln (Relative Affinity) | Binding Energy |
|---|---|---|---|---|
| H97Y | 101Y | 14 | 2.639 | −59.065 |
| S100aT | 105T | 1.9 | 0.642 | −57.465 |
| T28D | 28D | 1.4 | 0.336 | −57.647 |
| 28D31H | 28D31H | 3.1 | 1.131 | −57.699 |
| 28D31H97Y100aT | 28D31H101Y105T | 20 | 2.996 | −59.518 |
| N31H | 31H | 3.6 | 1.281 | −57.724 |
| Y53W | 54W | 1.3 | 0.262 | −57.504 |
| 71I73K | 72I74K | 0.9 | −0.105 | −57.158 |
| 71V73V | 72V74V | 0.3 | −1.204 | −57.314 |
| WT | WT | 1 | 0.000 | −57.404 |

As is clear from the Examples above, the simulation can be extrapolated to identify higher affinity mutants without the use of in vitro experimentation. Additionally, it is clear that this approach is useful for different antibodies and for different peptides. This methodology can be generally applied to perform affinity maturation in silico, using only a high-resolution antibody-antigen complex structure. In one embodiment, this use of in silico affinity maturation will save tremendous amounts of time and resource.

Example 41

Determination of Canonical Classes of Antibodies

Chothia, et al have described antibody structure in terms of "canonical classes" for the hypervariable regions of each immunoglobulin chain (J. Mol. Biol. 1987 Aug. 20; 196(4): 901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved beta-sheet framework. By examining sequences of immunoglobulins having unknown structure, Chothia, et al show that many immunoglobulins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures". Further work by Chothia, et al. (Nature. 1989 Dec. 21-28; 342(6252):877-83) and others (Martin, et al. J Mol. Biol. 1996 Nov. 15; 263(5):800-15) confirmed that that there is a small repertoire of main-chain conformations for at least five of the six hypervariable regions of antibodies.

Some of the antibodies described above were analyzed to determine the canonical class for each of the antibody's complementarity determining regions (CDRs). As is known, canonical classes have only been assigned for CDR1 and CDR2 of the antibody heavy chain, along with CDR1, CDR2 and CDR3 of the antibody light chain. The table below (41.1) summarizes the results of the analysis. The Canonical Class data is in the form of *HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical class 1, a HCDR2 that falls into canonical class 3, a LCDR1 that falls into canonical class 2, a LCDR2 that falls into canonical class 1, and a LCDR3 that falls into canonical class 5.

TABLE 41.1

| mAb | H1-H2-L1-L2-L3 |
|---|---|
| 139 | 1-3-2-1-1 |
| 250 | 1-3-2-1-1 |
| 123 | 1-3-4-1-1 |
| 131 | 1-3-4-1-1 |
| 13_1_2 | 1-3-4-1-1 |
| 211 | 1-3-4-1-1 |

TABLE 41.1-continued

| mAb | H1-H2-L1-L2-L3 |
|---|---|
| 318 | 1-3-4-1-1 |
| 333 | 1-3-4-1-1 |
| 342 | 1-3-4-1-1 |
| 95  | 3-1-4-1-1 |
| 150 | 3-Y-4-1-1 |
| 170 | 3-Y-4-1-1 |

Each CDR (except for H3) was assigned to a canonical structure if it satisfies the length requirement and matches the key residues defined in the canonical class. The amino acids defined for each antibody can be found, for example, in the articles by Chothia, et al. referred to above.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:
1. A method of inhibiting cell proliferation associated with the expression of EGFRvIII that comprises the amino acid sequence of SEQ ID NO: 56, said method comprising treating cells expressing EGFRvIII with an effective amount of an antibody, wherein said antibody binds to LEEKKGNYVVTDHC (SEQ ID NO: 56) of EGFRvIII and wherein the antibody is
   a) an antibody comprising a heavy chain variable region amino acid sequence of SEQ ID NO: 142 and a light chain variable region amino acid sequence of SEQ ID NO: 144,
   b) an antibody comprising a heavy chain variable region amino acid sequence of SEQ ID NO: 2 and a light chain variable region amino acid sequence of SEQ ID NO: 19,
   c) an antibody comprising a heavy chain variable region amino acid sequence of SEQ ID NO: 4 and a light chain variable region amino acid sequence of SEQ ID NO: 20,
   d) an antibody comprising a heavy chain variable region amino acid sequence of SEQ ID NO: 5 and a light chain variable region amino acid sequence of SEQ ID NO: 21,
   e) an antibody comprising a heavy chain variable region amino acid sequence of SEQ ID NO: 7 and a light chain variable region amino acid sequence of SEQ ID NO: 23,
   f) an antibody comprising a heavy chain variable region amino acid sequence of SEQ ID NO: 9 and a light chain variable region amino acid sequence of SEQ ID NO: 26,
   g) an antibody comprising a heavy chain variable region amino acid sequence of SEQ ID NO: 10 and a light chain variable region amino acid sequence of SEQ ID NO: 25,
   h) an antibody comprising a heavy chain variable region amino acid sequence of SEQ ID NO: 12 and a light chain variable region amino acid sequence of SEQ ID NO: 28,
   b) an antibody comprising a heavy chain variable region amino acid sequence of SEQ ID NO: 13 and a light chain variable region amino acid sequence of SEQ ID NO: 29,
   j) an antibody comprising a heavy chain variable region amino acid sequence of SEQ ID NO: 15 and a light chain variable region amino acid sequence of SEQ ID NO: 33,
   k) an antibody comprising a heavy chain variable region amino acid sequence of SEQ ID NO: 16 and a light chain variable region amino acid sequence of SEQ ID NO: 31, or
   l) an antibody comprising a heavy chain variable region amino acid sequence of SEQ ID NO: 17 and a light chain variable region amino acid sequence of SEQ ID NO: 32.

2. The method of claim 1, wherein the method is performed in vivo.

3. The method of claim 1, wherein the method is performed on mammal.

4. The method of claim 3, wherein the mammal is a human.

5. The method of claim 3, wherein the mammal suffers from a cancer involving epithelial cell proliferation associated with the expression of EGFRvIII.

6. The method of claim 5, wherein the cancer comprises a lung, colon, gastric, renal, prostate, breast, glioblastoma or ovarian carcinoma.

7. A method of inhibiting cell proliferation associated with the expression of EGFRvIII, that comprises the amino acid sequence of SEQ ID NO: 56, said method comprising treating cells expressing EGFRvIII with an effective amount of an isolated antibody that binds to LEEKKGNYVVTDHC (SEQ ID NO: 56) of EGFRvIII, wherein the antibody is
   (a) an antibody comprising a heavy chain polypeptide comprising the following complementarity determining regions (CDRs): a heavy chain CDR1 that is a CDR1 in SEQ ID NO: 142; a heavy chain CDR2 that is a CDR2 in SEQ ID NO: 142; a heavy chain CDR3 that is a CDR3 in SEQ ID NO: 142; and a light chain polypeptide comprising the following CDRs: a light chain CDR1 that is a CDR1 in SEQ ID NO: 144; a light chain CDR2 that is a CDR2 in SEQ ID NO: 144; and a light chain CDR3 that is a CDR3 in SEQ ID NO: 144,
   (b) an antibody comprising a heavy chain polypeptide comprising the following complementarity determining regions (CDRs): a heavy chain CDR1 that is a CDR1 in SEQ ID NO: 2; a heavy chain CDR2 that is a CDR2 in SEQ ID NO: 2; a heavy chain CDR3 that is a CDR3 in SEQ ID NO: 2; and a light chain polypeptide comprising the following CDRs: a light chain CDR1 that is a CDR1 in SEQ ID NO: 19; a light chain CDR2 that is a CDR2 in SEQ ID NO: 19; and a light chain CDR3 that is a CDR3 in SEQ ID NO: 19,
   (c) an antibody comprising a heavy chain polypeptide comprising the following complementarity determining regions (CDRs): a heavy chain CDR1 that is a CDR1 in SEQ ID NO: 4; a heavy chain CDR2 that is a CDR2 in SEQ ID NO: 4; a heavy chain CDR3 that is a CDR3 in SEQ ID NO: 4; and a light chain polypeptide comprising the following CDRs: a light chain CDR1 that is a CDR1 in SEQ ID NO: 20; a light chain CDR2 that is a CDR2 in SEQ ID NO: 20; and a light chain CDR3 that is a CDR3 in SEQ ID NO: 20,
   (d) an antibody comprising a heavy chain polypeptide comprising the following complementarity determining regions (CDRs): a heavy chain CDR1 that is a CDR1 in SEQ ID NO: 5; a heavy chain CDR2 that is a CDR2 in SEQ ID NO: 5; a heavy chain CDR3 that is a CDR3 in SEQ ID NO: 5; and a light chain polypeptide comprising the following CDRs: a light chain CDR1 that is a CDR1 in SEQ ID NO: 21; a light chain CDR2 that is a CDR2 in SEQ ID NO: 21; and a light chain CDR3 that is a CDR3 in SEQ ID NO: 21,
   (e) an antibody comprising a heavy chain polypeptide comprising the following complementarity determining regions (CDRs): a heavy chain CDR1 that is a CDR1 in SEQ ID NO: 7; a heavy chain CDR2 that is a CDR2 in SEQ ID NO: 7; a heavy chain CDR3 that is a CDR3 in SEQ ID NO: 7; and a light chain polypeptide comprising the following CDRs: a light chain CDR1 that is a CDR1 in SEQ ID NO: 23; a light chain CDR2 that is a CDR2 in SEQ ID NO: 23; and a light chain CDR3 that is a CDR3 in SEQ ID NO: 23,
   (f) an antibody comprising a heavy chain polypeptide comprising the following complementarity determining regions (CDRs): a heavy chain CDR1 that is a CDR1 in SEQ ID NO: 9; a heavy chain CDR2 that is a CDR2 in SEQ ID NO: 9; a heavy chain CDR3 that is a CDR3 in SEQ ID NO: 9; and a light chain polypeptide comprising the following CDRs: a light chain CDR1 that is a CDR1 in SEQ ID NO: 26; a light chain CDR2 that is a CDR2 in SEQ ID NO: 26; and a light chain CDR3 that is a CDR3 in SEQ ID NO: 26,
   (g) an antibody comprising a heavy chain polypeptide comprising the following complementarity determining regions (CDRs): a heavy chain CDR1 that is a CDR1 in SEQ ID NO: 10; a heavy chain CDR2 that is a CDR2 in SEQ ID NO: 10; a heavy chain CDR3 that is a CDR3 in SEQ ID NO: 10; and a light chain polypeptide comprising the following CDRs: a light chain CDR1 that is a CDR1 in SEQ ID NO: 25; a light chain CDR2 that is a CDR2 in SEQ ID NO: 25; and a light chain CDR3 that is a CDR3 in SEQ ID NO: 25, (h) an antibody comprising a heavy chain polypeptide comprising the following complementarity determining regions (CDRs): a heavy chain CDR1 that is a CDR1 in SEQ ID NO: 12; a heavy chain CDR2 that is a CDR2 in SEQ ID NO: 12; a heavy chain CDR3 that is a CDR3 in SEQ ID NO: 12; and a light chain polypeptide comprising the following CDRs: a light chain CDR1 that is a CDR1 in SEQ ID NO: 28; a light chain CDR2 that is a CDR2 in SEQ ID NO: 28; and a light chain CDR3 that is a CDR3 in SEQ ID NO: 28, (i) an antibody comprising a heavy chain polypeptide comprising the following complementarity determining regions (CDRs): a heavy chain CDR1 that is a CDR1 in SEQ ID NO: 13; a heavy chain CDR2 that is a CDR2 in SEQ ID NO: 13; a heavy chain CDR3 that is a CDR3 in SEQ ID NO: 13; and a light chain polypeptide comprising the following CDRs: a light chain CDR1 that is a CDR1 in SEQ ID NO: 29; a light chain CDR2 that is a CDR2 in SEQ ID NO: 29; and a light chain CDR3 that is a CDR3 in SEQ ID NO: 29, (j) an antibody comprising a heavy chain polypeptide comprising the following complementarity determining regions (CDRs): a heavy chain CDR1 that is a CDR1 in SEQ ID NO: 15; a heavy chain CDR2 that is a CDR2 in SEQ ID NO: 15; a heavy chain CDR3 that is a CDR3 in SEQ ID NO: 15; and a light chain polypeptide comprising the following CDRs: a light chain CDR1 that is a CDR1 in SEQ ID NO: 33; a light chain CDR2 that is a CDR2 in SEQ ID NO: 33; and a light chain CDR3 that is a CDR3 in SEQ ID NO: 33, (k) an antibody comprising a heavy chain polypeptide comprising the following complementarity determining regions (CDRs): a heavy chain CDR1 that is a CDR1 in SEQ ID NO: 16; a heavy chain CDR2 that is a CDR2 in SEQ ID NO: 16; a heavy chain CDR3 that is a CDR3 in SEQ ID NO: 16; and a light chain polypeptide comprising the following CDRs: a light chain CDR1 that is a CDR1 in SEQ ID NO: 31; a light chain CDR2 that is a CDR2 in SEQ ID NO: 31; and a light chain CDR3 that is a CDR3 in SEQ ID NO: 31, (l) an antibody comprising a heavy chain polypeptide comprising the following complementarity determining regions (CDRs): a heavy chain CDR1 that is a CDR1 in SEQ ID NO: 17; a heavy chain CDR2 that is a CDR2 in SEQ ID NO: 17; a heavy chain CDR3 that is a CDR3 in SEQ ID NO: 17; and a light chain polypeptide comprising the following CDRs: a light chain CDR1 that is a CDR1 in SEQ ID NO: 32; a light chain CDR2 that is a CDR2 in SEQ ID NO: 32; and a light chain CDR3 that is a CDR3 in SEQ ID NO: 32.

8. The method of claim 7, wherein the method is performed in vivo.

9. The method of claim 7, wherein the method is performed on mammal.

10. The method of claim 9, wherein the mammal is a human.

11. The method of claim 9, wherein the mammal suffers from a cancer involving epithelial cell proliferation associated with the expression of EGFRvIII.

12. The method of claim 11, wherein the cancer comprises a lung, colon, gastric, renal, prostate, breast, glioblastoma or ovarian carcinoma.

13. A method of inhibiting cell proliferation associated with the expression of EGFRvIII that comprises the amino acid sequence of SEQ ID NO: 56, said method comprising treating cells expressing EGFRvIII with an effective amount of an isolated antibody that binds to EGFRvIII, wherein the antibody is a) an antibody comprising a heavy chain polypeptide comprising the following complementarity determining regions (CDRs): a heavy chain CDR1 that is a CDR1 in SEQ ID NO: 142; a heavy chain CDR2 that is a CDR2 in SEQ ID NO: 142; a heavy chain CDR3 that is a CDR3 in SEQ ID NO: 142; and a light polypeptide comprising the following CDRs: a light chain CDR1 that is a CDR1 in SEQ ID NO: 144; a light chain CDR2 that is a CDR2 in SEQ ID NO: 144; and a light chain CDR3 that is a CDR3 in SEQ ID NO: 144, b) an antibody comprising a heavy chain polypeptide comprising the following complementarity determining regions (CDRs): a heavy chain CDR1 that is a CDR1 in SEQ ID NO: 2; a heavy chain CDR2 that is a CDR2 in SEQ ID NO: 2; a heavy chain CDR3 that is a CDR3 in SEQ ID NO: 2; and a light polypeptide comprising the following CDRs: a light chain CDR1 that is a CDR1 in SEQ ID NO: 19; a light chain CDR2 that is a CDR2 in SEQ ID NO: 19; and a light chain CDR3 that is a CDR3 in SEQ ID NO: 19, c) an antibody comprising a heavy chain polypeptide comprising the following complementarity determining regions (CDRs): a heavy chain CDR1 that is a CDR1 in SEQ ID NO: 4; a heavy chain CDR2 that is a CDR2 in SEQ ID NO: 4; a heavy chain CDR3 that is a CDR3 in SEQ ID NO: 4; and a light polypeptide comprising the following CDRs: a light chain CDR1 that is a CDR1 in SEQ ID NO: 20; a light chain CDR2 that is a CDR2 in SEQ ID NO: 20; and a light chain CDR3 that is a CDR3 in SEQ ID NO: 20, d) an antibody comprising a heavy chain polypeptide comprising the following complementarity determining regions (CDRs): a heavy chain CDR1 that is a CDR1 in SEQ ID NO: 5; a heavy chain CDR2 that is a CDR2 in SEQ ID NO: 5; a heavy chain CDR3 that is a CDR3 in SEQ ID NO: 5; and a light polypeptide comprising the following CDRs: a light chain CDR1 that is a CDR1 in SEQ ID NO: 21; a light chain CDR2 that is a CDR2 in SEQ ID NO: 21; and a light chain CDR3 that is a CDR3 in SEQ ID NO: 21, e) an antibody comprising a heavy chain polypeptide comprising the following complementarity determining regions (CDRs): a heavy chain CDR1 that is a CDR1 in SEQ ID NO: 7; a heavy chain CDR2 that is a CDR2 in SEQ ID NO: 7; a heavy chain CDR3 that is a CDR3 in SEQ ID NO: 7; and a light polypeptide comprising the following CDRs: a light chain CDR1 that is a CDR1 in SEQ ID NO: 23; a light chain CDR2 that is a CDR2 in SEQ ID NO: 23; and a light chain CDR3 that is a CDR3 in SEQ ID NO: 23, f) an antibody comprising a heavy chain polypeptide comprising the following complementarity determining regions (CDRs): a heavy chain CDR1 that is a CDR1 in SEQ ID NO: 9; a heavy chain CDR2 that is a CDR2 in SEQ ID NO: 9; a heavy chain CDR3 that is a CDR3 in SEQ ID NO: 9; and a light polypeptide comprising the following CDRs: a light chain CDR1 that is a CDR1 in SEQ ID NO: 26; a light chain CDR2 that is a CDR2 in SEQ ID NO: 26; and a light chain CDR3 that is a CDR3 in SEQ ID NO: 26, g) an antibody comprising a heavy chain polypeptide comprising the following complementarity determining regions (CDRs): a heavy chain CDR1 that is a CDR1 in SEQ ID NO: 10; a heavy chain CDR2 that is a CDR2 in SEQ ID NO: 10; a heavy chain CDR3 that is a CDR3 in SEQ ID NO: 10; and a light polypeptide comprising the following CDRs: a light chain CDR1 that is a CDR1 in SEQ ID NO: 25; a light chain CDR2 that is a CDR2 in SEQ ID NO: 25; and a light chain CDR3 that is a CDR3 in SEQ ID NO: 25, h) an antibody comprising a heavy chain polypeptide comprising the following complementarity determining regions (CDRs): a heavy chain CDR1 that is a CDR1 in SEQ ID NO: 12; a heavy chain CDR2 that is a CDR2 in SEQ ID NO: 12; a heavy chain CDR3 that is a CDR3 in SEQ ID NO: 12; and a light polypeptide comprising the following CDRs: a light chain CDR1 that is a CDR1 in SEQ ID NO: 28; a light chain CDR2 that is a CDR2 in SEQ ID NO: 28; and a light chain CDR3 that is a CDR3 in SEQ ID NO: 28, i) an antibody comprising a heavy chain polypeptide comprising the following complementarity determining regions (CDRs): a heavy chain CDR1 that is a CDR1 in SEQ ID NO: 13; a heavy chain CDR2 that is a CDR2 in SEQ ID NO: 13; a heavy chain CDR3 that is a CDR3 in SEQ ID NO: 13; and a light polypeptide comprising the following CDRs: a light chain CDR1 that is a CDR1 in SEQ ID NO: 29; a light chain CDR2 that is a CDR2 in SEQ ID NO: 29; and a light chain CDR3 that is a CDR3 in SEQ ID NO: 29, j) an antibody comprising a heavy chain polypeptide comprising the following complementarity determining regions (CDRs): a heavy chain CDR1 that is a CDR1 in SEQ ID NO: 15; a heavy chain CDR2 that is a CDR2 in SEQ ID NO: 15; a heavy chain CDR3 that is a CDR3 in SEQ ID NO: 15; and a light polypeptide comprising the following CDRs: a light chain CDR1 that is a CDR1 in SEQ ID NO: 33; a light chain CDR2 that is a CDR2 in SEQ ID NO: 33; and a light chain CDR3 that is a CDR3 in SEQ ID NO: 33, k) an antibody comprising a heavy chain polypeptide comprising the following complementarity determining regions (CDRs): a heavy chain CDR1 that is a CDR1 in SEQ ID NO: 16; a heavy chain CDR2 that is a CDR2 in SEQ ID NO: 16; a heavy chain CDR3 that is a CDR3 in SEQ ID NO: 16; and a light polypeptide comprising the following CDRs: a light chain CDR1 that is a CDR1 in SEQ ID NO: 31; a light chain CDR2 that is a CDR2 in SEQ ID NO: 31; and a light chain CDR3 that is a CDR3 in SEQ ID NO: 31, l) an antibody comprising a heavy chain polypeptide comprising the following complementarity determining regions (CDRs): a heavy chain CDR1 that is a CDR1 in SEQ ID NO: 17; a heavy chain CDR2 that is a CDR2 in SEQ ID NO: 17; a heavy chain CDR3 that is a CDR3 in SEQ ID NO: 17; and a light polypeptide comprising the following CDRs: a light chain CDR1 that is a CDR1 in SEQ ID NO: 32; a light chain CDR2 that is a CDR2 in SEQ ID NO: 32; and a light chain CDR3 that is a CDR3 in SEQ ID NO: 32, wherein each CDR is defined in accordance with the CDR definition of Kabat or Chothia.

14. The method of claim 13, wherein each CDR is defined in accordance with the CDR definition of Kabat.

15. The method of claim 13, wherein each CDR is defined in accordance with the CDR definition of Chothia.

16. The method of claim 13, wherein the antibody comprises a heavy chain polypeptide comprising the following complementarity determining regions (CDRs): a heavy chain CDR1 that is a CDR1 in SEQ ID NO: 2; a heavy chain CDR2 that is a CDR2 in SEQ ID NO: 2; a heavy chain CDR3 that is a CDR3 in SEQ ID NO: 2; and a light chain polypeptide comprising the following CDRs: a light chain CDR1 that is a CDR1 in SEQ ID NO: 19; a light chain CDR2 that is a CDR2 in SEQ ID NO: 19; and a light chain CDR3 that is a CDR3 in SEQ ID NO: 19.

17. The method of claim 16, wherein the method is performed in vivo.

18. The method of claim 16, wherein the method is performed on mammal.

19. The method of claim 16, wherein the mammal is a human.

20. The method of claim 16, wherein the mammal suffers from a cancer involving epithelial cell proliferation associated with the expression of EGFRvIII.

21. The method of claim 16, wherein the cancer comprises a lung, colon, gastric, renal, prostate, breast, glioblastoma or ovarian carcinoma.

22. A method of inhibiting cell proliferation associated with the expression of EGFRvIII that comprises the amino acid sequence of SEQ ID NO: 56, said method, comprising treating cells expressing EGFRvIII with an effective amount of an isolated antibody that binds to LEEKKGNYVVTDHC (SEQ ID NO: 56) of EGFRvIII and wherein the antibody comprises:

a heavy chain polypeptide, wherein CDR3 of the heavy chain polypeptide comprises the amino acid sequence in SEQ ID NO: 112, wherein CDR2 of the heavy chain polypeptide comprises the amino acid sequence in SEQ ID NO: 110, and wherein CDR1 of the heavy chain polypeptide comprises the amino acid sequence in SEQ ID NO: 108; and a light chain polypeptide, wherein CDR3 of the heavy chain polypeptide comprises the amino acid sequence in SEQ ID NO: 105, wherein CDR2 of the light chain polypeptide comprises the amino acid sequence in SEQ ID NO: 103, and wherein CDR1 of the light chain polypeptide comprises the amino acid sequence in SEQ ID NO: 101.

23. The method of claim 1, wherein the antibody comprises a heavy chain variable region amino acid sequence of SEQ ID NO: 2 and a light chain variable region amino acid sequence of SEQ ID NO: 19.

24. The method of claim 7, wherein the antibody comprises a heavy chain polypeptide comprising the following complementarity determining regions (CDRs): a heavy chain CDR1 that is a CDR1 in SEQ ID NO: 2; a heavy chain CDR2 that is a CDR2 in SEQ ID NO: 2; a heavy chain CDR3 that is a CDR3 in SEQ ID NO: 2; and a light chain polypeptide comprising the following CDRs: a light chain CDR1 that is a CDR1 in SEQ ID NO: 19; a light chain CDR2 that is a CDR2 in SEQ ID NO: 19; and a light chain CDR3 that is a CDR3 in SEQ ID NO: 19.

25. The method of claim 1, wherein the antibody comprises a heavy chain variable region amino acid sequence of SEQ ID NO: 142 and a light chain variable region amino acid sequence of SEQ ID NO: 144.

26. The method of claim 7, wherein the antibody comprises a heavy chain polypeptide comprising the following complementarity determining regions (CDRs): a heavy chain CDR1 that is a CDR1 in SEQ ID NO: 142; a heavy chain CDR2 that is a CDR2 in SEQ ID NO: 142; a heavy chain CDR3 that is a CDR3 in SEQ ID NO: 142; and a light chain polypeptide comprising the following CDRs: a light chain CDR1 that is a CDR1 in SEQ ID NO: 144; a light chain CDR2 that is a CDR2 in SEQ ID NO: 144; and a light chain CDR3 that is a CDR3 in SEQ ID NO: 144.

* * * * *

SEQUENCE LISTING

```
<160> NUMBER OF SEQ ID NOS: 144

<210> SEQ ID NO 1
<211> LENGTH: 109
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 2
<211> LENGTH: 124
<212> TYPE: PRT
<213> ORGANISM: Homo sapiens

<400> SEQUENCE: 2

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asp Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
```

```
            100                 105                 110
Tyr Trp Gly Gln Gly Thr Leu Val Thr Val Ser Ser
        115                 120

<210> SEQ ID NO 3
<211> LENGTH: 112
<212> TYPE: PRT
<213> ORGANISM: Homo sapiens

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Gly Gln Gly Thr Leu Val Thr Val Ser Ser
            100                 105                 110

<210> SEQ ID NO 4
<211> LENGTH: 118
<212> TYPE: PRT
<213> ORGANISM: Homo sapiens

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Ala Trp Asn Trp Ile Arg Gln Ser Pro Ala Arg Gly Leu Glu
        35                  40                  45

Trp Leu Gly Arg Thr Tyr Tyr Arg Ser Lys Trp Tyr Asn Asp Tyr Val
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Val Arg Ala Thr Ala Phe Asp Tyr Trp Gly Gln Gly Thr
            100                 105                 110

Leu Val Thr Val Ser Ser
        115

<210> SEQ ID NO 5
<211> LENGTH: 118
<212> TYPE: PRT
<213> ORGANISM: Homo sapiens

<400> SEQUENCE: 5

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30
```

Ser Ser Ala Trp Asn Trp Ile Arg Gln Ser Pro Ser Arg Gly Leu Glu
            35                  40                  45

Trp Leu Gly Arg Ala Tyr His Arg Ser Arg Trp Tyr Tyr Glu Tyr Ala
 50                  55                  60

Val Ser Val Lys Ser Arg Ile Asn Ile Thr Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Gly Ser Arg Phe Asp Tyr Trp Gly Gln Gly Thr
            100                 105                 110

Leu Val Thr Val Ser Ser
            115

<210> SEQ ID NO 6
<211> LENGTH: 110
<212> TYPE: PRT
<213> ORGANISM: Homo sapiens

<400> SEQUENCE: 6

Gln Val Gln Leu Gln Glu Ser Gly Pro Phe Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Trp Gly Gln Gly Thr Leu Val Thr Val Ser Ser
            100                 105                 110

<210> SEQ ID NO 7
<211> LENGTH: 126
<212> TYPE: PRT
<213> ORGANISM: Homo sapiens

<400> SEQUENCE: 7

Gln Val Gln Leu Gln Glu Ser Gly Pro Phe Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Phe Ile Tyr Arg Gly Asn Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Gly Tyr Cys Ser Arg Thr Gly Cys Tyr Gly Gly Trp
            100                 105                 110

Phe Asp Pro Trp Gly Gln Gly Thr Leu Val Thr Val Ser Pro
            115                 120                 125

```
<210> SEQ ID NO 8
<211> LENGTH: 109
<212> TYPE: PRT
<213> ORGANISM: Homo sapiens

<400> SEQUENCE: 8
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Trp | Gly | Gln | Gly | Thr | Leu | Val | Thr | Val | Ser | Ser |
|---|---|---|---|---|---|---|---|---|---|---|---|---|
| | | | 100 | | | | | 105 | | | | |

```
<210> SEQ ID NO 9
<211> LENGTH: 116
<212> TYPE: PRT
<213> ORGANISM: Homo sapiens

<400> SEQUENCE: 9
```

| Glu | Gly | Gln | Leu | Leu | Glu | Ser | Gly | Gly | Gly | Trp | Val | Gln | Pro | Gly | Glu |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Asn | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Val | Asn | Ser | Leu | Arg | Val | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Gly | Ser | Ser | Gly | Trp | Ser | Glu | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

```
<210> SEQ ID NO 10
<211> LENGTH: 116
<212> TYPE: PRT
<213> ORGANISM: Homo sapiens

<400> SEQUENCE: 10
```

| Glu | Val | Gln | Val | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

```
Ser Ala Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Ser Gly Trp Ser Glu Tyr Trp Gly Gln Gly Thr Leu Val
            100                 105                 110

Thr Val Ser Ser
        115

<210> SEQ ID NO 11
<211> LENGTH: 109
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Thr Val Thr Val Ser Ser
            100                 105

<210> SEQ ID NO 12
<211> LENGTH: 128
<212> TYPE: PRT
<213> ORGANISM: Homo sapiens

<400> SEQUENCE: 12

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Leu Ser Ser Tyr
                20                  25                  30

Gly Met His Trp Val Arg Gln Ala Pro Gly Lys Gly Leu Glu Trp Val
            35                  40                  45

Ala Val Thr Ser Tyr Asp Gly Ser Lys Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Ser Glu Gly Tyr Cys Ser Ser Ser Cys Tyr Lys Tyr Tyr Tyr
            100                 105                 110

Tyr Gly Met Asp Val Trp Gly Gln Gly Thr Thr Val Thr Val Ser Ser
            115                 120                 125

<210> SEQ ID NO 13
<211> LENGTH: 128
```

<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Lys Glu Asp Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Val Ser Glu Gly Tyr Cys Ser Ser Arg Ser Cys Tyr Lys Tyr Tyr Tyr
            100                 105                 110

Tyr Gly Met Asp Val Trp Gly Gln Gly Thr Thr Val Thr Val Ser Ser
        115                 120                 125

<210> SEQ ID NO 14
<211> LENGTH: 109
<212> TYPE: PRT
<213> ORGANISM: Homo sapiens

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Thr Val Thr Val Ser Ser
            100                 105

<210> SEQ ID NO 15
<211> LENGTH: 128
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Thr Ser Tyr Asp Gly Ser Lys Lys Tyr Ala Asp Ser Val
    50                  55                  60

Lys Gly Arg Phe Thr Ile Ser Arg Asp Asn Ser Lys Asn Thr Leu Tyr

```
65                  70                  75                  80
Leu Gln Met Asn Ser Leu Arg Ala Glu Asp Thr Ala Val Tyr Tyr Cys
                85                  90                  95
Val Ser Glu Gly Tyr Cys Asp Ser Ser Cys Tyr Lys Tyr Tyr Tyr
               100                 105                 110
Tyr Gly Met Asp Val Trp Gly Gln Gly Thr Thr Val Thr Val Ser Ser
               115                 120                 125
```

```
<210> SEQ ID NO 16
<211> LENGTH: 128
<212> TYPE: PRT
<213> ORGANISM: Homo sapiens

<400> SEQUENCE: 16

Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Leu Ser Ser Tyr
                20                  25                  30
Gly Met His Trp Val Arg Gln Ala Pro Gly Lys Gly Leu Glu Trp Val
            35                  40                  45
Ala Val Thr Ser Tyr Asp Gly Ser Lys Lys Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Ser Glu Gly Tyr Cys Asp Ser Thr Ser Cys Tyr Lys Tyr Tyr Tyr
               100                 105                 110
Tyr Gly Met Asp Val Trp Gly Gln Gly Thr Thr Val Thr Val Ser Ser
               115                 120                 125
```

```
<210> SEQ ID NO 17
<211> LENGTH: 128
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Leu Ser Ser Tyr
                20                  25                  30
Gly Met His Trp Val Arg Gln Ala Leu Gly Lys Gly Leu Glu Trp Val
            35                  40                  45
Ala Val Thr Ser Tyr Asp Gly Ser Lys Lys Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Ser Glu Gly Tyr Cys Asp Ser Thr Ser Cys Tyr Lys Tyr Tyr Tyr
               100                 105                 110
Tyr Gly Met Asp Val Trp Gly Gln Gly Thr Thr Val Thr Val Ser Ser
               115                 120                 125
```

```
<210> SEQ ID NO 18
<211> LENGTH: 112
<212> TYPE: PRT
```

<213> ORGANISM: Homo sapiens

<400> SEQUENCE: 18

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110

<210> SEQ ID NO 19
<211> LENGTH: 112
<212> TYPE: PRT
<213> ORGANISM: Homo sapiens

<400> SEQUENCE: 19

Asp Thr Val Met Thr Gln Thr Pro Leu Ser Ser His Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Arg Ile Ser Arg Arg Phe Ser Gly Val Pro
    50                  55                  60

Asp Arg Phe Ser Gly Ser Gly Ala Gly Thr Asp Phe Thr Leu Glu Ile
65                  70                  75                  80

Ser Arg Val Glu Ala Glu Asp Val Gly Val Tyr Tyr Cys Met Gln Ser
                85                  90                  95

Thr His Val Pro Arg Thr Phe Gly Gln Gly Thr Lys Val Glu Ile Lys
            100                 105                 110

<210> SEQ ID NO 20
<211> LENGTH: 112
<212> TYPE: PRT
<213> ORGANISM: Homo sapiens

<400> SEQUENCE: 20

Ala Ile Val Leu Thr Gln Thr Pro Leu Ser Ser Pro Val Thr Leu Gly
1               5                   10                  15

Gln Pro Ala Ser Ile Ser Cys Arg Ser Ser Gln Ser Leu Val His Arg
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Pro Asp Asp Val Gly Val Tyr Tyr Cys Met His Thr
                85                  90                  95

Thr Gln Leu Pro Trp Thr Phe Gly Gln Gly Thr Lys Val Glu Ile Lys
            100                 105                 110

<210> SEQ ID NO 21
<211> LENGTH: 112
<212> TYPE: PRT
<213> ORGANISM: Homo sapiens

<400> SEQUENCE: 21

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Arg
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Phe Cys Met His Thr
                85                  90                  95

Thr Gln Phe Pro Trp Thr Phe Gly Gln Gly Thr Arg Val Glu Ile Lys
            100                 105                 110

<210> SEQ ID NO 22
<211> LENGTH: 112
<212> TYPE: PRT
<213> ORGANISM: Homo sapiens

<400> SEQUENCE: 22

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Ile Thr Phe Gly Gln Gly Thr Arg Leu Glu Ile Lys
            100                 105                 110

<210> SEQ ID NO 23
<211> LENGTH: 112
<212> TYPE: PRT
<213> ORGANISM: Homo sapiens

<400> SEQUENCE: 23

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Ile His Thr
            20                  25                  30

Asp Gly Asn Ile Tyr Leu Ser Trp Leu Gln Gln Arg Pro Gly Gln Pro
        35                  40                  45

```
Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr Gln Phe Pro Ile Thr Phe Gly Gln Gly Thr Arg Leu Glu Ile Lys
            100                 105                 110
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105
```

<210> SEQ ID NO 25
<211> LENGTH: 107
<212> TYPE: PRT
<213> ORGANISM: Homo sapiens

<400> SEQUENCE: 25

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asn
                 20                  25                  30

Leu Ala Trp Tyr Gln Gln Lys Pro Gly Lys Ala Pro Lys Arg Leu Ile
            35                  40                  45

Tyr Ala Ala Ser Asn Leu Gln Ser Gly Val Pro Ser Arg Phe Thr Gly
 50                  55                  60

Ser Gly Ser Gly Thr Glu Phe Thr Leu Ile Val Ser Ser Leu Gln Pro
 65                  70                  75                  80

Glu Asp Phe Ala Thr Tyr Tyr Cys Leu Gln His His Ser Tyr Pro Leu
                 85                  90                  95

Thr Ser Gly Gly Gly Thr Lys Val Glu Ile Lys
            100                 105
```

<210> SEQ ID NO 26
<211> LENGTH: 107
<212> TYPE: PRT
<213> ORGANISM: Homo sapiens

<400> SEQUENCE: 26

```
Asp Ile Gln Met Thr Gln Ser Pro Ser Ser Leu Ser Ala Ser Val Gly
```

-continued

```
                1               5                  10                  15
Asp Ser Val Thr Ile Thr Cys Arg Thr Ser Gln Gly Ile Arg Lys Asn
                20                  25                  30

Leu Gly Trp Tyr Gln Gln Lys Pro Gly Lys Ala Pro Lys Arg Leu Ile
                35                  40                  45

Tyr Ala Ala Ser Ser Leu Gln Ser Gly Val Pro Ser Arg Phe Ser Gly
                50                  55                  60

Ser Gly Ser Gly Thr Glu Phe Thr Leu Thr Ile Ser Arg Leu Gln Pro
 65                 70                  75                  80

Glu Asp Phe Ala Thr Tyr Tyr Cys Leu Gln His His Ser Tyr Pro Leu
                85                  90                  95

Thr Phe Gly Gly Gly Thr Arg Val Glu Ile Arg
                100                 105
```

<210> SEQ ID NO 27
<211> LENGTH: 111
<212> TYPE: PRT
<213> ORGANISM: Homo sapiens

<400> SEQUENCE: 27

```
Asp Ile Val Met Thr Gln Ser Pro Leu Leu Pro Val Thr Pro Gly Glu
  1               5                  10                  15

Pro Ala Ser Ile Ser Cys Arg Ser Ser Gln Ser Leu Leu His Ser Asn
                20                  25                  30

Gly Tyr Asn Tyr Leu Asp Trp Tyr Leu Gln Lys Pro Gly Gln Ser Pro
                35                  40                  45

Gln Leu Leu Ile Tyr Leu Gly Ser Asn Arg Ala Ser Gly Val Pro Asp
                50                  55                  60

Arg Phe Ser Gly Ser Gly Ser Gly Thr Asp Phe Thr Leu Lys Ile Ser
 65                 70                  75                  80

Arg Val Glu Ala Glu Asp Val Gly Val Tyr Tyr Cys Met Gln Ala Leu
                85                  90                  95

Gln Thr Pro Trp Thr Phe Gly Gln Gly Thr Lys Val Glu Ile Lys
                100                 105                 110
```

<210> SEQ ID NO 28
<211> LENGTH: 112
<212> TYPE: PRT
<213> ORGANISM: Homo sapiens

<400> SEQUENCE: 28

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Tyr Arg
                20                  25                  30

Asn Gly Asn Asn Tyr Leu Asp Trp Tyr Leu Gln Arg Pro Gly Gln Ser
                35                  40                  45

Pro Gln Leu Leu Ile Tyr Leu Gly Ser Asn Arg Ala Ser Gly Val Pro
                50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
                100                 105                 110
```

```
<210> SEQ ID NO 29
<211> LENGTH: 112
<212> TYPE: PRT
<213> ORGANISM: Homo sapiens

<400> SEQUENCE: 29

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Arg
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly His Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 30
<211> LENGTH: 112
<212> TYPE: PRT
<213> ORGANISM: Homo sapiens

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 31
<211> LENGTH: 112
<212> TYPE: PRT
<213> ORGANISM: Homo sapiens

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Arg
            20                  25                  30

Asn Gly Asn Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
            85                  90                  95

Leu Gln Thr Pro Arg Thr Phe Gly Gln Gly Thr Lys Val Glu Ile Lys
            100                 105                 110

<210> SEQ ID NO 32
<211> LENGTH: 112
<212> TYPE: PRT
<213> ORGANISM: Homo sapiens

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Arg
            20                  25                  30

Asn Gly Asn Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Arg Thr Phe Gly Gln Gly Thr Lys Val Glu Ile Lys
            100                 105                 110

<210> SEQ ID NO 33
<211> LENGTH: 112
<212> TYPE: PRT
<213> ORGANISM: Homo sapiens

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Arg
            20                  25                  30

Asn Gly Asn Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Arg Thr Phe Gly Gln Gly Thr Lys Val Glu Ile Lys
            100                 105                 110

<210> SEQ ID NO 34
<211> LENGTH: 336
<212> TYPE: DNA
<213> ORGANISM: Homo sapiens

<400> SEQUENCE: 34
gatattgtga tgacccagac tccactctcc tcacctgtca cccttggaca gccggcctcc      60
atctcctgca ggtctagtca aagcctcata cacactgatg aaacatcta tttgagttgg     120 cttcagcaga ggccaggcca gcctccaaga ctcctaattt ataagatttc taatcggttc    180
tctggggtcc cagacagatt cagtggcagt ggggcaggga cagatttcac actgaagatc     240
agcagggtgg aagctgagga tgtggggtt tattactgca tgcaaggtac acaatttcct      300
atcaccttcg gccaagggac acgactggag attaaa                                336

<210> SEQ ID NO 35
<211> LENGTH: 375
<212> TYPE: DNA
<213> ORGANISM: Homo sapiens

<400> SEQUENCE: 35
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggttcatct attacagagg gaacacctac     180
tacaacccgt ccctcaagag tcgagttacc atatcagttg acacgtctaa gaaccagttc     240
tccctgaagc tgagctctgt gactgccgcg gacacggccg tgtattactg tgcgcgagac     300
ggatattgta gtagaaccgg ctgctatggc ggctggttcg acccctgggg ccagggaacc     360
ctggtcacgt ctcct                                                      375

<210> SEQ ID NO 36
<211> LENGTH: 335
<212> TYPE: DNA
<213> ORGANISM: Homo sapiens

<400> SEQUENCE: 36
atattgtgat gactcagtct ccactctccc tgcccgtcac cctggagag ccggcctcca      60 tctcctgcag gtctagtcag agcctcctgt atagaaatgg aaacaactat ttggattggt     120
atctgcagaa gccagggcag tctccacagc tcctgatcta tttgggttct aatcgggcct     180
ccggggtccc tgacaggttc agtggcagtg gatcgggcac agattttaca ctgaacatca     240
gcagagtgga ggctgaggat gttgggcatt attactgcat gcaggctcta caaactcctc     300
ggacgttcgg ccaagggacc aaggtggaaa tcaaa                                335

<210> SEQ ID NO 37
<211> LENGTH: 384
<212> TYPE: DNA
<213> ORGANISM: Homo sapiens

<400> SEQUENCE: 37
caggtgcagc tggtggagtc tgggggaggc gtggtccagc ctgggaggtc cctgagactc      60
tcctgtgcag cctccggatt caccctcagt agctatggca tgcactgggt ccgccaggct     120
ccaggcaagg gctggagtg gtggcagtt atgtcatatg atggaagtaa agaagactat      180
gcagactccg tgaagggccg attcaccatc tctagagaca attccgagaa catgctgtat     240
ctgcaaatga acagcctgag agctgaggac acggctgtat attactgtgt gagcgaagga     300
tattgtagta gtcgtagctg ctataagtac tactactacg gcatggacgt ctggggccaa     360
gggaccacgg tcaccgtctc ctca                                            384

<210> SEQ ID NO 38
<211> LENGTH: 336
<212> TYPE: DNA
<213> ORGANISM: Homo sapiens

<400> SEQUENCE: 38
gatactgtga tgacccagac tccactctcc tcacatgtaa cccttggaca gccggcctcc      60

```
atctcctgca ggtctagtca aagcctcgta cacagtgatg gaaacaccta cttgagttgg    120
cttcagcaga ggccaggcca acctccaaga ctcctaattt ataggatttc taggcggttc    180
tctggggtcc cagacagatt cagtggcagt ggggcaggga cagatttcac actggaaatc    240 agcaggtgg aggctgagga tgtcgggtt tattactgca tgcaatctac acacgttcct     300
cggacgttcg gccaagggac caaggtggag atcaaa                              336
```

```
<210> SEQ ID NO 39
<211> LENGTH: 372
<212> TYPE: DNA
<213> ORGANISM: Homo sapiens

<400> SEQUENCE: 39
caggtgcagc tggtggagtc tgggggaggc gtggtccagt ctggggggtc cctgagactc    60
tcctgtgcag cgtctggatt cacccttcaga aactatggca tgcactgggt ccgccaggct   120
ccaggcaagg ggctggagtg gtggcagtt atatggtatg atggaagtga taaatactat    180
gcagactccg tgaggggccg attcaccatc tccagagaca attccaagaa cacgctgtat   240
ctgcaaatga acagcctgag agccgaggac acggctgtgt attactgtgc gagagatggc   300
tacgatattt tgactggtaa tcctagggac tttgactact ggggccaggg aaccctggtc   360
accgtctcct ca                                                        372
```

```
<210> SEQ ID NO 40
<211> LENGTH: 348
<212> TYPE: DNA
<213> ORGANISM: Homo sapiens

<400> SEQUENCE: 40
gaggtgcagg tgttggagtc tgggggaggc ttggtacagc ctggggggtc cctgagactc    60
tcctgtgcag cctctggatt caccttttagc agctatgcca tgagctgggt ccgccaggct   120
ccagggaagg ggctggagtg ggtctcggct attagtggta gtggtggtag tacaaactac    180
gcagactccg tgaagggccg gttcaccatc tccagagaca attccaagaa cacactgtat   240
ctgcaaatga acagcctgag agccgaggac acggccgtct attactgtgc tgggagcagt   300
ggctggtccg agtactgggg ccagggaacc ctggtcaccg tctcctcg                 348
```

```
<210> SEQ ID NO 41
<211> LENGTH: 321
<212> TYPE: DNA
<213> ORGANISM: Homo sapiens

<400> SEQUENCE: 41
gacatccaga tgacccagtc tccatcctcc ctgtctgcat ctgtaggaga cagagtcacc    60
atcacttgcc gggctagtca gggcattaga aataatttag cctggtatca gcagaaacca   120
gggaaagccc ctaagcgcct gatctatgct gcctccaatt tgcaaagtgg gtcccatca    180 aggttcaccg gcagtggatc tgggacagaa ttcactctca tagtcagcag cctgcagcct   240
gaagattttg cgacttatta ctgtctacag catcacagtt acccgctcac ttccggcgga   300
gggaccaagg tggagatcaa a                                              321
```

```
<210> SEQ ID NO 42
<211> LENGTH: 336
<212> TYPE: DNA
<213> ORGANISM: Homo sapiens
```

<400> SEQUENCE: 42

```
gatattgtga tgacccagac tccactctcc tcacctgtca cccttggaca gccggcctcc    60
atctcctgca ggtctagtca aagcctcgta cacagggatg gaaataccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatt   240
agcagggtgg aagctgagga tgtcgggatt tatttctgca tgcatactac acaatttcct   300
tggacgttcg gccaagggac caggtgtggaa atcaaa                             336
```

<210> SEQ ID NO 43
<211> LENGTH: 354
<212> TYPE: DNA
<213> ORGANISM: Homo sapiens

<400> SEQUENCE: 43

```
caggtacagc tgcagcagtc aggtccagga ctggtgaagc cctcgcagac cctctcactc    60
acctgtgcca tctccgggga cagtgtctct agctacagtt ctgcttggaa ctggatcagg   120
cagtccccat cgagaggcct tgagtggctg ggaagggcat atcacaggtc caggtggtat   180
tacgagtatg cagtatcggt gaaaagtcga ataaacatca ccccagacac atccaagaac   240
cagttctccc tgcagctgaa ctctgtgact cccgaggaca cggctgtgta ttactgtgca   300
agaggcagtc gctttgacta ctggggccag ggaaccctgg tcaccgtctc ctca          354
```

<210> SEQ ID NO 44
<211> LENGTH: 354
<212> TYPE: DNA
<213> ORGANISM: Homo sapiens

<400> SEQUENCE: 44

```
caggtacagc tgcagcagtc aggtccagga ctggtgaagc cctcgcagac cctctcactc    60
acctgtgcca tctccgggga cagtgtctct agcaacaatg ctgcttggaa ctggatcagg   120
cagtccccag cgagaggcct tgagtggctg ggaaggacat actacaggtc caagtggtat   180
aatgattatg tagtatctgt gaaaagtcga ataaccatca acccagacac atccaagaac   240
cagttctccc tgcagctgaa ctctgtgact cccgaggaca cggctgtgta ttactgtgta   300
agaggcagtc gctttgacta ctggggccag ggaaccctgg tcaccgtctc ctca          354
```

<210> SEQ ID NO 45
<211> LENGTH: 336
<212> TYPE: DNA
<213> ORGANISM: Homo sapiens

<400> SEQUENCE: 45

```
gctattgtgt tgacccagac tccactctcc tcacctgtca cccttggaca gccggcctcc    60
atctcctgca ggtctagtca aagcctcgtt cacagggatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aacctgacga tgtcggggtt tattactgca tgcatactac acaacttcct   300
tggacgttcg gccaagggac caaggtggaa atcaaa                              336
```

<210> SEQ ID NO 46
<211> LENGTH: 336
<212> TYPE: DNA
<213> ORGANISM: Homo sapiens

<400> SEQUENCE: 46

```
gatattgtga tgactcagtc tccactctcc ctgcccgtca cccctggaga gccggcctcc      60
atctcctgca ggtctagtca gagcctccta tatagaaatg gaaacaacta tttggattgg     120
tatctgcaga ggccagggca gtctccacaa ctcctgatct atttgggttc taatcgggcc     180
tccggggtcc ctgacaggtt cagtggcagt ggatcaggca cagattttac attgaaaatc     240
ggcagagtgg aggctgagga tgttggggtt tattactgca tgcaggctct acaaactcct     300
cggacgttcg gccaagggac caaggtggaa atcaaa                               336
```

<210> SEQ ID NO 47
<211> LENGTH: 384
<212> TYPE: DNA
<213> ORGANISM: Homo sapiens

<400> SEQUENCE: 47

```
caggtgcagc tggtggagtc tgggggaggc gtggtccagc ctgggaggtc cctgagactc      60
tcctgtgtag cctctggatt caccctcagt agctatggca tgcactgggt ccgccaggct     120
ccaggcaagg ggctggagtg ggtggcagtg acatcatatg atggaagtaa aaaagactat     180
gcagactccg cgaagggccg attcaccatc tccagagaca attccaagaa cacgctgtat     240
ctgcaaatga acagcctgag agctgaggac acggctgtgt attactgtgt gagcaagga     300
tattgtagta gtagtagctg ctataagtac tactattacg gtatggacgt ctggggccaa     360
gggaccacgg tcaccgtctc ttca                                            384
```

<210> SEQ ID NO 48
<211> LENGTH: 348
<212> TYPE: DNA
<213> ORGANISM: Homo sapiens

<400> SEQUENCE: 48

```
gaggggcagc tgttggagtc tgggggaggc tgggtacagc ctggggagtc cctgagactc      60
tcctgtgcag cctctggatt cacctttagc agctatgcca tgagctgggt ccgccaggct     120
ccagggaagg ggctggagtg ggtctcggct attagtggta gtggtggtag cacaaattac     180
gcagactccg tgaagggccg gttcaccatc tccagagaca attccaagaa cacgctgtat     240
ctgcaagtga acagcctgag agtcgaggac acggccgtat attactgtgc tgggagcagt     300
ggctggtccg agtactgggg ccagggaacc ctggtcaccg tctcctca                  348
```

<210> SEQ ID NO 49
<211> LENGTH: 321
<212> TYPE: DNA
<213> ORGANISM: Homo sapiens

<400> SEQUENCE: 49

```
gacatccaga tgacccagtc tccatcctcc ctgtctgcat ctgtaggaga cagcgtcacc      60
atcacttgcc ggacaagtca gggcattaga aaaaatttag gctggtatca gcagaaacca     120
gggaaagccc ctaagcgcct gatctatgct gcatccagtt tacaaagtgg ggtcccatca     180
aggttcagcg gcagtggatc tgggacagaa ttcactctca caatccgcag cctgcagcct     240
gaagattttg caacttatta ctgtctccag catcatagtt acccgctcac tttcggcgga     300
gggaccaggg tggagatcag a                                               321
```

<210> SEQ ID NO 50

<211> LENGTH: 336
<212> TYPE: DNA
<213> ORGANISM: Homo sapiens

<400> SEQUENCE: 50

```
gatattgtga tgactcagtc tccactctcc ctgcccgtca cccctggaga gccggcctcc    60
atctcctgca ggtctagtca gagcctccta tatagaaatg gaaacaacta tttggattgg   120
tatctgcaga ggccagggca gtctccacaa ctcctgatct atttgggttc taatcgggcc   180
tccggggtcc ctgacaggtt cagtggcagt ggatcaggca cagatttac actgaaaatc    240
agcagagtgg aggctgagga tgttggggtt tattactgca tgcaggctct acaaactcct   300
cggacgttcg gccaagggac caaggtggaa atcaaa                             336
```

<210> SEQ ID NO 51
<211> LENGTH: 384
<212> TYPE: DNA
<213> ORGANISM: Homo sapiens

<400> SEQUENCE: 51

```
caggtgcagc tggtggagtc tgggggaggc gtggtccagc ctgggaggtc cctgagactc    60
tcctgtgtag cctctggatt caccctcagt agctatggca tgcactgggt ccgccaggct   120
ccaggcaagg ggctggagtg ggtggcagtg acatcatatg atggaagtaa aaaagactat   180
gcagactccg tgaagggccg attcaccatc tccagagaca attccaagaa cacgctgtat   240
ctgcaaatga acagcctgag agctgaggac acggctgtgt attactgtgt gagcgaagga   300
tattgtgata gtagtagctg ctataagtac tactactacg gtatggacgt ctggggccaa   360
gggaccacgg tcaccgtctc ttca                                          384
```

<210> SEQ ID NO 52
<211> LENGTH: 336
<212> TYPE: DNA
<213> ORGANISM: Homo sapiens

<400> SEQUENCE: 52

```
gatattgtga tgactcagtc tccactctcc ctgcccgtca cccctggaga gccggcctcc    60
atctcctgca ggtctagtca gagcctccta tatagaaatg gaaacaacta tttggattgg   120
tatctgcaga ggccagggca gtctccacaa ctcctgatct atttgggttc taatcgggcc   180
tccggggtcc ctgacaggtt cagtggcagt ggatcaggca cagatttac actgaaaatc    240
agcagagtgg aggctgagga tgttggggtt tattactgca tgcaggctct acaaactcct   300
cggacgttcg gccaagggac caaggtggaa atcaaa                             336
```

<210> SEQ ID NO 53
<211> LENGTH: 384
<212> TYPE: DNA
<213> ORGANISM: Homo sapiens

<400> SEQUENCE: 53

```
caggtgcagc tggtggagtc tgggggaggc gtggtccagc ctgggaggtc cctgagactc    60
tcctgtgtag cctctggatt caccctcagt agctatggca tgcactgggt ccgccaggct   120
ctaggcaagg ggctggagtg ggtggcagtg acatcatatg atggaagtaa aaaagactat   180
gcagactccg tgaagggccg attcaccatc tccagagaca attccaagaa cacgctgtat   240
ctgcaaatga acagcctgag agctgaggac acggctgtgt attactgtgt gagcgaagga   300
tattgtgata gtactagttg ctataagtac tactactacg gtatggacgt ctggggccaa   360
```

```
gggaccacgg tcaccgtctc ttca                                              384
```

```
<210> SEQ ID NO 54
<211> LENGTH: 336
<212> TYPE: DNA
<213> ORGANISM: Homo sapiens

<400> SEQUENCE: 54
gatattgtga tgactcagtc tccactctcc ctgcccgtca cccctggaga gccggcctcc       60
atctcctgca ggtctagtca gagcctccta tatagaaatg gaaacaacta tttggattgg     120
tatctgcaga ggccagggca gtctccacaa ctcctgatct atttgggttc aatcgggcc      180 tccggggtcc ctgacaggtt cagtggcagt ggatcaggca cagatttac actgaaaatc      240 agcagagtgg aggctgagga tgttggggtt tattactgca tgcaggctct acaaactcct     300
cggacgttcg gccaagggac caaggtggaa atcaaa                                336
```

```
<210> SEQ ID NO 55
<211> LENGTH: 384
<212> TYPE: DNA
<213> ORGANISM: Homo sapiens

<400> SEQUENCE: 55
caggtgcagc tggtggagtc tgggggaggc gtggtccagc ctgggaggtc cctgagactc       60
tcctgtgtag cctctggatt caccctcagt agctatggca tgcactgggt ccgccaggct     120
ccaggcaagg gctggagtg gtggcagtg acatcatatg atggaagtaa aaaagactat       180
gcagactccg tgaagggccg attcaccatc tccagagaca attccaagaa cacgctgtat     240
ctgcaaatga acagcctgag agctgaggac acggctgtgt attactgtgt gagcgaagga     300
tattgtgata gtactagctg ctataagtac tactactacg gtatggacgt ctggggccaa     360
gggaccacgg tcaccgtctc ttca                                              384
```

```
<210> SEQ ID NO 56
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 56

Leu Glu Glu Lys Lys Gly Asn Tyr Val Val Thr Asp His Cys
 1               5                  10
```

```
<210> SEQ ID NO 57
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 57

Glu Glu Lys Lys Gly Asn Tyr Val Val Thr
 1               5                  10
```

```
<210> SEQ ID NO 58
<211> LENGTH: 5
<212> TYPE: PRT
<213> ORGANISM: Artificial Sequence
<220> FEATURE:
<223> OTHER INFORMATION: Synthetic peptide sequence
```

<400> SEQUENCE: 58

Leu Glu Glu Lys Lys
 1               5

<210> SEQ ID NO 59
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 59

Leu Glu Glu Lys Lys Gly Asn Tyr Val Val Thr Asp
 1               5                  10

<210> SEQ ID NO 60
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 60

Glu Lys Asn Tyr
 1

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 61

Glu Glu Lys Gly Asn
 1               5

<210> SEQ ID NO 62
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 62
ggatctcgag ccagaccgga acgacaggcc acctc                              35

<210> SEQ ID NO 63
<211> LENGTH: 34
<212> TYPE: DNA
<213> ORGANISM: Artificial Sequence
<220> FEATURE:
<223> OTHER INFORMATION: Synthetic oligonucleotide primer sequence

<400> SEQUENCE: 63
cggatctcga gccggagccc agcactttga tctt                               34

<210> SEQ ID NO 64
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 64
cggatgaatt cccagaccgg acgacaggcc acctc                              35

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide primer sequence

<400> SEQUENCE: 65 ctttctttc ctccagagcc                                         20

<210> SEQ ID NO 66
<211> LENGTH: 21
<212> TYPE: DNA
<213> ORGANISM: Artificial Sequence
<220> FEATURE:
<223> OTHER INFORMATION: Synthetic oligonucleotide primer sequence

<400> SEQUENCE: 66
gtaattatgt ggtgacagat c                                      21

<210> SEQ ID NO 67
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 67
cggatctcga gctcaagaga gcttggttgg gagct                       35

<210> SEQ ID NO 68
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 68
ggtggcggta cctggacaag accgttgcg                              29

<210> SEQ ID NO 69
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 69
ataagaatgc ggccgctcat ttacccggag agcggga                     37

<210> SEQ ID NO 70
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 70
ctactagcta gccaccatgc gaccctccgg ga                          32

<210> SEQ ID NO 71
<211> LENGTH: 26
<212> TYPE: DNA
<213> ORGANISM: Artificial Sequence
<220> FEATURE:

<223> OTHER INFORMATION: Synthetic oligonucleotide primer sequence

<400> SEQUENCE: 71
cggggtaccc ggcgatggac gggatc                                              26

<210> SEQ ID NO 72
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 72

Ala Leu Glu Glu Lys Lys Gly Asn Tyr Val Val Thr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 73

Glu Glu Lys Lys Gly Asn Tyr Val Val Thr Asp His
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 74

Glu Lys Lys Gly Asn Tyr Val Val Thr Asp His Gly
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 75

Lys Lys Gly Asn Tyr Val Val Thr Asp His Gly Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 76

Lys Gly Asn Tyr Val Val Thr Asp His Gly Ser Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 77

Gly Asn Tyr Val Val Thr Asp His Gly Ser Cys Val
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 78

Asn Tyr Val Val Thr Asp His Gly Ser Cys Val Arg
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 79

Tyr Val Val Thr Asp His Gly Ser Cys Val Arg Ala
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 80

Ala Glu Glu Lys Lys Gly Asn Tyr Val Val Thr Asp
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 81

Leu Ala Glu Lys Lys Gly Asn Tyr Val Val Thr Asp
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 82

Leu Glu Ala Lys Lys Gly Asn Tyr Val Val Thr Asp
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 83

```
Leu Glu Glu Ala Lys Gly Asn Tyr Val Val Thr Asp
 1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 84

Leu Glu Glu Lys Ala Gly Asn Tyr Val Val Thr Asp
 1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 85

Leu Glu Glu Lys Lys Ala Asn Tyr Val Val Thr Asp
 1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 86

Leu Glu Glu Lys Lys Gly Ala Tyr Val Val Thr Asp
 1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 87

Leu Glu Glu Lys Lys Gly Asn Ala Val Val Thr Asp
 1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 88

Leu Glu Glu Lys Lys Gly Asn Tyr Ala Val Thr Asp
 1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 89
```

Leu Glu Glu Lys Lys Gly Asn Tyr Val Ala Thr Asp
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 90

Leu Glu Glu Lys Lys Gly Asn Tyr Val Val Ala Asp
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 91

Leu Glu Glu Lys Lys Gly Asn Tyr Val Val Thr Ala
1               5                   10

<210> SEQ ID NO 92
<211> LENGTH: 22
<212> TYPE: PRT
<213> ORGANISM: Artificial Sequence
<220> FEATURE:
<223> OTHER INFORMATION: Synthetic peptide sequence

<400> SEQUENCE: 92

Ala Thr Cys Val Lys Lys Cys Pro Arg Asn Tyr Val Val Thr Asp His
1               5                   10                  15

Gly Ser Cys Val Arg Ala
            20

<210> SEQ ID NO 93
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 93

Leu Glu Glu Lys Lys Gly Asn Tyr Val Val Thr Asp His Gly Ser Cys
1               5                   10                  15

Val Arg Ala

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 94

Glu Glu Lys Lys Gly Asn Tyr Val Val Thr
1               5                   10

<210> SEQ ID NO 95
<211> LENGTH: 12
<212> TYPE: PRT
<213> ORGANISM: Artificial Sequence
<220> FEATURE:

<223> OTHER INFORMATION: Synthetic peptide sequence

<400> SEQUENCE: 95

Leu Glu Glu Lys Lys Gly Asn Tyr Val Val Thr Asp
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 96

Tyr Val Val Thr Asp His
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 97

Tyr Val Val Thr Asp
1               5

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 98

Glu Glu Lys Lys Gly Asn Tyr Val Val Thr
1               5                   10

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 99

Gly Asn Tyr Val Val Thr
1               5

<210> SEQ ID NO 100
<211> LENGTH: 23
<212> TYPE: PRT
<213> ORGANISM: Artificial Sequence
<220> FEATURE:
<223> OTHER INFORMATION: Synthetic peptide sequence

<400> SEQUENCE: 100

Asp Thr Val Met Thr Gln Thr Pro Leu Ser Ser His Val Thr Leu Gly
1               5                   10                  15

Gln Pro Ala Ser Ile Ser Cys
            20

<210> SEQ ID NO 101
<211> LENGTH: 16
<212> TYPE: PRT

```
<213> ORGANISM: Artificial Sequence
<220> FEATURE:
<223> OTHER INFORMATION: Synthetic peptide sequence

<400> SEQUENCE: 101

Arg Ser Ser Gln Ser Leu Val His Ser Asp Gly Asn Thr Tyr Leu Ser
 1               5                  10                  15

<210> SEQ ID NO 102
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 102

Trp Leu Gln Gln Arg Pro Gly Pro Pro Arg Leu Leu Ile Tyr
 1               5                  10

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 103

Arg Ile Ser Arg Arg Phe Ser
 1               5

<210> SEQ ID NO 104
<211> LENGTH: 32
<212> TYPE: PRT
<213> ORGANISM: Artificial Sequence
<220> FEATURE:
<223> OTHER INFORMATION: Synthetic peptide sequence

<400> SEQUENCE: 104

Gly Val Pro Asp Arg Phe Ser Gly Ser Gly Ala Gly Thr Asp Phe Thr
 1               5                  10                  15

Leu Glu Ile Ser Arg Val Glu Ala Glu Asp Val Gly Val Tyr Tyr Cys
            20                  25                  30

<210> SEQ ID NO 105
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 105

Met Gln Ser Thr His Val Pro Arg Thr
 1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 106

Phe Gly Gln Thr Lys Val Glu Ile Lys
 1               5

<210> SEQ ID NO 107
```

```
<211> LENGTH: 30
<212> TYPE: PRT
<213> ORGANISM: Artificial Sequence
<220> FEATURE:
<223> OTHER INFORMATION: Synthetic peptide sequence

<400> SEQUENCE: 107

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg
            20                  25                  30

<210> SEQ ID NO 108
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 108

Asn Tyr Gly Met His
1               5

<210> SEQ ID NO 109
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 109

Trp Val Arg Gln Ala Pro Gly Lys Gly Leu Glu Trp Val Ala
1               5                   10

<210> SEQ ID NO 110
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 110

Val Ile Trp Tyr Asp Gly Ser Asp Lys Tyr Tyr Ala Asp Ser Val Arg
1               5                   10                  15

Gly

<210> SEQ ID NO 111
<211> LENGTH: 32
<212> TYPE: PRT
<213> ORGANISM: Artificial Sequence
<220> FEATURE:
<223> OTHER INFORMATION: Synthetic peptide sequence

<400> SEQUENCE: 111

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide sequence
```

<400> SEQUENCE: 112

Asp Gly Tyr Asp Ile Leu Thr Gly Asn Pro Arg Asp Phe Asp Tyr
1               5                   10                  15

<210> SEQ ID NO 113
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 113

Trp Gly Gln Gly Thr Leu Val Thr Val Ser Ser
1               5                   10

<210> SEQ ID NO 114
<211> LENGTH: 23
<212> TYPE: PRT
<213> ORGANISM: Artificial Sequence
<220> FEATURE:
<223> OTHER INFORMATION: Synthetic peptide sequence

<400> SEQUENCE: 114

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 115
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 115

Trp Leu His Gln Arg Pro Gly Gln Pro Pro Arg Leu Leu Ile Tyr
1               5                   10                  15

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 116

Lys Ile Ser Asn Arg Phe Ser
1               5

<210> SEQ ID NO 117
<211> LENGTH: 32
<212> TYPE: PRT
<213> ORGANISM: Artificial Sequence
<220> FEATURE:
<223> OTHER INFORMATION: Synthetic peptide sequence

<400> SEQUENCE: 117

Gly Val Pro Asp Arg Phe Ser Gly Ser Gly Ala Gly Thr Ala Phe Thr
1               5                   10                  15

Leu Lys Ile Ser Arg Val Glu Ala Glu Asp Val Gly Val Tyr Tyr Cys
            20                  25                  30

<210> SEQ ID NO 118
<211> LENGTH: 9

```
<212> TYPE: PRT
<213> ORGANISM: Artificial Sequence
<220> FEATURE:
<223> OTHER INFORMATION: Synthetic peptide sequence

<400> SEQUENCE: 118

Met Gln Ala Thr Gln Leu Pro Arg Thr
1               5

<210> SEQ ID NO 119
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 119

Phe Gly Gln Gly Thr Lys Val Glu Ile Lys Arg
1               5                   10

<210> SEQ ID NO 120
<211> LENGTH: 30
<212> TYPE: PRT
<213> ORGANISM: Artificial Sequence
<220> FEATURE:
<223> OTHER INFORMATION: Synthetic peptide sequence

<400> SEQUENCE: 120

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 121
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 121

Ser Tyr Gly Met His
1               5

<210> SEQ ID NO 122
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 122

Trp Val Arg Gln Ala Pro Gly Lys Gly Leu Glu Trp Val Ala
1               5                   10

<210> SEQ ID NO 123
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 123

Val Ile Trp Tyr Asp Gly Ser Asn Lys Tyr Tyr Val Asp Ser Val Lys
1               5                   10                  15

Gly
```

```
<210> SEQ ID NO 124
<211> LENGTH: 32
<212> TYPE: PRT
<213> ORGANISM: Artificial Sequence
<220> FEATURE:
<223> OTHER INFORMATION: Synthetic peptide sequence

<400> SEQUENCE: 124

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
                20                  25                  30

<210> SEQ ID NO 125
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 125

Asp Gly Trp Gln Gln Leu Ala Pro Phe Asp Tyr
 1               5                  10

<210> SEQ ID NO 126
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 126

Trp Gly Gln Gly Thr Leu Val Thr Val Ser Ser Ala
 1               5                  10

<210> SEQ ID NO 127
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 127

Glu Glu Lys Lys Gly Asn
 1               5

<210> SEQ ID NO 128
<211> LENGTH: 33
<212> TYPE: DNA
<213> ORGANISM: Artificial Sequence
<220> FEATURE:
<223> OTHER INFORMATION: Synthetic peptide sequence

<400> SEQUENCE: 128
ataaaagctt ctggaggaaa agaaaggtaa tta                            33

<210> SEQ ID NO 129
<211> LENGTH: 33
<212> TYPE: PRT
<213> ORGANISM: Artificial Sequence
<220> FEATURE:
<223> OTHER INFORMATION: Synthetic peptide sequence

<400> SEQUENCE: 129

Thr Thr Ala Thr Thr Gly Gly Thr Ala Cys Cys Thr Cys Ala Gly Gly
```

```
                1               5                  10                  15
Cys Gly Ala Thr Gly Gly Ala Cys Gly Gly Gly Ala Thr Cys Thr Thr
                20                  25                  30
Ala
```

<210> SEQ ID NO 130
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 130

```
Leu Glu Glu Lys Lys Gly Asn Tyr Val Val Thr Asp His Gly
 1               5                  10
```

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 131

```
Glu Glu Lys Lys Gly Asn Tyr
 1               5
```

<210> SEQ ID NO 132
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 132

```
Leu Glu Glu Lys Lys Gly Asn Tyr Val Val Thr
 1               5                  10
```

<210> SEQ ID NO 133
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 133

```
Leu Glu Glu Lys Lys Gly Asn Tyr
 1               5
```

<210> SEQ ID NO 134
<211> LENGTH: 1186
<212> TYPE: PRT
<213> ORGANISM: Homo sapiens

<400> SEQUENCE: 134

```
Leu Glu Glu Lys Lys Val Cys Gln Gly Thr Ser Asn Lys Leu Thr Gln
 1               5                  10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
                35                  40                  45

Asn Tyr Asp Leu Ser Phe Leu Lys Thr Ile Gln Glu Val Ala Gly Tyr
            50                  55                  60
```

```
Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
```

```
                485                 490                 495
Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Thr
            610                 615                 620

Gly Met Val Gly Ala Leu Leu Leu Leu Val Val Ala Leu Gly Ile Gly
625                 630                 635                 640

Gly Leu Phe Met Arg Arg Arg His Ile Val Arg Lys Arg Thr Leu Arg
                645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
            675                 680                 685

Lys Lys Ile Lys Val Leu Gly Ser Gly Ala Phe Gly Thr Val Tyr Lys
            690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
                725                 730                 735

Asp Glu Ala Tyr Val Met Ala Ser Val Asp Asn Pro His Val Cys Arg
            740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
            770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
                805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
            850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910
```

```
Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
    930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val Ala
        1010                1015                1020

Cys Ile Asp Arg Asn Gly Leu Gln Ser Cys Pro Ile Lys Glu Asp Ser
1025                1030                1035                1040

Phe Leu Gln Arg Tyr Ser Ser Asp Pro Thr Gly Ala Leu Thr Glu Asp
                1045                1050                1055

Ser Ile Asp Asp Thr Phe Leu Pro Val Pro Glu Tyr Ile Asn Gln Ser
            1060                1065                1070

Val Pro Lys Arg Pro Ala Gly Ser Val Gln Asn Pro Val Tyr His Asn
        1075                1080                1085

Gln Pro Leu Asn Pro Ala Pro Ser Arg Asp Pro His Tyr Gln Asp Pro
        1090                1095                1100

His Ser Thr Ala Val Gly Asn Pro Glu Tyr Leu Asn Thr Val Gln Pro
1105                1110                1115                1120

Thr Cys Val Asn Ser Thr Phe Asp Ser Pro Ala His Trp Ala Gln Lys
                1125                1130                1135

Gly Ser His Gln Ile Ser Leu Asp Asn Pro Asp Tyr Gln Gln Asp Phe
            1140                1145                1150

Phe Pro Lys Glu Ala Lys Pro Asn Gly Ile Phe Lys Gly Ser Thr Ala
        1155                1160                1165

Glu Asn Ala Glu Tyr Leu Arg Val Ala Pro Gln Ser Ser Glu Phe Ile
    1170                1175                1180

Gly Ala
1185

<210> SEQ ID NO 135
<211> LENGTH: 919
<212> TYPE: PRT
<213> ORGANISM: Homo sapiens

<400> SEQUENCE: 135

Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
        35                  40                  45

Ile Gly Ile Gly Glu Phe Lys Asp Ser Leu Ser Ile Asn Ala Thr Asn
    50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
```

```
                85                  90                  95
Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
            115                 120                 125

Phe Glu Asn Leu Glu Ile Ile Arg Gly Arg Thr Lys Gln His Gly Gln
            130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
            195                 200                 205

Lys Ala Thr Gly Gln Val Cys His Ala Leu Cys Ser Pro Glu Gly Cys
210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
            245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
            275                 280                 285

Ile Gln Cys Ala His Tyr Ile Asp Gly Pro His Cys Val Lys Thr Cys
290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
            325                 330                 335

Cys Thr Gly Pro Gly Leu Glu Gly Cys Pro Thr Asn Gly Pro Lys Ile
            340                 345                 350

Pro Ser Ile Ala Thr Gly Met Val Gly Ala Leu Leu Leu Leu Leu Val
            355                 360                 365

Val Ala Leu Gly Ile Gly Leu Phe Met Arg Arg Arg His Ile Val Arg
370                 375                 380

Lys Arg Thr Leu Arg Arg Leu Leu Gln Glu Arg Glu Leu Val Glu Pro
385                 390                 395                 400

Leu Thr Pro Ser Gly Glu Ala Pro Asn Gln Ala Leu Leu Arg Ile Leu
            405                 410                 415

Lys Glu Thr Glu Phe Lys Lys Ile Lys Val Leu Gly Ser Gly Ala Phe
            420                 425                 430

Gly Thr Val Tyr Lys Gly Leu Trp Ile Pro Glu Gly Glu Lys Val Lys
            435                 440                 445

Ile Pro Val Ala Ile Lys Glu Leu Arg Glu Ala Thr Ser Pro Lys Ala
450                 455                 460

Asn Lys Glu Ile Leu Asp Glu Ala Tyr Val Met Ala Ser Val Asp Asn
465                 470                 475                 480

Pro His Val Cys Arg Leu Leu Gly Ile Cys Leu Thr Ser Thr Val Gln
            485                 490                 495

Leu Ile Thr Gln Leu Met Pro Phe Gly Cys Leu Leu Asp Tyr Val Arg
            500                 505                 510
```

```
Glu His Lys Asp Asn Ile Gly Ser Gln Tyr Leu Leu Asn Trp Cys Val
            515                 520                 525

Gln Ile Ala Lys Gly Met Asn Tyr Leu Glu Asp Arg Arg Leu Val His
    530                 535                 540

Arg Asp Leu Ala Ala Arg Asn Val Leu Val Lys Thr Pro Gln His Val
545                 550                 555                 560

Lys Ile Thr Asp Phe Gly Leu Ala Lys Leu Leu Gly Ala Glu Glu Lys
                565                 570                 575

Glu Tyr His Ala Glu Gly Gly Lys Val Pro Ile Lys Trp Met Ala Leu
                580                 585                 590

Glu Ser Ile Leu His Arg Ile Tyr Thr His Gln Ser Asp Val Trp Ser
            595                 600                 605

Tyr Gly Val Thr Val Trp Glu Leu Met Thr Phe Gly Ser Lys Pro Tyr
        610                 615                 620

Asp Gly Ile Pro Ala Ser Glu Ile Ser Ser Ile Leu Glu Lys Gly Glu
625                 630                 635                 640

Arg Leu Pro Gln Pro Pro Ile Cys Thr Ile Asp Val Tyr Met Ile Met
                645                 650                 655

Val Lys Cys Trp Met Ile Asp Ala Asp Ser Arg Pro Lys Phe Arg Glu
                660                 665                 670

Leu Ile Ile Glu Phe Ser Lys Met Ala Arg Asp Pro Gln Arg Tyr Leu
            675                 680                 685

Val Ile Gln Gly Asp Glu Arg Met His Leu Pro Ser Pro Thr Asp Ser
        690                 695                 700

Asn Phe Tyr Arg Ala Leu Met Asp Glu Glu Asp Met Asp Asp Val Val
705                 710                 715                 720

Asp Ala Asp Glu Tyr Leu Ile Pro Gln Gln Gly Phe Phe Ser Ser Pro
                725                 730                 735

Ser Thr Ser Arg Thr Pro Leu Leu Ser Ser Leu Ser Ala Thr Ser Asn
            740                 745                 750

Asn Ser Thr Val Ala Cys Ile Asp Arg Asn Gly Leu Gln Ser Cys Pro
        755                 760                 765

Ile Lys Glu Asp Ser Phe Leu Gln Arg Tyr Ser Ser Asp Pro Thr Gly
    770                 775                 780

Ala Leu Thr Glu Asp Ser Ile Asp Asp Thr Phe Leu Pro Val Pro Glu
785                 790                 795                 800

Tyr Ile Asn Gln Ser Val Pro Lys Arg Pro Ala Gly Ser Val Gln Asn
                805                 810                 815

Pro Val Tyr His Asn Gln Pro Leu Asn Pro Ala Pro Ser Arg Asp Pro
                820                 825                 830

His Tyr Gln Asp Pro His Ser Thr Ala Val Gly Asn Pro Glu Tyr Leu
            835                 840                 845

Asn Thr Val Gln Pro Thr Cys Val Asn Ser Thr Phe Asp Ser Pro Ala
        850                 855                 860

His Trp Ala Gln Lys Gly Ser His Gln Ile Ser Leu Asp Asn Pro Asp
865                 870                 875                 880

Tyr Gln Gln Asp Phe Phe Pro Lys Glu Ala Lys Pro Asn Gly Ile Phe
                885                 890                 895

Lys Gly Ser Thr Ala Glu Asn Ala Glu Tyr Leu Arg Val Ala Pro Gln
                900                 905                 910

Ser Ser Glu Phe Ile Gly Ala
            915
```

<210> SEQ ID NO 136
<211> LENGTH: 268
<212> TYPE: PRT
<213> ORGANISM: Homo sapiens

<400> SEQUENCE: 136

Val Cys Gln Gly Thr Ser Asn Lys Leu Thr Gln Leu Gly Thr Phe Glu
1               5                   10                  15

Asp His Phe Leu Ser Leu Gln Arg Met Phe Asn Asn Cys Glu Val Val
            20                  25                  30

Leu Gly Asn Leu Glu Ile Thr Tyr Val Gln Arg Asn Tyr Asp Leu Ser
        35                  40                  45

Phe Leu Lys Thr Ile Gln Glu Val Ala Gly Tyr Val Leu Ile Ala Leu
50                  55                  60

Asn Thr Val Glu Arg Ile Pro Leu Glu Asn Leu Gln Ile Ile Arg Gly
65                  70                  75                  80

Asn Met Tyr Tyr Glu Asn Ser Tyr Ala Leu Ala Val Leu Ser Asn Tyr
                85                  90                  95

Asp Ala Asn Lys Thr Gly Leu Lys Glu Leu Pro Met Arg Asn Leu Gln
            100                 105                 110

Glu Ile Leu His Gly Ala Val Arg Phe Ser Asn Asn Pro Ala Leu Cys
        115                 120                 125

Asn Val Glu Ser Ile Gln Trp Arg Asp Ile Val Ser Ser Asp Phe Leu
130                 135                 140

Ser Asn Met Ser Met Asp Phe Gln Asn His Leu Gly Ser Cys Gln Lys
145                 150                 155                 160

Cys Asp Pro Ser Cys Pro Asn Gly Ser Cys Trp Gly Ala Gly Glu Glu
                165                 170                 175

Asn Cys Gln Lys Leu Thr Lys Ile Ile Cys Ala Gln Gln Cys Ser Gly
            180                 185                 190

Arg Cys Arg Gly Lys Ser Pro Ser Asp Cys Cys His Asn Gln Cys Ala
        195                 200                 205

Ala Gly Cys Thr Gly Pro Arg Glu Ser Asp Cys Leu Val Cys Arg Lys
210                 215                 220

Phe Arg Asp Glu Ala Thr Cys Lys Asp Thr Cys Pro Pro Leu Met Leu
225                 230                 235                 240

Tyr Asn Pro Thr Thr Tyr Gln Met Asp Val Asn Pro Glu Gly Lys Tyr
                245                 250                 255

Ser Phe Gly Ala Thr Cys Val Lys Lys Cys Pro Arg
            260                 265

<210> SEQ ID NO 137
<211> LENGTH: 512
<212> TYPE: DNA
<213> ORGANISM: Homo sapiens

<400> SEQUENCE: 137
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg gtggcagtt atatggtatg atggaagtaa taaatactat   180
gtagactccg tgaagggccg attcaccatc tccagagaca attccaagaa cacgctgtat   240
ctgcaaatga acagcctgag agccgaggac acggctgtgt attactgtgc gagagatgga   300
tggcagcagc tggcccccctt tgactactgg ggccagggaa ccctggtcac cgtctcctca   360

```
gcctccacca agggcccatc ggtcttcccc ctggcaccct ctagcaagag cacctctggg    420
ggcacagcgg ccctgggctg cctggtcaag gactacttcc ccgaaccggt gacggtgtcg    480
tggaactcag gcgccctgac cagcggcgtg ca                                 512
```

<210> SEQ ID NO 138
<211> LENGTH: 170
<212> TYPE: PRT
<213> ORGANISM: Homo sapiens

<400> SEQUENCE: 138

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Trp Gln Gln Leu Ala Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val
                165                 170
```

<210> SEQ ID NO 139
<211> LENGTH: 496
<212> TYPE: DNA
<213> ORGANISM: Homo sapiens

<400> SEQUENCE: 139

```
gatattgtga tgacccagac tccactctcc tcacctgtca cccttggaca gccggcctcc     60
atctcctgca ggtctagtca aagcctcgta catagtgatg aaacaccta cttgagttgg    120 cttcaccaga ggccaggcca gcctccaaga ctcctaattt ataagatttc taaccggttc    180
tctggggtcc cagacagatt cagtggcagt ggggcaggga cagctttcac actgaaaatc    240
agcagggtgg aagctgagga tgtcgggggtt tattactgca tgcaagctac acaacttcct    300
cggacgttcg gccaagggac caaggtggaa atcaaacgaa ctgtggctgc accatctgtc    360
ttcatcttcc cgccatctga tgagcagttg aaatctggaa ctgctagcgt tgtgtgcctg    420
ctgaataact tctatcccag agaggccaaa gtacagtgga aggtggataa cgccctccaa    480
tcgggtaact cccagg                                                   496
```

<210> SEQ ID NO 140
<211> LENGTH: 165
<212> TYPE: PRT
<213> ORGANISM: Homo sapiens -continued

```
<400> SEQUENCE: 140

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Ala Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Leu Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln
                165

<210> SEQ ID NO 141
<211> LENGTH: 110
<212> TYPE: PRT
<213> ORGANISM: Homo sapiens

<400> SEQUENCE: 141

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser Ala
            100                 105                 110

<210> SEQ ID NO 142
<211> LENGTH: 121
<212> TYPE: PRT
<213> ORGANISM: Homo sapiens

<400> SEQUENCE: 142

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
                35                  40                  45
Ala Val Ile Trp Tyr Asp Gly Ser Asn Lys Tyr Tyr Val Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gly Trp Gln Gln Leu Ala Pro Phe Asp Tyr Trp Gly Gln
            100                 105                 110
Gly Thr Leu Val Thr Val Ser Ser Ala
            115                 120

<210> SEQ ID NO 143
<211> LENGTH: 113
<212> TYPE: PRT
<213> ORGANISM: Homo sapiens

<400> SEQUENCE: 143

Asp Ile Val Met Thr Gln Thr Pro Leu Ser Ser Pro Val Thr Leu Gly
 1                   5                  10                  15
Gln Pro Ala Ser Ile Ser Cys Arg Ser Ser Gln Ser Leu Val His Ser
                 20                  25                  30
Asp Gly Asn Thr Tyr Leu Ser Trp Leu Gln Gln Arg Pro Gly Gln Pro
             35                  40                  45
Pro Arg Leu Leu Ile Tyr Lys Ile Ser Asn Arg Phe Ser Gly Val Pro
 50                  55                  60
Asp Arg Phe Ser Gly Ser Gly Ala Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Thr Gln Phe Pro Arg Thr Phe Gly Gln Gly Thr Lys Val Glu Ile Lys
            100                 105                 110
Arg

<210> SEQ ID NO 144
<211> LENGTH: 113
<212> TYPE: PRT
<213> ORGANISM: Homo sapiens

<400> SEQUENCE: 144

Asp Ile Val Met Thr Gln Thr Pro Leu Ser Ser Pro Val Thr Leu Gly
 1                   5                  10                  15
Gln Pro Ala Ser Ile Ser Cys Arg Ser Ser Gln Ser Leu Val His Ser
                 20                  25                  30
Asp Gly Asn Thr Tyr Leu Ser Trp Leu His Gln Arg Pro Gly Gln Pro
             35                  40                  45
Pro Arg Leu Leu Ile Tyr Lys Ile Ser Asn Arg Phe Ser Gly Val Pro
 50                  55                  60
Asp Arg Phe Ser Gly Ser Gly Ala Gly Thr Ala Phe Thr Leu Lys Ile
 65                  70                  75                  80
Ser Arg Val Glu Ala Glu Asp Val Gly Val Tyr Tyr Cys Met Gln Ala
                 85                  90                  95
Thr Gln Leu Pro Arg Thr Phe Gly Gln Gly Thr Lys Val Glu Ile Lys
            100                 105                 110
Arg
```